(12) United States Patent
Lollar

(10) Patent No.: US 7,635,763 B2
(45) Date of Patent: Dec. 22, 2009

(54) NUCLEIC ACID AND AMINO ACID SEQUENCES ENCODING HIGH-LEVEL EXPRESSOR FACTOR VIII POLYPEPTIDES AND METHODS OF USE

(75) Inventor: John S. Lollar, Decatur, GA (US)

(73) Assignee: Expression Therapeutics, LLC., Marietta, GA (US)

( * ) Notice: Subject to any disclaimer, the term of this patent is extended or adjusted under 35 U.S.C. 154(b) by 791 days.

(21) Appl. No.: 10/813,507

(22) Filed: Mar. 30, 2004

(65) Prior Publication Data

US 2005/0118684 A1 Jun. 2, 2005

Related U.S. Application Data

(63) Continuation of application No. PCT/US02/33403, filed on Oct. 7, 2002.

(60) Provisional application No. 60/327,388, filed on Oct. 5, 2001.

(51) Int. Cl.
*C07H 21/02* (2006.01)
*C07H 21/04* (2006.01)
*C12Q 1/68* (2006.01)
*C12P 21/06* (2006.01)
*C12P 19/34* (2006.01)
*C12N 5/02* (2006.01)

(52) U.S. Cl. .......................... 536/23.1; 536/23.4; 435/6; 435/69.1; 435/91.1; 435/325

(58) Field of Classification Search .............. 536/23.1, 536/24.3, 24.33; 435/6, 91.1, 325, 375
See application file for complete search history.

(56) References Cited

U.S. PATENT DOCUMENTS

| 5,364,771 A | 11/1994 | Lollar et al. |
| 5,583,209 A | 12/1996 | Lollar et al. |
| 5,663,060 A | 9/1997 | Lollar et al. |
| 5,744,446 A | 4/1998 | Lollar et al. |
| 5,859,204 A | 1/1999 | Lollar |

(Continued)

FOREIGN PATENT DOCUMENTS

| WO | WO 00/71141 A1 | 11/2000 |
| WO | WO 01/68109 A1 | 9/2001 |

OTHER PUBLICATIONS

Hemostasis, Thrombosis, and Vascular Biology; "*Reduction of the Antigenicity of Factor VIII Toward Complex Inhibitory Antibody Plasmas Using Multiply-Substituted Hybrid Human/Porcine Factor VIII Molecules*"; Rachel T. Barrow, John F. Healey, David Gailani, Dorothea Scandella, and Pete Lollar; 2000 by The American Society of Hematology; Blood, Jan. 15, 2000—vol. 95, No. 2.

(Continued)

*Primary Examiner*—Sean McGarry
*Assistant Examiner*—Terra Cotta Gibbs
(74) *Attorney, Agent, or Firm*—Brinks Hofer Gilson & Lione; Heather N. Schafer

(57) ABSTRACT

Methods and compositions are provided that allow for high-level expression of a factor VIII polypeptide. More specifically, methods and compositions are provided comprising nucleic acid and amino acid sequences comprising a modified factor VIII that result in high-level expression of the polypeptide. The methods and compositions of the invention find use in the treatment of factor VIII deficiency including, for example, hemophilia A.

14 Claims, 33 Drawing Sheets

U.S. PATENT DOCUMENTS

| | | | |
|---|---|---|---|
| 5,888,974 | A | 3/1999 | Lollar et al. |
| 5,935,935 | A | 8/1999 | Connelly et al. |
| 6,180,371 | B1 | 1/2001 | Lollar |
| 6,200,560 | B1 | 3/2001 | Couto et al. |
| 6,376,463 | B1 | 4/2002 | Lollar |
| 6,458,563 | B1 | 10/2002 | Lollar |
| 6,642,028 | B1 | 11/2003 | Ill et al. |
| 6,818,439 | B1 | 11/2004 | Jolly et al. |

OTHER PUBLICATIONS

The Journal of Biological Chemistry; "*High Level Expression of Recombinant Porcine Coagulation Factor VIII*"; Christopher B. Doering, John F. Healey, Ernest T. Parker, Rachel T. Barrow, and Pete Lollar; From the Winship Cancer Institute, Emory University, Atlanta, Georgia; 2002 By The American Society for Biochemistry and Molecular Biology, Inc.; vol. 277, No. 41, Issue of Oct. 11, pp. 38345-38349, 2002.

Barrow, R.T., et al., "Antigenicity of Putative Phospholipid Membrane-Binding Residues in Factor VIII," *Blood*, 2001, pp. 169-174, vol. 97 No. 1.

Barrow, R.T., et al., "Reduction of the Antigenicity of Factor VIII Toward Complex Inhibitory Antibody Plasmas Using Multiply-Substituted Hybrid Human/Porcine Factor VIII Molecules," *Blood*, 2000, pp. 564-568, vol. 95, No. 2.

Bowie, E.J., and C.A. Owen, "The Clinical and Laboratory Diagnosis of Hemorrhagic Disorders," *Grune & Stratton, Inc.*, Orlando, 1984, pp. 43-72.

Chang, J., et al., "Changing Residue 338 in Human Factor IX from Arginine to Alanine Causes an Increase in Catalytic Activity," *The Journal of Biological Chemistry*, 1998, pp. 12089-12094, vol. 273, No. 20, The American Society for Biochemistry and Molecular Biology, Inc., USA.

Doering, C.B., et al., "High Level Expression of Recombinant Porcine Coagulation Factor VIII," *The Journal of Biological Chemistry*, 2002, pp. 38345-38349, vol. 277, No. 41, The American Society for Biochemistry and Molecular Biology, Inc., USA.

Funk, W.D., et al., "Expression of the Amino-Terminal Half-Molecule of Human Serum Transferrin in Cultured Cells and Characterization of Recombinant Protein," *Biochemistry*, 1990, pp. 1654-1660, vol. 29, No. 6.

Healey, J.F., et al., "Residues Glu2181-Val2243 Contain a Major Determinant of the Inhibitory Epitope in the C2 Domain of Human Factor VIII," *Blood*, 1998, pp. 3701-3709, vol. 92, No. 10.

Healey, J.F., et al., "Residues 484-508 Contain a Major Determinant of the Inhibitory Epitope in the A2 Domain of Human Factor VIII," *The Journal of Biological Chemistry*, 1995, pp. 14505-14509, vol. 270, No. 24.

Kaufman, R.J., et al., "Biosynthesis, Assembly and Secretion of Coagulation Factor VIII," *Blood Coagulation and Fibrinolysis*, 1997, pp. S3-S14, vol. 8 (Suppl 2), Rapid science Publishers.

Lind, P., et al., "Novel Forms of B-Domain-Deleted Recombinant Factor VIII Molecules Construction and Biochemical Characterization," *Eur. J. Biochem.*, 1995, pp. 19-27, vol. 232.

Lollar, P., "Mapping factor VIII Inhibitor Epitopes Using Hybrid Human/Porcine Factor VIII Molecules," *Haematologica*, 2000, pp. 26-30, vol. 85 (Suppl. to n. 10).

Lubin, I.M., et al., "Elimination of a Major Inhibitor Epitope in Factor VIII," *The Journal of Biological Chemistry*, 1994, pp 8639-8641, vol. 269, No. 12, The American Society for Biochemistry and Molecular Biology, Inc., USA.

Prescott, R., et al., "The Inhibitor Antibody Response is More Complex in Hemophilia A Patients Than in Most Nonhemophiliacs with Factor VIII Autoantibodies," *Blood*, 1997, pp. 3663-3671, vol. 89, No. 10.

Vehar, G.A., et al., "Structure of Human Factor VIII," *Nature*, 1984, pp. 337-342, vol. 312.

Zhong, D., et al., "Some Human Inhibitor Antibodies Interfere with Factor VIII Binding to Factor IX," 1998, pp. 136-142, vol. 92, No. 1.

```
SIGNAL PEPTIDE
HUMAN  -19 MQIELSTCFF LCLLRFCFS
PIG        MQLELSTCVF LCLLPLGFS
MOUSE      MQIALFACFF LSLFNFCSS
           **  *  * ****   *
```

FIG. 1A

```
A1 DOMAIN
HUMAN   1 ATRRYYLGAV ELSWDYMQSD LG-ELPVDAR FPPRVPKSFP FNTSVVYKKT
PIG       AIRRYYLGAV ELSWDYRQSE LLRELHVDTR FPATAPGALP LGPSVLYKKT
MOUSE     AIRRYYLGAV ELSWNYIQSD LLSVLHTDSR FLPRMSTSFP FNTSIMYKKT
          ********** **** * **    *  * *  *         *    *  ****

50 LFVEFTDHLF NIAKPRPPWM GLLGPTIQAE VYDTVVITLK NMASHPVSLH
          VFVEFTDQLF SVARPRPPWM GLLGPTIQAE VYDTVVVTLK NMASHPVSLH
          VFVEYKDQLF NIAKPRPPWM GLLGPTIWTE VHDTVVITLK NMASHPVSLH
           ***   * **  * ****** ******* *  * **** *** **********

100 AVGVSYWKAS EGAEYDDQTS QREKEDDKVF PGGSHTYVWQ VLKENGPMAS
          AVGVSFWKSS EGAEYEDHTS QREKEDDKVL PGKSQTYVWQ VLKENGPTAS
          AVGVSYWKAS EGDEYEDQTS QMEKEDDKVF PGESHTYVWQ VLKENGPMAS
          ***** ** * ** **** ** * ******* **  * ***** *******  **

150 DPLCLTYSYL SHVDLVKDLN SGLIGALLVC REGSLAKEKT QTLHKFILLF
          DPPCLTYSYL SHVDLVKDLN SGLIGALLVC REGSLTRERT QNLHEFVLLF
          DPPCLTYSYM SHVDLVKDLN SGLIGALLVC KEGSLSKERT QMLYQFVLLF
          ** ******  ********** ********** ****  * ** *  * * ***

200 AVFDEGKSWH SETKNSLMQD RDAASARAWP KMHTVNGYVN RSLPGLIGCH
          AVFDEGKSWH SARNDSWTRA MDPAPARAQP AMHTVNGYVN RSLPGLIGCH
          AVFDEGKSWH SETNDSYTQS MDSASARDWP KMHTVNGYVN RSLPGLIGCH
          **********  *    *      *  **    ********* **********

250 RKSVYWHVIG MGTTPEVHSI FLEGHTFLVR NHRQASLEIS PITFLTAQTL
          KKSVYWHVIG MGTSPEVHSI FLEGHTFLVR HHRQASLEIS PLTFLTAQTF
          RKSVYWHVIG MGTTPEIHSI FLEGHTFFVR NHRQASLEIS PITFLTAQTL
           ********* *** ** *** ******* **  ********* ********
                                                  APC/IXa          ♦
      300 LMDLGQFLLF CHISSHQHDG MEAYVKVDSC PEEPQLRMKN NEEAEDYDDD
          LMDLGQFLLF CHISSHHHGG MEAHVRVESC AEEPQLRRKA DE-EEDYDDN
          LIDLGQFLLF CHISSHKHDG MEAYVKVDSC PEESQWQKKN NN-EEMEDYD
          * ******** ****** *   *** * * ** **  *    *   *   *  *
                                     IIa/Xa
      350 LTDSEMDVVR FDDDNSPSFI QIR
          LYDSDMDVVR LDGDDVSPFI QIR
          DDLYSEMDMF TLDYDSSPFI QIR
                            **  ***
```

FIG. 1B

```
A2 DOMAIN
HUMAN  373  SVAKKHPKTW  VHYIAAEEED  WDYAPLVLAP  DDRSYKSQYL  NNGPQRIGRK
PIG         SVAKKHPKTW  VHYISAEEED  WDYAPAVPSP  SDRSYKSLYL  NSGPQRIGRK
MOUSE       SVAKKYPKTW  IHYISAEEED  WDYAPSVPTS  DNGSYKSQYL  SNGPHRIGRK
            *****.****  ***.*****   ***** *     ****.**     **.*****

423  YKKVRFMAYT  DETFKTREAI  QHESGILGPL  LYGEVGDTLL  IIFKNQASRP
            YKKARFVAYT  DVTFKTRKAI  PYESGILGPL  LYGEVGDTLL  IIFKNKASRP
            YKKVRFIAYT  DETFKTRETI  QHESGLLGPL  LYGEVGDTLL  IIFKNQASRP
            ***.**.***  *.*****..*  .***.*****  **********  *****.****
                              A2 INHIBITOR EPITOPE
       473  YNIYPHGITD  VRPLYSRRLP  KGVKHLKDFP  ILPGEIFKYK  WTVTVEDGPT
            YNIYPHGITD  VSALHPGRLL  KGWKHLKDMP  ILPGETFKYK  WTVTVEDGPT
            YNIYPHGITD  VSPLHARRLP  RGIKHVKDLP  IHPGEIFKYK  WTVTVEDGPT
            **********  *. *.  .**  .*.**.**.*  *.***.****  **********
                                                F.IXa BINDING
                                              APC
       523  KSDPRCLTRY  YSSFVNMERD  LASGLIGPLL  ICYKE SVDQR  GNQIMSDKRN
            KSDPRCLTRY  YSSSINLEKD  LASGLIGPLL  ICYKE SVDQR  GNQMMSDKRN
            KSDPRCLTRY  YSSFINPERD  LASGLIGPLL  ICYKE SVDQR  GNQMMSDKRN
            **********  ***.*.  .*  **********  **********  ***.******

573  VILFSVFDEN  RSWYLTENIQ  RFLPNPAGVQ  LEDPEFQASN  IMHSINGYVF
            VILFSVFDEN  QSWYLAENIQ  RFLPNPDGLQ  PQDPEFQASN  IMHSINGYVF
            VILFSIFDEN  QSWYITENMQ  RFLPNAAKTQ  PQDPGFQASN  IMHSINGYVF
            *****.****  .***..**.*  *****.. .*  ..**.*****  **********

623  DSLQLSVCLH  EVAYWYILSI  GAQTDFLSVF  FSGYTFKHKM  VYEDTLTLFP
            DSLQLSVCLH  EVAYWYILSV  GAQTDFLSVF  FSGYTFKHKM  VYEDTLTLFP
            DSLELTVCLH  EVAYWHILSV  GAQTDFLSIF  FSGYTFKHKM  VYEDTLTLFP
            ***.*.****  *****.***.  ********.*  **********  **********
                                                                  ♦♦
       673  FSGETVFMSM  ENPGLWILGC  HNSDFRNRGM  TALLKVSSCD  KNTGDYYEDS
            FSGETVFMSM  ENPGLWVLGC  HNSDLRNRGM  TALLKVYSCD  RDIGDYYDNT
            FSGETVFMSM  ENPGLWVLGC  HNSDFRKRGM  TALLKVSSCD  KSTSDYYEEI
            **********  ******.***  ****.*.***  ******.***  *  .***
            ♦                   IIa/Xa/APC
       723  YEDISAYLLS  KNNAIEPR
            YEDIPGFLLS  GKNVIEPR
            YEDIPTQLVN  ENNVIDPR
            ****.   *   .* * **
```

FIG. 1C

```
B DOMAIN
HUMAN  741  SFSQNSRHPS TRQKQFNATT IPENDIEKTD PWFAHRTPMP KIQNVSSSDL
PIG         SFAQNSRPPS ASQKQFQTIT SPEDDVE-LD PQSGERTQAL EELSVPSGDG
MOUSE       SFFQNTNHPN TRKKKFKDST IPKNDMEKIE PQFEEIAEML KVQSVSVSDM
            ** **    *     *   *   *  * **    *         *    *  *

791  LMLLRQS-PT PHGLSLSDLQ EAKYETFSDD PSPGAIDSNN SLSEMTHFRP
            SMLLGQN-PA PHGSSSSDLQ EARNEA--DD YLPGARERNT APSAAARLRP
            LMLLGQSHPT PHGLFLSDGQ EAIYEAIHDD HSPNAIDSNE GPSKVTQLRP
            ***  *     ***     *  **   *  ** *  *  *  *        **

840  QLHHSGDMVF TPESGLQLRL NEKLGTTAAT ELKKLDFKVS ST-SNNLIS-
            ELHHSAERVL TPEP------ ------EK   ELKKLDSKMS SSSDLLKTSP
            ESHHSEKIVF TPQPGLQLRS NKSLETTIEV KWKKLGLQVS SLPSNLMTT-
             ***       **                    ***      *  *

888  TIPSDNLAAGT DNTSSLGPPS MPVHYDSQLD TTLFGKKSSP LTESGGPLSL
            TIPSDTLSAET ERTHSLGPPH PQVNFRSQLG AIVLGKNSSH FIGAGVPLGS
            TILSDNLKATF EKTDSSGFPD MPVHSSSKLS TTAFGKKAYS LVGSHVPLNA
            ** ** * *    *  *   *  *        * **             **

939  SEENNDSKLL ESGLMNSQES SWGKNVSSTE SGRLFKGKRA HGPALLTKDN
            TEED------ -------HES SLGENVSPVE SDGIFEKERA HGPASLTKDD
            SEENSDSNIL DSTLMYSQES LPRDNILSIE NDRLLREKRF HGIALLTKDN
            **                **    *    *           *  ** * ****

989  ALFKVSISLL KTNKTSNNSA TNRKTHIDGP SLLIENSPSV WQNILESDTE
            VLFKVNISLV KTNKARVYLK TNRKIHIDDA ALLTENRAS- ----------
            TLFKDNVSLM KTNKTYNHST TNEKLHTESP TSIENSTTDL QDAILKVNSE
             ***   **  ****       ** *  *

1039  FKKVTPLIHD RMLMDKNATA LRLNHMSNKT TSSKNMEMVQ QKKEGPIPPD
            ---------- ATFMDKNTTA SGLNHVSN-- ---------- ----------
            IQEVTALIHD GTLLGKNSTY LRLNHMLNRT TSTKNKDIFH RKDEDPIPQD
                *  ***      **     *** *

1089  AQNPDMSFFK MLFLPESARW IQRTHGKNSL NSGQGPSPKQ LVSLGPEKSV
            ---------- ---------W IKGPLGKNPL SSERGPSPEL LTSSGSGKSV
            EENTIMPFSK MLFLSESSNW FKKTNGNNSL NSEQEHSPKQ LVYLMFKKYV
                                *       *    * *  **    *    *

1139  EGQNFLSEKN KVVVGKEFT KDVGLKEMVF PSSRNLFLTN LDNHENNTH
            KGQSSGQGRI RVAVEEEELS KG---KEMML PNSELTFLTN SADVQGNDTH
            KNQSFLSEKN KVTVEQDGFT KNIGLKDMAF PHNMSIFLTT LSNVHENGRH
             *           *  *          * *  *    ***        *  *

1189  NQEKKIQEEI EKKETLIQEN VVLPQIHTVT GTKNFMKNLF LLSTRQNVEG
            SQGKKSREEM ERREKLVQEK VDLPQVYTAT GTKNFLRNIF HQSTEPSVEG
            NQEKNIQEEI EK-EALIEEK VVLPQVHEAT GSKNFLKDIL ILGTRQNI--
             *    *    **     *   * ***   *  * ***       **

1239  SYDGAYAPVL QDFRSLNDST NRTKKHTAHF SK--KGEEEN LEGLGNQTKQ
            FDGGSHAPVP QDSRSLNDSA ERAETHIAHF SAIR--EEAP LEAPGNRT--
            SLYEVHVPVL QNITSINNST NTVQIHMEHF FKRRKDKETN SEGLVNKTRE
                  * *   **   *  *      *  **          *   *    *
```

FIG. 1D-1

```
1287  IVEKYACTTR  ISPNTSQQNF  VTQRSKRALK  QFRLPLEETE  LEKRIIVDDT
      ----------  ---GPGPRSA  VPRRVKQSLK  QIRLPLEEIK  PERGVVLNAT
      MVKNYP----  -----SQKNI  TTQRSKRALG  QFRL------  ----------

1337  STQWSKNMKH  LTPSTLTQID  YNEKEKGAIT  QSPLSDCLTR  SHSIPQANRS
      STRWS-----  ----------  ----------  ----------  ----------
      STQWLKTINC  STQCIIKQID  HSKEMKKFIT  KSSLSDS-SV  IKSTTQTNSS
      **  *

1387  PLPIAKVSSF  PSIRPIYLTR  VLFQDNSSHL  PAASY----R  KKDSGVQESS
      ----------  ----------  ----------  ----------  -------ESS
      DSHIVKTSAF  P---PIDLKR  SPFQNKFSHV  QASSYIYDFK  TKSSRIQESN
                                                          **

1433  HFLQGAKKNN  LSLAILTLEM  TGDQREVGSL  GTSATNSVTY  KKVENTVLPK
      PILQGAKRNN  LSLPFLTLEM  AGGQGKISAL  GKSAAGPLAS  GKLEKAVLSS
      NFLKETKINN  PSLAILPWNM  FIDQGKFTSP  GKSNTNSVTY  KKRENIIFLK
       *   * **  **  *   *       *          *  *        *  *

1483  PDLPKTSGKV  ELLPKVHIYQ  KDLFPTETSN  GSPGHLDLVE  GSLLQGTEGA
      AGLSEASGKA  EFLPKVRVHR  EDLLPQKTSN  VSCAHGDLGQ  EIFLQKTRGP
      PTLPEESGKI  ELLPQVSIQE  EEILPTETSH  GSPGHLNLMK  EVFLQKIQGP
          ***    *  **  *       *   *     *      *    ***   *

1533  IKWNEANRPG  KVPFLRVATE  SSAKTPSKLL  DPLAWDNHYG  TQIPKEEWKS
      VNLNKVNRPG  ----------  ---RTPSKLL  ---------G  PPMPKE-WES
      TKWNKAKRHG  ESIKGKTES-  -SKNTRSKLL  NHHAWDYHYA  AQIPKDMWKS
       *    *  *                * ****                  * *   *

1583  QEKSPEKTAF  KKKDTI-LSLN  ACESNHAIAA  INEGQNKPEI  EVTWAKQGRT
      LEKSPKSTAL  RTKDIISLPLD  RHESNHSIAA  KNEGQAETQR  EAAWTKQGGP
      KEKSPEIISI  KQEDTI-LSLR  PHGNSHSIGA  -NEKQNWPQR  ETTWVKQGQT
       ****         *    *       **  *     **   *       * ***

1633  ERLCSONPPY  LKRHQR
      GRLCAPKPPV  LRRHQR
      QRTCSQIPPV  LKRHQR
        *   ***  *  ****
```

FIG. 1D-2

```
LIGHT CHAIN ACTIVATION PEPTIDE
                              ♦                  ♦    IIa/Xa
HUMAN 1649 EITRTTLQSDQEEIDYDDTISVEMKKEDFDIYDEDENQSPR
PIG        DISLPTFQPEEDKMDYDDIFSTETKGEDFDIYGEDENQDPR
MOUSE      EL--SAFQSEQEATDYDDAITIET-IEDFDIYSEDIKQGPR
             *    *       ****   *   ****** **  * **
```

FIG. 1E

A3 DOMAIN

```
                                           IXa Xa
HUMAN 1690 SFQKKTRHYF IAAVERLWDY GMSSSPHVLR NRAQSGSVPQ FKKVVFQEFT
PIG        SFQKRTRHYF IAAVEQLWDY GMSESPRALR NRAQNGEVPR FKKVVFREFA
MOUSE      SVQQKTRHYF IAAVERLWDY GMSTS-HVLR NRYQSDNVPQ FKKVVFQEFT
           * *  ***** ***** **** *** *   ** ** *   **  ****** **

1740 DGSFTQPLYR GELNEHLGLL GPYIRAEVED NIMVTFRNQA SRPYSFYSSL
           DGSFTQPSYR GELNKHLGLL GPYIRAEVED NIMVTFKNQA SRPYSFYSSL
           DGSFSQPLYR GELNEHLGLL GPYIRAEVED NIMVTFKNQA SRPYSFYSSL
           **** ** ** **** ***** ********** ****** *** **********
                                       FACTOR IXa BINDING
      1790 ISYEEDQRQG AEPRKNFVKP NETKTYFWKV QHHMAPTKDE FDCKAWAYFS
           ISYPDDQEQG AEPRHNFVQP NETRTYFWKV QHHMAPTEDE FDCKAWAYFS
           ISYKEDQR-G EEPRRNFVKP NETKIYFWKV QHHMAPTEDE FDCKAWAYFS
           *** ** *   *** *** * *** ***** ********** **********

1840 DVDLEKDVHS GLIGPLLVCH TNTLNPAHGR QVTVQEFALF FTIFDETKSW
           DVDLEKDVHS GLIGPLLICR ANTLNAAHGR QVTVQEFALF FTIFDETKSW
           DVDLERDMHS GLIGPLLICH ANTLNPAHGR QVSVQEFALL FTIFDETKSW
           ***** * ** ******* *  **** **** ** ****** **********

1890 YFTENMERNC RAPCNIQMED PTFKENYRFH AINGYIMDTL PGLVMAQDQR
           YFTENVERNC RAPCHLQMED PTLKENYRFH AINGYVMDTL PGLVMAQNQR
           YFTENVKRNC KTPCNFQMED PTLKENYRFH AINGYVMDTL PGLVMAQDQR
           *****  ***    **  **** ** ******* ********** ******* **

1940 IRWYLLSMGS NENIHSIHFS GHVFTVRKKE EYKMALYNLY PGVFETVEML
           IRWYLLSMGS NENIHSIHFS GHVFSVRKKE EYKMAVYNLY PGVFETVEML
           IRWYLLSMGN NENIQSIHFS GHVFTVRKKE EYKMAVYNLY PGVFETLEMI
           *********  ****  **** **** ***** ***** **** ****** **
                         PROTEIN C BINDING
      1990 PSKAGIWRVE CLIGEHLHAG MSTLFLVYSN
           PSKVGIWRIE CLIGEHLQAG MSTTFLVYSK
           PSRAGIWRVE CLIGEHLQAG MSTLFLVYSK
           **  **** * ******* ** *** ******
```

FIG. 1F

```
C1 DOMAIN
HUMAN  2020  KCQTPLGMAS  GHIRDFQITA  SGQYGQWAPK  LARLHYSGSI  NAWSTKEPFS
PIG          ECQAPLGMAS  GRIRDFQITA  SGQYGQWAPK  LARLHYSGSI  NAWSTKDPHS
MOUSE        QCQIPLGMAS  GSIRDFQITA  SGHYGQWAPN  LARLHYSGSI  NAWSTKEPFS
              ** ******  * ********  ** ******  **********  ****** * *

2070  WIKVDLLAPM  IIHGIKTQGA  RQKFSSLYIS  QFIIMYSLDG  KKWQTYRGNS
             WIKVDLLAPM  IIHGIMTQGA  RQKFSSLYIS  QFIIMYSLDG  RNWQSYRGNS
             WIKVDLLAPM  IVHGIKTQGA  RQKFSSLYIS  QFIIMYSLDG  KKWLSYQGNS
             **********  * *** ****  **********  **********   *  * ***

2120  TGTLMVFFGN  VDSSGIKHNI  FNPPIIARYI  RLHPTHYSIR  STLRMELMGCDLN
             TGTLMVFFGN  VDASGIKHNI  FNPPIVARYI  RLHPTHYSIR  STLRMELMGCDLN
             TGTLMVFFGN  VDSSGIKHNS  FNPPIIARYI  RLHPTHSSIR  STLRMELMGCDLN
             **********  ** ******  ***** ****  ****** ***  *************
```

FIG. 1G

```
C2 DOMAIN                        INHIBITOR EPITOPE
HUMAN  2173  SCSMPLGMES  KAISDAQITA  SSYFTNMFAT  WSPSKARLHL  QGRSNAWRPQ
PIG          SCSMPLGMQN  KAISDSQITA  SSHLSNIFAT  WSPSQARLHL  QGRTNAWRPR
MOUSE        SCSIPLGMES  KVISDTQITA  SSYFTNMFAT  WSPSQARLHL  QGRTNAWRPQ
             *** ****   * *** ****  **   * ***  **** *****  *** *****
                                                 C2
       2223  VNNPKEWLQV  DFQKTMKVTG  VTTQGVKSLL  TSMYVKEFLI  SSSQDGHQWT
             VSSAEEWLQV  DLQKTVKVTG  ITTQGVKSLL  SSMYVKEFLV  SSSQDGRRWT
             VNDPKQWLQV  DLQKTMKVTG  IITQGVKSLF  TMSFVKEFLI  SSSQDGHHWT
             *    ****  * *** ****  ********   ** *****  ******  **
                                                     PHOSPHOLIPID
       2273  LFFQNGKVKV  FQGNQDSFTP  VVNSLDPPLL  TRYLRIHPQS  WVHQIALRME
             LFLQDGHTKV  FQGNQDSSTP  VVNALDPPLF  TRYLRIHPTS  WAQHIALRLE
             QILYNGKVKV  FQGNQDSSTP  MMNSLDPPLL  TRYLRIHPQI  WEHQIALRLE
             *  **      **********      *****   ********   *   **** *
             BINDING
       2323  VLGCEAQDLY
             VLGCEAQDLY
             ILGCEAQQQY
             ****** *
```

FIG. 1H

AMINO ACID SEQUENCE OF HP44/OL

```
   1  MQLELSTCVF LCLLPLGFSA IRRYYLGAVE LSWDYRQSEL LRELHVDTRF
  51  PATAPGALPL GPSVLYKKTV FVEFTDQLFS VARPRPPWMG LLGPTIQAEV
 101  YDTVVVTLKN MASHPVSLHA VGVSFWKSSE GAEYEDHTSQ REKEDDKVLP
 151  GKSQTYVWQV LKENGPTASD PPCLTYSYLS HVDLVKDLNS GLIGALLVCR
 201  EGSLTRERTQ NLHEFVLLFA VFDEGKSWHS ARNDSWTRAM DPAPARAQPA
 251  MHTVNGYVNR SLPGLIGCHK KSVYWHVIGM GTSPEVHSIF LEGHTFLVRH
 301  HRQASLEISP LTFLTAQTFL MDLGQFLLFC HISSHHHGGM EAHVRVESCA
 351  EEPQLRRKAD EEEDYDDNLY DSDMDVVRLD GDDVSPFIQI RSVAKKHPKT
 401  WVHYISAEEE DWDYAPAVPS PSDRSYKSLY LNSGPQRIGR KYKKARFVAY
 451  TDVTFKTRKA IPYESGILGP LLYGEVGDTL LIIFKNKASR PYNIYPHGIT
 501  DVSALHPGRL LKGWKHLKDM PILPGETFKY KWTVTVEDGP TKSDPRCLTR
 551  YYSSSINLEK DLASGLIGPL LICYKESVDQ RGNQMMSDKR NVILFSVFDE
 601  NQSWYLAENI QRFLPNPDGL QPQDPEFQAS NIMHSINGYV FDSLQLSVCL
 651  HEVAYWYILS VGAQTDFLSV FFSGYTFKHK MVYEDTLTLF PFSGETVFMS
 701  MENPGLWVLG CHNSDLRNRG MTALLKVYSC DRDIGDYYDN TYEDIPGFLL
 751  SGKNVIEPRS FAQNSRPPSA SAPKPPVLRR HQRDISLPTF QPEEDKMDYD
 801  DIFSTETKGE DFDIYGEDEN QDPRSFQKRT RHYFIAAVEQ LWDYGMSESP
 851  RALRNRAQNG EVPRFKKVVF REFADGSFTQ PSYRGELNKH LGLLGPYIRA
 901  EVEDNIMVTF KNQASRPYSF YSSLISYPDD QEQGAEPRHN FVQPNETRTY
 951  FWKVQHHMAP TEDEFDCKAW AWFSDVDLEK DVHSGLIGPL LICRANTLNA
1001  AHGRQVTVQE FALFFTIFDE TKSWYFTENV ERNCRAPCHL QMEDPTLKEN
1051  YRFHAINGYV MDTLPGLVMA QNQRIRWYLL SMGSNENIHS IHFSGHVFSV
1101  RKKEEYKMAV YNLYPGVFET VEMLPSKVGI WRIECLIGEH LQAGMSTTFL
1151  VYSKKCQTPL GMASGHIRDF QITASGQYGQ WAPKLARLHY SGSINAWSTK
1201  EPFSWIKVDL LAPMIIHGIK TQGARQKFSS LYISQFIIMY SLDGKKWQTY
1251  RGNSTGTLMV FFGNVDSSGI KHNIFNPPII ARYIRLHPTH YSIRSTLRME
1301  LMGCDLNSCS MPLGMESKAI SDAQITASSY FTNMFATWSP SKARLHLQGR
1351  SNAWRPQVNN PKEWLQVDFQ KTMKVTGVTT QGVKSLLTSM YVKEFLISSS
1401  QDGHQWTLFF QNGKVKVFQG NQDSFTPVVN SLDPPLLTRY LRIHPQSWVH
1451  QIALRMEVLG CEAQDLY*
```

1-19 SIGNAL PEPTIDE
20-391 A1 DOMAIN
392-759 A2 DOMAIN
760-783 OL LINKER
784-1154 ap-A3
1155-1307 C1 DOMAIN
1308-1467 C2 DOMAIN

FIG. 4

HP44/OL NUCLEOTIDE SEQUENCE

```
   1  ATGCAGCTAG AGCTCTCCAC CTGTGTCTTT CTGTGTCTCT TGCCACTCGG
      TACGTCGATC TCGAGAGGTG GACACAGAAA GACACAGAGA ACGGTGAGCC
  51  CTTTAGTGCC ATCAGGAGAT ACTACCTGGG CGCAGTGGAA CTGTCCTGGG
      GAAATCACGG TAGTCCTCTA TGATGGACCC GCGTCACCTT GACAGGACCC
 101  ACTACCGGCA AAGTGAACTC CTCCGTGAGC TGCACGTGGA CACCAGATTT
      TGATGGCCGT TTCACTTGAG GAGGCACTCG ACGTGCACCT GTGGTCTAAA
 151  CCTGCTACAG CGCCAGGAGC TCTTCCGTTG GGCCCGTCAG TCCTGTACAA
      GGACGATGTC GCGGTCCTCG AGAAGGCAAC CCGGGCAGTC AGGACATGTT
 201  AAAGACTGTG TTCGTAGAGT TCACGGATCA ACTTTTCAGC GTTGCCAGGC
      TTTCTGACAC AAGCATCTCA AGTGCCTAGT TGAAAAGTCG CAACGGTCCG
 251  CCAGGCCACC ATGGATGGGT CTGCTGGGTC CTACCATCCA GGCTGAGGTT
      GGTCCGGTGG TACCTACCCA GACGACCCAG GATGGTAGGT CCGACTCCAA
 301  TACGACACGG TGGTCGTTAC CCTGAAGAAC ATGGCTTCTC ATCCCGTTAG
      ATGCTGTGCC ACCAGCAATG GGACTTCTTG TACCGAAGAG TAGGGCAATC
 351  TCTTCACGCT GTCGGCGTCT CCTTCTGGAA ATCTTCCGAA GGCGCTGAAT
      AGAAGTGCGA CAGCCGCAGA GGAAGACCTT TAGAAGGCTT CCGCGACTTA
 401  ATGAGGATCA CACCAGCCAA AGGGAGAAGG AAGACGATAA AGTCCTTCCC
      TACTCCTAGT GTGGTCGGTT TCCCTCTTCC TTCTGCTATT TCAGGAAGGG
 451  GGTAAAAGCC AAACCTACGT CTGGCAGGTC CTGAAAGAAA ATGGTCCAAC
      CCATTTTCGG TTTGGATGCA GACCGTCCAG GACTTTCTTT TACCAGGTTG
 501  AGCCTCTGAC CCACCATGTC TTACCTACTC ATACCTGTCT CACGTGGACC
      TCGGAGACTG GGTGGTACAG AATGGATGAG TATGGACAGA GTGCACCTGG
 551  TGGTGAAAGA CCTGAATTCG GGCCTCATTG GAGCCCTGCT GGTTTGTAGA
      ACCACTTTCT GGACTTAAGC CCGGAGTAAC CTCGGGACGA CCAAACATCT
 601  GAAGGGAGTC TGACCAGAGA AAGGACCCAG AACCTGCACG AATTTGTACT
      CTTCCCTCAG ACTGGTCTCT TTCCTGGGTC TTGGACGTGC TTAAACATGA
 651  ACTTTTTGCT GTCTTTGATG AAGGGAAAAG TTGGCACTCA GCAAGAAATG
      TGAAAAACGA CAGAAACTAC TTCCCTTTTC AACCGTGAGT CGTTCTTTAC
 701  ACTCCTGGAC ACGGGCCATG GATCCCGCAC CTGCCAGGGC CAGCCTGCA
      TGAGGACCTG TGCCCGGTAC CTAGGGCGTG GACGGTCCCG GTCGGACGT
 751  ATGCACACAG TCAATGGCTA TGTCAACAGG TCTCTGCCAG GTCTGATCGG
      TACGTGTGTC AGTTACCGAT ACAGTTGTCC AGAGACGGTC CAGACTAGCC
 801  ATGTCATAAG AAATCAGTCT ACTGGCACGT GATTGGAATG GCACCAGCC
      TACAGTATTC TTTAGTCAGA TGACCGTGCA CTAACCTTAC CCGTGGTCGG
 851  CGGAAGTGCA CTCCATTTTT CTTGAAGGCC ACACGTTTCT CGTGAGGCAC
      GCCTTCACGT GAGGTAAAAA GAACTTCCGG TGTGCAAAGA GCACTCCGTG
 901  CATCGCCAGG CTTCCTTGGA GATCTCGCCA CTAACTTTCC TCACTGCTCA
      GTAGCGGTCC GAAGGAACCT CTAGAGCGGT GATTGAAAGG AGTGACGAGT
 951  GACATTCCTG ATGGACCTTG GCCAGTTCCT ACTGTTTTGT CATATCTCTT
      CTGTAAGGAC TACCTGGAAC CGGTCAAGGA TGACAAAACA GTATAGAGAA
1001  CCCACCACCA TGGTGGCATG GAGGCTCACG TCAGAGTAGA AAGCTGCGCC
      GGGTGGTGGT ACCACCGTAC CTCCGAGTGC AGTCTCATCT TTCGACGCGG
1051  GAGGAGCCCC AGCTGCGGAG GAAAGCTGAT GAAGAGGAAG ATTATGATGA
      CTCCTCGGGG TCGACGCCTC CTTTCGACTA CTTCTCCTTC TAATACTACT
1101  CAATTTGTAC GACTCGGACA TGGACGTGGT CCGGCTCGAT GGTGACGACG
      GTTAAACATG CTGAGCCTGT ACCTGCACCA GGCCGAGCTA CCACTGCTGC
1151  TGTCTCCCTT TATCCAAATC CGCTCGGTTG CCAAGAAGCA TCCCAAAACC
      ACAGAGGGAA ATAGGTTTAG GCGAGCCAAC GGTTCTTCGT AGGGTTTTGG
1201  TGGGTGCACT ACATCTCTGC AGAGGAGGAG GACTGGGACT ACGCCCCGC
      ACCCACGTGA TGTAGAGACG TCTCCTCCTC CTGACCCTGA TGCGGGGCG
1251  GGTCCCCAGC CCCAGTGACA GAAGTTATAA AGTCTCTAC TTGAACAGTG
      CCAGGGGTCG GGGTCACTGT CTTCAATATT TCAGAGATG AACTTGTCAC
1301  GTCCTCAGCG AATTGGTAGG AAATACAAAA AAGCTCGATT CGTCGCTTAC
      CAGGAGTCGC TTAACCATCC TTTATGTTTT TTCGAGCTAA GCAGCGAATG
```

FIG. 5A

```
1351  ACGGATGTAA CATTTAAGAC TCGTAAAGCT ATTCCGTATG AATCAGGAAT
      TGCCTACATT GTAAATTCTG AGCATTTCGA TAAGGCATAC TTAGTCCTTA
1401  CCTGGGACCT TTACTTTATG GAGAAGTTGG AGACACACTT TTGATTATAT
      GGACCCTGGA AATGAAATAC CTCTTCAACC TCTGTGTGAA AACTAATATA
1451  TTAAGAATAA AGCGAGCCGA CCATATAACA TCTACCCTCA TGGAATCACT
      AATTCTTATT TCGCTCGGCT GGTATATTGT AGATGGGAGT ACCTTAGTGA
1501  GATGTCAGCG CTTTGCACCC AGGGAGACTT CTAAAAGGTT GGAAACATTT
      CTACAGTCGC GAAACGTGGG TCCCTCTGAA GATTTTCCAA CCTTTGTAAA
1551  GAAAGACATG CCAATTCTGC AGGAGAGAC TTTCAAGTAT AAATGGACAG
      CTTTCTGTAC GGTTAAGACG GTCCTCTCTG AAAGTTCATA TTTACCTGTC
1601  TGACTGTGGA AGATGGGCCA ACCAAGTCCG ATCCTCGGTG CCTGACCCGC
      ACTGACACCT TCTACCCGGT TGGTTCAGGC TAGGAGCCAC GGACTGGGCG
1651  TACTACTCGA GCTCCATTAA TCTAGAGAAA GATCTGGCTT CGGGACTCAT
      ATGATGAGCT CGAGGTAATT AGATCTCTTT CTAGACCGAA GCCCTGAGTA
1701  TGGCCCTCTC CTCATCTGCT ACAAAGAATC TGTAGACCAA AGAGGAAACC
      ACCGGGAGAG GAGTAGACGA TGTTTCTTAG ACATCTGGTT TCTCCTTTGG
1751  AGATGATGTC AGACAAGAGA AACGTCATCC TGTTTTCTGT ATTCGATGAG
      TCTACTACAG TCTGTTCTCT TTGCAGTAGG ACAAAAGACA TAAGCTACTC
1801  AATCAAAGCT GGTACCTCGC AGAGAATATT CAGCGCTTCC TCCCCAATCC
      TTAGTTTCGA CCATGGAGCG TCTCTTATAA GTCGCGAAGG AGGGGTTAGG
1851  GGATGGATTA CAGCCCCAGG ATCCAGAGTT CCAAGCTTCT AACATCATGC
      CCTACCTAAT GTCGGGGTCC TAGGTCTCAA GGTTCGAAGA TTGTAGTACG
1901  ACAGCATCAA TGGCTATGTT TTTGATAGCT TGCAGCTGTC GGTTTGTTTG
      TGTCGTAGTT ACCGATACAA AAACTATCGA ACGTCGACAG CCAAACAAAC
1951  CACGAGGTGG CATACTGGTA CATTCTAAGT GTTGGAGCAC AGACGGACTT
      GTGCTCCACC GTATGACCAT GTAAGATTCA CAACCTCGTG TCTGCCTGAA
2001  CCTCTCCGTC TTCTTCTCTG GCTACACCTT CAAACACAAA ATGGTCTATG
      GGAGAGGCAG AAGAAGAGAC CGATGTGGAA GTTTGTGTTT TACCAGATAC
2051  AAGACACACT CACCCTGTTC CCCTTCTCAG GAGAAACGGT CTTCATGTCA
      TTCTGTGTGA GTGGGACAAG GGGAAGAGTC CTCTTTGCCA GAAGTACAGT
2101  ATGGAAAACC CAGGTCTCTG GGTCCTTGGG TGCCACAACT CAGACTTGCG
      TACCTTTTGG GTCCAGAGAC CCAGGAACCC ACGGTGTTGA GTCTGAACGC
2151  GAACAGAGGG ATGACAGCCT TACTGAAGGT GTATAGTTGT GACAGGGACA
      CTTGTCTCCC TACTGTCGGA ATGACTTCCA CATATCAACA CTGTCCCTGT
2201  TTGGTGATTA TTATGACAAC ACTTATGAAG ATATTCCAGG CTTCTTGCTG
      AACCACTAAT AATACTGTTG TGAATACTTC TATAAGGTCC GAAGAACGAC
2251  AGTGGAAAGA ATGTCATTGA ACCTAGGAGC TTTGCCCAGA ATTCAAGACC
      TCACCTTTCT TACAGTAACT TGGATCCTCG AAACGGGTCT TAAGTTCTGG
2301  CCCTAGTGCG AGCGCTCCAA AGCCTCCGGT CCTGCGACGG CATCAGAGGG
      GGGATCACGC TCGCGAGGTT TCGGAGGCCA GGACGCTGCC GTAGTCTCCC
2351  ACATAAGCCT TCCTACTTTT CAGCCGGAGG AAGACAAAAT GGACTATGAT
      TGTATTCGGA AGGATGAAAA GTCGGCCTCC TTCTGTTTTA CCTGATACTA
2401  GATATCTTCT CAACTGAAAC GAAGGGAGAA GATTTTGACA TTTACGGTGA
      CTATAGAAGA GTTGACTTTG CTTCCCTCTT CTAAAACTGT AAATGCCACT
2451  GGATGAAAAT CAGGACCCTC GCAGCTTTCA GAAGAGAACC CGACACTATT
      CCTACTTTTA GTCCTGGGAG CGTCGAAAGT CTTCTCTTGG GCTGTGATAA
2501  TCATTGCTGC GGTGGAGCAG CTCTGGGATT ACGGGATGAG CGAATCCCCC
      AGTAACGACG CCACCTCGTC GAGACCCTAA TGCCCTACTC GCTTAGGGGG
2551  CGGGCGCTAA GAAACAGGGC TCAGAACGGA GAGGTGCCTC GGTTCAAGAA
      GCCCGCGATT CTTTGTCCCG AGTCTTGCCT CTCCACGGAG CCAAGTTCTT
2601  GGTGGTCTTC CGGGAATTTG CTGACGGCTC CTTCACGCAG CCGTCGTACC
      CCACCAGAAG GCCCTTAAAC GACTGCCGAG GAAGTGCGTC GGCAGCATGG
2651  GCGGGGAACT CAACAAACAC TTGGGGCTCT TGGGACCCTA CATCAGAGCG
      CGCCCCTTGA GTTGTTTGTG AACCCCGAGA ACCCTGGGAT GTAGTCTCGC
2701  GAAGTTGAAG ACAACATCAT GGTAACTTTC AAAAACCAGG CGTCTCGTCC
      CTTCAACTTC TGTTGTAGTA CCATTGAAAG TTTTTGGTCC GCAGAGCAGG
2751  CTATTCCTTC TACTCGAGCC TTATTTCTTA TCCGGATGAT CAGGAGCAAG
```

FIG. 5B

```
          GATAAGGAAG ATGAGCTCGG AATAAAGAAT AGGCCTACTA GTCCTCGTTC
2801      GGGCAGAACC TCGACACAAC TTCGTCCAGC CAAATGAAAC CAGAACTTAC
          CCCGTCTTGG AGCTGTGTTG AAGCAGGTCG GTTTACTTTG GTCTTGAATG
2851      TTTTGGAAAG TGCAGCATCA CATGGCACCC ACAGAAGACG AGTTTGACTG
          AAAACCTTTC ACGTCGTAGT GTACCGTGGG TGTCTTCTGC TCAAACTGAC
2901      CAAAGCCTGG GCCTACTTTT CTGATGTTGA CCTGGAAAAA GATGTGCACT
          GTTTCGGACC CGGATGAAAA GACTACAACT GGACCTTTTT CTACACGTGA
2951      CAGGCTTGAT CGGCCCCCTT CTGATCTGCC GCGCCAACAC CCTGAACGCT
          GTCCGAACTA GCCGGGGAA GACTAGACGG CGCGGTTGTG GGACTTGCGA
3001      GCTCACGGTA GACAAGTGAC CGTGCAAGAA TTTGCTCTGT TTTTCACTAT
          CGAGTGCCAT CTGTTCACTG GCACGTTCTT AAACGAGACA AAAAGTGATA
3051      TTTTGATGAG ACAAAGAGCT GGTACTTCAC TGAAAATGTG GAAAGGAACT
          AAAACTACTC TGTTTCTCGA CCATGAAGTG ACTTTTACAC CTTTCCTTGA
3101      GCCGGGCCCC CTGCCATCTG CAGATGGAGG ACCCCACTCT GAAAGAAAAC
          CGGCCCGGGG GACGGTAGAC GTCTACCTCC TGGGGTGAGA CTTTCTTTTG
3151      TATCGCTTCC ATGCAATCAA TGGCTATGTG ATGGATACAC TCCCTGGCTT
          ATAGCGAAGG TACGTTAGTT ACCGATACAC TACCTATGTG AGGGACCGAA
3201      AGTAATGGCT CAGAATCAAA GGATCCGATG GTATCTGCTC AGCATGGGCA
          TCATTACCGA GTCTTAGTTT CCTAGGCTAC CATAGACGAG TCGTACCCGT
3251      GCAATGAAAA TATCCATTCG ATTCATTTTA GCGGACACGT GTTCAGTGTA
          CGTTACTTTT ATAGGTAAGC TAAGTAAAAT CGCCTGTGCA CAAGTCACAT
3301      CGGAAAAAGG AGGAGTATAA AATGGCCGTG TACAATCTCT ATCCGGGTGT
          GCCTTTTTCC TCCTCATATT TTACCGGCAC ATGTTAGAGA TAGGCCCACA
3351      CTTTGAGACA GTGGAAATGC TACCGTCCAA AGTTGGAATT TGGCGAATAG
          GAAACTCTGT CACCTTTACG ATGGCAGGTT TCAACCTTAA ACCGCTTATC
3401      AATGCCTGAT TGGCGAGCAC CTGCAAGCTG GGATGAGCAC GACTTTCCTG
          TTACGGACTA ACCGCTCGTG GACGTTCGAC CCTACTCGTG CTGAAAGGAC
3451      GTGTACAGCA AGAAGTGTCA GACTCCCCTG GAATGGCTT CTGGACACAT
          CACATGTCGT TCTTCACAGT CTGAGGGGAC CCTTACCGAA GACCTGTGTA
3501      TAGAGATTTT CAGATTACAG CTTCAGGACA ATATGGACAG TGGGCCCCAA
          ATCTCTAAAA GTCTAATGTC GAAGTCCTGT TATACCTGTC ACCCGGGGTT
3551      AGCTGGCCAG ACTTCATTAT TCCGGATCAA TCAATGCCTG GAGCACCAAG
          TCGACCGGTC TGAAGTAATA AGGCCTAGTT AGTTACGGAC CTCGTGGTTC
3601      GAGCCCTTTT CTTGGATCAA GGTGGATCTG TTGGCACCAA TGATTATTCA
          CTCGGGAAAA GAACCTAGTT CCACCTAGAC AACCGTGGTT ACTAATAAGT
3651      CGGCATCAAG ACCCAGGGTG CCCGTCAGAA GTTCTCCAGC CTCTACATCT
          GCCGTAGTTC TGGGTCCCAC GGGCAGTCTT CAAGAGGTCG GAGATGTAGA
3701      CTCAGTTTAT CATCATGTAT AGTCTTGATG GGAAGAAGTG GCAGACTTAT
          GAGTCAAATA GTAGTACATA TCAGAACTAC CCTTCTTCAC CGTCTGAATA
3751      CGAGGAAATT CCACTGGAAC CTTAATGGTC TTCTTTGGCA ATGTGGATTC
          GCTCCTTTAA GGTGACCTTG GAATTACCAG AAGAAACCGT TACACCTAAG
3801      ATCTGGGATA AAACACAATA TTTTTAACCC TCCAATTATT GCTCGATACA
          TAGACCCTAT TTTGTGTTAT AAAAATTGGG AGGTTAATAA CGAGCTATGT
3851      TCCGTTTGCA CCCAACTCAT TATAGCATTC GCAGCACTCT TCGCATGGAG
          AGGCAAACGT GGGTTGAGTA ATATCGTAAG CGTCGTCAGA AGCGTACCTC
3901      TTGATGGGCT GTGATTTAAA TAGTTGCAGC ATGCCATTGG GAATGGAGAG
          AACTACCCGA CACTAAATTT ATCAACGTCG TACGGTAACC CTTACCTCTC
3951      TAAAGCAATA TCAGATGCAC AGATTACTGC TTCATCCTAC TTTACCAATA
          ATTTCGTTAT AGTCTACGTG TCTAATGACG AAGTAGGATG AAATGGTTAT
4001      TGTTTGCCAC CTGGTCTCCT TCAAAAGCTC GACTTCACCT CCAAGGGAGG
          ACAAACGGTG GACCAGAGGA AGTTTTCGAG CTGAAGTGGA GGTTCCCTCC
4051      AGTAATGCCT GGAGACCTCA GGTGAATAAT CCAAAAGAGT GGCTGCAAGT
          TCATTACGGA CCTCTGGAGT CCACTTATTA GGTTTTCTCA CCGACGTTCA
4101      GGACTTCCAG AAGACAATGA AAGTCACAGG AGTAACTACT CAGGGAGTAA
          CCTGAAGGTC TTCTGTTACT TTCAGTGTCC TCATTGATGA GTCCCTCATT
4151      AATCTCTGCT TACCAGCATG TATGTGAAGG AGTTCCTCAT CTCCAGCAGT
          TTAGAGACGA ATGGTCGTAC ATACACTTCC TCAAGGAGTA GAGGTCGTCA
```

FIG. 5C

```
4201   CAAGATGGCC ATCAGTGGAC TCTCTTTTTT CAGAATGGCA AAGTAAAGGT
       GTTCTACCGG TAGTCACCTG AGAGAAAAAA GTCTTACCGT TTCATTTCCA
4251   TTTTCAGGGA AATCAAGACT CCTTCACACC TGTGGTGAAC TCTCTAGACC
       AAAAGTCCCT TTAGTTCTGA GGAAGTGTGG ACACCACTTG AGAGATCTGG
4301   CACCGTTACT GACTCGCTAC CTTCGAATTC ACCCCAGAG TTGGGTGCAC
       GTGGCAATGA CTGAGCGATG GAAGCTTAAG TGGGGGTCTC AACCCACGTG
4351   CAGATTGCCC TGAGGATGGA GGTTCTGGGC TGCGAGGCAC AGGACCTCTA
       GTCTAACGGG ACTCCTACCT CCAAGACCCG ACGCTCCGTG TCCTGGAGAT
4401   C
       G
```

1-57 SIGNAL PEPTIDE
58-1173 A1 DOMAIN
1174-2277 A2 DOMAIN
2278-2349 OL LINKER
2350-3462 ap-A3 DOMAINS
3463-3921 C1 DOMAIN
3922-4401 C2 DOMAIN

FIG. 5D

AMINO ACID SEQUENCE OF HP46/SQ

```
   1  MQLELSTCVF  LCLLPLGFSA  IRRYYLGAVE  LSWDYRQSEL  LRELHVDTRF
  51  PATAPGALPL  GPSVLYKKTV  FVEFTDQLFS  VARPRPPWMG  LLGPTIQAEV
 101  YDTVVVTLKN  MASHPVSLHA  VGVSFWKSSE  GAEYEDHTSQ  REKEDDKVLP
 151  GKSQTYVWQV  LKENGPTASD  PPCLTYSYLS  HVDLVKDLNS  GLIGALLVCR
 201  EGSLTRERTQ  NLHEFVLLFA  VFDEGKSWHS  ARNDSWTRAM  DPAPARAQPA
 251  MHTVNGYVNR  SLPGLIGCHK  KSVYWHVIGM  GTSPEVHSIF  LEGHTFLVRH
 301  HRQASLEISP  LTFLTAQTFL  MDLGQFLLFC  HISSHHHGGM  EAHVRVESCA
 351  EEPQLRRKAD  EEEDYDDNLY  DSDMDVVRLD  GDDVSPFIQI  RSVAKKHPKT
 401  WVHYIAAEEE  DWDYAPLVLA  PDDRSYKSQY  LNNGPQRIGR  KYKKVRFMAY
 451  TDETFKTREA  IQHESGILGP  LLYGEVGDTL  LIIFKNQASR  PYNIYPHGIT
 501  DVRPLYSRRL  PKGVKHLKDF  PILPGEIFKY  KWTVTVEDGP  TKSDPRCLTR
 551  YYSSFVNMER  DLASGLIGPL  LICYKESVDQ  RGNQIMSDKR  NVILFSVFDE
 601  NRSWYLTENI  QRFLPNPAGV  QLEDPEFQAS  NIMHSINGYV  FDSLQLSVCL
 651  HEVAYWYILS  IGAQTDFLSV  FFSGYTFKHK  MVYEDTLTLF  PFSGETVFMS
 701  MENPGLWILG  CHNSFLRNRG  MTALLKVSSC  DKNTGDYYED  SYEDISAYLL
 751  SKNNAIEPRS  FSQNPPVLKR  HQREITRTTL  QSDQEEIDYD  DTISVEMKKE
 801  DFDIYDEDEN  QSPRSFQKKT  RHYFIAAVER  LWDYGMSSSP  HVLRNRAQSG
 851  SVPQFKKVVF  QEFTDGSFTQ  PLYRGELNEH  LGLLGPYIRA  EVEDNIMVTF
 901  RNQASRPYSF  YSSLISYEED  QRQGAEPRKN  FVKPNETKTY  FWKVQHHMAP
 951  TKDEFDCKAW  AYFSDVDLEK  DVHSGLIGPL  LVCHTNTLNP  AHGRQVTVQE
1001  FALFFTIFDE  TKSWYFTENM  ERNCRAPCNI  QMEDPTFKEN  YRFHAINGYI
1051  MDTLPGLVMA  QDQRIRWYLL  SMGSNENIHS  IHFSGHVFTV  RKKEEYKMAL
1101  YNLYPGVFET  VEMLPSKAGI  WRVECLIGEH  LHAGMSTLFL  VYSNKCQTPL
1151  GMASGHIRDF  QITASGQYGQ  WAPKLARLHY  SGSINAWSTK  EPFSWIKVDL
1201  LAPMIIHGIK  TQGARQKFSS  LYISQFIIMY  SLDGKKWQTY  RGNSTGTLMV
1251  FFGNVDSSGI  KHNIFNPPII  ARYIRLHPTH  YSIRSTLRME  LMGCDLNSCS
1301  MPLGMESKAI  SDAQITASSY  FTNMFATWSP  SKARLHLQGR  SNAWRPQVNN
1351  PKEWLQVDFQ  KTMKVTGVTT  QGVKSLLTSM  YVKEFLISSS  QDGHQWTLFF
1401  QNGKVKVFQG  NQDSFTPVVN  SLDPPLLTRY  LRIHPQSWVH  QIALRMEVLG
1451  CEAQDLY*
```

1-19 SIGNAL PEPTIDE
20-391 A1 DOMAIN
392-759 A2 DOMAIN
760-773 SQ LINKER
774-1144 ap-A3
1145-1297 C1 DOMAIN
1298-1457 C2 DOMAIN

FIG. 6

HP46/SQ NUCLEOTIDE SEQUENCE

```
   1 ATGCAGCTAG AGCTCTCCAC CTGTGTCTTT CTGTGTCTCT TGCCACTCGG
     TACGTCGATC TCGAGAGGTG GACACAGAAA GACACAGAGA ACGGTGAGCC
  51 CTTTAGTGCC ATCAGGAGAT ACTACCTGGG CGCAGTGGAA CTGTCCTGGG
     GAAATCACGG TAGTCCTCTA TGATGGACCC GCGTCACCTT GACAGGACCC
 101 ACTACCGGCA AAGTGAACTC CTCCGTGAGC TGCACGTGGA CACCAGATTT
     TGATGGCCGT TTCACTTGAG GAGGCACTCG ACGTGCACCT GTGGTCTAAA
 151 CCTGCTACAG CGCCAGGAGC TCTTCCGTTG GGCCCGTCAG TCCTGTACAA
     GGACGATGTC GCGGTCCTCG AGAAGGCAAC CCGGGCAGTC AGGACATGTT
 201 AAAGACTGTG TTCGTAGAGT TCACGGATCA ACTTTTCAGC GTTGCCAGGC
     TTTCTGACAC AAGCATCTCA AGTGCCTAGT TGAAAAGTCG CAACGGTCCG
 251 CCAGGCCACC ATGGATGGGT CTGCTGGGTC CTACCATCCA GGCTGAGGTT
     GGTCCGGTGG TACCTACCCA GACGACCCAG GATGGTAGGT CCGACTCCAA
 301 TACGACACGG TGGTCGTTAC CCTGAAGAAC ATGGCTTCTC ATCCCGTTAG
     ATGCTGTGCC ACCAGCAATG GGACTTCTTG TACCGAAGAG TAGGGCAATC
 351 TCTTCACGCT GTCGGCGTCT CCTTCTGGAA ATCTTCCGAA GGCGCTGAAT
     AGAAGTGCGA CAGCCGCAGA GGAAGACCTT TAGAAGGCTT CCGCGACTTA
 401 ATGAGGATCA CACCAGCCAA AGGGAGAAGG AAGACGATAA AGTCCTTCCC
     TACTCCTAGT GTGGTCGGTT TCCCTCTTCC TTCTGCTATT TCAGGAAGGG
 451 GGTAAAAGCC AAACCTACGT CTGGCAGGTC CTGAAAGAAA ATGGTCCAAC
     CCATTTTCGG TTTGGATGCA GACCGTCCAG GACTTTCTTT TACCAGGTTG
 501 AGCCTCTGAC CCACCATGTC TTACCTACTC ATACCTGTCT CACGTGGACC
     TCGGAGACTG GGTGGTACAG AATGGATGAG TATGGACAGA GTGCACCTGG
 551 TGGTGAAAGA CCTGAATTCG GGCCTCATTG GAGCCCTGCT GGTTTGTAGA
     ACCACTTTCT GGACTTAAGC CCGGAGTAAC CTCGGGACGA CCAAACATCT
 601 GAAGGGAGTC TGACCAGAGA AAGGACCCAG AACCTGCACG AATTTGTACT
     CTTCCCTCAG ACTGGTCTCT TTCCTGGGTC TTGGACGTGC TTAAACATGA
 651 ACTTTTTGCT GTCTTTGATG AAGGGAAAAG TTGGCACTCA GCAAGAAATG
     TGAAAAACGA CAGAAACTAC TTCCCTTTTC AACCGTGAGT CGTTCTTTAC
 701 ACTCCTGGAC ACGGGCCATG GATCCCGCAC CTGCCAGGGC CCAGCCTGCA
     TGAGGACCTG TGCCCGGTAC CTAGGGCGTG GACGGTCCCG GGTCGGACGT
 751 ATGCACACAG TCAATGGCTA TGTCAACAGG TCTCTGCCAG GTCTGATCGG
     TACGTGTGTC AGTTACCGAT ACAGTTGTCC AGAGACGGTC CAGACTAGCC
 801 ATGTCATAAG AAATCAGTCT ACTGGCACGT GATTGGAATG GGCACCAGCC
     TACAGTATTC TTTAGTCAGA TGACCGTGCA CTAACCTTAC CCGTGGTCGG
 851 CGGAAGTGCA CTCCATTTTT CTTGAAGGCC ACACGTTTCT CGTGAGGCAC
     GCCTTCACGT GAGGTAAAAA GAACTTCCGG TGTGCAAAGA GCACTCCGTG
 901 CATCGCCAGG CTTCCTTGGA GATCTCGCCA CTAACTTTCC TCACTGCTCA
     GTAGCGGTCC GAAGGAACCT CTAGAGCGGT GATTGAAAGG AGTGACGAGT
 951 GACATTCCTG ATGGACCTTG GCCAGTTCCT ACTGTTTTGT CATATCTCTT
     CTGTAAGGAC TACCTGGAAC CGGTCAAGGA TGACAAAACA GTATAGAGAA
1001 CCCACCACCA TGGTGGCATG GAGGCTCACG TCAGAGTAGA AAGCTGCGCC
     GGGTGGTGGT ACCACCGTAC CTCCGAGTGC AGTCTCATCT TTCGACGCGG
1051 GAGGAGCCCC AGCTGCGGAG GAAAGCTGAT GAAGAGGAAG ATTATGATGA
     CTCCTCGGGG TCGACGCCTC CTTTCGACTA CTTCTCCTTC TAATACTACT
1101 CAATTTGTAC GACTCGGACA TGGACGTGGT CCGGCTCGAT GGTGACGACG
     GTTAAACATG CTGAGCCTGT ACCTGCACCA GGCCGAGCTA CCACTGCTGC
1151 TGTCTCCCTT TATCCAAATC CGCTCAGTTG CCAAGAAGCA TCCTAAAACT
     ACAGAGGGAA ATAGGTTTAG GCGAGTCAAC GGTTCTTCGT AGGATTTTGA
1201 TGGGTACATT ACATTGCTGC TGAAGAGGAG GACTGGGACT ATGCTCCCTT
```

FIG. 7A

```
      ACCCATGTAA TGTAACGACG ACTTCTCCTC CTGACCCTGA TACGAGGGAA
1251  AGTCCTCGCC CCCGATGACA GAAGTTATAA AAGTCAATAT TTGAACAATG
      TCAGGAGCGG GGGCTACTGT CTTCAATATT TTCAGTTATA AACTTGTTAC
1301  GCCCTCAGCG GATTGGTAGG AAGTACAAAA AAGTCCGATT TATGGCATAC
      CGGGAGTCGC CTAACCATCC TTCATGTTTT TTCAGGCTAA ATACCGTATG
1351  ACAGATGAAA CCTTTAAGAC GCGTGAAGCT ATTCAGCATG AATCAGGAAT
      TGTCTACTTT GGAAATTCTG CGCACTTCGA TAAGTCGTAC TTAGTCCTTA
1401  CTTGGGACCT TTACTTTATG GGGAAGTTGG AGACACACTG TTGATTATAT
      GAACCCTGGA AATGAAATAC CCCTTCAACC TCTGTGTGAC AACTAATATA
1451  TTAAGAATCA AGCAAGCAGA CCATATAACA TCTACCCTCA CGGAATCACT
      AATTCTTAGT TCGTTCGTCT GGTATATTGT AGATGGGAGT GCCTTAGTGA
1501  GATGTCCGTC CTTTGTATTC AAGGAGATTA CCAAAAGGTG TAAAACATTT
      CTACAGGCAG GAAACATAAG TTCCTCTAAT GGTTTTCCAC ATTTTGTAAA
1551  GAAGGATTTT CCAATTCTGC CAGGAGAAAT ATTCAAATAT AAATGGACAG
      CTTCCTAAAA GGTTAAGACG GTCCTCTTTA TAAGTTTATA TTTACCTGTC
1601  TGACTGTAGA AGATGGGCCA ACTAAATCAG ATCCGCGGTG CCTGACCCGC
      ACTGACATCT TCTACCCGGT TGATTTAGTC TAGGCGCCAC GGACTGGGCG
1651  TATTACTCTA GTTTCGTTAA TATGGAGAGA GATCTAGCTT CAGGACTCAT
      ATAATGAGAT CAAAGCAATT ATACCTCTCT CTAGATCGAA GTCCTGAGTA
1701  TGGCCCTCTC CTCATCTGCT ACAAAGAATC TGTAGTCCAA AGAGGAAACC
      ACCGGGAGAG GAGTAGACGA TGTTTCTTAG ACATCAGTT TCTCCTTTGG
1751  AGATAATGTC AGACAAGAGG AATGTCATCC TGTTTCTGT ATTTGATGAG
      TCTATTACAG TCTGTTCTCC TTACAGTAGG ACAAAGACA TAAACTACTC
1801  AACCGAAGCT GGTACCTCAC AGAGAATATA CAACGCTTTC TCCCCAATCC
      TTGGCTTCGA CCATGGAGTG TCTCTTATAT GTTGCGAAAG AGGGGTTAGG
1851  AGCTGGAGTA CAGCTTGAGG ATCCAGAGTT CCAAGCCTCC AACATCATGC
      TCGACCTCAT GTCGAACTCC TAGGTCTCAA GGTTCGAAGG TTGTAGTACG
1901  ACAGCATCAA TGGCTATGTT TTTGATAGTT TGCAGTTGTC AGTTTGTTTG
      TGTCGTAGTT ACCGATACAA AAACTATCAA ACGTCAACAG TCAAACAAAC
1951  CATGAGGTGG CATACTGGTA CATTCTAAGC ATTGGAGCAC AGACTGACTT
      GTACTCCACC GTATGACCAT GTAAGATTCG TAACCTCGTG TCTGACTGAA
2001  CCTTTCTGTC TTCTTCTCTG GATATACCTT CAAACACAAA ATGGTCTATG
      GGAAAGACAG AAGAAGAGAC CTATATGGAA GTTTGTGTTT TACCAGATAC
2051  AAGACACACT CACCCTATTC CCATTCTCAG GAGAAACTGT CTTCATGTCG
      TTCTGTGTGA GTGGGATAAG GGTAAGAGTC CTCTTTGACA GAAGTACAGC
2101  ATGGAAAACC CAGGTCTATG GATTCTGGGG TGCCACAACT CAGACTTTCG
      TACCTTTTGG GTCCAGATAC CTAAGACCCC ACGGTGTTGA GTCTGAAAGC
2151  GAACAGAGGC ATGACCGCCT TACTGAAGGT TTCTAGTTGT GACAAGAACA
      CTTGTCTCCG TACTGGCGGA ATGACTTCCA AAGATCAACA CTGTTCTTGT
2201  CTGGTGATTA TTACGAGGAC AGTTATGAAG ATATTTCAGC ATACTTGCTG
      GACCACTAAT AATGCTCCTG TCAATACTTC TATAAAGTCG TATGAACGAC
2251  AGTAAAAACA ATGCCATTGA ACCTAGGAGC TTCTCTCAGA ATCCACCAGT
      TCATTTTTGT TACGGTAACT TGGATCCTCG AAGAGAGTCT AGGTGGTCA
2301  CTTGAAACGC CATCAACGGG AAATAACTCG TACTACTCTT CAGTCAGATC
      GAACTTTGCG GTAGTTGCCC TTATTGAGC ATGATGAGAA GTCAGTCTAG
2351  AAGAGGAAAT TGACTATGAT GATACCATAT CAGTTGAAAT GAAGAAGGAA
      TTCCTCTTTA ACTGATACTA CTATGGTATA GTCAACTTTA CTTCTTCCTT
2401  GATTTTGACA TTTATGATGA GGATGAAAAT CAGAGCCCCC GCAGCTTTCA
      CTAAAACTGT AAATACTACT CCTACTTTTA GTCTCGGGGG CGTCGAAAGT
2451  AAAGAAAACA CGACACTATT TTATTGCTGC AGTGGAGAGG CTCTGGGATT
      TTTCTTTTGT GCTGTGATAA AATAACGACG TCACCTCTCC GAGACCCTAA
2501  ATGGGATGAG TAGCTCCCCA CATGTTCTAA GAAACAGGGC TCAGAGTGGC
```

FIG. 7B

```
       TACCCTACTC ATCGAGGGGT GTACAAGATT CTTTGTCCCG AGTCTCAGCG
2551   AGTGTCCTC  AGTTCAAGAA AGTTGTTTTC CAGGAATTTA CTGATGGCTC
       TCACAGGGAG TCAAGTTCTT TCAACAAAAG GTCCTTAAAT GACTACCGAG
2601   CTTTACTCAG CCCTTATACC GTGGAGAACT AAATGAACAT TTGGGACTCC
       GAAATGAGTC GGGAATATGG CACCTCTTGA TTTACTTGTA AACCCTGAGG
2651   TGGGGCCATA TATAAGAGCA GAAGTTGAAG ATAATATCAT GGTAACTTTC
       ACCCCGGTAT ATATTCTCGT CTTCAACTTC TATTATAGTA CCATTGAAAG
2701   AGAAATCAGG CCTCTCGTCC CTATTCCTTC TATTCTAGCC TTATTTCTTA
       TCTTTAGTCC GGAGAGCAGG GATAAGGAAG ATAAGATCGG AATAAAGAAT
2751   TGAGGAAGAT CAGAGGCAAG GAGCAGAACC TAGAAAAAAC TTTGTCAAGC
       ACTCCTTCTA GTCTCCGTTC CTCGTCTTGG ATCTTTTTTG AAACAGTTCG
2801   CTAATGAAAC CAAAACTTAC TTTTGGAAAG TGCAACATCA TATGGCACCC
       GATTACTTTG GTTTTGAATG AAAACCTTTC ACGTTGTAGT ATACCGTGGG
2851   ACTAAAGATG AGTTTGACTG CAAAGCCTGG GCTTATTTCT CTGATGTTGA
       TGATTTCTAC TCAAACTGAC GTTTCGGACC CGAATAAAGA GACTACAACT
2901   CCTGGAAAAA GATGTGCACT CAGGCCTGAT TGGACCCCTT CTGGTCTGCC
       GGACCTTTTT CTACACGTGA GTCCGGACTA ACCTGGGGAA GACCAGACGG
2951   ACACTAACAC ACTGAACCCT GCTCATGGGA GACAAGTGAC AGTACAGGAA
       TGTGATTGTG TGACTTGGGA CGAGTACCCT CTGTTCACTG TCATGTCATT
3001   TTTGCTCTGT TTTTCACCAT CTTTGATGAG ACCAAAAGCT GGTACTTCAC
       AAACGAGACA AAAAGTGGTA GAAACTACTC TGGTTTTCGA CCATGAAGTG
3051   TGAAAATATG GAAAGAAACT GCAGGGCTCC CTGCAATATC CAGATGGAAG
       ACTTTTATAC CTTTCTTTGA CGTCCCGAGG GACGTTATAG GTCTACCTTC
3101   ATCCCACTTT TAAAGAGAAT TATCGCTTCC ATGCAATCAA TGGCTACATA
       TAGGGTGAAA ATTTCTCTTA ATAGCGAAGG TACGTTAGTT ACCGATGTAT
3151   ATGGATACAC TACCTGGCTT AGTAATGGCT CAGGATCAAA GGATTCGATG
       TACCTATGTG ATGGACCGAA TCATTACCGA GTCCTAGTTT CCTAAGCTAC
3201   GTATCTGCTC AGCATGGGCA GCAATGAAAA CATCCATTCT ATTCATTTCA
       CATAGACGAG TCGTACCCGT CGTTACTTTT GTAGGTAAGA TAAGTAAAGT
3251   GTGGACATGT GTTCACTGTA CGAAAAAAAG AGGAGTATAA AATGGCACTG
       CACCTGTACA CAAGTGACAT GCTTTTTTTC TCCTCATATT TTACCGTGAC
3301   TACAATCTCT ATCCAGGTGT TTTTGAGACA GTGGAAATGT TACCATCCAA
       ATGTTAGAGA TAGGTCCACA AAAACTCTGT CACCTTTACA ATGGTAGGTT
3351   AGCTGGAATT TGGCGGGTGG AATGCCTTAT GGCGAGCAT  CTACATGCTG
       TCGACCTTAA ACCGCCCACC TTACGGAATA CCGCTCGTA  GATGTACGAC
3401   GGATGAGCAC ACTTTTTCTG GTGTACAGCA ATAAGTGTCA GACTCCCCTG
       CCTACTCGTG TGAAAAAGAC CACATGTCGT TATTCACAGT CTGAGGGGAC
3451   GGAATGGCTT CTGGACACAT TAGAGATTTT CAGATTACAG CTTCAGGACA
       CCTTACCGAA GACCTGTGTA ATCTCTAAAA GTCTAATGTC GAAGTCCTGT
3501   ATATGGACAG TGGGCCCCAA AGCTGGCCAG ACTTCATTAT TCCGGATCAA
       TATACCTGTC ACCCGGGGTT TCGACCGGTC TGAAGTAATA AGGCCTAGTT
3551   TCAATGCCTG GAGCACCAAG GAGCCCTTTT CTTGGATCAA GGTGGATCTG
       AGTTACGGAC CTCGTGGTTC CTCGGGAAAA GAACCTAGTT CCACCTAGAC
3601   TTGGCACCAA TGATTATTCA CGGCATCAAG ACCCAGGGTG CCCGTCAGAA
       AACCGTGGTT GCCGTAGTTC GCCGTAGTTC TGGGTCCCAC GGGCAGTCTT
3651   GTTCTCCAGC CTCTACATCT CTCAGTTTAT CATCATGTAT AGTCTTGATG
       CAAGAGGTCG GAGATGTAGA GAGTCAAATA GTAGTACATA TCAGAACTAC
3701   GGAAGAAGTG GCAGACTTAT CGAGGAAATT CCACTGGAAC CTTAATGGTC
       CCTTCTTCAC CGTCTGAATA GCTCCTTTAA GGTGACCTTG GAATTACCAG
3751   TTCTTTGGCA ATGTGGATTC ATCTGGGATA AAACACAATA TTTTTAACCC
       AAGAAACCGT TACACCTAAG TAGACCCTAT TTTGTGTTAT AAAAATTGGG
3801   TCCAATTATT GCTCGATACA TCCGTTTGCA CCCAACTCAT TATAGCATTC
```

FIG. 7C

```
           AGGTTAATAA CGAGCTATGT AGGCAAAGCT GGGTTGAGTA ATATCGTAAG
3851  GCAGCACTCT TCGCATGGAG TTGATGGGCT GTGATTTAAA TAGTTGCAGC
      CGTCGTGAGA AGCGTACCTC AACTACCCGA CACTAAATTT ATCAACGTCG
3901  ATGCCATTGG GAATGGAGAG TAAAGCAATA TCAGATGCAC AGATTACTGC
      TACGGTAACC CTTACCTCTC ATTTCGTTAT AGTCTACGTG TCTAATGACG
3951  TTCATCCTAC TTTACCAATA TGTTTGCCAC CTGGTCTCCT TCAAAAGCTC
      AAGTAGGATG AAATGGTTAT ACAAACGGTG GACCAGAGGA AGTTTTCGAG
4001  GACTTCACCT CCAAGGGAGG AGTAATGCCT GGAGACCTCA GGTGAATAAT
      CTGAAGTGGA GGTTCCCTCC TCATTACGGA CCTCTGGAGT CCACTTATTA
4051  CCAAAAGAGT GGCTGCAAGT GGACTTCCAG AAGACAATGA AAGTCACAGG
      GGTTTTCTCA CCGACGTTCA CCTGAAGGTC TTCTGTTACT TTCAGTGTCC
4101  AGTAACTACT CAGGGAGTAA AATCTCTGCT TACCAGCATG TATGTGAAGG
      TCATTGATGA GTCCCTCATT TTAGAGACGA ATGGTCGTAC ATACACTTCC
4151  AGTTCCTCAT CTCCAGCAGT CAAGATGGCC ATCAGTGGAC TCTCTTTTTT
      TCAAGGAGTA GAGGTCGTCA GTTCTACCGG TAGTCACCTG AGAGAAAAAA
4201  CAGAATGGCA AAGTAAAGGT TTTTCAGGGA AATCAAGACT CCTTCACACC
      GTCTTACCGT TTCATTTCCA AAAAGTCCCT TTAGTTCTGA GGAAGTGTGG
4251  TGTGGTGAAC TCTCTAGACC CACCGTTACT GACTCGCTAC CTTCGAATTC
      ACACCACTTG AGAGATCTGG GTGGCAATGA CTGAGCGATG GAAGCTTAAG
4301  ACCCCAGAG TTGGGTGCAC CAGATTGCCC TGAGGATGGA GGTTCTGGGC
      TGGGGGTCTC AACCCACGTG GTCTAACGGG ACTCCTACCT CCAAGACCCG
4351  TGCGAGGCAC AGGACCTCTA C
      ACGCTCCGTG TCCTGGAGAT G
```

1-57 SIGNAL PEPTIDE
58-1173 A1 DOMAIN
1174-2277 A2 DOMAIN
2278-2319 SQ LINKER
2320-3432 ap-A3 DOMAINS
3433-3891 C1 DOMAIN
3892-4371 C2 DOMAIN

FIG. 7D

AMINO ACID SEQUENCE OF HP47/OL

```
   1  MQLELSTCVF  LCLLPLGFSA  IRRYYLGAVE  LSWDYRQSEL  LRELHVDTRF
  51  PATAPGALPL  GPSVLYKKTV  FVEFTDQLFS  VARPRPPWMG  LLGPTIQAEV
 101  YDTVVVTLKN  MASHPVSLHA  VGVSFWKSSE  GAEYEDHTSQ  REKEDDKVLP
 151  GKSQTYVWQV  LKENGPTASD  PPCLTYSYLS  HVDLVKDLNS  GLIGALLVCR
 201  EGSLTRERTQ  NLHEFVLLFA  VFDEGKSWHS  ARNDSWTRAM  DPAPARAQPA
 251  MHTVNGYVNR  SLPGLIGCHK  KSVYWHVIGM  GTSPEVHSIF  LEGHTFLVRH
 301  HRQASLEISP  LTFLTAQTFL  MDLGQFLLFC  HISSHHHGGM  EAHVRVESCA
 351  EEPQLRRKAD  EEEDYDDNLY  DSDMDVVRLD  GDDVSPFIQI  RSVAKKHPKT
 401  WVHYIAAEEE  DWDYAPLVLA  PDDRSYKSQY  LNNGPQRIGR  KYKKVRFMAY
 451  TDETFKTREA  IQHESGILGP  LLYGEVGDTL  LIIFKNQASR  PYNIYPHGIT
 501  DVRPLYSRRL  PKGVKHLKDF  PILPGEIFKY  KWTVTVEDGP  TKSDPRCLTR
 551  YYSSFVNMER  DLASGLIGPL  LICYKESVDQ  RGNQIMSDKR  NVILFSVFDE
 601  NRSWYLTENI  QRFLPNPAGV  QLEDPEFQAS  NIMHSINGYV  FDSLQLSVCL
 651  HEVAYWYILS  IGAQTDFLSV  FFSGYTFKHK  MVYEDTLTLF  PFSGETVFMS
 701  MENPGLWILG  CHNSDFRNRG  MTALLKVSSC  DKNTGDYYED  SYEDISAYLL
 751  SKNNAIEPRS  FAQNSRPPSA  SAPKPPVLRR  HQRDISLPTF  QPEEDKMDYD
 801  DIFSTETKGE  DFDIYGEDEN  QDPRSFQKRT  RHYFIAAVEQ  LWDYGMSESP
 851  RALRNRAQNG  EVPRFKKVVF  REFADGSFTQ  PSYRGELNKH  LGLLGPYIRA
 901  EVEDNIMVTF  KNQASRPYSF  YSSLISYPDD  QEQGAEPRHN  FVQPNETRTY
 951  FWKVQHHMAP  TEDEFDCKAW  AYFSDVDLEK  DVHSGLIGPL  LICRANTLNA
1001  AHGRQVTVQE  FALFFTIFDE  TKSWYFTENV  ERNCRAPCHL  QMEDPTLKEN
1051  YRFHAINGYV  MDTLPGLVMA  QNQRIRWYLL  SMGSNENIHS  IHFSGHVFSV
1101  RKKEEYKMAV  YNLYPGVFET  VEMLPSKVGI  WRIECLIGEH  LQAGMSTTFL
1151  VYSKKCQTPL  GMASGHIRDF  QITASGQYGQ  WAPKLARLHY  SGSINAWSTK
1201  EPFSWIKVDL  LAPMIIHGIK  TQGARQKFSS  LYISQFIIMY  SLDGKKWQTY
1251  RGNSTGTLMV  FFGNVDSSGI  KHNIFNPPII  ARYIRLHPTH  YSIRSTLRME
1301  LMGCDLNSCS  MPLGMESKAI  SDAQITASSY  FTNMFATWSP  SKARLHLQGR
1351  SNAWRPQVNN  PKEWLQVDFQ  KTMKVTGVTT  QGVKSLLTSM  YVKEFLISSS
1401  QDGHQWTLFF  QNGKVKVFQG  NQDSFTPVVN  SLDPPLLTRY  LRIHPQSWVH
1451  QIALRMEVLG  CEAQDLY*
```

1-19 SIGNAL PEPTIDE
20-391 A1 DOMAIN
392-759 A2 DOMAIN
760-783 OL LINKER
784-1154 ap-A3
1155-1307 C1 DOMAIN
1308-1467 C2 DOMAIN

FIG. 8

HP47/OL NUCLEOTIDE SEQUENCE

```
   1 ATGCAGCTAG AGCTCTCCAC CTGTGTCTTT CTGTGTCTCT TGCCACTCGG
     TACGTCGATC TCGAGAGGTG GACACAGAAA GACACAGAGA ACGGTGAGCC
  51 CTTTAGTGCC ATCAGGAGAT ACTACCTGGG CGCAGTGGAA CTGTCCTGGG
     GAAATCACGG TAGTCCTCTA TGATGGACCC GCGTCACCTT GACAGGACCC
 101 ACTACCGGCA AAGTGAACTC CTCCGTGAGC TGCACGTGGA CACCAGATTT
     TGATGGCCGT TTCACTTGAG GAGGCACTCG ACGTGCACCT GTGGTCTAAA
 151 CCTGCTACAG CGCCAGGAGC TCTTCCGTTG GCCCGTCAG TCCTGTACAA
     GGACGATGTC GCGGTCCTCG AGAAGGCAAC CCGGGCAGTC AGGACATGTT
 201 AAAGACTGTG TTCGTAGAGT TCACGGATCA ACTTTTCAGC GTTGCCAGGC
     TTTCTGACAC AAGCATCTCA AGTGCCTAGT TGAAAAGTCG CAACGGTCCG
 251 CCAGGCCACC ATGGATGGGT CTGCTGGGTC CTACCATCCA GGCTGAGGTT
     GGTCCGGTGG TACCTACCCA GACGACCCAG GATGGTAGGT CCGACTCCAA
 301 TACGACACGG TGGTCGTTAC CCTGAAGAAC ATGGCTTCTC ATCCCGTTAG
     ATGCTGTGCC ACCAGCAATG GGACTTCTTG TACCGAAGAG TAGGGCAATC
 351 TCTTCACGCT GTCGGCGTCT CCTTCTGGAA ATCTTCCGAA GGCGCTGAAT
     AGAAGTGCGA CAGCCGCAGA GGAAGACCTT TAGAAGGCTT CCGCGACTTA
 401 ATGAGGATCA CACCAGCCAA AGGGAGAAGG AAGACGATAA AGTCCTTCCC
     TACTCCTAGT GTGGTCGGTT TCCCTCTTCC TTCTGCTATT TCAGGAAGGG
 451 GGTAAAAGCC AAACCTACGT CTGGCAGGTC CTGAAAGAAA ATGGTCCAAC
     CCATTTTCGG TTTGGATGCA GACCGTCCAG GACTTTCTTT TACCAGGTTG
 501 AGCCTCTGAC CCACCATGTC TTACCTACTC ATACCTGTCT CACGTGGACC
     TCGGAGACTG GGTGGTACAG AATGGATGAG TATGGACAGA GTGCACCTGG
 551 TGGTGAAAGA CCTGAATTCG GGCCTCATTG GAGCCCTGCT GGTTTGTAGA
     ACCACTTTCT GGACTTAAGC CCGGAGTAAC CTCGGGACGA CCAAACATCT
 601 GAAGGGAGTC TGACCAGAGA AAGGACCCAG AACCTGCACG AATTTGTACT
     CTTCCCTCAG ACTGGTCTCT TTCCTGGGTC TTGGACGTGC TTAAACATGA
 651 ACTTTTTGCT GTCTTTGATG AAGGGAAAAG TTGGCACTCA GCAAGAAATG
     TGAAAAACGA CAGAAACTAC TTCCCTTTTC AACCGTGAGT CGTTCTTTAC
 701 ACTCCTGGAC ACGGGCCATG GATCCCGCAC CTGCCAGGGC CCAGCCTGCA
     TGAGGACCTG TGCCCGGTAC CTAGGGCGTG GACGGTCCCG GGTCGGACGT
 751 ATGCACACAG TCAATGGCTA TGTCAACAGG TCTCTGCCAG GTCTGATCGG
     TACGTGTGTC AGTTACCGAT ACAGTTGTCC AGAGACGGTC CAGACTAGCC
 801 ATGTCATAAG AAATCAGTCT ACTGGCACGT GATTGGAATG GGCACCAGCC
     TACAGTATTC TTTAGTCAGA TGACCGTGCA CTAACCTTAC CCGTGGTCGG
 851 CGGAAGTGCA CTCCATTTTT CTTGAAGGCC ACACGTTTCT CGTGAGGCAC
     GCCTTCACGT GAGGTAAAAA GAACTTCCGG TGTGCAAAGA GCACTCCGTG
 901 CATCGCCAGG CTTCCTTGGA GATCTCGCCA CTAACTTTCC TCACTGCTCA
     GTAGCGGTCC GAAGGAACCT CTAGAGCGGT GATTGAAAGG AGTGACGAGT
 951 GACATTCCTG ATGGACCTTG CCAGTTCCT ACTGTTTTGT CATATCTCTT
     CTGTAAGGAC TACCTGGAAC CGGTCAAGGA TGACAAAACA GTATAGAGAA
1001 CCCACCACCA TGGTGGCATG GAGGCTCACG TCAGAGTAGA AAGCTGCGCC
     GGGTGGTGGT ACCACCGTAC CTCCGAGTGC AGTCTCATCT TTCGACGCGG
1051 GAGGAGCCCC AGCTGCGGAG GAAAGCTGAT GAAGAGGAAG ATTATGATGA
     CTCCTCGGGG TCGACGCCTC CTTTCGACTA CTTCTCCTTC TAATACTACT
1101 CAATTTGTAC GACTCGGACA TGGACGTGGT CCGGCTCGAT GGTGACGACG
     GTTAAACATG CTGAGCCTGT ACCTGCACCA GGCCGAGCTA CCACTGCTGC
1151 TGTCTCCCTT TATCCAAATC CGCTCGGTTG CCAAGAAGCA TCCTAAAACT
     ACAGAGGGAA ATAGGTTTAG GCGAGCCAAC GGTTCTTCGT AGGATTTTGA
1201 TGGGTACATT ACATTGCTGC TGAAGAGGAG GACTGGGACT ATGCTCCCTT
```

FIG. 9A

```
      ACCCATGTAA TGTAACGACG ACTTCTCCTC CTGACCCTGA TACGAGGGAA
1251  AGTCCTCGCC CCCGATGACA GAAGTTATAA AAGTCAATAT TTGAACAATG
      TCAGGAGCGG GGGCTACTGT CTTCAATATT TTCAGTTATA AACTTGTTAC
1301  GCCCTCAGCG GATTGGTAGG AAGTACAAAA AAGTCCGATT TATGGCATAC
      CGGGAGTCGC CTAACCATCC TTCATGTTTT TTCAGGCTAA ATACCGTATG
1351  ACAGATGAAA CCTTTAAGAC GCGTGAAGCT ATTCAGCATG AATCAGGAAT
      TGTCTACTTT GGAAATTCTG CGCACTTCGA TAAGTCGTAC TTAGTCCTTA
1401  CTTGGGACCT TTACTTTATG GGGAAGTTGG AGACACACTG TTGATTATAT
      GAACCCTGGA AATGAAATAC CCCTTCAACC TCTGTGTGAC AACTAATATA
1451  TTAAGAATCA AGCAAGCAGA CCATATAACA TCTACCCTCA CGGAATCACT
      AATTCTTAGT TCGTTCGTCT GGTATATTGT AGATGGGAGT GCCTTAGTGA
1501  GATGTCCGTC CTTTGTATTC AAGGAGATTA CCAAAAGGTG TAAAACATTT
      CTACAGGCAG GAAACATAAG TTCCTCTAAT GGTTTTCCAC ATTTTGTAAA
1551  GAAGGATTTT CCAATTCTGC CAGGAGAAAT ATTCAAATAT AAATGGACAG
      CTTCCTAAAA GGTTAAGACG GTCCTCTTTA TAAGTTTATA TTTACCTGTC
1601  TGACTGTAGA AGATGGGCCA ACTAAATCAG ATCCGCGGTG CCTGACCCGC
      ACTGACATCT TCTACCCGGT TGATTTAGTC TAGGCGCCAC GGACTGGGCG
1651  TATTACTCTA GTTTCGTTAA TATGGAGAGA GATCTAGCTT CAGGACTCAT
      ATAATGAGAT CAAAGCAATT ATACCTCTCT CTAGATCGAA GTCCTGAGTA
1701  TGGCCCTCTC CTCATCTGCT ACAAAGAATC TGTAGATCAA AGAGGAAACC
      ACCGGGAGAG GAGTAGACGA TGTTTCTTAG ACATCTAGTT TCTCCTTTGG
1751  AGATAATGTC AGACAAGAGG AATGTCATCC TGTTTTCTGT ATTTGATGAG
      TCTATTACAG TCTGTTCTCC TTACAGTAGG ACAAAAGACA TAAACTACTC
1801  AACCGAAGCT GGTACCTCAC AGAGAATATA CAACGCTTTC TCCCCAATCC
      TTGGCTTCGA CCATGGAGTG TCTCTTATAT GTTGCGAAAG AGGGGTTAGG
1851  AGCTGGAGTG CAGCTTGAGG ATCCAGAGTT CCAAGCCTCC AACATCATGC
      TCGACCTCAC GTCGAACTCC TAGGTCTCAA GGTTCGGAGG TTGTAGTACG
1901  ACAGCATCAA TGGCTATGTT TTTGATAGTT TGCAGTTGTC AGTTTGTTTG
      TGTCGTAGTT ACCGATACAA AAACTATCAA ACGTCAACAG TCAAACAAAC
1951  CATGAGGTGG CATACTGGTA CATTCTAAGC ATTGGAGCAC AGACTGACTT
      GTACTCCACC GTATGACCAT GTAAGATTCG TAACCTCGTG TCTGACTGAA
2001  CCTTTCTGTC TTCTTCTCTG GATATACCTT CAAACACAAA ATGGTCTATG
      GGAAAGACAG AAGAAGAGAC CTATATGGAA GTTTGTGTTT TACCAGATAC
2051  AAGACACACT CACCCTATTC CCATTCTCAG GAGAAACTGT CTTCATGTCG
      TTCTGTGTGA GTGGGATAAG GGTAAGAGTC CTCTTTGACA GAAGTACAGC
2101  ATGGAAAACC CAGGTCTATG GATTCTGGGG TGCCACAACT CAGACTTTCG
      TACCTTTTGG GTCCAGATAC CTAAGACCCC ACGGTGTTGA GTCTGAAAGC
2151  GAACAGAGGC ATGACCGCCT TACTGAAGGT TTCTAGTTGT GACAAGAACA
      CTTGTCTCCG TACTGGCGGA ATGACTTCCA AAGATCAACA CTGTTCTTGT
2201  CTGGTGATTA TTACGAGGAC AGTTATGAAG ATATTTCAGC ATACTTGCTG
      GACCACTAAT TTACGAGGAC TCAATACTTC TATAAAGTCG TATGAACGAC
2251  AGTAAAAACA ATGCCATTGA ACCTAGGAGC TTTGCCCAGA ATTCAAGACC
      TCATTTTTGT TACGGTAACT TGGATCCTCG AAACGGGTCT TAAGTTCTGG
2301  CCCTAGTGCG AGCGCTCCAA AGCCTCCGGT CCTGCGACGG CATCAGAGGG
      GGGATCACGC TCGCGAGGTT TCGGAGGCCA GGACGCTGCC GTAGTCTCCC
2351  ACATAAGCCT TCCTACTTTT CAGCCGGAGG AAGACAAAAT GGACTATGAT
      TGTATTCGGA AGGATGAAAA GTCGGCCTCC TTCTGTTTTA CCTGATACTA
2401  GATATCTTCT CAACTGAAAC GAAGGGAGAA GATTTTGACA TTTACGGTGA
      CTATAGAAGA GTTGACTTTG CTTCCCTCTT CTAAAACTGT AAATGCCACT
2451  GGATGAAAAT CAGGACCCTC GCAGCTTTCA GAAGAGAACC CGACACTATT
      CCTACTTTTA GTCCTGGGAG CGTCGAAAGT CTTCTCTTGG GCTGTGATAA
2501  TCATTGCTGC GGTGGAGCAG CTCTGGGATT ACGGGATGAG CGAATCCCCC
```

FIG. 9B

```
       AGTAACGACG CCACCTCGTC GAGACCCTAA TGCCCTACTC GCTTAGGGGG
2551   CGGGCGCTAA GAAACAGGGC TCAGAACGGA GAGGTGCCTC GGTTCAAGAA
       GCCCGCGATT CTTTGTCCCG AGTCTTGCCT CTCCACGGAG CCAAGTTCTT
2601   GGTGGTCTTC CGGGAATTTG CTGACGGCTC CTTCACGCAG CCGTCGTACC
       CCACCAGAAG GCCCTTAAAC GACTGCCGAG GAAGTGCGTC GGCAGCATGG
2651   GCGGGGAACT CAACAAACAC TTGGGGCTCT TGGGACCCTA CATCAGAGCG
       CGCCCCTTGA GTTGTTTGTG AACCCCGAGA ACCCTGGGAT GTAGTCTCGC
2701   GAAGTTGAAG ACAACATCAT GGTAACTTTC AAAAACCAGG CGTCTCGTCC
       CTTCAACTTC TGTTGTAGTA CCATTGAAAG TTTTTGGTCC GCAGAGCAGG
2751   CTATTCCTTC TACTCGAGCC TTATTTCTTA TCCGGATGAT CAGGAGCAAG
       GATAAGGAAG ATGAGCTCGG AATAAAGAAT AGGCCTACTA GTCCTCGTTC
2801   GGGCAGAACC TCGACACAAC TTCGTCCAGC CAAATGAAAC CAGAACTTAC
       CCCGTCTTGG AGCTGTGTTG AAGCAGGTCG GTTTACTTTG GTCTTGAATG
2851   TTTTGGAAAG TGCAGCATCA CATGGCACCC ACAGAAGACG AGTTTGACTG
       AAAACCTTTC ACGTCGTAGT GTACCGTGGG TGTCTTCTGC TCAAACTGAC
2901   CAAAGCCTGG GCCTACTTTT CTGATGTTGA CCTGGAAAAA GATGTGCACT
       GTTTCGGACC CGGATGAAAA GACTACAACT GGACCTTTTT CTACACGTGA
2951   CAGGCTTGAT CGGCCCCCTT CTGATCTGCC GCGCCAACAC CCTGAACGCT
       GTCCGAACTA GCCGGGGAA GACTAGACGG CGCGGTTGTG GGACTTGCGA
3001   GCTCACGGTA GACAAGTGAC CGTGCAAGAA TTTGCTCTGT TTTTCACTAT
       CGAGTGCCAT CTGTTCACTG GCACGTTCTT AAACGAGACA AAAAGTGATA
3051   TTTTGATGAG ACAAAGAGCT GGTACTTCAC TGAAAATGTG GAAAGGAACT
       AAAACTACTC TGTTTCTCGA CCATGAAGTG ACTTTTACAC CTTTCCTTGA
3101   GCCGGGCCCC CTGCCATCTG CAGATGGAGG ACCCCACTCT GAAAGAAAAC
       CGGCCCGGGG GACGGTAGAC GTCTACCTCC TGGGGTGAGA CTTTCTTTTG
3151   TATCGCTTCC ATGCAATCAA TGGCTATGTG ATGGATACAC TCCCTGGCTT
       ATAGCGAAGG TACGTTAGTT ACCGATACAC TACCTATGTG AGGGACCGAA
3201   AGTAATGGCT CAGAATCAAA GGATCCGATG GTATCTGCTC AGCATGGGCA
       TCATTACCGA GTCTTAGTTT CCTAGGCTAC CATAGACGAG TCGTACCCGT
3251   GCAATGAAAA TATCCATTCG ATTCATTTTA GCGGACACGT GTTCAGTGTA
       CGTTACTTTT ATAGGTAAGC TAAGTAAAAT CGCCTGTGCA CAAGTCACAT
3301   CGGAAAAAGG AGGAGTATAA AATGGCCGTG TACAATCTCT ATCCGGGTGT
       GCCTTTTTCC TCCTCATATT TTACCGGCAC ATGTTAGAGA TAGGCCCACA
3351   CTTTGAGACA GTGGAAATGC TACCGTCCAA AGTTGGAATT TGGCGAATAG
       GAAACTCTGT CACCTTTACG ATGGCAGGTT TCAACCTTAA ACCGCTTATC
3401   AATGCCTGAT TGGCGAGCAC CTGCAAGCTG GATGAGCAC GACTTTCCTG
       TTACGGACTA ACCGCTCGTG GACGTTCGAC CCTACTCGTG CTGAAAGGAC
3451   GTGTACAGCA AGAAGTGTCA GACTCCCTG GGAATGGCTT CTGGACACAT
       CACATGTCGT TCTTCACAGT CTGAGGGGAC CCTTACCGAA GACCTGTGTA
3501   TAGAGATTTT CAGATTACAG CTTCAGGACA ATATGGACAG TGGGCCCCAA
       ATCTCTAAAA GTCTAATGTC GAAGTCCTGT TATACCTGTC ACCCGGGGTT
3551   AGCTGGCCAG ACTTCATTAT TCCGGATCAA TCAATGCCTG GAGCACCAAG
       TCGACCGGTC TGAAGTAATA AGGCCTAGTT AGTTACGGAC CTCGTGGTTC
3601   GAGCCCTTTT CTTGGATCAA GGTGGATCTG TTGGCACCAA TGATTATTCA
       CTCGGGAAAA GAACCTAGTT CCACCTAGAC AACCGTGGTT ACTAATAAGT
3651   CGGCATCAAG ACCCAGGGTG CCCGTCAGAA GTTCTCCAGC CTCTACATCT
       GCCGTAGTTC TGGGTCCCAC GGGCAGTCTT CAAGAGGTCG GAGATGTAGA
3701   CTCAGTTTAT CATCATGTAT AGTCTTGATG GAAGAAGTG GCAGACTTAT
       GAGTCAAATA GTAGTACATA TCAGAACTAC CCTTCTTCAC CGTCTGAATA
3751   CGAGGAAATT CCACTGGAAC CTTAATGGTC TTCTTTGGCA ATGTGGATTC
       GCTCCTTTAA GGTGACCTTG GAATTACCAG AAGAAACCGT TACACCTAAG
3801   ATCTGGGATA AAACACAATA TTTTTAACCC TCCAATTATT GCTCGATACA
```

FIG. 9C

```
      TAGACCCTAT TTTGTGTTAT AAAAATTGGG AGGTTAATAA CGAGCTATGT
3851  TCCGTTTGCA CCCAACTCAT TATAGCATTC GCAGCACTCT TCGCATGGAG
      AGGCAAACGT GGGTTGAGTA ATATCGTAAG CGTCGTGAGA AGCGTACCTC
3901  TTGATGGGCT GTGATTTAAA TAGTTGCAGC ATGCCATTGG GAATGGAGAG
      AACTACCCGA CACTAAATTT ATCAACGTCG TACGGTAACC CTTACCTCTC
3951  TAAAGCAATA TCAGATGCAC AGATTACTGC TTCATCCTAC TTTACCAATA
      ATTTCGTTAT AGTCTACGTG TCTAATGACG AAGTAGGATG AAATGGTTAT
4001  TGTTTGCCAC CTGGTCTCCT TCAAAAGCTC GACTTCACCT CCAAGGGAGG
      ACAAACGGTG GACCAGAGGA AGTTTTCGAG CTGAAGTGGA GGTTCCCTCC
4051  AGTAATGCCT GGAGACCTCA GGTGAATAAT CCAAAAGAGT GGCTGCAAGT
      TCATTACGGA CCTCTGGAGT CCACTTATTA GGTTTTCTCA CCGACGTTCA
4101  GGACTTCCAG AAGACAATGA AAGTCACAGG AGTAACTACT CAGGGAGTAA
      CCTGAAGGTC TTCTGTTACT TTCAGTGTCC TCATTGATGA GTCCCTCATT
4151  AATCTCTGCT TACCAGCATG TATGTGAAGG AGTTCCTCAT CTCCAGCAGT
      TTAGAGACGA ATGGTCGTAC ATACACTTCC TCAAGGAGTA GAGGTCGTCA
4201  CAAGATGGCC ATCAGTGGAC TCTCTTTTTT CAGAATGGCA AAGTAAAGGT
      GTTCTACCGG TAGTCACCTG AGAGAAAAAA GTCTTACCGT TTCATTTCCA
4251  TTTTCAGGGA AATCAAGACT CCTTCACACC TGTGGTGAAC TCTCTAGACC
      AAAAGTCCCT TTAGTTCTGA GGAAGTGTGG ACACCACTTG AGAGATCTGG
4301  CACCGTTACT GACTCGCTAC CTTCGAATTC ACCCCAGAG TTGGGTGCAC
      GTGGCAATGA CTGAGCGATG GAAGCTTAAG TGGGGGTCTC AACCCACGTG
4351  CAGATTGCCC TGAGGATGGA GGTTCTGGGC TGCGAGGCAC AGGACCTCTA
      GTCTAACGGG ACTCCTACCT CCAAGACCCG ACGCTCCGTG TCCTGGAGAT
4401  C
      G
```

FIG. 9D

AMINO ACID SEQUENCE OF HUMAN B DOMAIN-DELETED FACTOR VIII (HSQ)

```
Met Gln Ile Glu Leu Ser Thr Cys Phe Phe Leu Cys Leu Leu Arg Phe
 1            5                  10                  15
Cys Phe Ser Ala Thr Arg Arg Tyr Tyr Leu Gly Ala Val Glu Leu Ser
            20              25                  30
Trp Asp Tyr Met Gln Ser Asp Leu Gly Glu Leu Pro Val Asp Ala Arg
        35              40                  45
Phe Pro Pro Arg Val Pro Lys Ser Phe Pro Phe Asn Thr Ser Val Val
    50              55              60
Tyr Lys Lys Thr Leu Phe Val Glu Phe Thr Val His Leu Phe Asn Ile
65              70              75                      80
Ala Lys Pro Arg Pro Pro Trp Met Gly Leu Leu Gly Pro Thr Ile Gln
            85              90                      95
Ala Glu Val Tyr Asp Tyr Val Val Ile Thr Leu Lys Asn Met Ala Ser
            100             105                 110
His Pro Val Ser Leu His Ala Val Gly Val Ser Tyr Trp Lys Ala Ser
        115             120                 125
Glu Gly Ala Glu Thr Asp Asp Gln Thr Ser Gln Arg Glu Lys Glu Asp
    130             135                 140
Asp Lys Val Phe Pro Gly Gly Ser His Thr Tyr Val Trp Gln Val Leu
145             150             155                     160
Lys Glu Asn Gly Pro Met Ala Ser Asp Pro Leu Cys Leu Thr Tyr Ser
            165             170                 175
Tyr Leu Ser His Val Asp Leu Val Lys Asp Leu Asn Ser Gly Leu Ile
        180             185                 190
Gly Ala Leu Leu Val Cys Arg Glu Gly Ser Leu Ala Lys Glu Lys Thr
        195             200                 205
Gln Thr Leu His Lys Phe Ile Leu Leu Phe Ala Val Phe Asp Glu Gly
    210             215                 220
Lys Ser Trp His Ser Glu Thr Lys Asn Ser Leu Met Gln Asp Arg Asp
225             230             235                     240
Ala Ala Ser Ala Arg Ala Trp Pro Lys Met His Thr Val Asn Gly Tyr
            245             250                 255
Val Asn Arg Ser Leu Pro Gly Leu Ile Gly Cys His Arg Lys Ser Val
            260             265                 270
Tyr Trp His Val Ile Gly Met Gly Thr Thr Pro Glu Val His Ser Ile
        275             280                 285
Phe Leu Glu Gly His Thr Phe Leu Val Arg Asn His Arg Gln Ala Ser
    290             295                 300
Leu Glu Ile Ser Pro Ile Thr Phe Leu Thr Ala Gln Thr Leu Leu Met
305             310             315                     320
Asp Leu Gly Gln Phe Leu Leu Phe Cys His Ile Ser Ser His Gln His
            325             330                 335
Asp Gly Met Glu Ala Tyr Val Lys Val Asp Ser Cys Pro Glu Glu Pro
            340             345                 350
Gln Leu Arg Met Lys Asn Asn Glu Glu Ala Glu Asp Tyr Asp Asp Asp
        355             360                 365
Leu Thr Asp Ser Glu Met Asp Val Val Arg Phe Asp Asp Asp Asn Ser
    370             375                 380
Pro Ser Phe Ile Gln Ile Arg Ser Val Ala Lys Lys His Pro Lys Thr
385             390             395                     400
Trp Val His Tyr Ile Ala Ala Glu Glu Asp Trp Asp Tyr Ala Pro
```

FIG. 10A

```
                        405                      410                      415
Leu Val Leu Ala Pro Asp Asp Arg Ser Tyr Lys Ser Gln Tyr Leu Asn
                420                      425                  430
Asn Gly Pro Gln Arg Ile Gly Arg Lys Tyr Lys Lys Val Arg Phe Met
            435                      440                  445
Ala Tyr Thr Asp Glu Thr Phe Lys Thr Arg Glu Ala Ile Gln His Glu
        450                      455                  460
Ser Gly Ile Leu Gly Pro Leu Leu Tyr Gly Glu Val Gly Asp Thr Leu
465                      470                      475                  480
Leu Ile Ile Phe Lys Asn Gln Ala Ser Arg Pro Tyr Asn Ile Tyr Pro
                485                      490                  495
His Gly Ile Thr Asp Val Arg Pro Leu Tyr Ser Arg Arg Leu Pro Lys
            500                      505                  510
Gly Val Lys His Leu Lys Asp Phe Pro Ile Leu Pro Gly Glu Ile Phe
        515                      520                  525
Lys Tyr Lys Trp Thr Val Thr Val Glu Asp Gly Pro Thr Lys Ser Asp
    530                      535                  540
Pro Arg Cys Leu Thr Arg Tyr Tyr Ser Ser Phe Val Asn Met Glu Arg
545                      550                      555                  560
Asp Leu Ala Ser Gly Leu Ile Gly Pro Leu Leu Ile Cys Tyr Lys Glu
                565                      570                  575
Ser Val Asp Gln Arg Gly Asn Gln Ile Met Ser Asp Lys Arg Asn Val
            580                      585                  590
Ile Leu Phe Ser Val Phe Asp Glu Asn Arg Ser Trp Tyr Leu Thr Glu
        595                      600                  605
Asn Ile Gln Arg Phe Leu Pro Asn Pro Ala Gly Val Gln Leu Glu Asp
    610                      615                  620
Pro Glu Phe Gln Ala Ser Asn Ile Met His Ser Ile Asn Gly Tyr Val
625                      630                      635                  640
Phe Asp Ser Leu Gln Leu Ser Val Cys Leu His Glu Val Ala Tyr Trp
                645                      650                  655
Tyr Ile Leu Ser Ile Gly Ala Gln Thr Asp Phe Leu Ser Val Phe Phe
            660                      665                  670
Ser Gly Tyr Thr Phe Lys His Lys Met Val Tyr Glu Asp Thr Leu Thr
        675                      680                  685
Leu Phe Pro Phe Ser Gly Glu Thr Val Phe Met Ser Met Glu Asn Pro
    690                      695                  700
Gly Leu Trp Ile Leu Gly Cys His Asn Ser Asp Phe Arg Asn Arg Gly
705                      710                      715                  720
Met Thr Ala Leu Leu Lys Val Ser Ser Cys Asp Lys Asn Thr Gly Asp
                725                      730                  735
Tyr Tyr Glu Asp Ser Tyr Glu Asp Ile Ser Ala Tyr Leu Leu Ser Lys
            740                      745                  750
Asn Asn Ala Ile Glu Pro Arg Ser Phe Ser Gln Asn Pro Pro Val Leu
        755                      760                  765
Lys Arg His Gln Arg Glu Ile Thr Arg Thr Thr Leu Gln Ser Asp Gln
    770                      775                  780
Glu Glu Ile Asp Tyr Asp Asp Thr Ile Ser Val Glu Met Lys Lys Glu
785                      790                      795                  800
Asp Phe Asp Ile Tyr Asp Glu Asp Asn Gln Ser Pro Arg Ser Phe
                805                      810                  815
Gln Lys Lys Thr Arg His Hyr Phe Ile Ala Ala Val Glu Arg Leu Trp
            820                      825                  830
Asp Tyr Gly Met Ser Ser Ser Pro His Val Leu Arg Asn Atg Ala Gln
        835                      840                  845
Ser Gly Ser Val Pro Gln Phe Lys Lys Val Val Phe Gln Glu Phe Thr
    850                      855                  860
```

FIG. 10B

```
Asp Gly Ser Phe Thr Gln Pro Leu Tyr Arg Gly Glu Leu Asn Glu His
865                 870                 875                 880
Leu Gly Leu Leu Gly Pro Tyr Ile Arg Ala Glu Val Glu Asp Asn Ile
                885                 890                 895
Met Val Thr Phe Arg Asn Gln Ala Ser Arg Pro Tyr Ser Phe Tyr Ser
            900                 905                 910
Ser Leu Ile Ser Tyr Glu Glu Asp Gln Arg Gln Gly Ala Glu Pro Arg
        915                 920                 925
Lys Asn Phe Val Lys Pro Asn Glu Thr Lys Thr Tyr Phe Trp Lys Val
    930                 935                 940
Gln His His Met Ala Pro Thr Lys Asp Glu Phe Asp Cys Lys Ala Trp
945                 950                 955                 960
Ala Tyr Phe Ser Asp Val Asp Leu Glu Lys Asp Val His Ser Gly Leu
                965                 970                 975
Ile Gly Pro Leu Leu Val Cys His Thr Asn Thr Leu Asn Pro Ala His
            980                 985                 990
Gly Arg Gln Val Thr Val Gln Glu Phe Ala Leu Phe Phe Thr Ile Phe
        995                 1000                1005
Asp Glu Thr Lys Ser Trp Tyr Phe Thr Glu Asn Met Glu Arg Asn Cys
    1010                1015                1020
Arg Ala Pro Cys Asn Ile Gln Met Glu Asp Pro Thr Phe Lys Glu Asn
1025                1030                1035                1040
Tyr Arg Phe His Ala Ile Asn Gly Tyr Ile Met Asp Thr Leu Pro Gly
                1045                1050                1055
Leu Val Met Ala Gln Asp Gln Arg Ile Arg Trp Tyr Leu Leu Ser Met
            1060                1065                1070
Gly Ser Asn Glu Asn Ile His Ser Ile His Phe Ser Gly His Val Phe
        1075                1080                1085
Thr Val Arg Lys Lys Glu Glu Tyr Lys Met Ala Leu Tyr Asn Leu Tyr
    1090                1095                1100
Pro Gly Val Phe Glu Thr Val Glu Met Leu Pro Ser Lys Ala Gly Ile
1105                1110                1115                1120
Trp Arg Val Glu Cys Leu Ile Gly Glu His Leu His Ala Gly Met Ser
                1125                1130                1135
Thr Leu Phe Leu Val Tyr Ser Asn Lys Cys Gln Thr Pro Leu Gly Met
            1140                1145                1150
Ala Ser Gly His Ile Arg Asp Phe Gln Ile Thr Ala Ser Gly Gln Tyr
        1155                1160                1165
Gly Gln Trp Ala Pro Lys Leu Ala Arg Leu His Tyr Ser Gly Ser Ile
    1170                1175                1180
Asn Ala Trp Ser Thr Lys Glu Pro Phe Ser Trp Ile Lys Val Asp Leu
1185                1190                1195                1200
Leu Ala Pro Met Ile Ile His Gly Ile Lys Thr Gln Gly Ala Arg Gln
                1205                1210                1215
Lys Phe Ser Ser Leu Tyr Ile Ser Gln Phe Ile Ile Met Tyr Ser Leu
            1220                1225                1230
Asp Gly Lys Lys Trp Gln Thr Tyr Arg Gly Asn Ser Thr Gly Thr Leu
        1235                1240                1245
Met Val Phe Phe Gly Asn Val Asp Ser Ser Gly Ile Lys His Asn Ile
    1250                1255                1260
Phe Asn Pro Pro Ile Ile Ala Arg Tyr Ile Arg Leu His Pro Thr His
1265                1270                1275                1280
Tyr Ser Ile Arg Ser Thr Leu Arg Met Glu Leu Met Gly Cys Asp Leu
                1285                1290                1295
Asn Ser Cys Ser Met Pro Leu Gly Met Glu Ser Lys Ala Ile Ser Asp
            1300                1305                1310
Ala Gln Ile Thr Ala Ser Ser Tyr Phe Thr Asn Met Phe Ala Thr Trp
```

FIG. 10C

```
              1315                    1320                       1325
Ser Pro Ser Lys Ala Arg Leu His Leu Gln Gly Arg Ser Asn Ala Trp
      1330                 1335                 1340
Arg Pro Gln Val Asn Asn Pro Lys Glu Trp Leu Gln Val Asp Phe Gln
1345                1350                   1355                   1360
Lys Thr Met Lys Val Thr Gly Val Thr Thr Gln Gly Val Lys Ser Leu
                1365                   1370                  1375
Leu Thr Ser Met Tyr Val Lys Glu Phe Leu Ile Ser Ser Ser Gln Asp
             1380                   1385                   1390
Gly His Gln Trp Thr Leu Phe Phe Gln Asn Gly Lys Val Lys Val Phe
           1395                 1400                      1405
Gln Gly Asn Gln Asp Ser Phe Thr Pro Val Val Asn Ser Leu Asp Pro
      1410                   1415                  1420
Pro Leu Leu Thr Arg Tyr Leu Arg Ile His Pro Gln Ser Trp Val His
1425                  1430                    1435                   1440
Gln Ile Ala Leu Arg Met Glu Val Leu Gly Cys Glu Ala Gln Asp Leu
                1445                   1450                   1455
Tyr
```

FIG. 10D

NUCLEOTIDE SEQUENCE OF HUMAN B DOMAIN-DELETED FACTOR VIII(HSQ)

```
   1 ATGCAAATAG AGCTCTCCAC CTGCTTCTTT CTGTGCCTTT TGCGATTCTG
  51 CTTTAGTGCC ACCAGAAGAT ACTACCTGGG TGCAGTGGAA CTGTCATGGG
 101 ACTATATGCA AAGTGATCTC GGTGAGCTGC CTGTGGACGC AAGATTTCCT
 151 CCTAGAGTGC CAAAATCTTT TCCATTCAAC ACCTCAGTCG TGTACAAAAA
 201 GACTCTGTTT GTAGAATTCA CGGTTCACCT TTTCAACATC GCTAAGCCAA
 251 GGCCACCCTG GATGGGTCTG CTAGGTCCTA CCATCCAGGC TGAGGTTTAT
 301 GATACAGTGG TCATTACACT TAAGAACATG GCTTCCATC CTGTCAGTCT
 351 TCATGCTGTT GGTGTATCCT ACTGGAAAGC TTCTGAGGGA GCTGAATATG
 401 ATGATCAGAC CAGTCAAAGG GAGAAAGAAG ATGATAAAGT CTTCCCTGGT
 451 GGAAGCCATA CATATGTCTG GCAGGTCCTG AAAGAGAATG GTCCAATGGC
 501 CTCTGACCCA CTGTGCCTTA CCTACTCATA TCTTTCTCAT GTGGACCTGG
 551 TAAAAGACTT GAATTCAGGC CTCATTGGAG CCCTACTAGT ATGTAGAGAA
 601 GGGAGTCTGG CCAAGGAAAA GACACAGACC TTGCACAAAT TTATACTACT
 651 TTTTGCTGTA TTTGATGAAG GGAAAAGTTG GCACTCAGAA ACAAAGAACT
 701 CCTTGATGCA GGATAGGGAT GCTGCATCTG CTCGGGCCTG GCCTAAAATG
 751 CACACAGTCA ATGGTTATGT AAACAGGTCT CTGCCAGGTC TGATTGGATG
 801 CCACAGGAAA TCAGTCTATT GGCATGTGAT TGGAATGGGC ACCACTCCTG
 851 AAGTGCACTC AATATTCCTC GAAGGTCACA CATTTCTTGT GAGGAACCAT
 901 CGCCAGGCGT CCTTGGAAAT CTCGCCAATA ACTTTCCTTA CTGCTCAAAC
 951 ACTCTTGATG GACCTTGGAC AGTTTCTACT GTTTTGTCAT ATCTCTTCCC
1001 ACCAACATGA TGGCATGGAA GCTTATGTCA AAGTAGACAG CTGTCCAGAG
1051 GAACCCCAAC TACGAATGAA AAATAATGAA GAAGCGGAAG ACTATGATGA
1101 TGATCTTACT GATTCTGAAA TGGATGTGGT CAGGTTTGAT GATGACAACT
1151 CTCCTTCCTT TATCCAAATT CGCTCAGTTG CCAAGAAGCA TCCTAAAACT
1201 TGGGTACATT ACATTGCTGC TGAAGAGGAG GACTGGGACT ATGCTCCCTT
1251 AGTCCTCGCC CCCGATGACA GAAGTTATAA AAGTCAATAT TTGAACAATG
1301 GCCCTCAGCG GATTGGTAGG AAGTACAAAA AAGTCCGATT TATGGCATAC
1351 ACAGATGAAA CCTTTAAGAC GCGTGAAGCT ATTCAGCATG AATCAGGAAT
1401 CTTGGGACCT TTACTTTATG GGGAAGTTGG AGACACACTG TTGATTATAT
1451 TTAAGAATCA AGCAAGCAGA CCATATAACA TCTACCCTCA CGGAATCACT
1501 GATGTCCGTC CTTTGTATTC AAGGAGATTA CCAAAAGGTG TAAAACATTT
1551 GAAGGATTTT CCAATTCTGC CAGGAGAAAT ATTCAAATAT AAATGGACAG
1601 TGACTGTAGA AGATGGGCCA ACTAAATCAG ATCCGCGGTG CCTGACCCGC
1651 TATTACTCTA GTTTCGTTAA TATGGAGAGA GATCTAGCTT CAGGACTCAT
1701 TGGCCCTCTC CTCATCTGCT ACAAAGAATC TGTAGATCAA AGAGGAAACC
1751 AGATAATGTC AGACAAGAGG AATGTCATCC TGTTTTCTGT ATTTGATGAG
1801 AACCGAAGCT GGTACCTCAC AGAGAATATA CAACGCTTTC TCCCCAATCC
1851 AGCTGGAGTG CAGCTTGAGG ATCCAGAGTT CCAAGCCTCC AACATCATGC
1901 ACAGCATCAA TGGCTATGTT TTTGATAGTT TGCAGTTGTC AGTTTGTTTG
1951 CATGAGGTGG CATACTGGTA CATTCTAAGC ATTGGAGCAC AGACTGACTT
2001 CCTTTCTGTC TTCTTCTCTG GATATACCTT CAAACACAAA ATGGTCTATG
2051 AAGACACACT CACCCTATTC CCATTCTCAG GAGAAACTGT CTTCATGTCG
2100 ATGGAAAACC CAGGTCTATG GATTCTGGGG TGCCACAACT CAGACTTTCG
2151 GAACAGAGGC ATGACCGCCT TACTGAAGGT TTCTAGTTGT GACAAGAACA
2201 CTGGTGATTA TTACGAGGAC AGTTATGAAG ATATTTCAGC ATACTTGCTG
2251 AGTAAAAACA ATGCCATTGA ACCTAGGAGC TTCTCTCAGA ATCCACCAGT
2301 CTTGAAACGC CATCAACGGG AAATAACTCG TACTACTCTT CAGTCAGATC
2351 AAGAGGAAAT TGACTATGAT GATACCATAT CAGTTGAAAT GAAGAAGGAA
2401 GATTTTGACA TTTATGATGA GGATGAAAAT CAGAGCCCCC GCAGCTTTCA
```

FIG. 11A

```
2451  AAAGAAAACA CGACACTATT TTATTGCTGC AGTGGAGAGG CTCTGGGATT
2501  ATGGGATGAG TAGCTCCCCA CATGTTCTAA GAAACAGGGC TCAGAGTGGC
2551  AGTGTCCCTC AGTTCAAGAA AGTTGTTTTC CAGGAATTTA CTGATGGCTC
2601  CTTTACTCAG CCCTTATACC GTGGAGAACT AAATGAACAT TTGGGACTCC
2651  TGGGGCCATA TATAAGAGCA GAAGTTGAAG ATAATATCAT GGTAACTTTC
2701  AGAAATCAGG CCTCTCGTCC CTATTCCTTC TATTCTAGCC TTATTTCTTA
2751  TGAGGAAGAT CAGAGGCAAG GAGCAGAACC TAGAAAAAC TTTGTCAAGC
2801  CTAATGAAAC CAAAACTTAC TTTTGAAAG TGCAACATCA TATGGCACCC
2851  ACTAAGATG AGTTTGACTG CAAAGCCTGG GCTTATTTCT CTGATGTTGA
2901  CCTGGAAAAA GATGTGCACT CAGGCCTGAT TGGACCCCTT CTGGTCTGCC
2951  ACACTAACAC ACTGAACCCT GCTCATGGGA GACAAGTGAC AGTACAGGAA
3001  TTTGCTCTGT TTTTCACCAT CTTTGATGAG ACCAAAAGCT GGTACTTCAC
3051  TGAAAATATG GAAAGAAACT GCAGGGCTCC CTGCAATATC CAGATGGAAG
3101  ATCCCACTTT TAAAGAGAAT TATCGCTTCC ATGCAATCAA TGGCTACATA
3151  ATGGATACAC TACCTGGCTT AGTAATGGCT CAGGATCAAA GGATTCGATG
3201  GTATCTGCTC AGCATGGGCA GCAATGAAAA CATCCATTCT ATTCATTTCA
3251  GTGGACATGT GTTCACTGTA CGAAAAAAG AGGAGTATAA AATGGCACTG
3301  TACAATCTCT ATCCAGGTGT TTTGAGACA GTGGAAATGT TACCATCCAA
3351  AGCTGGAATT TGGCGGGTGG AATGCCTTAT TGGCGAGCAT CTACATGCTG
3401  GGATGAGCAC ACTTTTTCTG GTGTACAGCA ATAAGTGTCA GACTCCCCTG
3451  GGAATGGCTT CTGGACACAT TAGAGATTTT CAGATTACAG CTTCAGGACA
3501  ATATGGACAG TGGGCCCCAA AGCTGGCCAG ACTTCATTAT TCCGGATCAA
3551  TCAATGCCTG GAGCACCAAG GAGCCCTTTT CTTGGATCAA GGTGGATCTG
3601  TTGGCACCAA TGATTATTCA CGGCATCAAG ACCCAGGGTG CCCGTCAGAA
3651  GTTCTCCAGC CTCTACATCT CTCAGTTTAT CATCATGTAT AGTCTTGATG
3701  GGAAGAAGTG GCAGACTTAT CGAGGAAATT CCACTGGAAC CTTAATGGTC
3751  TTCTTTGGCA ATGTGGATTC ATCTGGGATA AAACACAATA TTTTTAACCC
3801  TCCAATTATT GCTCGATACA TCCGTTTGCA CCCAACTCAT TATAGCATTC
3851  GCAGCACTCT TCGCATGGAT TTGATGGGCT GTGATTTAAA TAGTTGCAGC
3901  ATGCCATTGG GAATGGAGAG TAAAGCAATA TCAGATGCAC AGATTACTGC
3951  TTCATCCTAC TTTACCAATA TGTTTGCCAC CTGGTCTCCT TCAAAAGCTC
4001  GACTTCACCT CCAAGGGAGG AGTAATGCCT GGAGACCTCA GGTGAATAAT
4051  CCAAAAGAGT GGCTGCAAGT GGACTTCCAG AAGACAATGA AAGTCACAGG
4101  AGTAACTACT CAGGGAGTAA AATCTCTGCT TACCAGCATG TATGTGAAGG
4151  AGTTCCTCAT CTCCAGCAGT CAAGATGGCC ATCAGTGGAC TCTCTTTTTT
4201  CAGAATGGCA AAGTAAAGGT TTTTCAGGGA AATCAAGACT CCTTCACACC
4251  TGTGGTGAAC TCTCTAGACC CACCGTTACT GACTCGCTAC CTTCGAATTC
4301  ACCCCCAGAG TTGGGTGCAC CAGATTGCCC TGAGGATGGA GGTTCTGGGC
4351  TGCGAGGCAC AGGACCTCTA C
```

FIG. 11B

AMINO ACID SEQUENCE OF HP630L

```
   1  MQLELSTCVF  LCLLPLGFSA  IRRYYLGAVE  LSWDYRQSEL  LRELHVDTRF
  51  PATAPGALPL  GPSVLYKKTV  FVEFTDQLFS  VARPRPPWMG  LLGPTIQAEV
 101  YDTVVVTLKN  MASHPVSLHA  VGVSFWKSSE  GAEYEDHTSQ  REKEDDKVLP
 151  GKSQTYVWQV  LKENGPTASD  PPCLTYSYLS  HVDLVKDLNS  GLIGALLVCR
 201  EGSLTRERTQ  NLHEFVLLFA  VFDEGKSWHS  ARNDSWTRAM  DPAPARAQPA
 251  MHTVNGYVNR  SLPGLIGCHK  KSVYWHVIGM  GTSPEVHSIF  LEGHTFLVRH
 301  HRQASLEISP  LTFLTAQTFL  MDLGQFLLFC  HISSHHHGGM  EAHVRVESCA
 351  EEPQLRRKAD  EEEDYDDNLY  DSDMDVVRLD  GDDVSPFIQI  RSVAKKHPKT
 401  WVHYIAAEEE  DWDYAPLVLA  PDDRSYKSQY  LNNGPQRIGR  KYKKVRFMAY
 451  TDETFKTREA  IQHESGILGP  LLYGEVGDTL  LIIFKNQASR  PYNIYPHGIT
 501  DVRPLYSRRL  PKGVKHLKDF  PILPGEIFKY  KWTVTVEDGP  TKSDPRCLTR
 551  YYSSFVNMER  DLASGLIGPL  LICYKESVDQ  RGNQIMSDKR  NVILFSVFDE
 601  NRSWYLTENI  QRFLPNPAGV  QLEDPEFQAS  NIMHSINGYV  FDSLQLSVCL
 651  HEVAYWYILS  IGAQTDFLSV  FFSGYTFKHK  MVYEDTLTLF  PFSGETVFMS
 701  MENPGLWILG  CHNSDFRNRG  MTALLKVSSC  DKNTGDYYED  SYEDISAYLL
 751  SKNNAIEPRS  FSQNSRHPST  RSQNPPVLKR  HQREITRTTL  QSDQEEIDYD
 801  DTISVEMKKE  DFDIYDEDEN  QSPRSFQKRT  RHYFIAAVEQ  LWDYGMSESP
 851  RALRNRAQNG  EVPRFKKVVF  REFADGSFTQ  PSYRGELNKH  LGLLGPYIRA
 901  EVEDNIMVTF  KNQASRPYSF  YSSLISYPDD  QEQGAEPRKN  FVKPNETKTY
 951  FWKVQHHMAP  TEDEFDCKAW  AYFSDVDLEK  DVHSGLIGPL  LICRANTLNA
1001  AHGRQVTVQE  FALFFTIFDE  TKSWYFTENV  ERNCRAPCHL  QMEDPTLKEN
1051  YRFHAINGYV  MDTLPGLVMA  QNQRIRWYLL  SMGSNENIHS  IHFSGHVFSV
1101  RKKEEYKMAV  YNLYPGVFET  VEMLPSKVGI  WRNRCLIGEH  LQAGMSTTFL
1151  VYSKKCQTPL  GMASGHIRDF  QITASGQYGQ  WAPKLARLHY  SGSINAWSTK
1201  EPFSWIKVDL  LAPMIIHGIK  TQGARQKFSS  LYISQFIIMY  SLDGKKWQTY
1251  RGNSTGTLMV  FFGNVDSSGI  KHNIFNPPII  ARYIRLHPTH  YSIRSTLRME
1301  LMGCDLNSCS  MPLGMESKAI  SDAQITASSY  FTNMFATWSP  SKARLHLQGR
1351  SNAWRPQVNN  PKEWLQVDFQ  KTMKVTGVTT  QGVKSLLTSM  YVKEFLISSS
1401  QDGHQWTLFF  QNGKVKVFQG  NQDSFTPVVN  SLDPPLLTRY  LRIHPQSWVH
1451  QIALRMEVLG  CEAQDLY
```

FIG. 13

NUCLEOTIDE SEQUENCE OF HP63/OL

```
   1  ATGCAGCTAG AGCTCTCCAC CTGTGTCTTT CTGTGTCTCT TGCCACTCGG
  51  CTTTAGTGCC ATCAGGAGAT ACTACCTGGG CGCAGTGGAA CTGTCCTGGG
 101  ACTACCGGCA AAGTGAACTC CTCCGTGAGC TGCACGTGGA CACCAGATTT
 151  CCTGCTACAG CGCCAGGAGC TCTTCCGTTG GGCCCGTCAG TCCTGTACAA
 201  AAAGACTGTG TTCGTAGAGT TCACGGATCA ACTTTTCAGC GTTGCCAGGC
 251  CCAGGCCACC ATGGATGGGT CTGCTGGGTC CTACCATCCA GGCTGAGGTT
 301  TACGACACGG TGGTCGTTAC CCTGAAGAAC ATGGCTTCTC ATCCCGTTAG
 351  TCTTCACGCT GTCGGCGTCT CCTTCTGGAA ATCTTCCGAA GGCGCTGAAT
 401  ATGAGGATCA CACCAGCCAA AGGGAGAAGG AAGACGATAA AGTCCTTCCC
 451  GGTAAAAGCC AAACCTACGT CTGGCAGGTC CTGAAAGAAA ATGGTCCAAC
 501  AGCCTCTGAC CCACCATGTC TTACCTACTC ATACCTGTCT CACGTGGACC
 551  TGGTGAAAGA CCTGAATTCG GGCCTCATTG GAGCCCTGCT GGTTTGTAGA
 601  GAAGGGAGTC TGACCAGAGA AAGGACCCAG AACCTGCACG AATTTGTACT
 651  ACTTTTTGCT GTCTTTGATG AAGGGAAAAG TTGGCACTCA GCAAGAAATG
 701  ACTCCTGGAC ACGGGCCATG GATCCGCAC CTGCCAGGGC CAGCCTGCA
 751  ATGCACACAG TCAATGGCTA TGTCAACAGG TCTCTGCCAG GTCTGATCGG
 801  ATGTCATAAG AAATCAGTCT ACTGGCACGT GATTGGAATG GGCACCAGCC
 851  CGGAAGTGCA CTCCATTTTT CTTGAAGGCC ACACGTTTCT CGTGAGGCAC
 901  CATCGCCAGG CTTCCTTGGA GATCTCGCCA CTAACTTTCC TCACTGCTCA
 951  GACATTCCTG ATGGACCTTG GCCAGTTCCT ACTGTTTTGT CATATCTCTT
1001  CCCACCACCA TGGTGGCATG GAGGCTCACG TCAGAGTAGA AAGCTGCGCC
1051  GAGGAGCCCC AGCTGCGGAG GAAAGCTGAT GAAGAGGAAG ATTATGATGA
1101  CAATTTGTAC GACTCGGACA TGGACGTGGT CCGGCTCGAT GGTGACGACG
1151  TGTCTCCCTT TATCCAAATC CGCTCAGTTG CCAAGAAGCA TCCTAAAACT
1201  TGGGTACATT ACATTGCTGC TGAAGAGGAG GACTGGGACT ATGCTCCCTT
1251  AGTCCTCGCC CCCGATGACA GAAGTTATAA AAGTCAATAT TTGAACAATG
1301  GCCCTCAGCG GATTGGTAGG AAGTACAAAA AAGTCCGATT TATGGCATAC
1351  ACAGATGAAA CCTTTAAGAC TCGTGAAGCT ATTCAGCATG AATCAGGAAT
1401  CTTGGGACCT TTACTTTATG GGGAAGTTGG AGACACACTG TTGATTATAT
1451  TTAAGAATCA AGCAAGCAGA CCATATAACA TCTACCCTCA CGGAATCACT
1501  GATGTCCGTC CTTTGTATTC AAGGAGATTA CCAAAAGGTG TAAAACATTT
1551  GAAGGATTTT CCAATTCTGC CAGGAGAAAT ATTCAAATAT AAATGGACAG
1601  TGACTGTAGA AGATGGGCCA ACTAAATCAG ATCCTCGGTG CCTGACCCGC
1651  TATTACTCTA GTTTCGTTAA TATGGAGAGA GATCTAGCTT CAGGACTCAT
1701  TGGCCCTCTC CTCATCTGCT ACAAAGAATC TGTAGATCAA AGAGGAAACC
1751  AGATAATGTC AGACAAGAGG AATGTCATCC TGTTTTCTGT ATTTGATGAG
1801  AACCGAAGCT GGTACCTCAC AGAGAATATA CAACGCTTTC TCCCCAATCC
1851  AGCTGGAGTG CAGCTTGAGG ATCCAGAGTT CCAAGCCTCC AACATCATGC
1901  ACAGCATCAA TGGCTATGTT TTTGATAGTT TGCAGTTGTC AGTTTGTTTG
1951  CATGAGGTGG CATACTGGTA CATTCTAAGC ATTGGAGCAC AGACTGACTT
2001  CCTTTCTGTC TTCTTCTCTG GATATACCTT CAAACACAAA ATGGTCTATG
2051  AAGACACACT CACCCTATTC CCATTCTCAG GAGAAACTGT CTTCATGTCG
2101  ATGGAAAACC CAGGTCTATG GATTCTGGGG TGCCACAACT CAGACTTTCG
2151  GAACAGAGGC ATGACCGCCT TACTGAAGGT TTCTAGTTGT GACAAGAACA
2201  CTGGTGATTA TTACGAGGAC AGTTATGAAG ATATTTCAGC ATACTTGCTG
2251  AGTAAAAACA ATGCCATTGA ACCTAGGAGC TTCTCCCAGA ATTCAAGACA
2301  CCCTAGCACT AGGTCTCAAA ACCACCAGT CTTGAAACGC ATCAACGGG
2351  AAATAACTCG TACTACTCTT CAGTCAGATC AAGAGGAAAT TGACTATGAT
```

FIG. 14A

```
2401  GATACCATAT CAGTTGAAAT GAAGAAGGAA GATTTTGACA TTTATGATGA
2451  GGATGAAAAT CAGAGCCCCC GCAGCTTTCA AAAGAGAACC CGACACTATT
2501  TCATTGCTGC GGTGGAGCAG CTCTGGGATT ACGGGATGAG CGAATCCCCC
2551  CGGGCGCTAA GAAACAGGGC TCAGAACGGA GAGGTGCCTC GGTTCAAGAA
2601  GGTGGTCTTC CGGGAATTTG CTGACGGCTC CTTCACGCAG CCGTCGTACC
2651  GCGGGGAACT CAACAAACAC TTGGGGCTCT TGGACCCTA CATCAGAGCG
2701  GAAGTTGAAG ACAACATCAT GGTAACTTTC AAAAACCAGG CGTCTCGTCC
2751  CTATTCCTTC TACTCGAGCC TTATTTCTTA TCCGGATGAT CAGGAGCAAG
2801  GGGCAGAACC TCGAAAAAC TTTGTCAAGC CTAATGAAAC CAAAACTTAC
2851  TTTTGGAAAC TGCAGCATCA CATGGCACCC ACAGAAGACG AGTTTGACTG
2901  CAAAGCCTGG GCCTACTTTT CTGATGTTGA CCTGGAAAAA GATGTGCACT
2951  CAGGCTTGAT CGGCCCCCTT CTGATCTGCC GCGCCAACAC CCTGAACGCT
3001  GCTCACGGTA GACAAGTGAC CGTGCAAGAA TTTGCTCTGT TTTTCACTAT
3051  TTTTGATGAG ACAAAGAGCT GGTACTTCAC TGAAAATGTG GAAAGGAACT
3101  GCCGGGCCCC CTGCCATCTG CAGATGGAGG ACCCCACTCT GAAAGAAAAC
3151  TATCGCTTCC ATGCAATCAA TGGCTATGTG ATGGATACAC TCCCTGGCTT
3201  AGTAATGGCT CAGAATCAAA GGATCCGATG GTATCTGCTC AGCATGGCA
3251  GCAATGAAAA TATCCATTCG ATTCATTTTA GCGGACACGT GTTCAGTGTA
3301  CGGAAAAAGG AGGAGTATAA AATGGCCGTG TACAATCTCT ATCCGGGTGT
3351  CTTTGAGACA GTGGAAATGC TACCGTCCAA AGTTGGAATT TGGCGGAATA
3401  GATGCCTGAT TGGCGAGCAC CTGCAAGCTG GGATGAGCAC GACTTTCCTG
3451  GTGTACAGCA AGAAGTGTCA GACTCCCTG GAATGGCTT CTGGACACAT
3501  TAGAGATTTT CAGATTACAG CTTCAGGACA ATATGGACAG TGGGCCCCAA
3551  AGCTGGCCAG ACTTCATTAT TCCGGATCAA TCAATGCCTG GAGCACCAAG
3601  GAGCCCTTTT CTTGGATCAA GGTGGATCTG TTGGCACCAA TGATTATTCA
3651  CGGCATCAAG ACCCAGGGTG CCCGTCAGAA GTTCTCCAGC CTCTACATCT
3701  CTCAGTTTAT CATCATGTAT AGTCTTGATG GAAGAAGTG GCAGACTTAT
3751  CGAGGAAATT CCACTGGAAC CTTAATGGTC TTCTTTGGCA ATGTGGATTC
3801  ATCTGGGATA AAACACAATA TTTTTAACCC TCCAATTATT GCTCGATACA
3851  TCCGTTTGCA CCCAACTCAT TATAGCATTC GCAGCACTCT TCGCATGGAG
3901  TTGATGGGCT GTGATTTAAA TAGTTGCAGC ATGCCATTGG GAATGGAGAG
3951  TAAAGCAATA TCAGATGCAC AGATTACTGC TTCATCCTAC TTTACCAATA
4001  TGTTTGCCAC CTGGTCTCCT TCAAAAGCTC GACTTCACCT CCAAGGGAGG
4051  AGTAATGCCT GGAGACCTCA GGTGAATAAT CCAAAAGAGT GGCTGCAAGT
4101  GGACTTCCAG AAGACAATGA AAGTCACAGG AGTAACTACT CAGGGAGTAA
4151  AATCTCTGCT TACCAGCATG TATGTGAAGG AGTTCCTCAT CTCCAGCAGT
4201  CAAGATGGCC ATCAGTGGAC TCTCTTTTTT CAGAATGGCA AAGTAAAGGT
4251  TTTTCAGGGA AATCAAGACT CCTTCACACC TGTGGTGAAC TCTCTAGACC
4301  CACCGTTACT GACTCGCTAC CTTCGAATTC ACCCCCAGAG TTGGGTGCAC
4351  CAGATTGCCC TGAGGATGGA GGTTCTGGGC TGCGAGGCAC AGGACCTCTA
4401  C
```

FIG. 14B

SEQUENCE LISTING

```
<160> NUMBER OF SEQ ID NOS: 21

<210> SEQ ID NO 1
<211> LENGTH: 6402
<212> TYPE: DNA
<213> ORGANISM: Sus scrofa
<220> FEATURE:
<221> NAME/KEY: gene
<222> LOCATION: (1)...(6399)
<223> OTHER INFORMATION: Factor VIII-- Full Length
<220> FEATURE:
<221> NAME/KEY: CDS
<222> LOCATION: (1)...(6399)

<400> SEQUENCE: 1 atg cag cta gag ctc tcc acc tgt gtc ttt ctg tgt ctc ttg cca ctc        48
Met Gln Leu Glu Leu Ser Thr Cys Val Phe Leu Cys Leu Leu Pro Leu
  1               5                  10                  15 ggc ttt agt gcc atc agg aga tac tac ctg ggc gca gtg gaa ctg tcc        96
Gly Phe Ser Ala Ile Arg Arg Tyr Tyr Leu Gly Ala Val Glu Leu Ser
             20                  25                  30 tgg gac tac cgg caa agt gaa ctc ctc cgt gag ctg cac gtg gac acc       144
Trp Asp Tyr Arg Gln Ser Glu Leu Leu Arg Glu Leu His Val Asp Thr
         35                  40                  45 aga ttt cct gct aca gcg cca gga gct ctt ccg ttg ggc ccg tca gtc       192
Arg Phe Pro Ala Thr Ala Pro Gly Ala Leu Pro Leu Gly Pro Ser Val
     50                  55                  60 ctg tac aaa aag act gtg ttc gta gag ttc acg gat caa ctt ttc agc       240
Leu Tyr Lys Lys Thr Val Phe Val Glu Phe Thr Asp Gln Leu Phe Ser
 65                  70                  75                  80 gtt gcc agg ccc agg cca cca tgg atg ggt ctg ctg ggt cct acc atc       288
Val Ala Arg Pro Arg Pro Pro Trp Met Gly Leu Leu Gly Pro Thr Ile
                 85                  90                  95 cag gct gag gtt tac gac acg gtg gtc gtt acc ctg aag aac atg gct       336
Gln Ala Glu Val Tyr Asp Thr Val Val Val Thr Leu Lys Asn Met Ala
            100                 105                 110 tct cat ccc gtt agt ctt cac gct gtc ggc gtc tcc ttc tgg aaa tct       384
Ser His Pro Val Ser Leu His Ala Val Gly Val Ser Phe Trp Lys Ser
        115                 120                 125 tcc gaa ggc gct gaa tat gag gat cac acc agc caa agg gag aag gaa       432
Ser Glu Gly Ala Glu Tyr Glu Asp His Thr Ser Gln Arg Glu Lys Glu
    130                 135                 140 gac gat aaa gtc ctt ccc ggt aaa agc caa acc tac gtc tgg cag gtc       480
Asp Asp Lys Val Leu Pro Gly Lys Ser Gln Thr Tyr Val Trp Gln Val
145                 150                 155                 160 ctg aaa gaa aat ggt cca aca gcc tct gac cca cca tgt ctc acc tac       528
Leu Lys Glu Asn Gly Pro Thr Ala Ser Asp Pro Pro Cys Leu Thr Tyr
                165                 170                 175
```

-continued

| | |
|---|---|
| tca tac ctg tct cac gtg gac ctg gtg aaa gac ctg aat tcg ggc ctc<br>Ser Tyr Leu Ser His Val Asp Leu Val Lys Asp Leu Asn Ser Gly Leu<br>          180                   185                   190 | 576 |
| att gga gcc ctg ctg gtt tgt aga gaa ggg agt ctg acc aga gaa agg<br>Ile Gly Ala Leu Leu Val Cys Arg Glu Gly Ser Leu Thr Arg Glu Arg<br>        195                 200                   205 | 624 |
| acc cag aac ctg cac gaa ttt gta cta ctt ttt gct gtc ttt gat gaa<br>Thr Gln Asn Leu His Glu Phe Val Leu Leu Phe Ala Val Phe Asp Glu<br>210                   215                   220 | 672 |
| ggg aaa agt tgg cac tca gca aga aat gac tcc tgg aca cgg gcc atg<br>Gly Lys Ser Trp His Ser Ala Arg Asn Asp Ser Trp Thr Arg Ala Met<br>225                   230                   235                   240 | 720 |
| gat ccc gca cct gcc agg gcc cag cct gca atg cac aca gtc aat ggc<br>Asp Pro Ala Pro Ala Arg Ala Gln Pro Ala Met His Thr Val Asn Gly<br>                  245                   250                   255 | 768 |
| tat gtc aac agg tct ctg cca ggt ctg atc gga tgt cat aag aaa tca<br>Tyr Val Asn Arg Ser Leu Pro Gly Leu Ile Gly Cys His Lys Lys Ser<br>                 260                   265                   270 | 816 |
| gtc tac tgg cac gtg att gga atg ggc acc agc ccg gaa gtg cac tcc<br>Val Tyr Trp His Val Ile Gly Met Gly Thr Ser Pro Glu Val His Ser<br>        275                 280                   285 | 864 |
| att ttt ctt gaa ggc cac acg ttt ctc gtg agg cac cat cgc cag gct<br>Ile Phe Leu Glu Gly His Thr Phe Leu Val Arg His His Arg Gln Ala<br>290                   295                   300 | 912 |
| tcc ttg gag atc tcg cca cta act ttc ctc act gct cag aca ttc ctg<br>Ser Leu Glu Ile Ser Pro Leu Thr Phe Leu Thr Ala Gln Thr Phe Leu<br>305                   310                   315                   320 | 960 |
| atg gac ctt ggc cag ttc cta ctg ttt tgt cat atc tcc tcc cac cac<br>Met Asp Leu Gly Gln Phe Leu Leu Phe Cys His Ile Ser Ser His His<br>                  325                   330                   335 | 1008 |
| cat ggt ggc atg gag gct cac gtc aga gta gaa agc tgc gcc gag gag<br>His Gly Gly Met Glu Ala His Val Arg Val Glu Ser Cys Ala Glu Glu<br>                  340                   345                   350 | 1056 |
| ccc cag ctg cgg agg aaa gct gat gaa gag gaa gat tat gat gac aat<br>Pro Gln Leu Arg Arg Lys Ala Asp Glu Glu Glu Asp Tyr Asp Asp Asn<br>        355                 360                   365 | 1104 |
| ttg tac gac tcg gac atg gac gtg gtc cgg ctc gat ggt gac gac gtg<br>Leu Tyr Asp Ser Asp Met Asp Val Val Arg Leu Asp Gly Asp Asp Val<br>370                   375                   380 | 1152 |
| tct ccc ttt atc caa atc cgc tcg gtt gcc aag aag cat ccc aaa acc<br>Ser Pro Phe Ile Gln Ile Arg Ser Val Ala Lys Lys His Pro Lys Thr<br>385                   390                   395                   400 | 1200 |
| tgg gtg cac tac atc tct gca gag gag gag gac tgg gac tac gcc ccc<br>Trp Val His Tyr Ile Ser Ala Glu Glu Glu Asp Trp Asp Tyr Ala Pro<br>                  405                   410                   415 | 1248 |
| gcg gtc ccc agc ccc agt gac aga agt tat aaa agt ctc tac ttg aac<br>Ala Val Pro Ser Pro Ser Asp Arg Ser Tyr Lys Ser Leu Tyr Leu Asn<br>                  420                   425                   430 | 1296 |
| agt ggt cct cag cga att ggt agg aaa tac aaa aaa gct cga ttc gtc<br>Ser Gly Pro Gln Arg Ile Gly Arg Lys Tyr Lys Lys Ala Arg Phe Val<br>        435                 440                   445 | 1344 |
| gct tac acg gat gta aca ttt aag act cgt aaa gct att ccg tat gaa<br>Ala Tyr Thr Asp Val Thr Phe Lys Thr Arg Lys Ala Ile Pro Tyr Glu<br>450                   455                   460 | 1392 |
| tca gga atc ctg gga cct tta ctt tat gga gaa gtt gga gac aca ctt<br>Ser Gly Ile Leu Gly Pro Leu Leu Tyr Gly Glu Val Gly Asp Thr Leu<br>465                   470                   475                   480 | 1440 |
| ttg att ata ttt aag aat aaa gcg agc cga cca tat aac atc tac cct<br>Leu Ile Ile Phe Lys Asn Lys Ala Ser Arg Pro Tyr Asn Ile Tyr Pro<br>                  485                   490                   495 | 1488 |

```
                                                     -continued
cat gga atc act gat gtc agc gct ttg cac cca ggg aga ctt cta aaa       1536
His Gly Ile Thr Asp Val Ser Ala Leu His Pro Gly Arg Leu Leu Lys
            500                 505                 510 ggt tgg aaa cat ttg aaa gac atg cca att ctg cca gga gag act ttc       1584
Gly Trp Lys His Leu Lys Asp Met Pro Ile Leu Pro Gly Glu Thr Phe
        515                 520                 525 aag tat aaa tgg aca gtg act gtg gaa gat ggg cca acc aag tcc gat       1632
Lys Tyr Lys Trp Thr Val Thr Val Glu Asp Gly Pro Thr Lys Ser Asp
530                 535                 540 cct cgg tgc ctg acc cgc tac tac tcg agc tcc att aat cta gag aaa       1680
Pro Arg Cys Leu Thr Arg Tyr Tyr Ser Ser Ser Ile Asn Leu Glu Lys
545                 550                 555                 560 gat ctg gct tcg gga ctc att ggc cct ctc ctc atc tgc tac aaa gaa       1728
Asp Leu Ala Ser Gly Leu Ile Gly Pro Leu Leu Ile Cys Tyr Lys Glu
                565                 570                 575 tct gta gac caa aga gga aac cag atg atg tca gac aag aga aac gtc       1776
Ser Val Asp Gln Arg Gly Asn Gln Met Met Ser Asp Lys Arg Asn Val
                580                 585                 590 atc ctg ttt tct gta ttc gat gag aat caa agc tgg tac ctc gca gag       1824
Ile Leu Phe Ser Val Phe Asp Glu Asn Gln Ser Trp Tyr Leu Ala Glu
            595                 600                 605 aat att cag cgc ttc ctc ccc aat ccg gat gga tta cag ccc cag gat       1872
Asn Ile Gln Arg Phe Leu Pro Asn Pro Asp Gly Leu Gln Pro Gln Asp
        610                 615                 620 cca gag ttc caa gct tct aac atc atg cac agc atc aat ggc tat gtt       1920
Pro Glu Phe Gln Ala Ser Asn Ile Met His Ser Ile Asn Gly Tyr Val
625                 630                 635                 640 ttt gat agc ttg cag ctg tcg gtt tgt ttg cac gag gtg gca tac tgg       1968
Phe Asp Ser Leu Gln Leu Ser Val Cys Leu His Glu Val Ala Tyr Trp
                645                 650                 655 tac att cta agt gtt gga gca cag acg gac ttc ctc tcc gtc ttc ttc       2016
Tyr Ile Leu Ser Val Gly Ala Gln Thr Asp Phe Leu Ser Val Phe Phe
                660                 665                 670 tct ggc tac acc ttc aaa cac aaa atg gtc tat gaa gac aca ctc acc       2064
Ser Gly Tyr Thr Phe Lys His Lys Met Val Tyr Glu Asp Thr Leu Thr
            675                 680                 685 ctg ttc ccc ttc tca gga gaa acg gtc ttc atg tca atg gaa aac cca       2112
Leu Phe Pro Phe Ser Gly Glu Thr Val Phe Met Ser Met Glu Asn Pro
        690                 695                 700 ggt ctc tgg gtc cta ggg tgc cac aac tca gac ttg cgg aac aga ggg       2160
Gly Leu Trp Val Leu Gly Cys His Asn Ser Asp Leu Arg Asn Arg Gly
705                 710                 715                 720 atg aca gcc tta ctg aag gtg tat agt tgt gac agg gac att ggt gat       2208
Met Thr Ala Leu Leu Lys Val Tyr Ser Cys Asp Arg Asp Ile Gly Asp
                725                 730                 735 tat tat gac aac act tat gaa gat att cca ggc ttc ttg ctg agt gga       2256
Tyr Tyr Asp Asn Thr Tyr Glu Asp Ile Pro Gly Phe Leu Leu Ser Gly
                740                 745                 750 aag aat gtc att gaa ccc aga agc ttt gcc cag aat tca aga ccc cct       2304
Lys Asn Val Ile Glu Pro Arg Ser Phe Ala Gln Asn Ser Arg Pro Pro
            755                 760                 765 agt gcg agc caa aag caa ttc caa acc atc aca agt cca gaa gat gac       2352
Ser Ala Ser Gln Lys Gln Phe Gln Thr Ile Thr Ser Pro Glu Asp Asp
        770                 775                 780 gtg gag ctt gac ccg cag tct gga gag aga acc caa gca ctg gaa gaa       2400
Val Glu Leu Asp Pro Gln Ser Gly Glu Arg Thr Gln Ala Leu Glu Glu
785                 790                 795                 800 cta agt gtc ccc tct ggt gat ggg tcg atg ctc ttg gga cag aat cct       2448
Leu Ser Val Pro Ser Gly Asp Gly Ser Met Leu Leu Gly Gln Asn Pro
                805                 810                 815
```

-continued

| | |
|---|---|
| gct cca cat ggc tca tcc tca tct gat ctt caa gaa gcc agg aat gag<br>Ala Pro His Gly Ser Ser Ser Ser Asp Leu Gln Glu Ala Arg Asn Glu<br>820                          825                     830 | 2496 |
| gct gat gat tat tta cct gga gca aga gaa aga ggc acg gcc cca tcc<br>Ala Asp Asp Tyr Leu Pro Gly Ala Arg Glu Arg Gly Thr Ala Pro Ser<br>835                         840                        845 | 2544 |
| gca gcg gca cgt ctc aga cca gag ctg cat cac agt gcc gaa aga gta<br>Ala Ala Ala Arg Leu Arg Pro Glu Leu His His Ser Ala Glu Arg Val<br>850                       855                     860 | 2592 |
| ctt act cct gag cca gag aaa gag ttg aag aaa ctt gat tca aaa atg<br>Leu Thr Pro Glu Pro Glu Lys Glu Leu Lys Lys Leu Asp Ser Lys Met<br>865                         870                     875              880 | 2640 |
| tct agt tca tca gac ctt cta aag act tcg cca aca att cca tca gac<br>Ser Ser Ser Ser Asp Leu Leu Lys Thr Ser Pro Thr Ile Pro Ser Asp<br>                       885                     890                     895 | 2688 |
| acg ttg tca gcg gag act gaa agg aca cat tcc tta ggc ccc cca cac<br>Thr Leu Ser Ala Glu Thr Glu Arg Thr His Ser Leu Gly Pro Pro His<br>900                         905                     910 | 2736 |
| ccg cag gtt aat ttc agg agt caa tta ggt gcc att gta ctt ggc aaa<br>Pro Gln Val Asn Phe Arg Ser Gln Leu Gly Ala Ile Val Leu Gly Lys<br>               915                     920                     925 | 2784 |
| aat tca tct cac ttt att ggg gct ggt gtc cct ttg ggc tcg act gag<br>Asn Ser Ser His Phe Ile Gly Ala Gly Val Pro Leu Gly Ser Thr Glu<br>930                         935                     940 | 2832 |
| gag gat cat gaa agc tcc ctg gga gaa aat gta tca cca gtg gag agt<br>Glu Asp His Glu Ser Ser Leu Gly Glu Asn Val Ser Pro Val Glu Ser<br>945                         950                     955              960 | 2880 |
| gac ggg ata ttt gaa aag gaa aga gct cat gga cct gct tca ctg acc<br>Asp Gly Ile Phe Glu Lys Glu Arg Ala His Gly Pro Ala Ser Leu Thr<br>                       965                     970                     975 | 2928 |
| aaa gac gat gtt tta ttt aaa gtt aat atc tct ttg gta aag aca aac<br>Lys Asp Asp Val Leu Phe Lys Val Asn Ile Ser Leu Val Lys Thr Asn<br>980                         985                     990 | 2976 |
| aag gca cga gtt tac tta aaa act aat aga aag att cac att gat gac<br>Lys Ala Arg Val Tyr Leu Lys Thr Asn Arg Lys Ile His Ile Asp Asp<br>               995                   1000                1005 | 3024 |
| gca gct tta tta act gag aat agg gca tct gca acg ttt atg gac aaa<br>Ala Ala Leu Leu Thr Glu Asn Arg Ala Ser Ala Thr Phe Met Asp Lys<br>1010                      1015                   1020 | 3072 |
| aat act aca gct tcg gga tta aat cat gtg tca aat tgg ata aaa ggg<br>Asn Thr Thr Ala Ser Gly Leu Asn His Val Ser Asn Trp Ile Lys Gly<br>1025                    1030                   1035                1040 | 3120 |
| ccc ctt ggc aag aac ccc cta agc tcg gag cga ggc ccc agt cca gag<br>Pro Leu Gly Lys Asn Pro Leu Ser Ser Glu Arg Gly Pro Ser Pro Glu<br>                    1045                   1050                1055 | 3168 |
| ctt ctg aca tct tca gga tca gga aaa tct gtg aaa ggt cag agt tct<br>Leu Leu Thr Ser Ser Gly Ser Gly Lys Ser Val Lys Gly Gln Ser Ser<br>1060                      1065                   1070 | 3216 |
| ggg cag ggg aga ata cgg gtg gca gtg gaa gag gaa gaa ctg agc aaa<br>Gly Gln Gly Arg Ile Arg Val Ala Val Glu Glu Glu Glu Leu Ser Lys<br>               1075                    1080                  1085 | 3264 |
| ggc aaa gag atg atg ctt ccc aac agc gag ctc acc ttt ctc act aac<br>Gly Lys Glu Met Met Leu Pro Asn Ser Glu Leu Thr Phe Leu Thr Asn<br>1090                      1095                   1100 | 3312 |
| tcg gct gat gtc caa gga aac gat aca cac agt caa gga aaa aag tct<br>Ser Ala Asp Val Gln Gly Asn Asp Thr His Ser Gln Gly Lys Lys Ser<br>1105                      1110                   1115                1120 | 3360 |
| cgg gaa gag atg gaa agg aga gaa aaa tta gtc caa gaa aaa gtc gac<br>Arg Glu Glu Met Glu Arg Arg Glu Lys Leu Val Gln Glu Lys Val Asp<br>                    1125                   1130                1135 | 3408 |

```
ttg cct cag gtg tat aca gcg act gga act aag aat ttc ctg aga aac    3456
Leu Pro Gln Val Tyr Thr Ala Thr Gly Thr Lys Asn Phe Leu Arg Asn
            1140                1145                1150 att ttt cac caa agc act gag ccc agt gta gaa ggg ttt gat ggg ggg    3504
Ile Phe His Gln Ser Thr Glu Pro Ser Val Glu Gly Phe Asp Gly Gly
        1155                1160                1165 tca cat gcg ccg gtg cct caa gac agc agg tca tta aat gat tcg gca    3552
Ser His Ala Pro Val Pro Gln Asp Ser Arg Ser Leu Asn Asp Ser Ala
    1170                1175                1180 gag aga gca gag act cac ata gcc cat ttc tca gca att agg gaa gag    3600
Glu Arg Ala Glu Thr His Ile Ala His Phe Ser Ala Ile Arg Glu Glu
1185                1190                1195                1200 gca ccc ttg gaa gcc ccg gga aat cga aca ggt cca ggt ccg agg agt    3648
Ala Pro Leu Glu Ala Pro Gly Asn Arg Thr Gly Pro Gly Pro Arg Ser
                1205                1210                1215 gcg gtt ccc cgc cgc gtt aag cag agc ttg aaa cag atc aga ctc ccg    3696
Ala Val Pro Arg Arg Val Lys Gln Ser Leu Lys Gln Ile Arg Leu Pro
            1220                1225                1230 cta gaa gaa ata aag cct gaa agg ggg gtg gtt ctg aat gcc acc tca    3744
Leu Glu Glu Ile Lys Pro Glu Arg Gly Val Val Leu Asn Ala Thr Ser
        1235                1240                1245 acc cgg tgg tct gaa agc agt cct atc tta caa gga gcc aaa aga aat    3792
Thr Arg Trp Ser Glu Ser Ser Pro Ile Leu Gln Gly Ala Lys Arg Asn
    1250                1255                1260 aac ctt tct tta cct ttc ctg acc ttg gaa atg gcc gga ggt caa gga    3840
Asn Leu Ser Leu Pro Phe Leu Thr Leu Glu Met Ala Gly Gly Gln Gly
1265                1270                1275                1280 aag atc agc gcc ctg ggg aaa agt gcc gca ggc ccg ctg gcg tcc ggg    3888
Lys Ile Ser Ala Leu Gly Lys Ser Ala Ala Gly Pro Leu Ala Ser Gly
                1285                1290                1295 aag ctg gag aag gct gtt ctc tct tca gca ggc ttg tct gaa gca tct    3936
Lys Leu Glu Lys Ala Val Leu Ser Ser Ala Gly Leu Ser Glu Ala Ser
            1300                1305                1310 ggc aaa gct gag ttt ctt cct aaa gtt cga gtt cat cgg gaa gac ctg    3984
Gly Lys Ala Glu Phe Leu Pro Lys Val Arg Val His Arg Glu Asp Leu
        1315                1320                1325 ttg cct caa aaa acc agc aat gtt tct tgc gca cac ggg gat ctc ggc    4032
Leu Pro Gln Lys Thr Ser Asn Val Ser Cys Ala His Gly Asp Leu Gly
    1330                1335                1340 cag gag atc ttc ctg cag aaa aca cgg gga cct gtt aac ctg aac aaa    4080
Gln Glu Ile Phe Leu Gln Lys Thr Arg Gly Pro Val Asn Leu Asn Lys
1345                1350                1355                1360 gta aat aga cct gga agg act ccc tcc aag ctt ctg ggt ccc ccg atg    4128
Val Asn Arg Pro Gly Arg Thr Pro Ser Lys Leu Leu Gly Pro Pro Met
                1365                1370                1375 ccc aaa gag tgg gaa tcc cta gag aag tca cca aaa agc aca gct ctc    4176
Pro Lys Glu Trp Glu Ser Leu Glu Lys Ser Pro Lys Ser Thr Ala Leu
            1380                1385                1390 agg acg aaa gac atc atc agt tta ccc ctg gac cgt cac gaa agc aat    4224
Arg Thr Lys Asp Ile Ile Ser Leu Pro Leu Asp Arg His Glu Ser Asn
        1395                1400                1405 cat tca ata gca gca aaa aat gaa gga caa gcc gag acc caa aga gaa    4272
His Ser Ile Ala Ala Lys Asn Glu Gly Gln Ala Glu Thr Gln Arg Glu
    1410                1415                1420 gcc gcc tgg acg aag cag gga ggg cct gga agg ctg tgc gct cca aag    4320
Ala Ala Trp Thr Lys Gln Gly Gly Pro Gly Arg Leu Cys Ala Pro Lys
1425                1430                1435                1440 cct ccg gtc ctg cga cgg cat cag agg gac ata agc ctt cct act ttt    4368
Pro Pro Val Leu Arg Arg His Gln Arg Asp Ile Ser Leu Pro Thr Phe
                1445                1450                1455
```

```
                                                         -continued cag ccg gag gaa gac aaa atg gac tat gat gat atc ttc tca act gaa      4416
Gln Pro Glu Glu Asp Lys Met Asp Tyr Asp Asp Ile Phe Ser Thr Glu
        1460                1465                1470 acg aag gga gaa gat ttt gac att tac ggt gag gat gaa aat cag gac      4464
Thr Lys Gly Glu Asp Phe Asp Ile Tyr Gly Glu Asp Glu Asn Gln Asp
    1475                1480                1485 cct cgc agc ttt cag aag aga acc cga cac tat ttc att gct gcg gtg      4512
Pro Arg Ser Phe Gln Lys Arg Thr Arg His Tyr Phe Ile Ala Ala Val
1490                1495                1500 gag cag ctc tgg gat tac ggg atg agc gaa tcc ccc cgg gcg cta aga      4560
Glu Gln Leu Trp Asp Tyr Gly Met Ser Glu Ser Pro Arg Ala Leu Arg
1505                1510                1515                1520 aac agg gct cag aac gga gag gtg cct cgg ttc aag aag gtg gtc ttc      4608
Asn Arg Ala Gln Asn Gly Glu Val Pro Arg Phe Lys Lys Val Val Phe
                1525                1530                1535 cgg gaa ttt gct gac ggc tcc ttc acg cag ccg tcg tac cgc ggg gaa      4656
Arg Glu Phe Ala Asp Gly Ser Phe Thr Gln Pro Ser Tyr Arg Gly Glu
            1540                1545                1550 ctc aac aaa cac ttg ggg ctc ttg gga ccc tac atc aga gcg gaa gtt      4704
Leu Asn Lys His Leu Gly Leu Leu Gly Pro Tyr Ile Arg Ala Glu Val
        1555                1560                1565 gaa gac aac atc atg gta act ttc aaa aac cag gcg tct cgt ccc tat      4752
Glu Asp Asn Ile Met Val Thr Phe Lys Asn Gln Ala Ser Arg Pro Tyr
    1570                1575                1580 tcc ttc tac tcg agc ctt att tct tat ccg gat gat cag gag caa ggg      4800
Ser Phe Tyr Ser Ser Leu Ile Ser Tyr Pro Asp Asp Gln Glu Gln Gly
1585                1590                1595                1600 gca gaa cct cga cac aac ttc gtc cag cca aat gaa acc aga act tac      4848
Ala Glu Pro Arg His Asn Phe Val Gln Pro Asn Glu Thr Arg Thr Tyr
                1605                1610                1615 ttt tgg aaa gtg cag cat cac atg gca ccc aca gaa gac gag ttt gac      4896
Phe Trp Lys Val Gln His His Met Ala Pro Thr Glu Asp Glu Phe Asp
            1620                1625                1630 tgc aaa gcc tgg gcc tac ttt tct gat gtt gac ctg gaa aaa gat gtg      4944
Cys Lys Ala Trp Ala Tyr Phe Ser Asp Val Asp Leu Glu Lys Asp Val
        1635                1640                1645 cac tca ggc ttg atc ggc ccc ctt ctg atc tgc cgc gcc aac acc ctg      4992
His Ser Gly Leu Ile Gly Pro Leu Leu Ile Cys Arg Ala Asn Thr Leu
    1650                1655                1660 aac gct gct cac ggt aga caa gtg acc gtg caa gaa ttt gct ctg ttt      5040
Asn Ala Ala His Gly Arg Gln Val Thr Val Gln Glu Phe Ala Leu Phe
1665                1670                1675                1680 ttc act att ttt gat gag aca aag agc tgg tac ttc act gaa aat gtg      5088
Phe Thr Ile Phe Asp Glu Thr Lys Ser Trp Tyr Phe Thr Glu Asn Val
                1685                1690                1695 gaa agg aac tgc cgg gcc ccc tgc cac ctg cag atg gag gac ccc act      5136
Glu Arg Asn Cys Arg Ala Pro Cys His Leu Gln Met Glu Asp Pro Thr
            1700                1705                1710 ctg aaa gaa aac tat cgc ttc cat gca atc aat ggc tat gtg atg gat      5184
Leu Lys Glu Asn Tyr Arg Phe His Ala Ile Asn Gly Tyr Val Met Asp
        1715                1720                1725 aca ctc cct ggc tta gta atg gct cag aat caa agg atc cga tgg tat      5232
Thr Leu Pro Gly Leu Val Met Ala Gln Asn Gln Arg Ile Arg Trp Tyr
    1730                1735                1740 ctg ctc agc atg ggc agc aat gaa aat atc cat tcg att cat ttt agc      5280
Leu Leu Ser Met Gly Ser Asn Glu Asn Ile His Ser Ile His Phe Ser
1745                1750                1755                1760 gga cac gtg ttc agt gta cgg aaa aag gag gag tat aaa atg gcc gtg      5328
Gly His Val Phe Ser Val Arg Lys Lys Glu Glu Tyr Lys Met Ala Val
                1765                1770                1775
```

```
tac aat ctc tat ccg ggt gtc ttt gag aca gtg gaa atg cta ccg tcc      5376
Tyr Asn Leu Tyr Pro Gly Val Phe Glu Thr Val Glu Met Leu Pro Ser
            1780                1785                1790 aaa gtt gga att tgg cga ata gaa tgc ctg att ggc gag cac ctg caa      5424
Lys Val Gly Ile Trp Arg Ile Glu Cys Leu Ile Gly Glu His Leu Gln
        1795                1800                1805 gct ggg atg agc acg act ttc ctg gtg tac agc aag gag tgt cag gct      5472
Ala Gly Met Ser Thr Thr Phe Leu Val Tyr Ser Lys Glu Cys Gln Ala
    1810                1815                1820 cca ctg gga atg gct tct gga cgc att aga gat ttt cag atc aca gct      5520
Pro Leu Gly Met Ala Ser Gly Arg Ile Arg Asp Phe Gln Ile Thr Ala
1825                1830                1835                1840 tca gga cag tat gga cag tgg gcc cca aag ctg gcc aga ctt cat tat      5568
Ser Gly Gln Tyr Gly Gln Trp Ala Pro Lys Leu Ala Arg Leu His Tyr
                1845                1850                1855 tcc gga tca atc aat gcc tgg agc acc aag gat ccc cac tcc tgg atc      5616
Ser Gly Ser Ile Asn Ala Trp Ser Thr Lys Asp Pro His Ser Trp Ile
            1860                1865                1870 aag gtg gat ctg ttg gca cca atg atc att cac ggc atc atg acc cag      5664
Lys Val Asp Leu Leu Ala Pro Met Ile Ile His Gly Ile Met Thr Gln
        1875                1880                1885 ggt gcc cgt cag aag ttt tcc agc ctc tac atc tcc cag ttt atc atc      5712
Gly Ala Arg Gln Lys Phe Ser Ser Leu Tyr Ile Ser Gln Phe Ile Ile
    1890                1895                1900 atg tac agt ctt gac ggg agg aac tgg cag agt tac cga ggg aat tcc      5760
Met Tyr Ser Leu Asp Gly Arg Asn Trp Gln Ser Tyr Arg Gly Asn Ser
1905                1910                1915                1920 acg ggc acc tta atg gtc ttc ttt ggc aat gtg gac gca tct ggg att      5808
Thr Gly Thr Leu Met Val Phe Phe Gly Asn Val Asp Ala Ser Gly Ile
                1925                1930                1935 aaa cac aat att ttt aac cct ccg att gtg gct cgg tac atc cgt ttg      5856
Lys His Asn Ile Phe Asn Pro Pro Ile Val Ala Arg Tyr Ile Arg Leu
            1940                1945                1950 cac cca aca cat tac agc atc cgc agc act ctt cgc atg gag ttg atg      5904
His Pro Thr His Tyr Ser Ile Arg Ser Thr Leu Arg Met Glu Leu Met
        1955                1960                1965 ggc tgt gat tta aac agt tgc agc atg ccc ctg gga atg cag aat aaa      5952
Gly Cys Asp Leu Asn Ser Cys Ser Met Pro Leu Gly Met Gln Asn Lys
    1970                1975                1980 gcg ata tca gac tca cag atc acg gcc tcc tcc cac cta agc aat ata      6000
Ala Ile Ser Asp Ser Gln Ile Thr Ala Ser Ser His Leu Ser Asn Ile
1985                1990                1995                2000 ttt gcc acc tgg tct cct tca caa gcc cga ctt cac ctc cag ggg cgg      6048
Phe Ala Thr Trp Ser Pro Ser Gln Ala Arg Leu His Leu Gln Gly Arg
                2005                2010                2015 acg aat gcc tgg cga ccc cgg gtg agc agc gca gag gag tgg ctg cag      6096
Thr Asn Ala Trp Arg Pro Arg Val Ser Ser Ala Glu Glu Trp Leu Gln
            2020                2025                2030 gtg gac ctg cag aag acg gtg aag gtc aca ggc atc acc acc cag ggc      6144
Val Asp Leu Gln Lys Thr Val Lys Val Thr Gly Ile Thr Thr Gln Gly
        2035                2040                2045 gtg aag tcc ctg ctc agc agc atg tat gtg aag gag ttc ctc gtg tcc      6192
Val Lys Ser Leu Leu Ser Ser Met Tyr Val Lys Glu Phe Leu Val Ser
    2050                2055                2060 agt agt cag gac ggc cgc cgc tgg acc ctg ttt ctt cag gac ggc cac      6240
Ser Ser Gln Asp Gly Arg Arg Trp Thr Leu Phe Leu Gln Asp Gly His
2065                2070                2075                2080 acg aag gtt ttt cag ggc aat cag gac tcc tcc acc ccc gtg gtg aac      6288
Thr Lys Val Phe Gln Gly Asn Gln Asp Ser Ser Thr Pro Val Val Asn
                2085                2090                2095
```

```
gct ctg gac ccc ccg ctg ttc acg cgc tac ctg agg atc cac ccc acg    6336
Ala Leu Asp Pro Pro Leu Phe Thr Arg Tyr Leu Arg Ile His Pro Thr
        2100                2105                2110 agc tgg gcg cag cac atc gcc ctg agg ctc gag gtt cta gga tgt gag    6384
Ser Trp Ala Gln His Ile Ala Leu Arg Leu Glu Val Leu Gly Cys Glu
            2115                2120                2125 gca cag gat ctc tac tga                                            6402
Ala Gln Asp Leu Tyr
    2130
```

<210> SEQ ID NO 2
<211> LENGTH: 2133
<212> TYPE: PRT
<213> ORGANISM: Sus scrofa

<400> SEQUENCE: 2

```
Met Gln Leu Glu Leu Ser Thr Cys Val Phe Leu Cys Leu Leu Pro Leu
 1               5                  10                  15

Gly Phe Ser Ala Ile Arg Arg Tyr Tyr Leu Gly Ala Val Glu Leu Ser
             20                  25                  30

Trp Asp Tyr Arg Gln Ser Glu Leu Leu Arg Glu Leu His Val Asp Thr
         35                  40                  45

Arg Phe Pro Ala Thr Ala Pro Gly Ala Leu Pro Leu Gly Pro Ser Val
     50                  55                  60

Leu Tyr Lys Lys Thr Val Phe Val Glu Phe Thr Asp Gln Leu Phe Ser
 65                  70                  75                  80

Val Ala Arg Pro Arg Pro Pro Trp Met Gly Leu Leu Gly Pro Thr Ile
                 85                  90                  95

Gln Ala Glu Val Tyr Asp Thr Val Val Val Thr Leu Lys Asn Met Ala
            100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285

Ile Phe Leu Glu Gly His Thr Phe Leu Val Arg His His Arg Gln Ala
    290                 295                 300

Ser Leu Glu Ile Ser Pro Leu Thr Phe Leu Thr Ala Gln Thr Phe Leu
305                 310                 315                 320
```

-continued

```
Met Asp Leu Gly Gln Phe Leu Phe Cys His Ile Ser Ser His His
            325                 330                 335

His Gly Gly Met Glu Ala His Val Arg Val Glu Ser Cys Ala Glu Glu
                340                 345                 350

Pro Gln Leu Arg Arg Lys Ala Asp Glu Glu Asp Tyr Asp Asp Asn
            355                 360                 365

Leu Tyr Asp Ser Asp Met Asp Val Val Arg Leu Asp Gly Asp Val
        370                 375                 380

Ser Pro Phe Ile Gln Ile Arg Ser Val Ala Lys Lys His Pro Lys Thr
385                 390                 395                 400

Trp Val His Tyr Ile Ser Ala Glu Glu Glu Asp Trp Asp Tyr Ala Pro
                405                 410                 415

Ala Val Pro Ser Pro Ser Asp Arg Ser Tyr Lys Ser Leu Tyr Leu Asn
            420                 425                 430

Ser Gly Pro Gln Arg Ile Gly Arg Lys Tyr Lys Lys Ala Arg Phe Val
            435                 440                 445

Ala Tyr Thr Asp Val Thr Phe Lys Thr Arg Lys Ala Ile Pro Tyr Glu
        450                 455                 460

Ser Gly Ile Leu Gly Pro Leu Leu Tyr Gly Glu Val Gly Asp Thr Leu
465                 470                 475                 480

Leu Ile Ile Phe Lys Asn Lys Ala Ser Arg Pro Tyr Asn Ile Tyr Pro
                485                 490                 495

His Gly Ile Thr Asp Val Ser Ala Leu His Pro Gly Arg Leu Leu Lys
            500                 505                 510

Gly Trp Lys His Leu Lys Asp Met Pro Ile Leu Pro Gly Glu Thr Phe
            515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Ser Ile Asn Leu Glu Lys
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Met Met Ser Asp Lys Arg Asn Val
            580                 585                 590

Ile Leu Phe Ser Val Phe Asp Glu Asn Gln Ser Trp Tyr Leu Ala Glu
        595                 600                 605

Asn Ile Gln Arg Phe Leu Pro Asn Pro Asp Gly Leu Gln Pro Gln Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Val Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
        690                 695                 700

Gly Leu Trp Val Leu Gly Cys His Asn Ser Asp Leu Arg Asn Arg Gly
705                 710                 715                 720

Met Thr Ala Leu Leu Lys Val Tyr Ser Cys Asp Arg Asp Ile Gly Asp
                725                 730                 735
```

```
Tyr Tyr Asp Asn Thr Tyr Glu Asp Ile Pro Gly Phe Leu Leu Ser Gly
            740                 745                 750
Lys Asn Val Ile Glu Pro Arg Ser Phe Ala Gln Asn Ser Arg Pro Pro
            755                 760                 765
Ser Ala Ser Gln Lys Gln Phe Gln Thr Ile Thr Ser Pro Glu Asp Asp
            770                 775                 780
Val Glu Leu Asp Pro Gln Ser Gly Glu Arg Thr Gln Ala Leu Glu Glu
785                 790                 795                 800
Leu Ser Val Pro Ser Gly Asp Gly Ser Met Leu Leu Gly Gln Asn Pro
                805                 810                 815
Ala Pro His Gly Ser Ser Ser Asp Leu Gln Glu Ala Arg Asn Glu
            820                 825                 830
Ala Asp Asp Tyr Leu Pro Gly Ala Arg Glu Arg Gly Thr Ala Pro Ser
            835                 840                 845
Ala Ala Ala Arg Leu Arg Pro Glu Leu His His Ser Ala Glu Arg Val
            850                 855                 860
Leu Thr Pro Glu Pro Glu Lys Glu Leu Lys Lys Leu Asp Ser Lys Met
865                 870                 875                 880
Ser Ser Ser Ser Asp Leu Leu Lys Thr Ser Pro Thr Ile Pro Ser Asp
                885                 890                 895
Thr Leu Ser Ala Glu Thr Glu Arg Thr His Ser Leu Gly Pro Pro His
            900                 905                 910
Pro Gln Val Asn Phe Arg Ser Gln Leu Gly Ala Ile Val Leu Gly Lys
            915                 920                 925
Asn Ser Ser His Phe Ile Gly Ala Gly Val Pro Leu Gly Ser Thr Glu
            930                 935                 940
Glu Asp His Glu Ser Ser Leu Gly Glu Asn Val Ser Pro Val Glu Ser
945                 950                 955                 960
Asp Gly Ile Phe Glu Lys Glu Arg Ala His Gly Pro Ala Ser Leu Thr
                965                 970                 975
Lys Asp Asp Val Leu Phe Lys Val Asn Ile Ser Leu Val Lys Thr Asn
            980                 985                 990
Lys Ala Arg Val Tyr Leu Lys Thr Asn Arg Lys Ile His Ile Asp Asp
            995                 1000                1005
Ala Ala Leu Leu Thr Glu Asn Arg Ala Ser Ala Thr Phe Met Asp Lys
            1010                1015                1020
Asn Thr Thr Ala Ser Gly Leu Asn His Val Ser Asn Trp Ile Lys Gly
1025                1030                1035                1040
Pro Leu Gly Lys Asn Pro Leu Ser Ser Glu Arg Gly Pro Ser Pro Glu
                1045                1050                1055
Leu Leu Thr Ser Ser Gly Ser Gly Lys Ser Val Lys Gly Gln Ser Ser
            1060                1065                1070
Gly Gln Gly Arg Ile Arg Val Ala Val Glu Glu Glu Leu Ser Lys
            1075                1080                1085
Gly Lys Glu Met Met Leu Pro Asn Ser Glu Leu Thr Phe Leu Thr Asn
            1090                1095                1100
Ser Ala Asp Val Gln Gly Asn Asp Thr His Ser Gln Gly Lys Lys Ser
1105                1110                1115                1120
Arg Glu Glu Met Glu Arg Arg Glu Lys Leu Val Gln Glu Lys Val Asp
                1125                1130                1135
Leu Pro Gln Val Tyr Thr Ala Thr Gly Thr Lys Asn Phe Leu Arg Asn
            1140                1145                1150
```

```
Ile Phe His Gln Ser Thr Glu Pro Ser Val Glu Gly Phe Asp Gly Gly
        1155                1160                1165

Ser His Ala Pro Val Pro Gln Asp Ser Arg Ser Leu Asn Asp Ser Ala
        1170                1175                1180

Glu Arg Ala Glu Thr His Ile Ala His Phe Ser Ala Ile Arg Glu Glu
1185                1190                1195                1200

Ala Pro Leu Glu Ala Pro Gly Asn Arg Thr Gly Pro Gly Pro Arg Ser
        1205                1210                1215

Ala Val Pro Arg Arg Val Lys Gln Ser Leu Lys Gln Ile Arg Leu Pro
        1220                1225                1230

Leu Glu Glu Ile Lys Pro Glu Arg Gly Val Val Leu Asn Ala Thr Ser
        1235                1240                1245

Thr Arg Trp Ser Glu Ser Ser Pro Ile Leu Gln Gly Ala Lys Arg Asn
        1250                1255                1260

Asn Leu Ser Leu Pro Phe Leu Thr Leu Glu Met Ala Gly Gly Gln Gly
1265                1270                1275                1280

Lys Ile Ser Ala Leu Gly Lys Ser Ala Ala Gly Pro Leu Ala Ser Gly
                1285                1290                1295

Lys Leu Glu Lys Ala Val Leu Ser Ala Gly Leu Ser Glu Ala Ser
        1300                1305                1310

Gly Lys Ala Glu Phe Leu Pro Lys Val Arg Val His Arg Glu Asp Leu
        1315                1320                1325

Leu Pro Gln Lys Thr Ser Asn Val Ser Cys Ala His Gly Asp Leu Gly
        1330                1335                1340

Gln Glu Ile Phe Leu Gln Lys Thr Arg Gly Pro Val Asn Leu Asn Lys
1345                1350                1355                1360

Val Asn Arg Pro Gly Arg Thr Pro Ser Lys Leu Leu Gly Pro Pro Met
                1365                1370                1375

Pro Lys Glu Trp Glu Ser Leu Glu Lys Ser Pro Lys Ser Thr Ala Leu
                1380                1385                1390

Arg Thr Lys Asp Ile Ile Ser Leu Pro Leu Asp Arg His Glu Ser Asn
        1395                1400                1405

His Ser Ile Ala Ala Lys Asn Glu Gly Gln Ala Glu Thr Gln Arg Glu
        1410                1415                1420

Ala Ala Trp Thr Lys Gln Gly Gly Pro Gly Arg Leu Cys Ala Pro Lys
1425                1430                1435                1440

Pro Pro Val Leu Arg Arg His Gln Arg Asp Ile Ser Leu Pro Thr Phe
                1445                1450                1455

Gln Pro Glu Glu Asp Lys Met Asp Tyr Asp Asp Ile Phe Ser Thr Glu
                1460                1465                1470

Thr Lys Gly Glu Asp Phe Asp Ile Tyr Gly Glu Asp Glu Asn Gln Asp
        1475                1480                1485

Pro Arg Ser Phe Gln Lys Arg Thr Arg His Tyr Phe Ile Ala Ala Val
        1490                1495                1500

Glu Gln Leu Trp Asp Tyr Gly Met Ser Glu Ser Pro Arg Ala Leu Arg
1505                1510                1515                1520

Asn Arg Ala Gln Asn Gly Glu Val Pro Arg Phe Lys Lys Val Val Phe
                1525                1530                1535

Arg Glu Phe Ala Asp Gly Ser Phe Thr Gln Pro Ser Tyr Arg Gly Glu
                1540                1545                1550

Leu Asn Lys His Leu Gly Leu Leu Gly Pro Tyr Ile Arg Ala Glu Val
                1555                1560                1565
```

-continued

```
Glu Asp Asn Ile Met Val Thr Phe Lys Asn Gln Ala Ser Arg Pro Tyr
    1570                1575                1580
Ser Phe Tyr Ser Ser Leu Ile Ser Tyr Pro Asp Asp Gln Glu Gln Gly
1585                1590                1595                1600
Ala Glu Pro Arg His Asn Phe Val Gln Pro Asn Glu Thr Arg Thr Tyr
                1605                1610                1615
Phe Trp Lys Val Gln His His Met Ala Pro Thr Glu Asp Glu Phe Asp
            1620                1625                1630
Cys Lys Ala Trp Ala Tyr Phe Ser Asp Val Asp Leu Glu Lys Asp Val
        1635                1640                1645
His Ser Gly Leu Ile Gly Pro Leu Leu Ile Cys Arg Ala Asn Thr Leu
    1650                1655                1660
Asn Ala Ala His Gly Arg Gln Val Thr Val Gln Glu Phe Ala Leu Phe
1665                1670                1675                1680
Phe Thr Ile Phe Asp Glu Thr Lys Ser Trp Tyr Phe Thr Glu Asn Val
                1685                1690                1695
Glu Arg Asn Cys Arg Ala Pro Cys His Leu Gln Met Glu Asp Pro Thr
            1700                1705                1710
Leu Lys Glu Asn Tyr Arg Phe His Ala Ile Asn Gly Tyr Val Met Asp
        1715                1720                1725
Thr Leu Pro Gly Leu Val Met Ala Gln Asn Gln Arg Ile Arg Trp Tyr
    1730                1735                1740
Leu Leu Ser Met Gly Ser Asn Glu Asn Ile His Ser Ile His Phe Ser
1745                1750                1755                1760
Gly His Val Phe Ser Val Arg Lys Lys Glu Glu Tyr Lys Met Ala Val
                1765                1770                1775
Tyr Asn Leu Tyr Pro Gly Val Phe Glu Thr Val Glu Met Leu Pro Ser
            1780                1785                1790
Lys Val Gly Ile Trp Arg Ile Glu Cys Leu Ile Gly Glu His Leu Gln
        1795                1800                1805
Ala Gly Met Ser Thr Thr Phe Leu Val Tyr Ser Lys Glu Cys Gln Ala
    1810                1815                1820
Pro Leu Gly Met Ala Ser Gly Arg Ile Arg Asp Phe Gln Ile Thr Ala
1825                1830                1835                1840
Ser Gly Gln Tyr Gly Gln Trp Ala Pro Lys Leu Ala Arg Leu His Tyr
                1845                1850                1855
Ser Gly Ser Ile Asn Ala Trp Ser Thr Lys Asp Pro His Ser Trp Ile
            1860                1865                1870
Lys Val Asp Leu Leu Ala Pro Met Ile Ile His Gly Ile Met Thr Gln
        1875                1880                1885
Gly Ala Arg Gln Lys Phe Ser Ser Leu Tyr Ile Ser Gln Phe Ile Ile
    1890                1895                1900
Met Tyr Ser Leu Asp Gly Arg Asn Trp Gln Ser Tyr Arg Gly Asn Ser
1905                1910                1915                1920
Thr Gly Thr Leu Met Val Phe Phe Gly Asn Val Asp Ala Ser Gly Ile
                1925                1930                1935
Lys His Asn Ile Phe Asn Pro Pro Ile Val Ala Arg Tyr Ile Arg Leu
            1940                1945                1950
His Pro Thr His Tyr Ser Ile Arg Ser Thr Leu Arg Met Glu Leu Met
        1955                1960                1965
Gly Cys Asp Leu Asn Ser Cys Ser Met Pro Leu Gly Met Gln Asn Lys
    1970                1975                1980
```

```
Ala Ile Ser Asp Ser Gln Ile Thr Ala Ser Ser His Leu Ser Asn Ile
1985                1990                1995                2000

Phe Ala Thr Trp Ser Pro Ser Gln Ala Arg Leu His Leu Gln Gly Arg
                2005                2010                2015

Thr Asn Ala Trp Arg Pro Arg Val Ser Ser Ala Glu Glu Trp Leu Gln
            2020                2025                2030

Val Asp Leu Gln Lys Thr Val Lys Val Thr Gly Ile Thr Thr Gln Gly
        2035                2040                2045

Val Lys Ser Leu Leu Ser Ser Met Tyr Val Lys Glu Phe Leu Val Ser
    2050                2055                2060

Ser Ser Gln Asp Gly Arg Arg Trp Thr Leu Phe Leu Gln Asp Gly His
2065                2070                2075                2080

Thr Lys Val Phe Gln Gly Asn Gln Asp Ser Ser Thr Pro Val Val Asn
                2085                2090                2095

Ala Leu Asp Pro Pro Leu Phe Thr Arg Tyr Leu Arg Ile His Pro Thr
            2100                2105                2110

Ser Trp Ala Gln His Ile Ala Leu Arg Leu Glu Val Leu Gly Cys Glu
        2115                2120                2125

Ala Gln Asp Leu Tyr
    2130

<210> SEQ ID NO 3
<211> LENGTH: 4404
<212> TYPE: DNA
<213> ORGANISM: Sus scrofa
<220> FEATURE:
<221> NAME/KEY: gene
<222> LOCATION: (1)...(4401)
<223> OTHER INFORMATION: Factor VIII-- B-domain deleted
<220> FEATURE:
<221> NAME/KEY: CDS
<222> LOCATION: (1)...(4401)

<400> SEQUENCE: 3 atg cag cta gag ctc tcc acc tgt gtc ttt ctg tgt ctc ttg cca ctc     48
Met Gln Leu Glu Leu Ser Thr Cys Val Phe Leu Cys Leu Leu Pro Leu
1               5                   10                  15 ggc ttt agt gcc atc agg aga tac tac ctg ggc gca gtg gaa ctg tcc     96
Gly Phe Ser Ala Ile Arg Arg Tyr Tyr Leu Gly Ala Val Glu Leu Ser
            20                  25                  30 tgg gac tac cgg caa agt gaa ctc ctc cgt gag ctg cac gtg gac acc    144
Trp Asp Tyr Arg Gln Ser Glu Leu Leu Arg Glu Leu His Val Asp Thr
        35                  40                  45 aga ttt cct gct aca gcg cca gga gct ctt ccg ttg ggc cca tca gtc    192
Arg Phe Pro Ala Thr Ala Pro Gly Ala Leu Pro Leu Gly Pro Ser Val
    50                  55                  60 ctg tac aaa aag act gtg ttc gta gag ttc acg gat caa ctt ttc agc    240
Leu Tyr Lys Lys Thr Val Phe Val Glu Phe Thr Asp Gln Leu Phe Ser
65                  70                  75                  80 gtt gcc agg ccc agg cca cca tgg atg ggt ctg ctg ggt cct acc atc    288
Val Ala Arg Pro Arg Pro Pro Trp Met Gly Leu Leu Gly Pro Thr Ile
                85                  90                  95 cag gct gag gtt tac gac acg gtg gtc gtt acc ctg aag aac atg gct    336
Gln Ala Glu Val Tyr Asp Thr Val Val Val Thr Leu Lys Asn Met Ala
            100                 105                 110 tct cat ccc gtt agt ctt cac gct gtc ggc gtc tcc ttc tgg aaa tct    384
Ser His Pro Val Ser Leu His Ala Val Gly Val Ser Phe Trp Lys Ser
        115                 120                 125
```

-continued

| | | |
|---|---|---|
| tcc gaa ggc gct gaa tat gag gat cac acc agc caa agg gag aag gaa<br>Ser Glu Gly Ala Glu Tyr Glu Asp His Thr Ser Gln Arg Glu Lys Glu<br>130                             135                          140 | | 432 |
| gac gat aaa gtc ctt ccc ggt aaa agc caa acc tac gtc tgg cag gtc<br>Asp Asp Lys Val Leu Pro Gly Lys Ser Gln Thr Tyr Val Trp Gln Val<br>145                     150                       155                   160 | | 480 |
| ctg aaa gaa aat ggt cca aca gcc tct gac cca cca tgt ctt acc tac<br>Leu Lys Glu Asn Gly Pro Thr Ala Ser Asp Pro Pro Cys Leu Thr Tyr<br>                   165                       170                   175 | | 528 |
| tca tac ctg tct cac gtg gac ctg gtg aaa gac ctg aat tcg ggc ctc<br>Ser Tyr Leu Ser His Val Asp Leu Val Lys Asp Leu Asn Ser Gly Leu<br>                 180                       185                   190 | | 576 |
| att gga gcc ctg ctg gtt tgt aga gaa ggg agt ctg acc aga gaa agg<br>Ile Gly Ala Leu Leu Val Cys Arg Glu Gly Ser Leu Thr Arg Glu Arg<br>         195                     200                     205 | | 624 |
| acc cag aac ctg cac gaa ttt gta cta ctt ttt gct gtc ttt gat gaa<br>Thr Gln Asn Leu His Glu Phe Val Leu Leu Phe Ala Val Phe Asp Glu<br>210                             215                       220 | | 672 |
| ggg aaa agt tgg cac tca gca aga aat gac tcc tgg aca cgg gcc atg<br>Gly Lys Ser Trp His Ser Ala Arg Asn Asp Ser Trp Thr Arg Ala Met<br>225                             230                       235                   240 | | 720 |
| gat ccc gca cct gcc agg gcc cag cct gca atg cac aca gtc aat ggc<br>Asp Pro Ala Pro Ala Arg Ala Gln Pro Ala Met His Thr Val Asn Gly<br>                   245                       250                   255 | | 768 |
| tat gtc aac agg tct ctg cca ggt ctg atc gga tgt cat aag aaa tca<br>Tyr Val Asn Arg Ser Leu Pro Gly Leu Ile Gly Cys His Lys Lys Ser<br>         260                     265                     270 | | 816 |
| gtc tac tgg cac gtg att gga atg ggc acc agc ccg gaa gtg cac tcc<br>Val Tyr Trp His Val Ile Gly Met Gly Thr Ser Pro Glu Val His Ser<br>               275                     280                   285 | | 864 |
| att ttt ctt gaa ggc cac acg ttt ctc gtg agg cac cat cgc cag gct<br>Ile Phe Leu Glu Gly His Thr Phe Leu Val Arg His His Arg Gln Ala<br>290                             295                       300 | | 912 |
| tcc ttg gag atc tcg cca cta act ttc ctc act gct cag aca ttc ctg<br>Ser Leu Glu Ile Ser Pro Leu Thr Phe Leu Thr Ala Gln Thr Phe Leu<br>305                             310                       315                   320 | | 960 |
| atg gac ctt ggc cag ttc cta ctg ttt tgt cat atc tct tcc cac cac<br>Met Asp Leu Gly Gln Phe Leu Leu Phe Cys His Ile Ser Ser His His<br>                   325                       330                   335 | | 1008 |
| cat ggt ggc atg gag gct cac gtc aga gta gaa agc tgc gcc gag gag<br>His Gly Gly Met Glu Ala His Val Arg Val Glu Ser Cys Ala Glu Glu<br>         340                     345                     350 | | 1056 |
| ccc cag ctg cgg agg aaa gct gat gaa gag gaa gat tat gat gac aat<br>Pro Gln Leu Arg Arg Lys Ala Asp Glu Glu Glu Asp Tyr Asp Asp Asn<br>               355                     360                   365 | | 1104 |
| ttg tac gac tcg gac atg gac gtg gtc cgg ctc gat ggt gac gac gtg<br>Leu Tyr Asp Ser Asp Met Asp Val Val Arg Leu Asp Gly Asp Asp Val<br>370                             375                       380 | | 1152 |
| tct ccc ttt atc caa atc cgc tcg gtt gcc aag aag cat ccc aaa acc<br>Ser Pro Phe Ile Gln Ile Arg Ser Val Ala Lys Lys His Pro Lys Thr<br>385                             390                       395                   400 | | 1200 |
| tgg gtg cac tac atc tct gca gag gag gag gac tgg gac tac gcc ccc<br>Trp Val His Tyr Ile Ser Ala Glu Glu Glu Asp Trp Asp Tyr Ala Pro<br>                   405                       410                   415 | | 1248 |
| gcg gtc ccc agc ccc agt gac aga agt tat aaa agt ctc tac ttg aac<br>Ala Val Pro Ser Pro Ser Asp Arg Ser Tyr Lys Ser Leu Tyr Leu Asn<br>         420                     425                     430 | | 1296 |
| agt ggt cct cag cga att ggt agg aaa tac aaa aaa gct cga ttc gtc<br>Ser Gly Pro Gln Arg Ile Gly Arg Lys Tyr Lys Lys Ala Arg Phe Val<br>               435                     440                   445 | | 1344 |

```
gct tac acg gat gta aca ttt aag act cgt aaa gct att ccg tat gaa    1392
Ala Tyr Thr Asp Val Thr Phe Lys Thr Arg Lys Ala Ile Pro Tyr Glu
450             455                 460 tca gga atc ctg gga cct tta ctt tat gga gaa gtt gga gac aca ctt    1440
Ser Gly Ile Leu Gly Pro Leu Leu Tyr Gly Glu Val Gly Asp Thr Leu
465                 470                 475                 480 ttg att ata ttt aag aat aaa gcg agc cga cca tat aac atc tac cct    1488
Leu Ile Ile Phe Lys Asn Lys Ala Ser Arg Pro Tyr Asn Ile Tyr Pro
                    485                 490                 495 cat gga atc act gat gtc agc gct ttg cac cca ggg aga ctt cta aaa    1536
His Gly Ile Thr Asp Val Ser Ala Leu His Pro Gly Arg Leu Leu Lys
                500                 505                 510 ggt tgg aaa cat ttg aaa gac atg cca att ctg cca gga gag act ttc    1584
Gly Trp Lys His Leu Lys Asp Met Pro Ile Leu Pro Gly Glu Thr Phe
            515                 520                 525 aag tat aaa tgg aca gtg act gtg gaa gat ggg cca acc aag tcc gat    1632
Lys Tyr Lys Trp Thr Val Thr Val Glu Asp Gly Pro Thr Lys Ser Asp
530                 535                 540 cct cgg tgc ctg acc cgc tac tac tcg agc tcc att aat cta gag aaa    1680
Pro Arg Cys Leu Thr Arg Tyr Tyr Ser Ser Ser Ile Asn Leu Glu Lys
545                 550                 555                 560 gat ctg gct tcg gga ctc att ggc cct ctc ctc atc tgc tac aaa gaa    1728
Asp Leu Ala Ser Gly Leu Ile Gly Pro Leu Leu Ile Cys Tyr Lys Glu
                565                 570                 575 tct gta gac caa aga gga aac cag atg atg tca gac aag aga aac gtc    1776
Ser Val Asp Gln Arg Gly Asn Gln Met Met Ser Asp Lys Arg Asn Val
                580                 585                 590 atc ctg ttt tct gta ttc gat gag aat caa agc tgg tac ctc gca gag    1824
Ile Leu Phe Ser Val Phe Asp Glu Asn Gln Ser Trp Tyr Leu Ala Glu
            595                 600                 605 aat att cag cgc ttc ctc ccc aat ccg gat gga tta cag ccc cag gat    1872
Asn Ile Gln Arg Phe Leu Pro Asn Pro Asp Gly Leu Gln Pro Gln Asp
        610                 615                 620 cca gag ttc caa gct tct aac atc atg cac agc atc aat ggc tat gtt    1920
Pro Glu Phe Gln Ala Ser Asn Ile Met His Ser Ile Asn Gly Tyr Val
625                 630                 635                 640 ttt gat agc ttg cag ctg tcg gtt tgt ttg cac gag gtg gca tac tgg    1968
Phe Asp Ser Leu Gln Leu Ser Val Cys Leu His Glu Val Ala Tyr Trp
                645                 650                 655 tac att cta agt gtt gga gca cag acg gac ttc ctc tcc gtc ttc ttc    2016
Tyr Ile Leu Ser Val Gly Ala Gln Thr Asp Phe Leu Ser Val Phe Phe
                660                 665                 670 tct ggc tac acc ttc aaa cac aaa atg gtc tat gaa gac aca ctc acc    2064
Ser Gly Tyr Thr Phe Lys His Lys Met Val Tyr Glu Asp Thr Leu Thr
            675                 680                 685 ctg ttc ccc ttc tca gga gaa acg gtc ttc atg tca atg gaa aac cca    2112
Leu Phe Pro Phe Ser Gly Glu Thr Val Phe Met Ser Met Glu Asn Pro
690                 695                 700 ggt ctc tgg gtc ctt ggg tgc cac aac tca gac ttg cgg aac aga ggg    2160
Gly Leu Trp Val Leu Gly Cys His Asn Ser Asp Leu Arg Asn Arg Gly
705                 710                 715                 720 atg aca gcc tta ctg aag gtg tat agt tgt gac agg gac att ggt gat    2208
Met Thr Ala Leu Leu Lys Val Tyr Ser Cys Asp Arg Asp Ile Gly Asp
                725                 730                 735 tat tat gac aac act tat gaa gat att cca ggc ttc ttg ctg agt gga    2256
Tyr Tyr Asp Asn Thr Tyr Glu Asp Ile Pro Gly Phe Leu Leu Ser Gly
            740                 745                 750 aag aat gtc att gaa cct agg agc ttt gcc cag aat tca aga ccc cct    2304
Lys Asn Val Ile Glu Pro Arg Ser Phe Ala Gln Asn Ser Arg Pro Pro
        755                 760                 765
```

```
agt gcg agc gct cca aag cct ccg gtc ctg cga cgg cat cag agg gac    2352
Ser Ala Ser Ala Pro Lys Pro Pro Val Leu Arg Arg His Gln Arg Asp
    770             775                 780 ata agc ctt cct act ttt cag ccg gag gaa gac aaa atg gac tat gat    2400
Ile Ser Leu Pro Thr Phe Gln Pro Glu Glu Asp Lys Met Asp Tyr Asp
785             790                 795                 800 gat atc ttc tca act gaa acg aag gga gaa gat ttt gac att tac ggt    2448
Asp Ile Phe Ser Thr Glu Thr Lys Gly Glu Asp Phe Asp Ile Tyr Gly
                805                 810                 815 gag gat gaa aat cag gac cct cgc agc ttt cag aag aga acc cga cac    2496
Glu Asp Glu Asn Gln Asp Pro Arg Ser Phe Gln Lys Arg Thr Arg His
            820                 825                 830 tat ttc att gct gcg gtg gag cag ctc tgg gat tac ggg atg agc gaa    2544
Tyr Phe Ile Ala Ala Val Glu Gln Leu Trp Asp Tyr Gly Met Ser Glu
        835                 840                 845 tcc ccc cgg gcg cta aga aac agg gct cag aac gga gag gtg cct cgg    2592
Ser Pro Arg Ala Leu Arg Asn Arg Ala Gln Asn Gly Glu Val Pro Arg
850                 855                 860 ttc aag aag gtg gtc ttc cgg gaa ttt gct gac ggc tcc ttc acg cag    2640
Phe Lys Lys Val Val Phe Arg Glu Phe Ala Asp Gly Ser Phe Thr Gln
865                 870                 875                 880 ccg tcg tac cgc ggg gaa ctc aac aaa cac ttg ggg ctc ttg gga ccc    2688
Pro Ser Tyr Arg Gly Glu Leu Asn Lys His Leu Gly Leu Leu Gly Pro
                885                 890                 895 tac atc aga gcg gaa gtt gaa gac aac atc atg gta act ttc aaa aac    2736
Tyr Ile Arg Ala Glu Val Glu Asp Asn Ile Met Val Thr Phe Lys Asn
            900                 905                 910 cag gcg tct cgt ccc tat tcc ttc tac tcg agc ctt att tct tat ccg    2784
Gln Ala Ser Arg Pro Tyr Ser Phe Tyr Ser Ser Leu Ile Ser Tyr Pro
        915                 920                 925 gat gat cag gag caa ggg gca gaa cct cga cac aac ttc gtc cag cca    2832
Asp Asp Gln Glu Gln Gly Ala Glu Pro Arg His Asn Phe Val Gln Pro
930                 935                 940 aat gaa acc aga act tac ttt tgg aaa gtg cag cat cac atg gca ccc    2880
Asn Glu Thr Arg Thr Tyr Phe Trp Lys Val Gln His His Met Ala Pro
945                 950                 955                 960 aca gaa gac gag ttt gac tgc aaa gcc tgg gcc tac ttt tct gat gtt    2928
Thr Glu Asp Glu Phe Asp Cys Lys Ala Trp Ala Tyr Phe Ser Asp Val
                965                 970                 975 gac ctg gaa aaa gat gtg cac tca ggc ttg atc ggc ccc ctt ctg atc    2976
Asp Leu Glu Lys Asp Val His Ser Gly Leu Ile Gly Pro Leu Leu Ile
            980                 985                 990 tgc cgc gcc aac acc ctg aac gct gct cac ggt aga caa gtg acc gtg    3024
Cys Arg Ala Asn Thr Leu Asn Ala Ala His Gly Arg Gln Val Thr Val
        995                 1000                1005 caa gaa ttt gct ctg ttt ttc act att ttt gat gag aca aag agc tgg    3072
Gln Glu Phe Ala Leu Phe Phe Thr Ile Phe Asp Glu Thr Lys Ser Trp
    1010                1015                1020 tac ttc act gaa aat gtg gaa agg aac tgc cgg gcc ccc tgc cat ctg    3120
Tyr Phe Thr Glu Asn Val Glu Arg Asn Cys Arg Ala Pro Cys His Leu
1025                1030                1035                1040 cag atg gag gac ccc act ctg aaa gaa aac tat cgc ttc cat gca atc    3168
Gln Met Glu Asp Pro Thr Leu Lys Glu Asn Tyr Arg Phe His Ala Ile
                1045                1050                1055 aat ggc tat gtg atg gat aca ctc cct ggc tta gta atg gct cag aat    3216
Asn Gly Tyr Val Met Asp Thr Leu Pro Gly Leu Val Met Ala Gln Asn
            1060                1065                1070 caa agg atc cga tgg tat ctg ctc agc atg ggc agc aat gaa aat atc    3264
Gln Arg Ile Arg Trp Tyr Leu Leu Ser Met Gly Ser Asn Glu Asn Ile
        1075                1080                1085
```

```
cat tcg att cat ttt agc gga cac gtg ttc agt gta cgg aaa aag gag     3312
His Ser Ile His Phe Ser Gly His Val Phe Ser Val Arg Lys Lys Glu
        1090            1095            1100 gag tat aaa atg gcc gtg tac aat ctc tat ccg ggt gtc ttt gag aca     3360
Glu Tyr Lys Met Ala Val Tyr Asn Leu Tyr Pro Gly Val Phe Glu Thr
1105            1110            1115            1120 gtg gaa atg cta ccg tcc aaa gtt gga att tgg cga ata gaa tgc ctg     3408
Val Glu Met Leu Pro Ser Lys Val Gly Ile Trp Arg Ile Glu Cys Leu
        1125            1130            1135 att ggc gag cac ctg caa gct ggg atg agc acg act ttc ctg gtg tac     3456
Ile Gly Glu His Leu Gln Ala Gly Met Ser Thr Thr Phe Leu Val Tyr
        1140            1145            1150 agc aag gag tgt cag gct cca ctg gga atg gct tct gga cgc att aga     3504
Ser Lys Glu Cys Gln Ala Pro Leu Gly Met Ala Ser Gly Arg Ile Arg
        1155            1160            1165 gat ttt cag atc aca gct tca gga cag tat gga cag tgg gcc cca aag     3552
Asp Phe Gln Ile Thr Ala Ser Gly Gln Tyr Gly Gln Trp Ala Pro Lys
        1170            1175            1180 ctg gcc aga ctt cat tat tcc gga tca atc aat gcc tgg agc acc aag     3600
Leu Ala Arg Leu His Tyr Ser Gly Ser Ile Asn Ala Trp Ser Thr Lys
1185            1190            1195            1200 gat ccc cac tcc tgg atc aag gtg gat ctg ttg gca cca atg atc att     3648
Asp Pro His Ser Trp Ile Lys Val Asp Leu Leu Ala Pro Met Ile Ile
        1205            1210            1215 cac ggc atc atg acc cag ggt gcc cgt cag aag ttt tcc agc ctc tac     3696
His Gly Ile Met Thr Gln Gly Ala Arg Gln Lys Phe Ser Ser Leu Tyr
        1220            1225            1230 atc tcc cag ttt atc atc atg tac agt ctt gac ggg agg aac tgg cag     3744
Ile Ser Gln Phe Ile Ile Met Tyr Ser Leu Asp Gly Arg Asn Trp Gln
        1235            1240            1245 agt tac cga ggg aat tcc acg ggc acc tta atg gtc ttc ttt ggc aat     3792
Ser Tyr Arg Gly Asn Ser Thr Gly Thr Leu Met Val Phe Phe Gly Asn
        1250            1255            1260 gtg gac gca tct ggg att aaa cac aat att ttt aac cct ccg att gtg     3840
Val Asp Ala Ser Gly Ile Lys His Asn Ile Phe Asn Pro Pro Ile Val
1265            1270            1275            1280 gct cgg tac atc cgt ttg cac cca aca cat tac agc atc cgc agc act     3888
Ala Arg Tyr Ile Arg Leu His Pro Thr His Tyr Ser Ile Arg Ser Thr
        1285            1290            1295 ctt cgc atg gag ttg atg ggc tgt gat tta aac agt tgc agc atg ccc     3936
Leu Arg Met Glu Leu Met Gly Cys Asp Leu Asn Ser Cys Ser Met Pro
        1300            1305            1310 ctg gga atg cag aat aaa gcg ata tca gac tca cag atc acg gcc tcc     3984
Leu Gly Met Gln Asn Lys Ala Ile Ser Asp Ser Gln Ile Thr Ala Ser
        1315            1320            1325 tcc cac cta agc aat ata ttt gcc acc tgg tct cct tca caa gcc cga     4032
Ser His Leu Ser Asn Ile Phe Ala Thr Trp Ser Pro Ser Gln Ala Arg
        1330            1335            1340 ctt cac ctc cag ggg cgg acg aat gcc tgg cga ccc cgg gtg agc agc     4080
Leu His Leu Gln Gly Arg Thr Asn Ala Trp Arg Pro Arg Val Ser Ser
1345            1350            1355            1360 gca gag gag tgg ctg cag gtg gac ctg cag aag acg gtg aag gtc aca     4128
Ala Glu Glu Trp Leu Gln Val Asp Leu Gln Lys Thr Val Lys Val Thr
        1365            1370            1375 ggc atc acc acc cag ggc gtg aag tcc ctg ctc agc agc atg tat gtg     4176
Gly Ile Thr Thr Gln Gly Val Lys Ser Leu Leu Ser Ser Met Tyr Val
        1380            1385            1390 aag gag ttc ctc gtg tcc agt agt cag gac ggc cgc cgc tgg acc ctg     4224
Lys Glu Phe Leu Val Ser Ser Ser Gln Asp Gly Arg Arg Trp Thr Leu
        1395            1400            1405
```

```
ttt ctt cag gac ggc cac acg aag gtt ttt cag ggc aat cag gac tcc    4272
Phe Leu Gln Asp Gly His Thr Lys Val Phe Gln Gly Asn Gln Asp Ser
        1410                1415                1420 tcc acc ccc gtg gtg aac gct ctg gac ccc ccg ctg ttc acg cgc tac    4320
Ser Thr Pro Val Val Asn Ala Leu Asp Pro Pro Leu Phe Thr Arg Tyr
1425                1430                1435                1440 ctg agg atc cac ccc acg agc tgg gcg cag cac atc gcc ctg agg ctc    4368
Leu Arg Ile His Pro Thr Ser Trp Ala Gln His Ile Ala Leu Arg Leu
                1445                1450                1455 gag gtt cta gga tgt gag gca cag gat ctc tac tga                     4404
Glu Val Leu Gly Cys Glu Ala Gln Asp Leu Tyr
                1460                1465
```

<210> SEQ ID NO 4
<211> LENGTH: 1467
<212> TYPE: PRT
<213> ORGANISM: Sus scrofa

<400> SEQUENCE: 4

```
Met Gln Leu Glu Leu Ser Thr Cys Val Phe Leu Cys Leu Leu Pro Leu
 1               5                   10                  15

Gly Phe Ser Ala Ile Arg Arg Tyr Tyr Leu Gly Ala Val Glu Leu Ser
                20                  25                  30

Trp Asp Tyr Arg Gln Ser Glu Leu Leu Arg Glu Leu His Val Asp Thr
            35                  40                  45

Arg Phe Pro Ala Thr Ala Pro Gly Ala Leu Pro Leu Gly Pro Ser Val
        50                  55                  60

Leu Tyr Lys Lys Thr Val Phe Val Glu Phe Thr Asp Gln Leu Phe Ser
65                  70                  75                  80

Val Ala Arg Pro Arg Pro Pro Trp Met Gly Leu Leu Gly Pro Thr Ile
                85                  90                  95

Gln Ala Glu Val Tyr Asp Thr Val Val Val Thr Leu Lys Asn Met Ala
            100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285
```

-continued

```
Ile Phe Leu Glu Gly His Thr Phe Leu Val Arg His His Arg Gln Ala
290                 295                 300
Ser Leu Glu Ile Ser Pro Leu Thr Phe Leu Thr Ala Gln Thr Phe Leu
305                 310                 315                 320
Met Asp Leu Gly Gln Phe Leu Leu Phe Cys His Ile Ser Ser His His
                325                 330                 335
His Gly Gly Met Glu Ala His Val Arg Val Glu Ser Cys Ala Glu Glu
            340                 345                 350
Pro Gln Leu Arg Arg Lys Ala Asp Glu Glu Asp Tyr Asp Asp Asn
        355                 360                 365
Leu Tyr Asp Ser Asp Met Asp Val Val Arg Leu Asp Gly Asp Asp Val
370                 375                 380
Ser Pro Phe Ile Gln Ile Arg Ser Val Ala Lys Lys His Pro Lys Thr
385                 390                 395                 400
Trp Val His Tyr Ile Ser Ala Glu Glu Glu Asp Trp Asp Tyr Ala Pro
                405                 410                 415
Ala Val Pro Ser Pro Ser Asp Arg Ser Tyr Lys Ser Leu Tyr Leu Asn
            420                 425                 430
Ser Gly Pro Gln Arg Ile Gly Arg Lys Tyr Lys Lys Ala Arg Phe Val
        435                 440                 445
Ala Tyr Thr Asp Val Thr Phe Lys Thr Arg Lys Ala Ile Pro Tyr Glu
450                 455                 460
Ser Gly Ile Leu Gly Pro Leu Leu Tyr Gly Glu Val Gly Asp Thr Leu
465                 470                 475                 480
Leu Ile Ile Phe Lys Asn Lys Ala Ser Arg Pro Tyr Asn Ile Tyr Pro
                485                 490                 495
His Gly Ile Thr Asp Val Ser Ala Leu His Pro Gly Arg Leu Leu Lys
            500                 505                 510
Gly Trp Lys His Leu Lys Asp Met Pro Ile Leu Pro Gly Glu Thr Phe
        515                 520                 525
Lys Tyr Lys Trp Thr Val Thr Val Glu Asp Gly Pro Thr Lys Ser Asp
530                 535                 540
Pro Arg Cys Leu Thr Arg Tyr Tyr Ser Ser Ile Asn Leu Glu Lys
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Met Met Ser Asp Lys Arg Asn Val
            580                 585                 590
Ile Leu Phe Ser Val Phe Asp Glu Asn Gln Ser Trp Tyr Leu Ala Glu
        595                 600                 605
Asn Ile Gln Arg Phe Leu Pro Asn Pro Asp Gly Leu Gln Pro Gln Asp
610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Val Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
690                 695                 700
```

-continued

Gly Leu Trp Val Leu Gly Cys His Asn Ser Asp Leu Arg Asn Arg Gly
705                 710                 715                 720

Met Thr Ala Leu Leu Lys Val Tyr Ser Cys Asp Arg Asp Ile Gly Asp
            725                 730                 735

Tyr Tyr Asp Asn Thr Tyr Glu Asp Ile Pro Gly Phe Leu Leu Ser Gly
        740                 745                 750

Lys Asn Val Ile Glu Pro Arg Ser Phe Ala Gln Asn Ser Arg Pro Pro
    755                 760                 765

Ser Ala Ser Ala Pro Lys Pro Pro Val Leu Arg Arg His Gln Arg Asp
770                 775                 780

Ile Ser Leu Pro Thr Phe Gln Pro Glu Glu Asp Lys Met Asp Tyr Asp
785                 790                 795                 800

Asp Ile Phe Ser Thr Glu Thr Lys Gly Glu Asp Phe Asp Ile Tyr Gly
                805                 810                 815

Glu Asp Glu Asn Gln Asp Pro Arg Ser Phe Gln Lys Arg Thr Arg His
            820                 825                 830

Tyr Phe Ile Ala Ala Val Glu Gln Leu Trp Asp Tyr Gly Met Ser Glu
        835                 840                 845

Ser Pro Arg Ala Leu Arg Asn Arg Ala Gln Asn Gly Glu Val Pro Arg
    850                 855                 860

Phe Lys Lys Val Val Phe Arg Glu Phe Ala Asp Gly Ser Phe Thr Gln
865                 870                 875                 880

Pro Ser Tyr Arg Gly Glu Leu Asn Lys His Leu Gly Leu Leu Gly Pro
                885                 890                 895

Tyr Ile Arg Ala Glu Val Glu Asp Asn Ile Met Val Thr Phe Lys Asn
            900                 905                 910

Gln Ala Ser Arg Pro Tyr Ser Phe Tyr Ser Ser Leu Ile Ser Tyr Pro
        915                 920                 925

Asp Asp Gln Glu Gln Gly Ala Glu Pro Arg His Asn Phe Val Gln Pro
    930                 935                 940

Asn Glu Thr Arg Thr Tyr Phe Trp Lys Val Gln His His Met Ala Pro
945                 950                 955                 960

Thr Glu Asp Glu Phe Asp Cys Lys Ala Trp Ala Tyr Phe Ser Asp Val
                965                 970                 975

Asp Leu Glu Lys Asp Val His Ser Gly Leu Ile Gly Pro Leu Leu Ile
            980                 985                 990

Cys Arg Ala Asn Thr Leu Asn Ala Ala His Gly Arg Gln Val Thr Val
        995                 1000                1005

Gln Glu Phe Ala Leu Phe Phe Thr Ile Phe Asp Glu Thr Lys Ser Trp
1010                1015                1020

Tyr Phe Thr Glu Asn Val Glu Arg Asn Cys Arg Ala Pro Cys His Leu
1025                1030                1035                1040

Gln Met Glu Asp Pro Thr Leu Lys Glu Asn Tyr Arg Phe His Ala Ile
                1045                1050                1055

Asn Gly Tyr Val Met Asp Thr Leu Pro Gly Leu Val Met Ala Gln Asn
            1060                1065                1070

Gln Arg Ile Arg Trp Tyr Leu Leu Ser Met Gly Ser Asn Glu Asn Ile
        1075                1080                1085

His Ser Ile His Phe Ser Gly His Val Phe Ser Val Arg Lys Lys Glu
    1090                1095                1100

Glu Tyr Lys Met Ala Val Tyr Asn Leu Tyr Pro Gly Val Phe Glu Thr
1105                1110                1115                1120

```
Val Glu Met Leu Pro Ser Lys Val Gly Ile Trp Arg Ile Glu Cys Leu
            1125                1130                1135

Ile Gly Glu His Leu Gln Ala Gly Met Ser Thr Thr Phe Leu Val Tyr
        1140                1145                1150

Ser Lys Glu Cys Gln Ala Pro Leu Gly Met Ala Ser Gly Arg Ile Arg
    1155                1160                1165

Asp Phe Gln Ile Thr Ala Ser Gly Gln Tyr Gly Gln Trp Ala Pro Lys
    1170                1175                1180

Leu Ala Arg Leu His Tyr Ser Gly Ser Ile Asn Ala Trp Ser Thr Lys
1185                1190                1195                1200

Asp Pro His Ser Trp Ile Lys Val Asp Leu Leu Ala Pro Met Ile Ile
                1205                1210                1215

His Gly Ile Met Thr Gln Gly Ala Arg Gln Lys Phe Ser Ser Leu Tyr
            1220                1225                1230

Ile Ser Gln Phe Ile Ile Met Tyr Ser Leu Asp Gly Arg Asn Trp Gln
        1235                1240                1245

Ser Tyr Arg Gly Asn Ser Thr Gly Thr Leu Met Val Phe Phe Gly Asn
    1250                1255                1260

Val Asp Ala Ser Gly Ile Lys His Asn Ile Phe Asn Pro Pro Ile Val
1265                1270                1275                1280

Ala Arg Tyr Ile Arg Leu His Pro Thr His Tyr Ser Ile Arg Ser Thr
                1285                1290                1295

Leu Arg Met Glu Leu Met Gly Cys Asp Leu Asn Ser Cys Ser Met Pro
            1300                1305                1310

Leu Gly Met Gln Asn Lys Ala Ile Ser Asp Ser Gln Ile Thr Ala Ser
        1315                1320                1325

Ser His Leu Ser Asn Ile Phe Ala Thr Trp Ser Pro Ser Gln Ala Arg
    1330                1335                1340

Leu His Leu Gln Gly Arg Thr Asn Ala Trp Arg Pro Arg Val Ser Ser
1345                1350                1355                1360

Ala Glu Glu Trp Leu Gln Val Asp Leu Gln Lys Thr Val Lys Val Thr
                1365                1370                1375

Gly Ile Thr Thr Gln Gly Val Lys Ser Leu Leu Ser Ser Met Tyr Val
            1380                1385                1390

Lys Glu Phe Leu Val Ser Ser Ser Gln Asp Gly Arg Arg Trp Thr Leu
        1395                1400                1405

Phe Leu Gln Asp Gly His Thr Lys Val Phe Gln Gly Asn Gln Asp Ser
    1410                1415                1420

Ser Thr Pro Val Val Asn Ala Leu Asp Pro Pro Leu Phe Thr Arg Tyr
1425                1430                1435                1440

Leu Arg Ile His Pro Thr Ser Trp Ala Gln His Ile Ala Leu Arg Leu
                1445                1450                1455

Glu Val Leu Gly Cys Glu Ala Gln Asp Leu Tyr
            1460                1465

<210> SEQ ID NO 5
<211> LENGTH: 9009
<212> TYPE: DNA
<213> ORGANISM: Homo sapiens
<220> FEATURE:
<221> NAME/KEY: gene
<222> LOCATION: (0)...(0)
<223> OTHER INFORMATION: Factor VIII- Full Length
<220> FEATURE:
<221> NAME/KEY: CDS
<222> LOCATION: (208)...(7203)
```

```
<400> SEQUENCE: 5
cagtgggtaa gttccttaaa tgctctgcaa agaaattggg acttttcatt aaatcagaaa      60
ttttactttt ttcccctcct gggagctaaa gatattttag agaagaatta accttttgct     120
tctccagttg aacatttgta gcaataagtc atgcaaatag agctctccac ctgcttcttt     180
ctgtgccttt tgcgattctg ctttagt gcc acc aga aga tac tac ctg ggt gca     234
                                Ala Thr Arg Arg Tyr Tyr Leu Gly Ala
                                 1               5 gtg gaa ctg tca tgg gac tat atg caa agt gat ctc ggt gag ctg cct       282
Val Glu Leu Ser Trp Asp Tyr Met Gln Ser Asp Leu Gly Glu Leu Pro
 10          15                  20                  25 gtg gac gca aga ttt cct cct aga gtg cca aaa tct ttt cca ttc aac       330
Val Asp Ala Arg Phe Pro Pro Arg Val Pro Lys Ser Phe Pro Phe Asn
                 30                  35                  40 acc tca gtc gtg tac aaa aag act ctg ttt gta gaa ttc acg gtt cac       378
Thr Ser Val Val Tyr Lys Lys Thr Leu Phe Val Glu Phe Thr Val His
             45                  50                  55 ctt ttc aac atc gct aag cca agg cca ccc tgg atg ggt ctg cta ggt       426
Leu Phe Asn Ile Ala Lys Pro Arg Pro Pro Trp Met Gly Leu Leu Gly
         60                  65                  70 cct acc atc cag gct gag gtt tat gat aca gtg gtc att aca ctt aag       474
Pro Thr Ile Gln Ala Glu Val Tyr Asp Thr Val Val Ile Thr Leu Lys
     75                  80                  85 aac atg gct tcc cat cct gtc agt ctt cat gct gtt ggt gta tcc tac       522
Asn Met Ala Ser His Pro Val Ser Leu His Ala Val Gly Val Ser Tyr
 90                  95                 100                 105 tgg aaa gct tct gag gga gct gaa tat gat gat cag acc agt caa agg       570
Trp Lys Ala Ser Glu Gly Ala Glu Tyr Asp Asp Gln Thr Ser Gln Arg
                110                 115                 120 gag aaa gaa gat gat aaa gtc ttc cct ggt gga agc cat aca tat gtc       618
Glu Lys Glu Asp Asp Lys Val Phe Pro Gly Gly Ser His Thr Tyr Val
            125                 130                 135 tgg cag gtc ctg aaa gag aat ggt cca atg gcc tct gac cca ctg tgc       666
Trp Gln Val Leu Lys Glu Asn Gly Pro Met Ala Ser Asp Pro Leu Cys
        140                 145                 150 ctt acc tac tca tat ctt tct cat gtg gac ctg gta aaa gac ttg aat       714
Leu Thr Tyr Ser Tyr Leu Ser His Val Asp Leu Val Lys Asp Leu Asn
    155                 160                 165 tca ggc ctc att gga gcc cta cta gta tgt aga gaa ggg agt ctg gcc       762
Ser Gly Leu Ile Gly Ala Leu Leu Val Cys Arg Glu Gly Ser Leu Ala
170                 175                 180                 185 aag gaa aag aca cag acc ttg cac aaa ttt ata cta ctt ttt gct gta       810
Lys Glu Lys Thr Gln Thr Leu His Lys Phe Ile Leu Leu Phe Ala Val
                190                 195                 200 ttt gat gaa ggg aaa agt tgg cac tca gaa aca aag aac tcc ttg atg       858
Phe Asp Glu Gly Lys Ser Trp His Ser Glu Thr Lys Asn Ser Leu Met
            205                 210                 215 cag gat agg gat gct gca tct gct cgg gcc tgg cct aaa atg cac aca       906
Gln Asp Arg Asp Ala Ala Ser Ala Arg Ala Trp Pro Lys Met His Thr
        220                 225                 230 gtc aat ggt tat gta aac agg tct ctg cca ggt ctg att gga tgc cac       954
Val Asn Gly Tyr Val Asn Arg Ser Leu Pro Gly Leu Ile Gly Cys His
    235                 240                 245 agg aaa tca gtc tat tgg cat gtg att gga atg ggc acc act cct gaa      1002
Arg Lys Ser Val Tyr Trp His Val Ile Gly Met Gly Thr Thr Pro Glu
250                 255                 260                 265 gtg cac tca ata ttc ctc gaa ggt cac aca ttt ctt gtg agg aac cat      1050
Val His Ser Ile Phe Leu Glu Gly His Thr Phe Leu Val Arg Asn His
                270                 275                 280
```

| | | |
|---|---|---|
| cgc cag gcg tcc ttg gaa atc tcg cca ata act ttc ctt act gct caa<br>Arg Gln Ala Ser Leu Glu Ile Ser Pro Ile Thr Phe Leu Thr Ala Gln<br>285 290 295 | | 1098 |
| aca ctc ttg atg gac ctt gga cag ttt cta ctg ttt tgt cat atc tct<br>Thr Leu Leu Met Asp Leu Gly Gln Phe Leu Leu Phe Cys His Ile Ser<br>300 305 310 | | 1146 |
| tcc cac caa cat gat ggc atg gaa gct tat gtc aaa gta gac agc tgt<br>Ser His Gln His Asp Gly Met Glu Ala Tyr Val Lys Val Asp Ser Cys<br>315 320 325 | | 1194 |
| cca gag gaa ccc caa cta cga atg aaa aat aat gaa gaa gcg gaa gac<br>Pro Glu Glu Pro Gln Leu Arg Met Lys Asn Asn Glu Glu Ala Glu Asp<br>330 335 340 345 | | 1242 |
| tat gat gat gat ctt act gat tct gaa atg gat gtg gtc agg ttt gat<br>Tyr Asp Asp Asp Leu Thr Asp Ser Glu Met Asp Val Val Arg Phe Asp<br>350 355 360 | | 1290 |
| gat gac aac tct cct tcc ttt atc caa att cgc tca gtt gcc aag aag<br>Asp Asp Asn Ser Pro Ser Phe Ile Gln Ile Arg Ser Val Ala Lys Lys<br>365 370 375 | | 1338 |
| cat cct aaa act tgg gta cat tac att gct gct gaa gag gag gac tgg<br>His Pro Lys Thr Trp Val His Tyr Ile Ala Ala Glu Glu Glu Asp Trp<br>380 385 390 | | 1386 |
| gac tat gct ccc tta gtc ctc gcc ccc gat gac aga agt tat aaa agt<br>Asp Tyr Ala Pro Leu Val Leu Ala Pro Asp Asp Arg Ser Tyr Lys Ser<br>395 400 405 | | 1434 |
| caa tat ttg aac aat ggc cct cag cgg att ggt agg aag tac aaa aaa<br>Gln Tyr Leu Asn Asn Gly Pro Gln Arg Ile Gly Arg Lys Tyr Lys Lys<br>410 415 420 425 | | 1482 |
| gtc cga ttt atg gca tac aca gat gaa acc ttt aag act cgt gaa gct<br>Val Arg Phe Met Ala Tyr Thr Asp Glu Thr Phe Lys Thr Arg Glu Ala<br>430 435 440 | | 1530 |
| att cag cat gaa tca gga atc ttg gga cct tta ctt tat ggg gaa gtt<br>Ile Gln His Glu Ser Gly Ile Leu Gly Pro Leu Leu Tyr Gly Glu Val<br>445 450 455 | | 1578 |
| gga gac aca ctg ttg att ata ttt aag aat caa gca agc aga cca tat<br>Gly Asp Thr Leu Leu Ile Ile Phe Lys Asn Gln Ala Ser Arg Pro Tyr<br>460 465 470 | | 1626 |
| aac atc tac cct cac gga atc act gat gtc cgt cct ttg tat tca agg<br>Asn Ile Tyr Pro His Gly Ile Thr Asp Val Arg Pro Leu Tyr Ser Arg<br>475 480 485 | | 1674 |
| aga tta cca aaa ggt gta aaa cat ttg aag gat ttt cca att ctg cca<br>Arg Leu Pro Lys Gly Val Lys His Leu Lys Asp Phe Pro Ile Leu Pro<br>490 495 500 505 | | 1722 |
| gga gaa ata ttc aaa tat aaa tgg aca gtg act gta gaa gat ggg cca<br>Gly Glu Ile Phe Lys Tyr Lys Trp Thr Val Thr Val Glu Asp Gly Pro<br>510 515 520 | | 1770 |
| act aaa tca gat cct cgg tgc ctg acc cgc tat tac tct agt ttc gtt<br>Thr Lys Ser Asp Pro Arg Cys Leu Thr Arg Tyr Tyr Ser Ser Phe Val<br>525 530 535 | | 1818 |
| aat atg gag aga gat cta gct tca gga ctc att ggc cct ctc ctc atc<br>Asn Met Glu Arg Asp Leu Ala Ser Gly Leu Ile Gly Pro Leu Leu Ile<br>540 545 550 | | 1866 |
| tgc tac aaa gaa tct gta gat caa aga gga aac cag ata atg tca gac<br>Cys Tyr Lys Glu Ser Val Asp Gln Arg Gly Asn Gln Ile Met Ser Asp<br>555 560 565 | | 1914 |
| aag agg aat gtc atc ctg ttt tct gta ttt gat gag aac cga agc tgg<br>Lys Arg Asn Val Ile Leu Phe Ser Val Phe Asp Glu Asn Arg Ser Trp<br>570 575 580 585 | | 1962 |

-continued

| | | |
|---|---|---|
| tac ctc aca gag aat ata caa cgc ttt ctc ccc aat cca gct gga gtg<br>Tyr Leu Thr Glu Asn Ile Gln Arg Phe Leu Pro Asn Pro Ala Gly Val<br>590         595         600 | | 2010 |
| cag ctt gag gat cca gag ttc caa gcc tcc aac atc atg cac agc atc<br>Gln Leu Glu Asp Pro Glu Phe Gln Ala Ser Asn Ile Met His Ser Ile<br>605         610         615 | | 2058 |
| aat ggc tat gtt ttt gat agt ttg cag ttg tca gtt tgt ttg cat gag<br>Asn Gly Tyr Val Phe Asp Ser Leu Gln Leu Ser Val Cys Leu His Glu<br>620         625         630 | | 2106 |
| gtg gca tac tgg tac att cta agc att gga gca cag act gac ttc ctt<br>Val Ala Tyr Trp Tyr Ile Leu Ser Ile Gly Ala Gln Thr Asp Phe Leu<br>635         640         645 | | 2154 |
| tct gtc ttc ttc tct gga tat acc ttc aaa cac aaa atg gtc tat gaa<br>Ser Val Phe Phe Ser Gly Tyr Thr Phe Lys His Lys Met Val Tyr Glu<br>650         655         660         665 | | 2202 |
| gac aca ctc acc cta ttc cca ttc tca gga gaa act gtc ttc atg tcg<br>Asp Thr Leu Thr Leu Phe Pro Phe Ser Gly Glu Thr Val Phe Met Ser<br>670         675         680 | | 2250 |
| atg gaa aac cca ggt cta tgg att ctg ggg tgc cac aac tca gac ttt<br>Met Glu Asn Pro Gly Leu Trp Ile Leu Gly Cys His Asn Ser Asp Phe<br>685         690         695 | | 2298 |
| cgg aac aga ggc atg acc gcc tta ctg aag gtt tct agt tgt gac aag<br>Arg Asn Arg Gly Met Thr Ala Leu Leu Lys Val Ser Ser Cys Asp Lys<br>700         705         710 | | 2346 |
| aac act ggt gat tat tac gag gac agt tat gaa gat att tca gca tac<br>Asn Thr Gly Asp Tyr Tyr Glu Asp Ser Tyr Glu Asp Ile Ser Ala Tyr<br>715         720         725 | | 2394 |
| ttg ctg agt aaa aac aat gcc att gaa cca aga agc ttc tcc cag aat<br>Leu Leu Ser Lys Asn Asn Ala Ile Glu Pro Arg Ser Phe Ser Gln Asn<br>730         735         740         745 | | 2442 |
| tca aga cac cct agc act agg caa aag caa ttt aat gcc acc aca att<br>Ser Arg His Pro Ser Thr Arg Gln Lys Gln Phe Asn Ala Thr Thr Ile<br>750         755         760 | | 2490 |
| cca gaa aat gac ata gag aag act gac cct tgg ttt gca cac aga aca<br>Pro Glu Asn Asp Ile Glu Lys Thr Asp Pro Trp Phe Ala His Arg Thr<br>765         770         775 | | 2538 |
| cct atg cct aaa ata caa aat gtc tcc tct agt gat ttg ttg atg ctc<br>Pro Met Pro Lys Ile Gln Asn Val Ser Ser Ser Asp Leu Leu Met Leu<br>780         785         790 | | 2586 |
| ttg cga cag agt cct act cca cat ggg cta tcc tta tct gat ctc caa<br>Leu Arg Gln Ser Pro Thr Pro His Gly Leu Ser Leu Ser Asp Leu Gln<br>795         800         805 | | 2634 |
| gaa gcc aaa tat gag act ttt tct gat gat cca tca cct gga gca ata<br>Glu Ala Lys Tyr Glu Thr Phe Ser Asp Asp Pro Ser Pro Gly Ala Ile<br>810         815         820         825 | | 2682 |
| gac agt aat aac agc ctg tct gaa atg aca cac ttc agg cca cag ctc<br>Asp Ser Asn Asn Ser Leu Ser Glu Met Thr His Phe Arg Pro Gln Leu<br>830         835         840 | | 2730 |
| cat cac agt ggg gac atg gta ttt acc cct gag tca ggc ctc caa tta<br>His His Ser Gly Asp Met Val Phe Thr Pro Glu Ser Gly Leu Gln Leu<br>845         850         855 | | 2778 |
| aga tta aat gag aaa ctg ggg aca act gca gca aca gag ttg aag aaa<br>Arg Leu Asn Glu Lys Leu Gly Thr Thr Ala Ala Thr Glu Leu Lys Lys<br>860         865         870 | | 2826 |
| ctt gat ttc aaa gtt tct agt aca tca aat aat ctg att tca aca att<br>Leu Asp Phe Lys Val Ser Ser Thr Ser Asn Asn Leu Ile Ser Thr Ile<br>875         880         885 | | 2874 |
| cca tca gac aat ttg gca gca ggt act gat aat aca agt cct tta gga<br>Pro Ser Asp Asn Leu Ala Ala Gly Thr Asp Asn Thr Ser Pro Leu Gly<br>890         895         900         905 | | 2922 |

```
ccc cca agt atg cca gtt cat tat gat agt caa tta gat acc act cta      2970
Pro Pro Ser Met Pro Val His Tyr Asp Ser Gln Leu Asp Thr Thr Leu
            910                 915                 920 ttt ggc aaa aag tca tct ccc ctt act gag tct ggt gga cct ctg agc      3018
Phe Gly Lys Lys Ser Ser Pro Leu Thr Glu Ser Gly Gly Pro Leu Ser
            925                 930                 935 ttg agt gaa gaa aat aat gat tca aag ttg tta gaa tca ggt tta atg      3066
Leu Ser Glu Glu Asn Asn Asp Ser Lys Leu Leu Glu Ser Gly Leu Met
            940                 945                 950 aat agc caa gaa agt tca tgg gga aaa aat gta tcg tca aca gag agt      3114
Asn Ser Gln Glu Ser Ser Trp Gly Lys Asn Val Ser Ser Thr Glu Ser
            955                 960                 965 ggt agg tta ttt aaa ggg aaa aga gct cat gga cct gct ttg ttg act      3162
Gly Arg Leu Phe Lys Gly Lys Arg Ala His Gly Pro Ala Leu Leu Thr
970                 975                 980                 985 aaa gat aat gcc tta ttc aaa gtt agc atc tct ttg tta aag aca aac      3210
Lys Asp Asn Ala Leu Phe Lys Val Ser Ile Ser Leu Leu Lys Thr Asn
                990                 995                 1000 aaa act tcc aat aat tca gca act aat aga aag act cac att gat ggc      3258
Lys Thr Ser Asn Asn Ser Ala Thr Asn Arg Lys Thr His Ile Asp Gly
            1005                1010                1015 cca tca tta tta att gag aat agt cca tca gtc tgg caa aat ata tta      3306
Pro Ser Leu Leu Ile Glu Asn Ser Pro Ser Val Trp Gln Asn Ile Leu
            1020                1025                1030 gaa agt gac act gag ttt aaa aaa gtg aca cct ttg att cat gac aga      3354
Glu Ser Asp Thr Glu Phe Lys Lys Val Thr Pro Leu Ile His Asp Arg
            1035                1040                1045 atg ctt atg gac aaa aat gct aca gct ttg agg cta aat cat atg tca      3402
Met Leu Met Asp Lys Asn Ala Thr Ala Leu Arg Leu Asn His Met Ser
1050                1055                1060                1065 aat aaa act act tca tca aaa aac atg gaa atg gtc caa cag aaa aaa      3450
Asn Lys Thr Thr Ser Ser Lys Asn Met Glu Met Val Gln Gln Lys Lys
                1070                1075                1080 gag ggc ccc att cca cca gat gca caa aat cca gat atg tcg ttc ttt      3498
Glu Gly Pro Ile Pro Pro Asp Ala Gln Asn Pro Asp Met Ser Phe Phe
            1085                1090                1095 aag atg cta ttc ttg cca gaa tca gca agg tgg ata caa agg act cat      3546
Lys Met Leu Phe Leu Pro Glu Ser Ala Arg Trp Ile Gln Arg Thr His
            1100                1105                1110 gga aag aac tct ctg aac tct ggg caa ggc ccc agt cca aag caa tta      3594
Gly Lys Asn Ser Leu Asn Ser Gly Gln Gly Pro Ser Pro Lys Gln Leu
            1115                1120                1125 gta tcc tta gga cca gaa aaa tct gtg gaa ggt cag aat ttc ttg tct      3642
Val Ser Leu Gly Pro Glu Lys Ser Val Glu Gly Gln Asn Phe Leu Ser
1130                1135                1140                1145 gag aaa aac aaa gtg gta gta gga aag ggt gaa ttt aca aag gac gta      3690
Glu Lys Asn Lys Val Val Val Gly Lys Gly Glu Phe Thr Lys Asp Val
                1150                1155                1160 gga ctc aaa gag atg gtt ttt cca agc agc aga aac cta ttt ctt act      3738
Gly Leu Lys Glu Met Val Phe Pro Ser Ser Arg Asn Leu Phe Leu Thr
            1165                1170                1175 aac ttg gat aat tta cat gaa aat aat aca cac aat caa gaa aaa aaa      3786
Asn Leu Asp Asn Leu His Glu Asn Asn Thr His Asn Gln Glu Lys Lys
            1180                1185                1190 att cag gaa gaa ata gaa aag aag gaa aca tta atc caa gag aat gta      3834
Ile Gln Glu Glu Ile Glu Lys Lys Glu Thr Leu Ile Gln Glu Asn Val
            1195                1200                1205 gtt ttg cct cag ata cat aca gtg act ggc act aag aat ttc atg aag      3882
Val Leu Pro Gln Ile His Thr Val Thr Gly Thr Lys Asn Phe Met Lys
1210                1215                1220                1225
```

```
aac ctt ttc tta ctg agc act agg caa aat gta gaa ggt tca tat gag    3930
Asn Leu Phe Leu Leu Ser Thr Arg Gln Asn Val Glu Gly Ser Tyr Glu
            1230                1235                1240 ggg gca tat gct cca gta ctt caa gat ttt agg tca tta aat gat tca    3978
Gly Ala Tyr Ala Pro Val Leu Gln Asp Phe Arg Ser Leu Asn Asp Ser
        1245                1250                1255 aca aat aga aca aag aaa cac aca gct cat ttc tca aaa aaa ggg gag    4026
Thr Asn Arg Thr Lys Lys His Thr Ala His Phe Ser Lys Lys Gly Glu
    1260                1265                1270 gaa gaa aac ttg gaa ggc ttg gga aat caa acc aag caa att gta gag    4074
Glu Glu Asn Leu Glu Gly Leu Gly Asn Gln Thr Lys Gln Ile Val Glu
1275                1280                1285 aaa tat gca tgc acc aca agg ata tct cct aat aca agc cag cag aat    4122
Lys Tyr Ala Cys Thr Thr Arg Ile Ser Pro Asn Thr Ser Gln Gln Asn
1290                1295                1300                1305 ttt gtc acg caa cgt agt aag aga gct ttg aaa caa ttc aga ctc cca    4170
Phe Val Thr Gln Arg Ser Lys Arg Ala Leu Lys Gln Phe Arg Leu Pro
        1310                1315                1320 cta gaa gaa aca gaa ctt gaa aaa agg ata att gtg gat gac acc tca    4218
Leu Glu Glu Thr Glu Leu Glu Lys Arg Ile Ile Val Asp Asp Thr Ser
    1325                1330                1335 acc cag tgg tcc aaa aac atg aaa cat ttg acc ccg agc acc ctc aca    4266
Thr Gln Trp Ser Lys Asn Met Lys His Leu Thr Pro Ser Thr Leu Thr
1340                1345                1350 cag ata gac tac aat gag aag gag aaa ggg gcc att act cag tct ccc    4314
Gln Ile Asp Tyr Asn Glu Lys Glu Lys Gly Ala Ile Thr Gln Ser Pro
        1355                1360                1365 tta tca gat tgc ctt acg agg agt cat agc atc cct caa gca aat aga    4362
Leu Ser Asp Cys Leu Thr Arg Ser His Ser Ile Pro Gln Ala Asn Arg
1370                1375                1380                1385 tct cca tta ccc att gca aag gta tca tca ttt cca tct att aga cct    4410
Ser Pro Leu Pro Ile Ala Lys Val Ser Ser Phe Pro Ser Ile Arg Pro
        1390                1395                1400 ata tat ctg acc agg gtc cta ttc caa gac aac tct tct cat ctt cca    4458
Ile Tyr Leu Thr Arg Val Leu Phe Gln Asp Asn Ser Ser His Leu Pro
    1405                1410                1415 gca gca tct tat aga aag aaa gat tct ggg gtc caa gaa agc agt cat    4506
Ala Ala Ser Tyr Arg Lys Lys Asp Ser Gly Val Gln Glu Ser Ser His
1420                1425                1430 ttc tta caa gga gcc aaa aaa aat aac ctt tct tta gcc att cta acc    4554
Phe Leu Gln Gly Ala Lys Lys Asn Asn Leu Ser Leu Ala Ile Leu Thr
        1435                1440                1445 ttg gag atg act ggt gat caa aga gag gtt ggc tcc ctg ggg aca agt    4602
Leu Glu Met Thr Gly Asp Gln Arg Glu Val Gly Ser Leu Gly Thr Ser
1450                1455                1460                1465 gcc aca aat tca gtc aca tac aag aaa gtt gag aac act gtt ctc ccg    4650
Ala Thr Asn Ser Val Thr Tyr Lys Lys Val Glu Asn Thr Val Leu Pro
        1470                1475                1480 aaa cca gac ttg ccc aaa aca tct ggc aaa gtt gaa ttg ctt cca aaa    4698
Lys Pro Asp Leu Pro Lys Thr Ser Gly Lys Val Glu Leu Leu Pro Lys
    1485                1490                1495 gtt cac att tat cag aag gac cta ttc cct acg gaa act agc aat ggg    4746
Val His Ile Tyr Gln Lys Asp Leu Phe Pro Thr Glu Thr Ser Asn Gly
1500                1505                1510 tct cct ggc cat ctg gat ctc gtg gaa ggg agc ctt ctt cag gga aca    4794
Ser Pro Gly His Leu Asp Leu Val Glu Gly Ser Leu Leu Gln Gly Thr
        1515                1520                1525 gag gga gcg att aag tgg aat gaa gca aac aga cct gga aaa gtt ccc    4842
Glu Gly Ala Ile Lys Trp Asn Glu Ala Asn Arg Pro Gly Lys Val Pro
1530                1535                1540                1545
```

```
ttt ctg aga gta gca aca gaa agc tct gca aag act ccc tcc aag cta    4890
Phe Leu Arg Val Ala Thr Glu Ser Ser Ala Lys Thr Pro Ser Lys Leu
            1550                1555                1560 ttg gat cct ctt gct tgg gat aac cac tat ggt act cag ata cca aaa    4938
Leu Asp Pro Leu Ala Trp Asp Asn His Tyr Gly Thr Gln Ile Pro Lys
        1565                1570                1575 gaa gag tgg aaa tcc caa gag aag tca cca gaa aaa aca gct ttt aag    4986
Glu Glu Trp Lys Ser Gln Glu Lys Ser Pro Glu Lys Thr Ala Phe Lys
    1580                1585                1590 aaa aag gat acc att ttg tcc ctg aac gct tgt gaa agc aat cat gca    5034
Lys Lys Asp Thr Ile Leu Ser Leu Asn Ala Cys Glu Ser Asn His Ala
1595                1600                1605 ata gca gca ata aat gag gga caa aat aag ccc gaa ata gaa gtc acc    5082
Ile Ala Ala Ile Asn Glu Gly Gln Asn Lys Pro Glu Ile Glu Val Thr
1610                1615                1620                1625 tgg gca aag caa ggt agg act gaa agg ctg tgc tct caa aac cca cca    5130
Trp Ala Lys Gln Gly Arg Thr Glu Arg Leu Cys Ser Gln Asn Pro Pro
            1630                1635                1640 gtc ttg aaa cgc cat caa cgg gaa ata act cgt act act ctt cag tca    5178
Val Leu Lys Arg His Gln Arg Glu Ile Thr Arg Thr Thr Leu Gln Ser
        1645                1650                1655 gat caa gag gaa att gac tat gat gat acc ata tca gtt gaa atg aag    5226
Asp Gln Glu Glu Ile Asp Tyr Asp Asp Thr Ile Ser Val Glu Met Lys
    1660                1665                1670 aag gaa gat ttt gac att tat gat gag gat gaa aat cag agc ccc cgc    5274
Lys Glu Asp Phe Asp Ile Tyr Asp Glu Asp Glu Asn Gln Ser Pro Arg
1675                1680                1685 agc ttt caa aag aaa aca cga cac tat ttt att gct gca gtg gag agg    5322
Ser Phe Gln Lys Lys Thr Arg His Tyr Phe Ile Ala Ala Val Glu Arg
1690                1695                1700                1705 ctc tgg gat tat ggg atg agt agc tcc cca cat gtt cta aga aac agg    5370
Leu Trp Asp Tyr Gly Met Ser Ser Ser Pro His Val Leu Arg Asn Arg
            1710                1715                1720 gct cag agt ggc agt gtc cct cag ttc aag aaa gtt gtt ttc cag gaa    5418
Ala Gln Ser Gly Ser Val Pro Gln Phe Lys Lys Val Val Phe Gln Glu
        1725                1730                1735 ttt act gat ggc tcc ttt act cag ccc tta tac cgt gga gaa cta aat    5466
Phe Thr Asp Gly Ser Phe Thr Gln Pro Leu Tyr Arg Gly Glu Leu Asn
    1740                1745                1750 gaa cat ttg gga ctc ctg ggg cca tat ata aga gca gaa gtt gaa gat    5514
Glu His Leu Gly Leu Leu Gly Pro Tyr Ile Arg Ala Glu Val Glu Asp
1755                1760                1765 aat atc atg gta act ttc aga aat cag gcc tct cgt ccc tat tcc ttc    5562
Asn Ile Met Val Thr Phe Arg Asn Gln Ala Ser Arg Pro Tyr Ser Phe
1770                1775                1780                1785 tat tct agc ctt att tct tat gag gaa gat cag agg caa gga gca gaa    5610
Tyr Ser Ser Leu Ile Ser Tyr Glu Glu Asp Gln Arg Gln Gly Ala Glu
            1790                1795                1800 cct aga aaa aac ttt gtc aag cct aat gaa acc aaa act tac ttt tgg    5658
Pro Arg Lys Asn Phe Val Lys Pro Asn Glu Thr Lys Thr Tyr Phe Trp
        1805                1810                1815 aaa gtg caa cat cat atg gca ccc act aaa gat gag ttt gac tgc aaa    5706
Lys Val Gln His His Met Ala Pro Thr Lys Asp Glu Phe Asp Cys Lys
    1820                1825                1830 gcc tgg gct tat ttc tct gat gtt gac ctg gaa aaa gat gtg cac tca    5754
Ala Trp Ala Tyr Phe Ser Asp Val Asp Leu Glu Lys Asp Val His Ser
1835                1840                1845 ggc ctg att gga ccc ctt ctg gtc tgc cac act aac aca ctg aac cct    5802
Gly Leu Ile Gly Pro Leu Leu Val Cys His Thr Asn Thr Leu Asn Pro
1850                1855                1860                1865
```

```
gct cat ggg aga caa gtg aca gta cag gaa ttt gct ctg ttt ttc acc    5850
Ala His Gly Arg Gln Val Thr Val Gln Glu Phe Ala Leu Phe Phe Thr
             1870                1875                1880 atc ttt gat gag acc aaa agc tgg tac ttc act gaa aat atg gaa aga    5898
Ile Phe Asp Glu Thr Lys Ser Trp Tyr Phe Thr Glu Asn Met Glu Arg
     1885                1890                1895 aac tgc agg gct ccc tgc aat atc cag atg gaa gat ccc act ttt aaa    5946
Asn Cys Arg Ala Pro Cys Asn Ile Gln Met Glu Asp Pro Thr Phe Lys
 1900                1905                1910 gag aat tat cgc ttc cat gca atc aat ggc tac ata atg gat aca cta    5994
Glu Asn Tyr Arg Phe His Ala Ile Asn Gly Tyr Ile Met Asp Thr Leu
         1915                1920                1925 cct ggc tta gta atg gct cag gat caa agg att cga tgg tat ctg ctc    6042
Pro Gly Leu Val Met Ala Gln Asp Gln Arg Ile Arg Trp Tyr Leu Leu
1930                1935                1940                1945 agc atg ggc agc aat gaa aac atc cat tct att cat ttc agt gga cat    6090
Ser Met Gly Ser Asn Glu Asn Ile His Ser Ile His Phe Ser Gly His
                 1950                1955                1960 gtg ttc act gta cga aaa aaa gag gag tat aaa atg gca ctg tac aat    6138
Val Phe Thr Val Arg Lys Lys Glu Glu Tyr Lys Met Ala Leu Tyr Asn
         1965                1970                1975 ctc tat cca ggt gtt ttt gag aca gtg gaa atg tta cca tcc aaa gct    6186
Leu Tyr Pro Gly Val Phe Glu Thr Val Glu Met Leu Pro Ser Lys Ala
     1980                1985                1990 gga att tgg cgg gtg gaa tgc ctt att ggc gag cat cta cat gct ggg    6234
Gly Ile Trp Arg Val Glu Cys Leu Ile Gly Glu His Leu His Ala Gly
 1995                2000                2005 atg agc aca ctt ttt ctg gtg tac agc aat aag tgt cag act ccc ctg    6282
Met Ser Thr Leu Phe Leu Val Tyr Ser Asn Lys Cys Gln Thr Pro Leu
2010                2015                2020                2025 gga atg gct tct gga cac att aga gat ttt cag att aca gct tca gga    6330
Gly Met Ala Ser Gly His Ile Arg Asp Phe Gln Ile Thr Ala Ser Gly
                 2030                2035                2040 caa tat gga cag tgg gcc cca aag ctg gcc aga ctt cat tat tcc gga    6378
Gln Tyr Gly Gln Trp Ala Pro Lys Leu Ala Arg Leu His Tyr Ser Gly
         2045                2050                2055 tca atc aat gcc tgg agc acc aag gag ccc ttt tct tgg atc aag gtg    6426
Ser Ile Asn Ala Trp Ser Thr Lys Glu Pro Phe Ser Trp Ile Lys Val
     2060                2065                2070 gat ctg ttg gca cca atg att att cac ggc atc aag acc cag ggt gcc    6474
Asp Leu Leu Ala Pro Met Ile Ile His Gly Ile Lys Thr Gln Gly Ala
 2075                2080                2085 cgt cag aag ttc tcc agc ctc tac atc tct cag ttt atc atc atg tat    6522
Arg Gln Lys Phe Ser Ser Leu Tyr Ile Ser Gln Phe Ile Ile Met Tyr
2090                2095                2100                2105 agt ctt gat ggg aag aag tgg cag act tat cga gga aat tcc act gga    6570
Ser Leu Asp Gly Lys Lys Trp Gln Thr Tyr Arg Gly Asn Ser Thr Gly
                 2110                2115                2120 acc tta atg gtc ttc ttt ggc aat gtg gat tca tct ggg ata aaa cac    6618
Thr Leu Met Val Phe Phe Gly Asn Val Asp Ser Ser Gly Ile Lys His
         2125                2130                2135 aat att ttt aac cct cca att att gct cga tac atc cgt ttg cac cca    6666
Asn Ile Phe Asn Pro Pro Ile Ile Ala Arg Tyr Ile Arg Leu His Pro
     2140                2145                2150 act cat tat agc att cgc agc act ctt cgc atg gag ttg atg ggc tgt    6714
Thr His Tyr Ser Ile Arg Ser Thr Leu Arg Met Glu Leu Met Gly Cys
 2155                2160                2165 gat tta aat agt tgc agc atg cca ttg gga atg gag agt aaa gca ata    6762
Asp Leu Asn Ser Cys Ser Met Pro Leu Gly Met Glu Ser Lys Ala Ile
2170                2175                2180                2185
```

| | | |
|---|---|---|
| tca gat gca cag att act gct tca tcc tac ttt acc aat atg ttt gcc<br>Ser Asp Ala Gln Ile Thr Ala Ser Ser Tyr Phe Thr Asn Met Phe Ala<br>              2190                         2195                   2200 | | 6810 |
| acc tgg tct cct tca aaa gct cga ctt cac ctc caa ggg agg agt aat<br>Thr Trp Ser Pro Ser Lys Ala Arg Leu His Leu Gln Gly Arg Ser Asn<br>              2205                       2210                   2215 | | 6858 |
| gcc tgg aga cct cag gtg aat aat cca aaa gag tgg ctg caa gtg gac<br>Ala Trp Arg Pro Gln Val Asn Asn Pro Lys Glu Trp Leu Gln Val Asp<br>              2220                       2225                   2230 | | 6906 |
| ttc cag aag aca atg aaa gtc aca gga gta act act cag gga gta aaa<br>Phe Gln Lys Thr Met Lys Val Thr Gly Val Thr Thr Gln Gly Val Lys<br>              2235                       2240                   2245 | | 6954 |
| tct ctg ctt acc agc atg tat gtg aag gag ttc ctc atc tcc agc agt<br>Ser Leu Leu Thr Ser Met Tyr Val Lys Glu Phe Leu Ile Ser Ser Ser<br>2250                       2255                     2260                   2265 | | 7002 |
| caa gat ggc cat cag tgg act ctc ttt ttt cag aat ggc aaa gta aag<br>Gln Asp Gly His Gln Trp Thr Leu Phe Phe Gln Asn Gly Lys Val Lys<br>              2270                       2275                   2280 | | 7050 |
| gtt ttt cag gga aat caa gac tcc ttc aca cct gtg gtg aac tct cta<br>Val Phe Gln Gly Asn Gln Asp Ser Phe Thr Pro Val Val Asn Ser Leu<br>              2285                       2290                   2295 | | 7098 |
| gac cca ccg tta ctg act cgc tac ctt cga att cac ccc cag agt tgg<br>Asp Pro Pro Leu Leu Thr Arg Tyr Leu Arg Ile His Pro Gln Ser Trp<br>              2300                       2305                   2310 | | 7146 |
| gtg cac cag att gcc ctg agg atg gag gtt ctg ggc tgc gag gca cag<br>Val His Gln Ile Ala Leu Arg Met Glu Val Leu Gly Cys Glu Ala Gln<br>              2315                       2320                   2325 | | 7194 |
| gac ctc tac tgagggtggc cactgcagca cctgccactg ccgtcacctc<br>Asp Leu Tyr<br>2330 | | 7243 |
| tccctcctca gctccagggc agtgtccctc cctggcttgc cttctacctt tgtgctaaat | | 7303 |
| cctagcagac actgccttga agcctcctga attaactatc atcagtcctg catttctttg | | 7363 |
| gtgggggggcc aggagggtgc atccaattta acttaactct tacctatttt ctgcagctgc | | 7423 |
| tcccagatta ctccttcctt ccaatataac taggcaaaaa gaagtgagga gaaacctgca | | 7483 |
| tgaaagcatt cttccctgaa aagttaggcc tctcagagtc accacttcct ctgttgtaga | | 7543 |
| aaaactatgt gatgaaactt tgaaaaagat atttatgatg ttaacatttc aggttaagcc | | 7603 |
| tcatacgttt aaaataaaac tctcagttgt ttattatcct gatcaagcat ggaacaaagc | | 7663 |
| atgtttcagg atcagatcaa tacaatcttg gagtcaaaag gcaaatcatt tggacaatct | | 7723 |
| gcaaaatgga gagaatacaa taactactac agtaaagtct gtttctgctt ccttacacat | | 7783 |
| agatataatt atgttattta gtcattatga ggggcacatt cttatctcca aaactagcat | | 7843 |
| tcttaaactg agaattatag atggggttca agaatcccta agtcccctga aattatataa | | 7903 |
| ggcattctgt ataaatgcaa atgtgcattt ttctgacgag tgtccataga tataaagcca | | 7963 |
| ttggtcttaa ttctgaccaa taaaaaaata agtcaggagg atgcaattgt tgaaagcttt | | 8023 |
| gaaataaaat aacatgtctt cttgaaattt gtgatggcca agaaagaaaa tgatgatgac | | 8083 |
| attaggcttc taaaggacat acatttaata tttctgtgga aatatgagga aaatccatgg | | 8143 |
| ttatctgaga taggagatac aaactttgta attctaataa tgcactcagt ttactctctc | | 8203 |
| cctctactaa tttcctgctg aaaataacac aacaaaaatg taacagggga aatttatatac | | 8263 |
| cgtgactgaa aactagagtc ctacttacat agttgaaata tcaaggaggt cagaagaaaa | | 8323 |
| ttggactggt gaaaacagaa aaaacactcc agtctgccat atcaccacac aataggatcc | | 8383 |
| cccttcttgc cctccacccc cataagattg tgaagggttt actgctcctt ccatctgcct | | 8443 |

```
gcaccccttc actatgacta cacagaactc tcctgatagt aaaggggct ggaggcaagg       8503 ataagttata gagcagttgg aggaagcatc caaagactgc aacccagggc aaatggaaaa      8563
caggagatcc taatatgaaa gaaaaatgga tcccaatctg agaaaaggca aaagaatggc      8623
tacttttttc tatgctggag tattttctaa taatcctgct tgacccttat ctgacctctt      8683
tggaaactat aacatagctg tcacagtata gtcacaatcc acaaatgatg caggtgcaaa      8743
tggtttatag ccctgtgaag ttcttaaagt ttagaggcta acttacagaa atgaataagt      8803
tgttttgttt tatagcccgg tagaggagtt aaccccaaag gtgatatggt tttatttcct      8863
gttatgttta acttgataat cttattttgg cattcttttc ccattgacta tatacatctc      8923
tatttctcaa atgttcatgg aactagctct tttattttcc tgctggtttc ttcagtaatg      8983
agttaaataa aacattgaca cataca                                           9009

<210> SEQ ID NO 6
<211> LENGTH: 2332
<212> TYPE: PRT
<213> ORGANISM: Homo sapiens

<400> SEQUENCE: 6

Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270
```

```
Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
        530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685
```

-continued

```
Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu Asn
1010                1015                1020

Ser Pro Ser Val Trp Gln Asn Ile Leu Glu Ser Asp Thr Glu Phe Lys
1025                1030                1035                1040

Lys Val Thr Pro Leu Ile His Asp Arg Met Leu Met Asp Lys Asn Ala
                1045                1050                1055

Thr Ala Leu Arg Leu Asn His Met Ser Asn Lys Thr Thr Ser Ser Lys
            1060                1065                1070

Asn Met Glu Met Val Gln Gln Lys Lys Glu Gly Pro Ile Pro Pro Asp
        1075                1080                1085

Ala Gln Asn Pro Asp Met Ser Phe Phe Lys Met Leu Phe Leu Pro Glu
1090                1095                1100
```

```
Ser Ala Arg Trp Ile Gln Arg Thr His Gly Lys Asn Ser Leu Asn Ser
1105                1110                1115                1120

Gly Gln Gly Pro Ser Pro Lys Gln Leu Val Ser Leu Gly Pro Glu Lys
            1125                1130                1135

Ser Val Glu Gly Gln Asn Phe Leu Ser Glu Lys Asn Lys Val Val Val
            1140                1145                1150

Gly Lys Gly Glu Phe Thr Lys Asp Val Gly Leu Lys Glu Met Val Phe
            1155                1160                1165

Pro Ser Ser Arg Asn Leu Phe Leu Thr Asn Leu Asp Asn Leu His Glu
            1170                1175                1180

Asn Asn Thr His Asn Gln Glu Lys Lys Ile Gln Glu Glu Ile Glu Lys
1185                1190                1195                1200

Lys Glu Thr Leu Ile Gln Glu Asn Val Val Leu Pro Gln Ile His Thr
                1205                1210                1215

Val Thr Gly Thr Lys Asn Phe Met Lys Asn Leu Phe Leu Leu Ser Thr
                1220                1225                1230

Arg Gln Asn Val Glu Gly Ser Tyr Glu Gly Ala Tyr Ala Pro Val Leu
                1235                1240                1245

Gln Asp Phe Arg Ser Leu Asn Asp Ser Thr Asn Arg Thr Lys Lys His
                1250                1255                1260

Thr Ala His Phe Ser Lys Lys Gly Glu Glu Asn Leu Glu Gly Leu
1265                1270                1275                1280

Gly Asn Gln Thr Lys Gln Ile Val Glu Lys Tyr Ala Cys Thr Thr Arg
                1285                1290                1295

Ile Ser Pro Asn Thr Ser Gln Gln Asn Phe Val Thr Gln Arg Ser Lys
                1300                1305                1310

Arg Ala Leu Lys Gln Phe Arg Leu Pro Leu Glu Glu Thr Glu Leu Glu
                1315                1320                1325

Lys Arg Ile Ile Val Asp Asp Thr Ser Thr Gln Trp Ser Lys Asn Met
                1330                1335                1340

Lys His Leu Thr Pro Ser Thr Leu Thr Gln Ile Asp Tyr Asn Glu Lys
1345                1350                1355                1360

Glu Lys Gly Ala Ile Thr Gln Ser Pro Leu Ser Asp Cys Leu Thr Arg
                1365                1370                1375

Ser His Ser Ile Pro Gln Ala Asn Arg Ser Pro Leu Pro Ile Ala Lys
                1380                1385                1390

Val Ser Ser Phe Pro Ser Ile Arg Pro Ile Tyr Leu Thr Arg Val Leu
                1395                1400                1405

Phe Gln Asp Asn Ser Ser His Leu Pro Ala Ala Ser Tyr Arg Lys Lys
                1410                1415                1420

Asp Ser Gly Val Gln Glu Ser Ser His Phe Leu Gln Gly Ala Lys Lys
1425                1430                1435                1440

Asn Asn Leu Ser Leu Ala Ile Leu Thr Leu Glu Met Thr Gly Asp Gln
                1445                1450                1455

Arg Glu Val Gly Ser Leu Gly Thr Ser Ala Thr Asn Ser Val Thr Tyr
                1460                1465                1470

Lys Lys Val Glu Asn Thr Val Leu Pro Lys Pro Asp Leu Pro Lys Thr
                1475                1480                1485

Ser Gly Lys Val Glu Leu Leu Pro Lys Val His Ile Tyr Gln Lys Asp
                1490                1495                1500

Leu Phe Pro Thr Glu Thr Ser Asn Gly Ser Pro Gly His Leu Asp Leu
1505                1510                1515                1520
```

```
Val Glu Gly Ser Leu Leu Gln Gly Thr Glu Gly Ala Ile Lys Trp Asn
            1525                1530                1535

Glu Ala Asn Arg Pro Gly Lys Val Pro Phe Leu Arg Val Ala Thr Glu
        1540                1545                1550

Ser Ser Ala Lys Thr Pro Ser Lys Leu Leu Asp Pro Leu Ala Trp Asp
    1555                1560                1565

Asn His Tyr Gly Thr Gln Ile Pro Lys Glu Glu Trp Lys Ser Gln Glu
1570                1575                1580

Lys Ser Pro Glu Lys Thr Ala Phe Lys Lys Asp Thr Ile Leu Ser
1585                1590                1595                1600

Leu Asn Ala Cys Glu Ser Asn His Ala Ile Ala Ile Asn Glu Gly
                1605                1610                1615

Gln Asn Lys Pro Glu Ile Glu Val Thr Trp Ala Lys Gln Gly Arg Thr
            1620                1625                1630

Glu Arg Leu Cys Ser Gln Asn Pro Pro Val Leu Lys Arg His Gln Arg
        1635                1640                1645

Glu Ile Thr Arg Thr Thr Leu Gln Ser Asp Gln Glu Glu Ile Asp Tyr
    1650                1655                1660

Asp Asp Thr Ile Ser Val Glu Met Lys Lys Glu Asp Phe Asp Ile Tyr
1665                1670                1675                1680

Asp Glu Asp Glu Asn Gln Ser Pro Arg Ser Phe Gln Lys Lys Thr Arg
                1685                1690                1695

His Tyr Phe Ile Ala Ala Val Glu Arg Leu Trp Asp Tyr Gly Met Ser
            1700                1705                1710

Ser Ser Pro His Val Leu Arg Asn Arg Ala Gln Ser Gly Ser Val Pro
        1715                1720                1725

Gln Phe Lys Lys Val Val Phe Gln Glu Phe Thr Asp Gly Ser Phe Thr
    1730                1735                1740

Gln Pro Leu Tyr Arg Gly Glu Leu Asn Glu His Leu Gly Leu Leu Gly
1745                1750                1755                1760

Pro Tyr Ile Arg Ala Glu Val Glu Asp Asn Ile Met Val Thr Phe Arg
                1765                1770                1775

Asn Gln Ala Ser Arg Pro Tyr Ser Phe Tyr Ser Ser Leu Ile Ser Tyr
            1780                1785                1790

Glu Glu Asp Gln Arg Gln Gly Ala Glu Pro Arg Lys Asn Phe Val Lys
        1795                1800                1805

Pro Asn Glu Thr Lys Thr Tyr Phe Trp Lys Val Gln His His Met Ala
    1810                1815                1820

Pro Thr Lys Asp Glu Phe Asp Cys Lys Ala Trp Ala Tyr Phe Ser Asp
1825                1830                1835                1840

Val Asp Leu Glu Lys Asp Val His Ser Gly Leu Ile Gly Pro Leu Leu
                1845                1850                1855

Val Cys His Thr Asn Thr Leu Asn Pro Ala His Gly Arg Gln Val Thr
            1860                1865                1870

Val Gln Glu Phe Ala Leu Phe Phe Thr Ile Phe Asp Glu Thr Lys Ser
        1875                1880                1885

Trp Tyr Phe Thr Glu Asn Met Glu Arg Asn Cys Arg Ala Pro Cys Asn
    1890                1895                1900

Ile Gln Met Glu Asp Pro Thr Phe Lys Glu Asn Tyr Arg Phe His Ala
1905                1910                1915                1920

Ile Asn Gly Tyr Ile Met Asp Thr Leu Pro Gly Leu Val Met Ala Gln
                1925                1930                1935
```

-continued

```
Asp Gln Arg Ile Arg Trp Tyr Leu Leu Ser Met Gly Ser Asn Glu Asn
            1940                1945                1950

Ile His Ser Ile His Phe Ser Gly His Val Thr Val Arg Lys Lys
            1955                1960                1965

Glu Glu Tyr Lys Met Ala Leu Tyr Asn Leu Tyr Pro Gly Val Phe Glu
            1970                1975                1980

Thr Val Glu Met Leu Pro Ser Lys Ala Gly Ile Trp Arg Val Glu Cys
1985                1990                1995                2000

Leu Ile Gly Glu His Leu His Ala Gly Met Ser Thr Leu Phe Leu Val
                2005                2010                2015

Tyr Ser Asn Lys Cys Gln Thr Pro Leu Gly Met Ala Ser Gly His Ile
            2020                2025                2030

Arg Asp Phe Gln Ile Thr Ala Ser Gly Gln Tyr Gly Gln Trp Ala Pro
            2035                2040                2045

Lys Leu Ala Arg Leu His Tyr Ser Gly Ser Ile Asn Ala Trp Ser Thr
            2050                2055                2060

Lys Glu Pro Phe Ser Trp Ile Lys Val Asp Leu Leu Ala Pro Met Ile
2065                2070                2075                2080

Ile His Gly Ile Lys Thr Gln Gly Ala Arg Gln Lys Phe Ser Ser Leu
            2085                2090                2095

Tyr Ile Ser Gln Phe Ile Ile Met Tyr Ser Leu Asp Gly Lys Lys Trp
            2100                2105                2110

Gln Thr Tyr Arg Gly Asn Ser Thr Gly Thr Leu Met Val Phe Phe Gly
            2115                2120                2125

Asn Val Asp Ser Ser Gly Ile Lys His Asn Ile Phe Asn Pro Pro Ile
            2130                2135                2140

Ile Ala Arg Tyr Ile Arg Leu His Pro Thr His Tyr Ser Ile Arg Ser
2145                2150                2155                2160

Thr Leu Arg Met Glu Leu Met Gly Cys Asp Leu Asn Ser Cys Ser Met
            2165                2170                2175

Pro Leu Gly Met Glu Ser Lys Ala Ile Ser Asp Ala Gln Ile Thr Ala
            2180                2185                2190

Ser Ser Tyr Phe Thr Asn Met Phe Ala Thr Trp Ser Pro Ser Lys Ala
            2195                2200                2205

Arg Leu His Leu Gln Gly Arg Ser Asn Ala Trp Arg Pro Gln Val Asn
            2210                2215                2220

Asn Pro Lys Glu Trp Leu Gln Val Asp Phe Gln Lys Thr Met Lys Val
2225                2230                2235                2240

Thr Gly Val Thr Thr Gln Gly Val Lys Ser Leu Leu Thr Ser Met Tyr
            2245                2250                2255

Val Lys Glu Phe Leu Ile Ser Ser Ser Gln Asp Gly His Gln Trp Thr
            2260                2265                2270

Leu Phe Phe Gln Asn Gly Lys Val Lys Val Phe Gln Gly Asn Gln Asp
            2275                2280                2285

Ser Phe Thr Pro Val Val Asn Ser Leu Asp Pro Pro Leu Leu Thr Arg
            2290                2295                2300

Tyr Leu Arg Ile His Pro Gln Ser Trp Val His Gln Ile Ala Leu Arg
2305                2310                2315                2320

Met Glu Val Leu Gly Cys Glu Ala Gln Asp Leu Tyr
            2325                2330
```

<210> SEQ ID NO 7
<211> LENGTH: 6996
<212> TYPE: DNA
<213> ORGANISM: Homo sapiens
<220> FEATURE:
<221> NAME/KEY: gene
<222> LOCATION: (0)...(0)
<223> OTHER INFORMATION: Factor VIII- Full Length coding sequence

<400> SEQUENCE: 7

| | | | | | | |
|---|---|---|---|---|---|---|
| gccaccagaa | gatactacct | gggtgcagtg | gaactgtcat | gggactatat | gcaaagtgat | 60 |
| ctcggtgagc | tgcctgtgga | cgcaagattt | cctcctagag | tgccaaaatc | ttttccattc | 120 |
| aacacctcag | tcgtgtacaa | aaagactctg | tttgtagaat | tcacggttca | ccttttcaac | 180 |
| atcgctaagc | caaggccacc | ctggatgggt | ctgctaggtc | ctaccatcca | ggctgaggtt | 240 |
| tatgatacag | tggtcattac | acttaagaac | atggcttccc | atcctgtcag | tcttcatgct | 300 |
| gttggtgtat | cctactggaa | agcttctgag | ggagctgaat | atgatgatca | gaccagtcaa | 360 |
| agggagaaag | aagatgataa | agtcttccct | ggtggaagcc | atacatatgt | ctggcaggtc | 420 |
| ctgaaagaga | tggtccaat | ggcctctgac | ccactgtgcc | ttacctactc | atatctttct | 480 |
| catgtggacc | tggtaaaaga | cttgaattca | ggcctcattg | gagccctact | agtatgtaga | 540 |
| gaagggagtc | tggccaagga | aaagacacag | accttgcaca | aatttatact | acttttgct | 600 |
| gtatttgatg | aagggaaaag | ttggcactca | gaaacaaaga | actccttgat | gcaggatagg | 660 |
| gatgctgcat | ctgctcgggc | ctggcctaaa | atgcacacag | tcaatggtta | tgtaaacagg | 720 |
| tctctgccag | gtctgattgg | atgccacagg | aaatcagtct | attggcatgt | gattggaatg | 780 |
| ggcaccactc | ctgaagtgca | ctcaatattc | ctcgaaggtc | acacatttct | tgtgaggaac | 840 |
| catcgccagg | cgtccttgga | aatctcgcca | ataactttcc | ttactgctca | aacactcttg | 900 |
| atggaccttg | gacagtttct | actgttttgt | catatctctt | cccaccaaca | tgatggcatg | 960 |
| gaagcttatg | tcaaagtaga | cagctgtcca | gaggaacccc | aactacgaat | gaaaaataat | 1020 |
| gaagaagcgg | aagactatga | tgatgatctt | actgattctg | aaatggatgt | ggtcaggttt | 1080 |
| gatgatgaca | actctccttc | ctttatccaa | attcgctcag | ttgccaagaa | gcatcctaaa | 1140 |
| acttgggtac | attacattgc | tgctgaagag | gaggactggg | actatgctcc | cttagtcctc | 1200 |
| gcccccgatg | acagaagtta | taaaagtcaa | tatttgaaca | atggccctca | gcggattggt | 1260 |
| aggaagtaca | aaaaagtccg | atttatggca | tacacagatg | aaaccttaa | gactcgtgaa | 1320 |
| gctattcagc | atgaatcagg | aatcttggga | cctttacttt | atggggaagt | ggagacaca | 1380 |
| ctgttgatta | tatttaagaa | tcaagcaagc | agaccatata | acatctaccc | tcacggaatc | 1440 |
| actgatgtcc | gtcctttgta | ttcaaggaga | ttaccaaaag | gtgtaaaaca | tttgaaggat | 1500 |
| tttccaattc | tgccaggaga | aatattcaaa | tataaatgga | cagtgactgt | agaagatggg | 1560 |
| ccaactaaat | cagatcctcg | gtgcctgacc | cgctattact | ctagtttcgt | taatatggag | 1620 |
| agagatctag | cttcaggact | cattggccct | ctcctcatct | gctacaaaga | atctgtagat | 1680 |
| caaagaggaa | accagataat | gtcagacaag | aggaatgtca | tcctgttttc | tgtatttgat | 1740 |
| gagaaccgaa | gctggtacct | cacagagaat | atacaacgct | ttctccccaa | tccagctgga | 1800 |
| gtgcagcttg | aggatccaga | gttccaagcc | tccaacatca | tgcacagcat | caatggctat | 1860 |
| gttttttgata | gtttgcagtt | gtcagtttgt | ttgcatgagg | tggcatactg | gtacattcta | 1920 |
| agcattggag | cacagactga | cttcctttct | gtcttcttct | ctggatatac | cttcaaacac | 1980 |
| aaaatggtct | atgaagacac | actcaccta | ttcccattct | caggagaaac | tgtcttcatg | 2040 |

```
tcgatggaaa acccaggtct atggattctg gggtgccaca actcagactt tcggaacaga    2100
ggcatgaccg ccttactgaa ggtttctagt tgtgacaaga acactggtga ttattacgag    2160
gacagttatg aagatatttc agcatacttg ctgagtaaaa acaatgccat tgaaccaaga    2220
agcttctccc agaattcaag acaccctagc actaggcaaa agcaatttaa tgccaccaca    2280
attccagaaa atgacataga gaagactgac ccttggtttg cacacagaac acctatgcct    2340
aaaatacaaa atgtctcctc tagtgatttg ttgatgctct tgcgacagag tcctactcca    2400
catgggctat ccttatctga tctccaagaa gccaaatatg acttttttc tgatgatcca    2460 tcacctggag caatagacag taataacagc ctgtctgaaa tgacacactt caggccacag    2520
ctccatcaca gtggggacat ggtatttacc cctgagtcag gcctccaatt aagattaaat    2580
gagaaactgg ggacaactgc agcaacagag ttgaagaaac ttgatttcaa agttctagt    2640 acatcaaata atctgatttc aacaattcca tcagacaatt tggcagcagg tactgataat    2700
acaagttcct taggaccccc aagtatgcca gttcattatg atagtcaatt agataccact    2760
ctatttggca aaaagtcatc tccccttact gagtctggtg gacctctgag cttgagtgaa    2820
gaaaataatg attcaaagtt gttagaatca ggtttaatga atagccaaga aagttcatgg    2880
ggaaaaaatg tatcgtcaac agagagtggt aggttattta agggaaaag agctcatgga    2940 cctgctttgt tgactaaaga taatgcctta ttcaaagtta gcatctcttt gttaaagaca    3000
aacaaaactt ccaataattc agcaactaat agaaagactc acattgatgg cccatcatta    3060
ttaattgaga atagtccatc agtctggcaa aatatattag aaagtgacac tgagtttaaa    3120
aaagtgacac ctttgattca tgacagaatg cttatggaca aaaatgctac agctttgagg    3180
ctaaatcata tgtcaaataa aactacttca tcaaaaaaca tggaaatggt ccaacagaaa    3240
aaagagggcc ccattccacc agatgcacaa aatccagata tgtcgttctt taagatgcta    3300
ttcttgccag aatcagcaag gtggatacaa aggactcatg gaaagaactc tctgaactct    3360
gggcaaggcc ccagtccaaa gcaattagta tccttaggac cagaaaaatc tgtggaaggt    3420
cagaatttct tgtctgagaa aaacaaagtg gtagtaggaa agggtgaatt tacaaaggac    3480
gtaggactca aagagatggt ttttccaagc agcagaaacc tatttcttac taacttggat    3540
aatttacatg aaaataatac acacaatcaa gaaaaaaaa ttcaggaaga aatagaaaag    3600
aaggaaacat taatccaaga gaatgtagtt ttgcctcaga tacatacagt gactggcact    3660
aagaatttca tgaagaacct tttcttactg agcactaggc aaaatgtaga aggttcatat    3720
gagggggcat atgctccagt acttcaagat tttaggtcat taaatgattc aacaaataga    3780
acaaagaaac acacagctca tttctcaaaa aaggggagg aagaaaactt ggaaggcttg    3840
ggaaatcaaa ccaagcaaat tgtagagaaa tatgcatgca ccacaaggat atctcctaat    3900
acaagccagc agaattttgt cacgcaacgt agtaagagag ctttgaaaca attcagactc    3960
ccactagaag aaacagaact tgaaaaaagg ataattgtgg atgacacctc aacccagtgg    4020
tccaaaaaca tgaaacattt gaccccgagc accctcacac agatagacta caatgagaag    4080
gagaaagggg ccattactca gtctccctta tcagattgcc ttacgaggag tcatagcatc    4140
cctcaagcaa atagatctcc attacccatt gcaaggtat catcatttcc atctattaga    4200
cctatatatc tgaccagggt cctattccaa gacaactctt ctcatcttcc agcagcatct    4260
tatagaaaga aagattctgg ggtccaagaa agcagtcatt tcttacaagg agccaaaaaa    4320 aataacccttt ctttagccat tctaaccttg gagatgactg tgatcaaag agaggttggc    4380 tccctgggga caagtgccac aaattcagtc acatacaaga aagttgagaa cactgttctc    4440
```

```
ccgaaaccag acttgcccaa aacatctggc aaagttgaat tgcttccaaa agttcacatt   4500
tatcagaagg acctattccc tacgaaaact agcaatgggc ctcctggcca tctggatctc   4560
gtggaaggga gccttcttca gggaacagag ggagcgatta agtggaatga agcaaacaga   4620
cctggaaaag ttcccttttct gagagtagca acagaaagct ctgcaaagac tccctccaag   4680
ctattggatc ctcttgcttg ggataaccac tatggtactc agataccaaa agaagagtgg   4740
aaatcccaag agaagtcacc agaaaaaaca gcttttaaga aaaaggatac cattttgtcc   4800
ctgaacgctt gtgaaagcaa tcatgcaata gcagcaataa atgagggaca aaataagccc   4860
gaaatagaag tcacctgggc aaagcaaggt aggactgaaa ggctgtgctc tcaaaaccca   4920
ccagtcttga aacgccatca acgggaaata actcgtacta ctcttcagtc agatcaagag   4980
gaaattgact atgatgatac catatcagtt gaaatgaaga aggaagattt tgacattttat   5040
gatgaggatg aaaatcagag cccccgcagc tttcaaaaga aaacacgaca ctattttatt   5100
gctgcagtgg agaggctctg ggattatggg atgagtagct ccccacatgt tctaagaaac   5160
agggctcaga gtggcagtgt ccctcagttc aagaaagttg ttttccagga atttactgat   5220
ggctccttta ctcagccctt ataccgtgga gaactaaatg aacatttggg actcctgggg   5280
ccatatataa gagcagaagt tgaagataat atcatggtaa ctttcagaaa tcaggcctct   5340
cgtcccctatt ccttctattc tagccttatt tcttatgagg aagatcagag gcaaggagca   5400
gaacctagaa aaaactttgt caagcctaat gaaaccaaaa cttactttttg gaaagtgcaa   5460
catcatatgg cacccactaa agatgagttt gactgcaaag cctgggctta tttctctgat   5520
gttgacctgg aaaagatgt gcactcaggc ctgattggac cccttctggt ctgccacact   5580
aacacactga accctgctca tgggagacaa gtgacagtac aggaatttgc tctgttttttc   5640
accatctttg atgagaccaa aagctggtac ttcactgaaa atatggaaag aaactgcagg   5700
gctccctgca atatccagat ggaagatccc acttttaaag agaattatcg cttccatgca   5760
atcaatggct acataatgga tacactacct ggcttagtaa tggctcagga tcaaaggatt   5820
cgatggtatc tgctcagcat gggcagcaat gaaaacatcc attctattca tttcagtgga   5880
catgtgttca ctgtacgaaa aaaagaggag tataaaatgg cactgtacaa tctctatcca   5940
ggtgtttttg agacagtgga aatgttacca tccaaagctg gaatttggcg ggtggaatgc   6000
cttattggcg agcatctaca tgctgggatg agcacacttt ttctggtgta cagcaataag   6060
tgtcagactc ccctgggaat ggcttctgga cacattagag attttcagat tacagcttca   6120
ggacaatatg gacagtgggc cccaaagctg gccagacttc attattccgg atcaatcaat   6180
gcctggagca ccaaggagcc cttttcttgg atcaaggtgg atctgttggc accaatgatt   6240
attcacggca tcaagaccca gggtgcccgt cagaagttct ccagcctcta catctctcag   6300
tttatcatca tgtatagtct tgatgggaag aagtggcaga cttatcgagg aaattccact   6360
ggaaccttaa tggtcttctt tggcaatgtg gattcatctg gataaaaca caatatttt   6420
aaccctccaa ttattgctcg atacatccgt ttgcacccaa ctcattatag cattcgcagc   6480
actcttcgca tggagttgat gggctgtgat ttaaatagtt gcagcatgcc attgggaatg   6540
gagagtaaag caatatcaga tgcacagatt actgcttcat cctactttac caatatgttt   6600
gccacctggt ctccttcaaa agctcgactt cacctccaag ggaggagtaa tgcctggaga   6660
cctcaggtga ataatccaaa agagtggctg caagtggact tccagaagac aatgaaagtc   6720
acaggagtaa ctactcaggg agtaaaaatct ctgcttacca gcatgtatgt gaaggagttc   6780
ctcatctcca gcagtcaaga tggccatcag tggactctct ttttttcagaa tggcaaagta   6840
```

```
aaggttttc agggaaatca agactccttc acacctgtgg tgaactctct agacccaccg   6900
ttactgactc gctaccttcg aattcacccc cagagttggg tgcaccagat tgccctgagg   6960
atggaggttc tgggctgcga ggcacaggac ctctac                            6996
```

<210> SEQ ID NO 8
<211> LENGTH: 2319
<212> TYPE: PRT
<213> ORGANISM: Mus musculus

<400> SEQUENCE: 8

```
Met Gln Ile Ala Leu Phe Ala Cys Phe Phe Leu Ser Leu Phe Asn Phe
 1               5                  10                  15

Cys Ser Ser Ala Ile Arg Arg Tyr Tyr Leu Gly Ala Val Glu Leu Ser
                20                  25                  30

Trp Asn Tyr Ile Gln Ser Asp Leu Leu Ser Val Leu His Thr Asp Ser
            35                  40                  45

Arg Phe Leu Pro Arg Met Ser Thr Ser Phe Pro Phe Asn Thr Ser Ile
        50                  55                  60

Met Tyr Lys Lys Thr Val Phe Val Glu Tyr Lys Asp Gln Leu Phe Asn
65                  70                  75                  80

Ile Ala Lys Pro Arg Pro Pro Trp Met Gly Leu Leu Gly Pro Thr Ile
                85                  90                  95

Trp Thr Glu Val His Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Asp Glu Tyr Glu Asp Gln Thr Ser Gln Met Glu Lys Glu
    130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Met Ser His Val Asp Leu Val Lys Asp Leu Asn Ser Gly Leu
            180                 185                 190

Ile Gly Ala Leu Leu Val Cys Lys Glu Gly Ser Leu Ser Lys Glu Arg
        195                 200                 205

Thr Gln Met Leu Tyr Gln Phe Val Leu Leu Phe Ala Val Phe Asp Glu
    210                 215                 220

Gly Lys Ser Trp His Ser Glu Thr Asn Asp Ser Tyr Thr Gln Ser Met
225                 230                 235                 240

Asp Ser Ala Ser Ala Arg Asp Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Ile His Ser
        275                 280                 285

Ile Phe Leu Glu Gly His Thr Phe Phe Val Arg Asn His Arg Gln Ala
    290                 295                 300

Ser Leu Glu Ile Ser Pro Ile Thr Phe Leu Thr Ala Gln Thr Leu Leu
305                 310                 315                 320

Ile Asp Leu Gly Gln Phe Leu Leu Phe Cys His Ile Ser Ser His Lys
                325                 330                 335

His Asp Gly Met Glu Ala Tyr Val Lys Val Asp Ser Cys Pro Glu Glu
            340                 345                 350
```

```
Ser Gln Trp Gln Lys Lys Asn Asn Glu Glu Met Glu Asp Tyr Asp
        355                 360                 365

Asp Asp Leu Tyr Ser Glu Met Asp Met Phe Thr Leu Asp Tyr Asp Ser
        370                 375                 380

Ser Pro Phe Ile Gln Ile Arg Ser Val Ala Lys Lys Tyr Pro Lys Thr
385                 390                 395                 400

Trp Ile His Tyr Ile Ser Ala Glu Glu Asp Trp Asp Tyr Ala Pro
                    405                 410                 415

Ser Val Pro Thr Ser Asp Asn Gly Ser Tyr Lys Ser Gln Tyr Leu Ser
            420                 425                 430

Asn Gly Pro His Arg Ile Gly Arg Lys Tyr Lys Val Arg Phe Ile
                435                 440                 445

Ala Tyr Thr Asp Glu Thr Phe Lys Thr Arg Glu Thr Ile Gln His Glu
        450                 455                 460

Ser Gly Leu Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Ser Pro Leu His Ala Arg Arg Leu Pro Arg
            500                 505                 510

Gly Ile Lys His Val Lys Asp Leu Pro Ile His Pro Gly Glu Ile Phe
        515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Ile Asn Pro Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Met Met Ser Asp Lys Arg Asn Val
            580                 585                 590

Ile Leu Phe Ser Ile Phe Asp Glu Asn Gln Ser Trp Tyr Ile Thr Glu
                595                 600                 605

Asn Met Gln Arg Phe Leu Pro Asn Ala Ala Lys Thr Gln Pro Gln Asp
        610                 615                 620

Pro Gly Phe Gln Ala Ser Asn Ile Met His Ser Ile Asn Gly Tyr Val
625                 630                 635                 640

Phe Asp Ser Leu Glu Leu Thr Val Cys Leu His Glu Val Ala Tyr Trp
                645                 650                 655

His Ile Leu Ser Val Gly Ala Gln Thr Asp Phe Leu Ser Ile Phe Phe
            660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
        690                 695                 700

Gly Leu Trp Val Leu Gly Cys His Asn Ser Asp Phe Arg Lys Arg Gly
705                 710                 715                 720

Met Thr Ala Leu Leu Lys Val Ser Ser Cys Asp Lys Ser Thr Ser Asp
                725                 730                 735

Tyr Tyr Glu Glu Ile Tyr Glu Asp Ile Pro Thr Gln Leu Val Asn Glu
            740                 745                 750

Asn Asn Val Ile Asp Pro Arg Ser Phe Phe Gln Asn Thr Asn His Pro
                755                 760                 765
```

-continued

```
Asn Thr Arg Lys Lys Lys Phe Lys Asp Ser Thr Ile Pro Lys Asn Asp
770                 775                 780

Met Glu Lys Ile Glu Pro Gln Phe Glu Glu Ile Ala Glu Met Leu Lys
785                 790                 795                 800

Val Gln Ser Val Ser Val Ser Asp Met Leu Met Leu Leu Gly Gln Ser
                805                 810                 815

His Pro Thr Pro His Gly Leu Phe Leu Ser Asp Gly Gln Glu Ala Ile
            820                 825                 830

Tyr Glu Ala Ile His Asp Asp His Ser Pro Asn Ala Ile Asp Ser Asn
        835                 840                 845

Glu Gly Pro Ser Lys Val Thr Gln Leu Arg Pro Glu Ser His His Ser
850                 855                 860

Glu Lys Ile Val Phe Thr Pro Gln Pro Gly Leu Gln Leu Arg Ser Asn
865                 870                 875                 880

Lys Ser Leu Glu Thr Thr Ile Glu Val Lys Trp Lys Lys Leu Gly Leu
                885                 890                 895

Gln Val Ser Ser Leu Pro Ser Asn Leu Met Thr Thr Ile Leu Ser
            900                 905                 910

Asp Asn Leu Lys Ala Thr Phe Glu Lys Thr Asp Ser Ser Gly Phe Pro
        915                 920                 925

Asp Met Pro Val His Ser Ser Lys Leu Ser Thr Ala Phe Gly
930                 935                 940

Lys Lys Ala Tyr Ser Leu Val Gly Ser His Val Pro Leu Asn Ala Ser
945                 950                 955                 960

Glu Glu Asn Ser Asp Ser Asn Ile Leu Asp Ser Thr Leu Met Tyr Ser
                965                 970                 975

Gln Glu Ser Leu Pro Arg Asp Asn Ile Leu Ser Ile Glu Asn Asp Arg
            980                 985                 990

Leu Leu Arg Glu Lys Arg Phe His Gly Ile Ala Leu Leu Thr Lys Asp
        995                 1000                1005

Asn Thr Leu Phe Lys Asp Asn Val Ser Leu Met Lys Thr Asn Lys Thr
        1010                1015                1020

Tyr Asn His Ser Thr Thr Asn Glu Lys Leu His Thr Glu Ser Pro Thr
1025                1030                1035                1040

Ser Ile Glu Asn Ser Thr Thr Asp Leu Gln Asp Ala Ile Leu Lys Val
            1045                1050                1055

Asn Ser Glu Ile Gln Glu Val Thr Ala Leu Ile His Asp Gly Thr Leu
        1060                1065                1070

Leu Gly Lys Asn Ser Thr Tyr Leu Arg Leu Asn His Met Leu Asn Arg
    1075                1080                1085

Thr Thr Ser Thr Lys Asn Lys Asp Ile Phe His Arg Lys Asp Glu Asp
        1090                1095                1100

Pro Ile Pro Gln Asp Glu Glu Asn Thr Ile Met Pro Phe Ser Lys Met
1105                1110                1115                1120

Leu Phe Leu Ser Glu Ser Ser Asn Trp Phe Lys Thr Asn Gly Asn
                1125                1130                1135

Asn Ser Leu Asn Ser Glu Gln Glu His Ser Pro Lys Gln Leu Val Tyr
            1140                1145                1150

Leu Met Phe Lys Lys Tyr Val Lys Asn Gln Ser Phe Leu Ser Glu Lys
        1155                1160                1165

Asn Lys Val Thr Val Glu Gln Asp Gly Phe Thr Lys Asn Ile Gly Leu
    1170                1175                1180
```

-continued

```
Lys Asp Met Ala Phe Pro His Asn Met Ser Ile Phe Leu Thr Thr Leu
1185                1190                1195                1200

Ser Asn Val His Glu Asn Gly Arg His Asn Gln Glu Lys Asn Ile Gln
            1205                1210                1215

Glu Glu Ile Glu Lys Glu Ala Leu Ile Glu Lys Val Val Leu Pro
        1220                1225                1230

Gln Val His Glu Ala Thr Gly Ser Lys Asn Phe Leu Lys Asp Ile Leu
            1235                1240                1245

Ile Leu Gly Thr Arg Gln Asn Ile Ser Leu Tyr Glu Val His Val Pro
        1250                1255                1260

Val Leu Gln Asn Ile Thr Ser Ile Asn Asn Ser Thr Asn Thr Val Gln
1265                1270                1275                1280

Ile His Met Glu His Phe Phe Lys Arg Arg Lys Asp Lys Glu Thr Asn
            1285                1290                1295

Ser Glu Gly Leu Val Asn Lys Thr Arg Glu Met Val Lys Asn Tyr Pro
        1300                1305                1310

Ser Gln Lys Asn Ile Thr Thr Gln Arg Ser Lys Arg Ala Leu Gly Gln
            1315                1320                1325

Phe Arg Leu Ser Thr Gln Trp Leu Lys Thr Ile Asn Cys Ser Thr Gln
        1330                1335                1340

Cys Ile Ile Lys Gln Ile Asp His Ser Lys Glu Met Lys Lys Phe Ile
1345                1350                1355                1360

Thr Lys Ser Ser Leu Ser Asp Ser Ser Val Ile Lys Ser Thr Thr Gln
            1365                1370                1375

Thr Asn Ser Ser Asp Ser His Ile Val Lys Thr Ser Ala Phe Pro Pro
        1380                1385                1390

Ile Asp Leu Lys Arg Ser Pro Phe Gln Asn Lys Phe Ser His Val Gln
            1395                1400                1405

Ala Ser Ser Tyr Ile Tyr Asp Phe Lys Thr Lys Ser Ser Arg Ile Gln
        1410                1415                1420

Glu Ser Asn Asn Phe Leu Lys Glu Thr Lys Ile Asn Asn Pro Ser Leu
1425                1430                1435                1440

Ala Ile Leu Pro Trp Asn Met Phe Ile Asp Gln Gly Lys Phe Thr Ser
            1445                1450                1455

Pro Gly Lys Ser Asn Thr Asn Ser Val Thr Tyr Lys Lys Arg Glu Asn
        1460                1465                1470

Ile Ile Phe Leu Lys Pro Thr Leu Pro Glu Glu Ser Gly Lys Ile Glu
            1475                1480                1485

Leu Leu Pro Gln Val Ser Ile Gln Glu Glu Ile Leu Pro Thr Glu
        1490                1495                1500

Thr Ser His Gly Ser Pro Gly His Leu Asn Leu Met Lys Glu Val Phe
1505                1510                1515                1520

Leu Gln Lys Ile Gln Gly Pro Thr Lys Trp Asn Lys Ala Lys Arg His
            1525                1530                1535

Gly Glu Ser Ile Lys Gly Lys Thr Glu Ser Ser Lys Asn Thr Arg Ser
        1540                1545                1550

Lys Leu Leu Asn His His Ala Trp Asp Tyr His Tyr Ala Ala Gln Ile
            1555                1560                1565

Pro Lys Asp Met Trp Lys Ser Lys Glu Lys Ser Pro Glu Ile Ile Ser
        1570                1575                1580

Ile Lys Gln Glu Asp Thr Ile Leu Ser Leu Arg Pro His Gly Asn Ser
1585                1590                1595                1600
```

-continued

```
His Ser Ile Gly Ala Asn Glu Lys Gln Asn Trp Pro Gln Arg Glu Thr
                1605                1610                1615
Thr Trp Val Lys Gln Gly Gln Thr Gln Arg Thr Cys Ser Gln Ile Pro
            1620                1625                1630
Pro Val Leu Lys Arg His Gln Arg Glu Leu Ser Ala Phe Gln Ser Glu
        1635                1640                1645
Gln Glu Ala Thr Asp Tyr Asp Asp Ala Ile Thr Ile Glu Thr Ile Glu
    1650                1655                1660
Asp Phe Asp Ile Tyr Ser Glu Asp Ile Lys Gln Gly Pro Arg Ser Phe
1665                1670                1675                1680
Gln Gln Lys Thr Arg His Tyr Phe Ile Ala Ala Val Glu Arg Leu Trp
                1685                1690                1695
Asp Tyr Gly Met Ser Thr Ser His Val Leu Arg Asn Arg Tyr Gln Ser
            1700                1705                1710
Asp Asn Val Pro Gln Phe Lys Lys Val Val Phe Gln Glu Phe Thr Asp
        1715                1720                1725
Gly Ser Phe Ser Gln Pro Leu Tyr Arg Gly Glu Leu Asn Glu His Leu
    1730                1735                1740
Gly Leu Leu Gly Pro Tyr Ile Arg Ala Glu Val Glu Asp Asn Ile Met
1745                1750                1755                1760
Val Thr Phe Lys Asn Gln Ala Ser Arg Pro Tyr Ser Phe Tyr Ser Ser
                1765                1770                1775
Leu Ile Ser Tyr Lys Glu Asp Gln Arg Gly Glu Glu Pro Arg Arg Asn
            1780                1785                1790
Phe Val Lys Pro Asn Glu Thr Lys Ile Tyr Phe Trp Lys Val Gln His
        1795                1800                1805
His Met Ala Pro Thr Glu Asp Glu Phe Asp Cys Lys Ala Trp Ala Tyr
    1810                1815                1820
Phe Ser Asp Val Asp Leu Glu Arg Asp Met His Ser Gly Leu Ile Gly
1825                1830                1835                1840
Pro Leu Leu Ile Cys His Ala Asn Thr Leu Asn Pro Ala His Gly Arg
                1845                1850                1855
Gln Val Ser Val Gln Glu Phe Ala Leu Leu Phe Thr Ile Phe Asp Glu
            1860                1865                1870
Thr Lys Ser Trp Tyr Phe Thr Glu Asn Val Lys Arg Asn Cys Lys Thr
        1875                1880                1885
Pro Cys Asn Phe Gln Met Glu Asp Pro Thr Leu Lys Glu Asn Tyr Arg
    1890                1895                1900
Phe His Ala Ile Asn Gly Tyr Val Met Asp Thr Leu Pro Gly Leu Val
1905                1910                1915                1920
Met Ala Gln Asp Gln Arg Ile Arg Trp Tyr Leu Leu Ser Met Gly Asn
                1925                1930                1935
Asn Glu Asn Ile Gln Ser Ile His Phe Ser Gly His Val Phe Thr Val
            1940                1945                1950
Arg Lys Lys Glu Glu Tyr Lys Met Ala Val Tyr Asn Leu Tyr Pro Gly
        1955                1960                1965
Val Phe Glu Thr Leu Glu Met Ile Pro Ser Arg Ala Gly Ile Trp Arg
    1970                1975                1980
Val Glu Cys Leu Ile Gly Glu His Leu Gln Ala Gly Met Ser Thr Leu
1985                1990                1995                2000
Phe Leu Val Tyr Ser Lys Gln Cys Gln Ile Pro Leu Gly Met Ala Ser
                2005                2010                2015
```

-continued

```
Gly Ser Ile Arg Asp Phe Gln Ile Thr Ala Ser Gly His Tyr Gly Gln
            2020                2025                2030

Trp Ala Pro Asn Leu Ala Arg Leu His Tyr Ser Gly Ser Ile Asn Ala
            2035                2040            2045

Trp Ser Thr Lys Glu Pro Phe Ser Trp Ile Lys Val Asp Leu Leu Ala
    2050                2055                2060

Pro Met Ile Val His Gly Ile Lys Thr Gln Gly Ala Arg Gln Lys Phe
2065            2070                2075                2080

Ser Ser Leu Tyr Ile Ser Gln Phe Ile Ile Met Tyr Ser Leu Asp Gly
                2085                2090                2095

Lys Lys Trp Leu Ser Tyr Gln Gly Asn Ser Thr Gly Thr Leu Met Val
            2100                2105                2110

Phe Phe Gly Asn Val Asp Ser Ser Gly Ile Lys His Asn Ser Phe Asn
            2115                2120                2125

Pro Pro Ile Ile Ala Arg Tyr Ile Arg Leu His Pro Thr His Ser Ser
2130                2135                2140

Ile Arg Ser Thr Leu Arg Met Glu Leu Met Gly Cys Asp Leu Asn Ser
2145                2150                2155                2160

Cys Ser Ile Pro Leu Gly Met Glu Ser Lys Val Ile Ser Asp Thr Gln
                2165                2170                2175

Ile Thr Ala Ser Ser Tyr Phe Thr Asn Met Phe Ala Thr Trp Ser Pro
            2180                2185                2190

Ser Gln Ala Arg Leu His Leu Gln Gly Arg Thr Asn Ala Trp Arg Pro
                2195                2200                2205

Gln Val Asn Asp Pro Lys Gln Trp Leu Gln Val Asp Leu Gln Lys Thr
    2210                2215                2220

Met Lys Val Thr Gly Ile Ile Thr Gln Gly Val Lys Ser Leu Phe Thr
2225                2230                2235                2240

Ser Met Phe Val Lys Glu Phe Leu Ile Ser Ser Ser Gln Asp Gly His
                2245                2250                2255

His Trp Thr Gln Ile Leu Tyr Asn Gly Lys Val Lys Val Phe Gln Gly
            2260                2265                2270

Asn Gln Asp Ser Ser Thr Pro Met Met Asn Ser Leu Asp Pro Pro Leu
            2275                2280                2285

Leu Thr Arg Tyr Leu Arg Ile His Pro Gln Ile Trp Glu His Gln Ile
    2290                2295                2300

Ala Leu Arg Leu Glu Ile Leu Gly Cys Glu Ala Gln Gln Gln Tyr
2305                2310                2315

<210> SEQ ID NO 9
<211> LENGTH: 14
<212> TYPE: PRT
<213> ORGANISM: Homo sapeins
<220> FEATURE:
<221> NAME/KEY: DOMAIN
<222> LOCATION: (1)...(14)
<223> OTHER INFORMATION: Linker sequence

<400> SEQUENCE: 9

Ser Phe Ser Gln Asn Pro Pro Val Leu Lys Arg His Gln Arg
 1               5                   10

<210> SEQ ID NO 10
<211> LENGTH: 4
<212> TYPE: PRT
<213> ORGANISM: Homo sapiens
```

-continued

```
<400> SEQUENCE: 10

Arg His Gln Arg
 1

<210> SEQ ID NO 11
<211> LENGTH: 24
<212> TYPE: PRT
<213> ORGANISM: Sus Scrofa
<220> FEATURE:
<221> NAME/KEY: DOMAIN
<222> LOCATION: (1)...(24)
<223> OTHER INFORMATION: Linker sequence

<400> SEQUENCE: 11

Ser Phe Ala Gln Asn Ser Arg Pro Pro Ser Ala Ser Ala Pro Lys Pro
 1               5                   10                  15

Pro Val Leu Arg Arg His Gln Arg
            20

<210> SEQ ID NO 12
<211> LENGTH: 4371
<212> TYPE: DNA
<213> ORGANISM: Homo sapiens
<220> FEATURE:
<221> NAME/KEY: CDS
<222> LOCATION: (1)...(4371)
<223> OTHER INFORMATION: B domain-deleted factor VIII
      (HSQ)

<400> SEQUENCE: 12
```

| | | | | | | | | | | | | | | | | |
|---|---|---|---|---|---|---|---|---|---|---|---|---|---|---|---|---|
| atg | caa | ata | gag | ctc | tcc | acc | tgc | ttc | ttt | ctg | tgc | ctt | ttg | cga | ttc | 48 |
| Met | Gln | Ile | Glu | Leu | Ser | Thr | Cys | Phe | Phe | Leu | Cys | Leu | Leu | Arg | Phe | |
| 1 | | | | 5 | | | | | 10 | | | | | 15 | | |
| tgc | ttt | agt | gcc | acc | aga | aga | tac | tac | ctg | ggt | gca | gtg | gaa | ctg | tca | 96 |
| Cys | Phe | Ser | Ala | Thr | Arg | Arg | Tyr | Tyr | Leu | Gly | Ala | Val | Glu | Leu | Ser | |
| | | | 20 | | | | | 25 | | | | | 30 | | | |
| tgg | gac | tat | atg | caa | agt | gat | ctc | ggt | gag | ctg | cct | gtg | gac | gca | aga | 144 |
| Trp | Asp | Tyr | Met | Gln | Ser | Asp | Leu | Gly | Glu | Leu | Pro | Val | Asp | Ala | Arg | |
| | | 35 | | | | | 40 | | | | | 45 | | | | |
| ttt | cct | cct | aga | gtg | cca | aaa | tct | ttt | cca | ttc | aac | acc | tca | gtc | gtg | 192 |
| Phe | Pro | Pro | Arg | Val | Pro | Lys | Ser | Phe | Pro | Phe | Asn | Thr | Ser | Val | Val | |
| | 50 | | | | | 55 | | | | | 60 | | | | | |
| tac | aaa | aag | act | ctg | ttt | gta | gaa | ttc | acg | gtt | cac | ctt | ttc | aac | atc | 240 |
| Tyr | Lys | Lys | Thr | Leu | Phe | Val | Glu | Phe | Thr | Val | His | Leu | Phe | Asn | Ile | |
| 65 | | | | | 70 | | | | | 75 | | | | | 80 | |
| gct | aag | cca | agg | cca | ccc | tgg | atg | ggt | ctg | cta | ggt | cct | acc | atc | cag | 288 |
| Ala | Lys | Pro | Arg | Pro | Pro | Trp | Met | Gly | Leu | Leu | Gly | Pro | Thr | Ile | Gln | |
| | | | 85 | | | | | 90 | | | | | 95 | | | |
| gct | gag | gtt | tat | gat | aca | gtg | gtc | att | aca | ctt | aag | aac | atg | gct | tcc | 336 |
| Ala | Glu | Val | Tyr | Asp | Thr | Val | Val | Ile | Thr | Leu | Lys | Asn | Met | Ala | Ser | |
| | | 100 | | | | | 105 | | | | | 110 | | | | |
| cat | cct | gtc | agt | ctt | cat | gct | gtt | ggt | gta | tcc | tac | tgg | aaa | gct | tct | 384 |
| His | Pro | Val | Ser | Leu | His | Ala | Val | Gly | Val | Ser | Tyr | Trp | Lys | Ala | Ser | |
| | 115 | | | | | 120 | | | | | 125 | | | | | |
| gag | gga | gct | gaa | tat | gat | gat | cag | acc | agt | caa | agg | gag | aaa | gaa | gat | 432 |
| Glu | Gly | Ala | Glu | Tyr | Asp | Asp | Gln | Thr | Ser | Gln | Arg | Glu | Lys | Glu | Asp | |
| | 130 | | | | | 135 | | | | | 140 | | | | | |
| gat | aaa | gtc | ttc | cct | ggt | gga | agc | cat | aca | tat | gtc | tgg | cag | gtc | ctg | 480 |
| Asp | Lys | Val | Phe | Pro | Gly | Gly | Ser | His | Thr | Tyr | Val | Trp | Gln | Val | Leu | |
| 145 | | | | | 150 | | | | | 155 | | | | | 160 | |
| aaa | gag | aat | ggt | cca | atg | gcc | tct | gac | cca | ctg | tgc | ctt | acc | tac | tca | 528 |
| Lys | Glu | Asn | Gly | Pro | Met | Ala | Ser | Asp | Pro | Leu | Cys | Leu | Thr | Tyr | Ser | |
| | | | 165 | | | | | 170 | | | | | 175 | | | |

```
tat ctt tct cat gtg gac ctg gta aaa gac ttg aat tca ggc ctc att         576
Tyr Leu Ser His Val Asp Leu Val Lys Asp Leu Asn Ser Gly Leu Ile
            180                 185                 190 gga gcc cta cta gta tgt aga gaa ggg agt ctg gcc aag gaa aag aca         624
Gly Ala Leu Leu Val Cys Arg Glu Gly Ser Leu Ala Lys Glu Lys Thr
        195                 200                 205 cag acc ttg cac aaa ttt ata cta ctt ttt gct gta ttt gat gaa ggg         672
Gln Thr Leu His Lys Phe Ile Leu Leu Phe Ala Val Phe Asp Glu Gly
    210                 215                 220 aaa agt tgg cac tca gaa aca aag aac tcc ttg atg cag gat agg gat         720
Lys Ser Trp His Ser Glu Thr Lys Asn Ser Leu Met Gln Asp Arg Asp
225                 230                 235                 240 gct gca tct gct cgg gcc tgg cct aaa atg cac aca gtc aat ggt tat         768
Ala Ala Ser Ala Arg Ala Trp Pro Lys Met His Thr Val Asn Gly Tyr
                245                 250                 255 gta aac agg tct ctg cca ggt ctg att gga tgc cac agg aaa tca gtc         816
Val Asn Arg Ser Leu Pro Gly Leu Ile Gly Cys His Arg Lys Ser Val
            260                 265                 270 tat tgg cat gtg att gga atg ggc acc act cct gaa gtg cac tca ata         864
Tyr Trp His Val Ile Gly Met Gly Thr Thr Pro Glu Val His Ser Ile
        275                 280                 285 ttc ctc gaa ggt cac aca ttt ctt gtg agg aac cat cgc cag gcg tcc         912
Phe Leu Glu Gly His Thr Phe Leu Val Arg Asn His Arg Gln Ala Ser
    290                 295                 300 ttg gaa atc tcg cca ata act ttc ctt act gct caa aca ctc ttg atg         960
Leu Glu Ile Ser Pro Ile Thr Phe Leu Thr Ala Gln Thr Leu Leu Met
305                 310                 315                 320 gac ctt gga cag ttt cta ctg ttt tgt cat atc tct tcc cac caa cat        1008
Asp Leu Gly Gln Phe Leu Leu Phe Cys His Ile Ser Ser His Gln His
                325                 330                 335 gat ggc atg gaa gct tat gtc aaa gta gac agc tgt cca gag gaa ccc        1056
Asp Gly Met Glu Ala Tyr Val Lys Val Asp Ser Cys Pro Glu Glu Pro
            340                 345                 350 caa cta cga atg aaa aat aat gaa gaa gcg gaa gac tat gat gat gat        1104
Gln Leu Arg Met Lys Asn Asn Glu Glu Ala Glu Asp Tyr Asp Asp Asp
        355                 360                 365 ctt act gat tct gaa atg gat gtg gtc agg ttt gat gat gac aac tct        1152
Leu Thr Asp Ser Glu Met Asp Val Val Arg Phe Asp Asp Asp Asn Ser
    370                 375                 380 cct tcc ttt atc caa att cgc tca gtt gcc aag aag cat cct aaa act        1200
Pro Ser Phe Ile Gln Ile Arg Ser Val Ala Lys Lys His Pro Lys Thr
385                 390                 395                 400 tgg gta cat tac att gct gct gaa gag gag gac tgg gac tat gct ccc        1248
Trp Val His Tyr Ile Ala Ala Glu Glu Glu Asp Trp Asp Tyr Ala Pro
                405                 410                 415 tta gtc ctc gcc ccc gat gac aga agt tat aaa agt caa tat ttg aac        1296
Leu Val Leu Ala Pro Asp Asp Arg Ser Tyr Lys Ser Gln Tyr Leu Asn
            420                 425                 430 aat ggc cct cag cgg att ggt agg aag tac aaa aaa gtc cga ttt atg        1344
Asn Gly Pro Gln Arg Ile Gly Arg Lys Tyr Lys Lys Val Arg Phe Met
        435                 440                 445 gca tac aca gat gaa acc ttt aag acg cgt gaa gct att cag cat gaa        1392
Ala Tyr Thr Asp Glu Thr Phe Lys Thr Arg Glu Ala Ile Gln His Glu
    450                 455                 460 tca gga atc ttg gga cct tta ctt tat ggg gaa gtt gga gac aca ctg        1440
Ser Gly Ile Leu Gly Pro Leu Leu Tyr Gly Glu Val Gly Asp Thr Leu
465                 470                 475                 480 ttg att ata ttt aag aat caa gca agc aga cca tat aac atc tac cct        1488
Leu Ile Ile Phe Lys Asn Gln Ala Ser Arg Pro Tyr Asn Ile Tyr Pro
                485                 490                 495
```

```
cac gga atc act gat gtc cgt cct ttg tat tca agg aga tta cca aaa      1536
His Gly Ile Thr Asp Val Arg Pro Leu Tyr Ser Arg Arg Leu Pro Lys
            500                 505                 510 ggt gta aaa cat ttg aag gat ttt cca att ctg cca gga gaa ata ttc      1584
Gly Val Lys His Leu Lys Asp Phe Pro Ile Leu Pro Gly Glu Ile Phe
            515                 520                 525 aaa tat aaa tgg aca gtg act gta gaa gat ggg cca act aaa tca gat      1632
Lys Tyr Lys Trp Thr Val Thr Val Glu Asp Gly Pro Thr Lys Ser Asp
530                 535                 540 ccg cgg tgc ctg acc cgc tat tac tct agt ttc gtt aat atg gag aga      1680
Pro Arg Cys Leu Thr Arg Tyr Tyr Ser Ser Phe Val Asn Met Glu Arg
545                 550                 555                 560 gat cta gct tca gga ctc att ggc cct ctc ctc atc tgc tac aaa gaa      1728
Asp Leu Ala Ser Gly Leu Ile Gly Pro Leu Leu Ile Cys Tyr Lys Glu
                565                 570                 575 tct gta gat caa aga gga aac cag ata atg tca gac aag agg aat gtc      1776
Ser Val Asp Gln Arg Gly Asn Gln Ile Met Ser Asp Lys Arg Asn Val
            580                 585                 590 atc ctg ttt tct gta ttt gat gag aac cga agc tgg tac ctc aca gag      1824
Ile Leu Phe Ser Val Phe Asp Glu Asn Arg Ser Trp Tyr Leu Thr Glu
            595                 600                 605 aat ata caa cgc ttt ctc ccc aat cca gct gga gtg cag ctt gag gat      1872
Asn Ile Gln Arg Phe Leu Pro Asn Pro Ala Gly Val Gln Leu Glu Asp
610                 615                 620 cca gag ttc caa gcc tcc aac atc atg cac agc atc aat ggc tat gtt      1920
Pro Glu Phe Gln Ala Ser Asn Ile Met His Ser Ile Asn Gly Tyr Val
625                 630                 635                 640 ttt gat agt ttg cag ttg tca gtt tgt ttg cat gag gtg gca tac tgg      1968
Phe Asp Ser Leu Gln Leu Ser Val Cys Leu His Glu Val Ala Tyr Trp
                645                 650                 655 tac att cta agc att gga gca cag act gac ttc ctt tct gtc ttc ttc      2016
Tyr Ile Leu Ser Ile Gly Ala Gln Thr Asp Phe Leu Ser Val Phe Phe
            660                 665                 670 tct gga tat acc ttc aaa cac aaa atg gtc tat gaa gac aca ctc acc      2064
Ser Gly Tyr Thr Phe Lys His Lys Met Val Tyr Glu Asp Thr Leu Thr
            675                 680                 685 cta ttc cca ttc tca gga gaa act gtc ttc atg tcg atg gaa aac cca      2112
Leu Phe Pro Phe Ser Gly Glu Thr Val Phe Met Ser Met Glu Asn Pro
690                 695                 700 ggt cta tgg att ctg ggg tgc cac aac tca gac ttt cgg aac aga ggc      2160
Gly Leu Trp Ile Leu Gly Cys His Asn Ser Asp Phe Arg Asn Arg Gly
705                 710                 715                 720 atg acc gcc tta ctg aag gtt tct agt tgt gac aag aac act ggt gat      2208
Met Thr Ala Leu Leu Lys Val Ser Ser Cys Asp Lys Asn Thr Gly Asp
                725                 730                 735 tat tac gag gac agt tat gaa gat att tca gca tac ttg ctg agt aaa      2256
Tyr Tyr Glu Asp Ser Tyr Glu Asp Ile Ser Ala Tyr Leu Leu Ser Lys
            740                 745                 750 aac aat gcc att gaa cct agg agc ttc tct cag aat cca cca gtc ttg      2304
Asn Asn Ala Ile Glu Pro Arg Ser Phe Ser Gln Asn Pro Pro Val Leu
            755                 760                 765 aaa cgc cat caa cgg gaa ata act cgt act act ctt cag tca gat caa      2352
Lys Arg His Gln Arg Glu Ile Thr Arg Thr Thr Leu Gln Ser Asp Gln
770                 775                 780 gag gaa att gac tat gat gat acc ata tca gtt gaa atg aag aag gaa      2400
Glu Glu Ile Asp Tyr Asp Asp Thr Ile Ser Val Glu Met Lys Lys Glu
785                 790                 795                 800 gat ttt gac att tat gat gag gat gaa aat cag agc ccc cgc agc ttt      2448
Asp Phe Asp Ile Tyr Asp Glu Asp Glu Asn Gln Ser Pro Arg Ser Phe
                805                 810                 815
```

-continued

| | | |
|---|---|---|
| caa aag aaa aca cga cac tat ttt att gct gca gtg gag agg ctc tgg<br>Gln Lys Lys Thr Arg His Tyr Phe Ile Ala Ala Val Glu Arg Leu Trp<br>        820                         825                      830 | 2496 |
| gat tat ggg atg agt agc tcc cca cat gtt cta aga aac agg gct cag<br>Asp Tyr Gly Met Ser Ser Pro His Val Leu Arg Asn Arg Ala Gln<br>        835                         840                      845 | 2544 |
| agt ggc agt gtc cct cag ttc aag aaa gtt gtt ttc cag gaa ttt act<br>Ser Gly Ser Val Pro Gln Phe Lys Lys Val Val Phe Gln Glu Phe Thr<br>850                         855                       860 | 2592 |
| gat ggc tcc ttt act cag ccc tta tac cgt gga gaa cta aat gaa cat<br>Asp Gly Ser Phe Thr Gln Pro Leu Tyr Arg Gly Glu Leu Asn Glu His<br>865                         870                      875                 880 | 2640 |
| ttg gga ctc ctg ggg cca tat ata aga gca gaa gtt gaa gat aat atc<br>Leu Gly Leu Leu Gly Pro Tyr Ile Arg Ala Glu Val Glu Asp Asn Ile<br>                       885                      890                      895 | 2688 |
| atg gta act ttc aga aat cag gcc tct cgt ccc tat tcc ttc tat tct<br>Met Val Thr Phe Arg Asn Gln Ala Ser Arg Pro Tyr Ser Phe Tyr Ser<br>        900                         905                      910 | 2736 |
| agc ctt att tct tat gag gaa gat cag agg caa gga gca gaa cct aga<br>Ser Leu Ile Ser Tyr Glu Glu Asp Gln Arg Gln Gly Ala Glu Pro Arg<br>        915                         920                      925 | 2784 |
| aaa aac ttt gtc aag cct aat gaa acc aaa act tac ttt tgg aaa gtg<br>Lys Asn Phe Val Lys Pro Asn Glu Thr Lys Thr Tyr Phe Trp Lys Val<br>930                         935                       940 | 2832 |
| caa cat cat atg gca ccc act aaa gat gag ttt gac tgc aaa gcc tgg<br>Gln His His Met Ala Pro Thr Lys Asp Glu Phe Asp Cys Lys Ala Trp<br>945                         950                       955                 960 | 2880 |
| gct tat ttc tct gat gtt gac ctg gaa aaa gat gtg cac tca ggc ctg<br>Ala Tyr Phe Ser Asp Val Asp Leu Glu Lys Asp Val His Ser Gly Leu<br>                       965                      970                      975 | 2928 |
| att gga ccc ctt ctg gtc tgc cac act aac aca ctg aac cct gct cat<br>Ile Gly Pro Leu Leu Val Cys His Thr Asn Thr Leu Asn Pro Ala His<br>                  980                       985                      990 | 2976 |
| ggg aga caa gtg aca gta cag gaa ttt gct ctg ttt ttc acc atc ttt<br>Gly Arg Gln Val Thr Val Gln Glu Phe Ala Leu Phe Phe Thr Ile Phe<br>        995                       1000                     1005 | 3024 |
| gat gag acc aaa agc tgg tac ttc act gaa aat atg gaa aga aac tgc<br>Asp Glu Thr Lys Ser Trp Tyr Phe Thr Glu Asn Met Glu Arg Asn Cys<br>1010                       1015                     1020 | 3072 |
| agg gct ccc tgc aat atc cag atg gaa gat ccc act ttt aaa gag aat<br>Arg Ala Pro Cys Asn Ile Gln Met Glu Asp Pro Thr Phe Lys Glu Asn<br>1025                       1030                     1035                     1040 | 3120 |
| tat cgc ttc cat gca atc aat ggc tac ata atg gat aca cta cct ggc<br>Tyr Arg Phe His Ala Ile Asn Gly Tyr Ile Met Asp Thr Leu Pro Gly<br>                       1045                     1050                     1055 | 3168 |
| tta gta atg gct cag gat caa agg att cga tgg tat ctg ctc agc atg<br>Leu Val Met Ala Gln Asp Gln Arg Ile Arg Trp Tyr Leu Leu Ser Met<br>                1060                     1065                     1070 | 3216 |
| ggc agc aat gaa aac atc cat tct att cat ttc agt gga cat gtg ttc<br>Gly Ser Asn Glu Asn Ile His Ser Ile His Phe Ser Gly His Val Phe<br>1075                       1080                     1085 | 3264 |
| act gta cga aaa aaa gag gag tat aaa atg gca ctg tac aat ctc tat<br>Thr Val Arg Lys Lys Glu Glu Tyr Lys Met Ala Leu Tyr Asn Leu Tyr<br>                1090                     1095                     1100 | 3312 |
| cca ggt gtt ttt gag aca gtg gaa atg tta cca tcc aaa gct gga att<br>Pro Gly Val Phe Glu Thr Val Glu Met Leu Pro Ser Lys Ala Gly Ile<br>1105                       1110                     1115                     1120 | 3360 |
| tgg cgg gtg gaa tgc ctt att ggc gag cat cta cat gct ggg atg agc<br>Trp Arg Val Glu Cys Leu Ile Gly Glu His Leu His Ala Gly Met Ser<br>                1125                     1130                     1135 | 3408 |

-continued

| | |
|---|---|
| aca ctt ttt ctg gtg tac agc aat aag tgt cag act ccc ctg gga atg<br>Thr Leu Phe Leu Val Tyr Ser Asn Lys Cys Gln Thr Pro Leu Gly Met<br>     1140                   1145                   1150 | 3456 |
| gct tct gga cac att aga gat ttt cag att aca gct tca gga caa tat<br>Ala Ser Gly His Ile Arg Asp Phe Gln Ile Thr Ala Ser Gly Gln Tyr<br>1155                  1160                  1165 | 3504 |
| gga cag tgg gcc cca aag ctg gcc aga ctt cat tat tcc gga tca atc<br>Gly Gln Trp Ala Pro Lys Leu Ala Arg Leu His Tyr Ser Gly Ser Ile<br>     1170                   1175                   1180 | 3552 |
| aat gcc tgg agc acc aag gag ccc ttt tct tgg atc aag gtg gat ctg<br>Asn Ala Trp Ser Thr Lys Glu Pro Phe Ser Trp Ile Lys Val Asp Leu<br>1185                  1190                  1195                 1200 | 3600 |
| ttg gca cca atg att att cac ggc atc aag acc cag ggt gcc cgt cag<br>Leu Ala Pro Met Ile Ile His Gly Ile Lys Thr Gln Gly Ala Arg Gln<br>                   1205                  1210                  1215 | 3648 |
| aag ttc tcc agc ctc tac atc tct cag ttt atc atc atg tat agt ctt<br>Lys Phe Ser Ser Leu Tyr Ile Ser Gln Phe Ile Ile Met Tyr Ser Leu<br>1220                  1225                  1230 | 3696 |
| gat ggg aag aag tgg cag act tat cga gga aat tcc act gga acc tta<br>Asp Gly Lys Lys Trp Gln Thr Tyr Arg Gly Asn Ser Thr Gly Thr Leu<br>     1235                   1240                   1245 | 3744 |
| atg gtc ttc ttt ggc aat gtg gat tca tct ggg ata aaa cac aat att<br>Met Val Phe Phe Gly Asn Val Asp Ser Ser Gly Ile Lys His Asn Ile<br>1250                  1255                  1260 | 3792 |
| ttt aac cct cca att att gct cga tac atc cgt ttg cac cca act cat<br>Phe Asn Pro Pro Ile Ile Ala Arg Tyr Ile Arg Leu His Pro Thr His<br>1265                  1270                  1275                 1280 | 3840 |
| tat agc att cgc agc act ctt cgc atg gag ttg atg ggc tgt gat tta<br>Tyr Ser Ile Arg Ser Thr Leu Arg Met Glu Leu Met Gly Cys Asp Leu<br>                 1285                  1290                  1295 | 3888 |
| aat agt tgc agc atg cca ttg gga atg gag agt aaa gca ata tca gat<br>Asn Ser Cys Ser Met Pro Leu Gly Met Glu Ser Lys Ala Ile Ser Asp<br>             1300                  1305                  1310 | 3936 |
| gca cag att act gct tca tcc tac ttt acc aat atg ttt gcc acc tgg<br>Ala Gln Ile Thr Ala Ser Ser Tyr Phe Thr Asn Met Phe Ala Thr Trp<br>1315                  1320                  1325 | 3984 |
| tct cct tca aaa gct cga ctt cac ctc caa ggg agg agt aat gcc tgg<br>Ser Pro Ser Lys Ala Arg Leu His Leu Gln Gly Arg Ser Asn Ala Trp<br>     1330                   1335                   1340 | 4032 |
| aga cct cag gtg aat aat cca aaa gag tgg ctg caa gtg gac ttc cag<br>Arg Pro Gln Val Asn Asn Pro Lys Glu Trp Leu Gln Val Asp Phe Gln<br>1345                  1350                  1355                 1360 | 4080 |
| aag aca atg aaa gtc aca gga gta act act cag gga gta aaa tct ctg<br>Lys Thr Met Lys Val Thr Gly Val Thr Thr Gln Gly Val Lys Ser Leu<br>             1365                  1370                  1375 | 4128 |
| ctt acc agc atg tat gtg aag gag ttc ctc atc tcc agc agt caa gat<br>Leu Thr Ser Met Tyr Val Lys Glu Phe Leu Ile Ser Ser Ser Gln Asp<br>1380                  1385                  1390 | 4176 |
| ggc cat cag tgg act ctc ttt ttt cag aat ggc aaa gta aag gtt ttt<br>Gly His Gln Trp Thr Leu Phe Phe Gln Asn Gly Lys Val Lys Val Phe<br>     1395                   1400                   1405 | 4224 |
| cag gga aat caa gac tcc ttc aca cct gtg gtg aac tct cta gac cca<br>Gln Gly Asn Gln Asp Ser Phe Thr Pro Val Val Asn Ser Leu Asp Pro<br>1410                  1415                  1420 | 4272 |
| ccg tta ctg act cgc tac ctt cga att cac ccc cag agt tgg gtg cac<br>Pro Leu Leu Thr Arg Tyr Leu Arg Ile His Pro Gln Ser Trp Val His<br>     1425                   1430                   1435                 1440 | 4320 |

```
cag att gcc ctg agg atg gag gtt ctg ggc tgc gag gca cag gac ctc    4368
Gln Ile Ala Leu Arg Met Glu Val Leu Gly Cys Glu Ala Gln Asp Leu
            1445                1450                1455 tac                                                                 4371
Tyr

<210> SEQ ID NO 13
<211> LENGTH: 1457
<212> TYPE: PRT
<213> ORGANISM: Homo sapiens

<400> SEQUENCE: 13

Met Gln Ile Glu Leu Ser Thr Cys Phe Phe Leu Cys Leu Leu Arg Phe
  1               5                  10                  15

Cys Phe Ser Ala Thr Arg Arg Tyr Tyr Leu Gly Ala Val Glu Leu Ser
                 20                  25                  30

Trp Asp Tyr Met Gln Ser Asp Leu Gly Glu Leu Pro Val Asp Ala Arg
             35                  40                  45

Phe Pro Pro Arg Val Pro Lys Ser Phe Pro Phe Asn Thr Ser Val Val
 50                  55                  60

Tyr Lys Lys Thr Leu Phe Val Glu Phe Thr Val His Leu Phe Asn Ile
65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335
```

-continued

```
Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
            370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
            530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750
```

-continued

```
Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
        770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Asn Gln Ser Pro Arg Ser Phe
                    805                 810                 815

Gln Lys Lys Thr Arg His Tyr Phe Ile Ala Ala Val Glu Arg Leu Trp
                820                 825                 830

Asp Tyr Gly Met Ser Ser Ser Pro His Val Leu Arg Asn Arg Ala Gln
                835                 840                 845

Ser Gly Ser Val Pro Gln Phe Lys Lys Val Val Phe Gln Glu Phe Thr
        850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                    885                 890                 895

Met Val Thr Phe Arg Asn Gln Ala Ser Arg Pro Tyr Ser Phe Tyr Ser
                900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
        930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                    965                 970                 975

Ile Gly Pro Leu Leu Val Cys His Thr Asn Thr Leu Asn Pro Ala His
                980                 985                 990

Gly Arg Gln Val Thr Val Gln Glu Phe Ala Leu Phe Phe Thr Ile Phe
        995                 1000                1005

Asp Glu Thr Lys Ser Trp Tyr Phe Thr Glu Asn Met Glu Arg Asn Cys
        1010                1015                1020

Arg Ala Pro Cys Asn Ile Gln Met Glu Asp Pro Thr Phe Lys Glu Asn
1025                1030                1035                1040

Tyr Arg Phe His Ala Ile Asn Gly Tyr Ile Met Asp Thr Leu Pro Gly
                    1045                1050                1055

Leu Val Met Ala Gln Asp Gln Arg Ile Arg Trp Tyr Leu Leu Ser Met
                1060                1065                1070

Gly Ser Asn Glu Asn Ile His Ser Ile His Phe Ser Gly His Val Phe
                1075                1080                1085

Thr Val Arg Lys Lys Glu Glu Tyr Lys Met Ala Leu Tyr Asn Leu Tyr
                1090                1095                1100

Pro Gly Val Phe Glu Thr Val Glu Met Leu Pro Ser Lys Ala Gly Ile
1105                1110                1115                1120

Trp Arg Val Glu Cys Leu Ile Gly Glu His Leu His Ala Gly Met Ser
                    1125                1130                1135

Thr Leu Phe Leu Val Tyr Ser Asn Lys Cys Gln Thr Pro Leu Gly Met
                1140                1145                1150

Ala Ser Gly His Ile Arg Asp Phe Gln Ile Thr Ala Ser Gly Gln Tyr
                1155                1160                1165
```

```
Gly Gln Trp Ala Pro Lys Leu Ala Arg Leu His Tyr Ser Gly Ser Ile
    1170            1175                1180

Asn Ala Trp Ser Thr Lys Glu Pro Phe Ser Trp Ile Lys Val Asp Leu
1185                1190                1195                1200

Leu Ala Pro Met Ile Ile His Gly Ile Lys Thr Gln Gly Ala Arg Gln
                1205                1210                1215

Lys Phe Ser Ser Leu Tyr Ile Ser Gln Phe Ile Ile Met Tyr Ser Leu
            1220                1225                1230

Asp Gly Lys Lys Trp Gln Thr Tyr Arg Gly Asn Ser Thr Gly Thr Leu
        1235                1240                1245

Met Val Phe Phe Gly Asn Val Asp Ser Ser Gly Ile Lys His Asn Ile
    1250                1255                1260

Phe Asn Pro Pro Ile Ile Ala Arg Tyr Ile Arg Leu His Pro Thr His
1265                1270                1275                1280

Tyr Ser Ile Arg Ser Thr Leu Arg Met Glu Leu Met Gly Cys Asp Leu
                1285                1290                1295

Asn Ser Cys Ser Met Pro Leu Gly Met Glu Ser Lys Ala Ile Ser Asp
            1300                1305                1310

Ala Gln Ile Thr Ala Ser Ser Tyr Phe Thr Asn Met Phe Ala Thr Trp
        1315                1320                1325

Ser Pro Ser Lys Ala Arg Leu His Leu Gln Gly Arg Ser Asn Ala Trp
    1330                1335                1340

Arg Pro Gln Val Asn Asn Pro Lys Glu Trp Leu Gln Val Asp Phe Gln
1345                1350                1355                1360

Lys Thr Met Lys Val Thr Gly Val Thr Thr Gln Gly Val Lys Ser Leu
                1365                1370                1375

Leu Thr Ser Met Tyr Val Lys Glu Phe Leu Ile Ser Ser Ser Gln Asp
            1380                1385                1390

Gly His Gln Trp Thr Leu Phe Phe Gln Asn Gly Lys Val Lys Val Phe
        1395                1400                1405

Gln Gly Asn Gln Asp Ser Phe Thr Pro Val Val Asn Ser Leu Asp Pro
    1410                1415                1420

Pro Leu Leu Thr Arg Tyr Leu Arg Ile His Pro Gln Ser Trp Val His
1425                1430                1435                1440

Gln Ile Ala Leu Arg Met Glu Val Leu Gly Cys Glu Ala Gln Asp Leu
                1445                1450                1455

Tyr

<210> SEQ ID NO 14
<211> LENGTH: 4401
<212> TYPE: DNA
<213> ORGANISM: Artificial Sequence
<220> FEATURE:
<223> OTHER INFORMATION: hybrid human and porcine factor VIII sequence
<220> FEATURE:
<221> NAME/KEY: CDS
<222> LOCATION: (1)...(4401)
<223> OTHER INFORMATION: HP44/OL-- factor VIII having the following
      domains: A1p-A2p-app-A3p-C1h-C2h

<400> SEQUENCE: 14 atg cag cta gag ctc tcc acc tgt gtc ttt ctg tgt ctc ttg cca ctc    48
Met Gln Leu Glu Leu Ser Thr Cys Val Phe Leu Cys Leu Leu Pro Leu
1               5                   10                  15 ggc ttt agt gcc atc agg aga tac tac ctg ggc gca gtg gaa ctg tcc    96
Gly Phe Ser Ala Ile Arg Arg Tyr Tyr Leu Gly Ala Val Glu Leu Ser
            20                  25                  30
```

```
tgg gac tac cgg caa agt gaa ctc ctc cgt gag ctg cac gtg gac acc    144
Trp Asp Tyr Arg Gln Ser Glu Leu Leu Arg Glu Leu His Val Asp Thr
         35                  40                  45 aga ttt cct gct aca gcg cca gga gct ctt ccg ttg ggc ccg tca gtc    192
Arg Phe Pro Ala Thr Ala Pro Gly Ala Leu Pro Leu Gly Pro Ser Val
 50                  55                  60 ctg tac aaa aag act gtg ttc gta gag ttc acg gat caa ctt ttc agc    240
Leu Tyr Lys Lys Thr Val Phe Val Glu Phe Thr Asp Gln Leu Phe Ser
 65                  70                  75                  80 gtt gcc agg ccc agg cca cca tgg atg ggt ctg ctg ggt cct acc atc    288
Val Ala Arg Pro Arg Pro Pro Trp Met Gly Leu Leu Gly Pro Thr Ile
                 85                  90                  95 cag gct gag gtt tac gac acg gtc gtt acc ctg aag aac atg gct        336
Gln Ala Glu Val Tyr Asp Thr Val Val Thr Leu Lys Asn Met Ala
            100                 105                 110 tct cat ccc gtt agt ctt cac gct gtc ggc gtc tcc ttc tgg aaa tct    384
Ser His Pro Val Ser Leu His Ala Val Gly Val Ser Phe Trp Lys Ser
        115                 120                 125 tcc gaa ggc gct gaa tat gag gat cac acc agc caa agg gag aag gaa    432
Ser Glu Gly Ala Glu Tyr Glu Asp His Thr Ser Gln Arg Glu Lys Glu
130                 135                 140 gac gat aaa gtc ctt ccc ggt aaa agc caa acc tac gtc tgg cag gtc    480
Asp Asp Lys Val Leu Pro Gly Lys Ser Gln Thr Tyr Val Trp Gln Val
145                 150                 155                 160 ctg aaa gaa aat ggt cca aca gcc tct gac cca cca tgt ctt acc tac    528
Leu Lys Glu Asn Gly Pro Thr Ala Ser Asp Pro Pro Cys Leu Thr Tyr
                165                 170                 175 tca tac ctg tct cac gtg gac ctg gtg aaa gac ctg aat tcg ggc ctc    576
Ser Tyr Leu Ser His Val Asp Leu Val Lys Asp Leu Asn Ser Gly Leu
                180                 185                 190 att gga gcc ctg ctg gtt tgt aga gaa ggg agt ctg acc aga gaa agg    624
Ile Gly Ala Leu Leu Val Cys Arg Glu Gly Ser Leu Thr Arg Glu Arg
            195                 200                 205 acc cag aac ctg cac gaa ttt gta cta ctt ttt gct gtc ttt gat gaa    672
Thr Gln Asn Leu His Glu Phe Val Leu Leu Phe Ala Val Phe Asp Glu
210                 215                 220 ggg aaa agt tgg cac tca gca aga aat gac tcc tgg aca cgg gcc atg    720
Gly Lys Ser Trp His Ser Ala Arg Asn Asp Ser Trp Thr Arg Ala Met
225                 230                 235                 240 gat ccc gca cct gcc agg gcc cag cct gca atg cac aca gtc aat ggc    768
Asp Pro Ala Pro Ala Arg Ala Gln Pro Ala Met His Thr Val Asn Gly
                245                 250                 255 tat gtc aac agg tct ctg cca ggt ctg atc gga tgt cat aag aaa tca    816
Tyr Val Asn Arg Ser Leu Pro Gly Leu Ile Gly Cys His Lys Lys Ser
                260                 265                 270 gtc tac tgg cac gtg att gga atg ggc acc agc ccg gaa gtg cac tcc    864
Val Tyr Trp His Val Ile Gly Met Gly Thr Ser Pro Glu Val His Ser
            275                 280                 285 att ttt ctt gaa ggc cac acg ttt ctc gtg agg cac cat cgc cag gct    912
Ile Phe Leu Glu Gly His Thr Phe Leu Val Arg His His Arg Gln Ala
290                 295                 300 tcc ttg gag atc tcg cca cta act ttc ctc act gct cag aca ttc ctg    960
Ser Leu Glu Ile Ser Pro Leu Thr Phe Leu Thr Ala Gln Thr Phe Leu
305                 310                 315                 320 atg gac ctt ggc cag ttc cta ctg ttt tgt cat atc tct tcc cac cac   1008
Met Asp Leu Gly Gln Phe Leu Leu Phe Cys His Ile Ser Ser His His
                325                 330                 335 cat ggt ggc atg gag gct cac gtc aga gta gaa agc tgc gcc gag gag   1056
His Gly Gly Met Glu Ala His Val Arg Val Glu Ser Cys Ala Glu Glu
            340                 345                 350
```

-continued

```
ccc cag ctg cgg agg aaa gct gat gaa gag gaa gat tat gat gac aat    1104
Pro Gln Leu Arg Arg Lys Ala Asp Glu Glu Glu Asp Tyr Asp Asp Asn
        355                 360                 365 ttg tac gac tcg gac atg gac gtg gtc cgg ctc gat ggt gac gac gtg    1152
Leu Tyr Asp Ser Asp Met Asp Val Val Arg Leu Asp Gly Asp Asp Val
370                 375                 380 tct ccc ttt atc caa atc cgc tcg gtt gcc aag aag cat ccc aaa acc    1200
Ser Pro Phe Ile Gln Ile Arg Ser Val Ala Lys Lys His Pro Lys Thr
385                 390                 395                 400 tgg gtg cac tac atc tct gca gag gag gag gac tgg gac tac gcc ccc    1248
Trp Val His Tyr Ile Ser Ala Glu Glu Glu Asp Trp Asp Tyr Ala Pro
            405                 410                 415 gcg gtc ccc agc ccc agt gac aga agt tat aaa agt ctc tac ttg aac    1296
Ala Val Pro Ser Pro Ser Asp Arg Ser Tyr Lys Ser Leu Tyr Leu Asn
        420                 425                 430 agt ggt cct cag cga att ggt agg aaa tac aaa aaa gct cga ttc gtc    1344
Ser Gly Pro Gln Arg Ile Gly Arg Lys Tyr Lys Lys Ala Arg Phe Val
        435                 440                 445 gct tac acg gat gta aca ttt aag act cgt aaa gct att ccg tat gaa    1392
Ala Tyr Thr Asp Val Thr Phe Lys Thr Arg Lys Ala Ile Pro Tyr Glu
450                 455                 460 tca gga atc ctg gga cct tta ctt tat gga gaa gtt gga gac aca ctt    1440
Ser Gly Ile Leu Gly Pro Leu Leu Tyr Gly Glu Val Gly Asp Thr Leu
465                 470                 475                 480 ttg att ata ttt aag aat aaa gcg agc cga cca tat aac atc tac cct    1488
Leu Ile Ile Phe Lys Asn Lys Ala Ser Arg Pro Tyr Asn Ile Tyr Pro
            485                 490                 495 cat gga atc act gat gtc agc gct ttg cac cca ggg aga ctt cta aaa    1536
His Gly Ile Thr Asp Val Ser Ala Leu His Pro Gly Arg Leu Leu Lys
        500                 505                 510 ggt tgg aaa cat ttg aaa gac atg cca att ctg cca gga gag act ttc    1584
Gly Trp Lys His Leu Lys Asp Met Pro Ile Leu Pro Gly Glu Thr Phe
        515                 520                 525 aag tat aaa tgg aca gtg act gtg gaa gat ggg cca acc aag tcc gat    1632
Lys Tyr Lys Trp Thr Val Thr Val Glu Asp Gly Pro Thr Lys Ser Asp
530                 535                 540 cct cgg tgc ctg acc cgc tac tac tcg agc tcc att aat cta gag aaa    1680
Pro Arg Cys Leu Thr Arg Tyr Tyr Ser Ser Ser Ile Asn Leu Glu Lys
545                 550                 555                 560 gat ctg gct tcg gga ctc att ggc cct ctc ctc atc tgc tac aaa gaa    1728
Asp Leu Ala Ser Gly Leu Ile Gly Pro Leu Leu Ile Cys Tyr Lys Glu
            565                 570                 575 tct gta gac caa aga gga aac cag atg atg tca gac aag aga aac gtc    1776
Ser Val Asp Gln Arg Gly Asn Gln Met Met Ser Asp Lys Arg Asn Val
        580                 585                 590 atc ctg ttt tct gta ttc gat gag aat caa agc tgg tac ctc gca gag    1824
Ile Leu Phe Ser Val Phe Asp Glu Asn Gln Ser Trp Tyr Leu Ala Glu
        595                 600                 605 aat att cag cgc ttc ctc ccc aat ccg gat gga tta cag ccc cag gat    1872
Asn Ile Gln Arg Phe Leu Pro Asn Pro Asp Gly Leu Gln Pro Gln Asp
610                 615                 620 cca gag ttc caa gct tct aac atc atg cac agc atc aat ggc tat gtt    1920
Pro Glu Phe Gln Ala Ser Asn Ile Met His Ser Ile Asn Gly Tyr Val
625                 630                 635                 640 ttt gat agc ttg cag ctg tcg gtt tgt ttg cac gag gtg gca tac tgg    1968
Phe Asp Ser Leu Gln Leu Ser Val Cys Leu His Glu Val Ala Tyr Trp
            645                 650                 655 tac att cta agt gtt gga gca cag acg gac ttc ctc tcc gtc ttc ttc    2016
Tyr Ile Leu Ser Val Gly Ala Gln Thr Asp Phe Leu Ser Val Phe Phe
        660                 665                 670
```

```
tct ggc tac acc ttc aaa cac aaa atg gtc tat gaa gac aca ctc acc      2064
Ser Gly Tyr Thr Phe Lys His Lys Met Val Tyr Glu Asp Thr Leu Thr
            675                 680                 685 ctg ttc ccc ttc tca gga gaa acg gtc ttc atg tca atg gaa aac cca      2112
Leu Phe Pro Phe Ser Gly Glu Thr Val Phe Met Ser Met Glu Asn Pro
    690                 695                 700 ggt ctc tgg gtc ctt ggg tgc cac aac tca gac ttg cgg aac aga ggg      2160
Gly Leu Trp Val Leu Gly Cys His Asn Ser Asp Leu Arg Asn Arg Gly
705                 710                 715                 720 atg aca gcc tta ctg aag gtg tat agt tgt gac agg gac att ggt gat      2208
Met Thr Ala Leu Leu Lys Val Tyr Ser Cys Asp Arg Asp Ile Gly Asp
                725                 730                 735 tat tat gac aac act tat gaa gat att cca ggc ttc ttg ctg agt gga      2256
Tyr Tyr Asp Asn Thr Tyr Glu Asp Ile Pro Gly Phe Leu Leu Ser Gly
            740                 745                 750 aag aat gtc att gaa cct agg agc ttt gcc cag aat tca aga ccc cct      2304
Lys Asn Val Ile Glu Pro Arg Ser Phe Ala Gln Asn Ser Arg Pro Pro
    755                 760                 765 agt gcg agc gct cca aag cct ccg gtc ctg cga cgg cat cag agg gac      2352
Ser Ala Ser Ala Pro Lys Pro Pro Val Leu Arg Arg His Gln Arg Asp
770                 775                 780 ata agc ctt cct act ttt cag ccg gag gaa gac aaa atg gac tat gat      2400
Ile Ser Leu Pro Thr Phe Gln Pro Glu Glu Asp Lys Met Asp Tyr Asp
785                 790                 795                 800 gat atc ttc tca act gaa acg aag gga gaa gat ttt gac att tac ggt      2448
Asp Ile Phe Ser Thr Glu Thr Lys Gly Glu Asp Phe Asp Ile Tyr Gly
                805                 810                 815 gag gat gaa aat cag gac cct cgc agc ttt cag aag aga acc cga cac      2496
Glu Asp Glu Asn Gln Asp Pro Arg Ser Phe Gln Lys Arg Thr Arg His
            820                 825                 830 tat ttc att gct gcg gtg gag cag ctc tgg gat tac ggg atg agc gaa      2544
Tyr Phe Ile Ala Ala Val Glu Gln Leu Trp Asp Tyr Gly Met Ser Glu
    835                 840                 845 tcc ccc cgg gcg cta aga aac agg gct cag aac gga gag gtg cct cgg      2592
Ser Pro Arg Ala Leu Arg Asn Arg Ala Gln Asn Gly Glu Val Pro Arg
850                 855                 860 ttc aag aag gtg gtc ttc cgg gaa ttt gct gac ggc tcc ttc acg cag      2640
Phe Lys Lys Val Val Phe Arg Glu Phe Ala Asp Gly Ser Phe Thr Gln
865                 870                 875                 880 ccg tcg tac cgc ggg gaa ctc aac aaa cac ttg ggg ctc ttg gga ccc      2688
Pro Ser Tyr Arg Gly Glu Leu Asn Lys His Leu Gly Leu Leu Gly Pro
                885                 890                 895 tac atc aga gcg gaa gtt gaa gac aac atc atg gta act ttc aaa aac      2736
Tyr Ile Arg Ala Glu Val Glu Asp Asn Ile Met Val Thr Phe Lys Asn
            900                 905                 910 cag gcg tct cgt ccc tat tcc ttc tac tcg agc ctt att tct tat ccg      2784
Gln Ala Ser Arg Pro Tyr Ser Phe Tyr Ser Ser Leu Ile Ser Tyr Pro
    915                 920                 925 gat gat cag gag caa ggg gca gaa cct cga cac aac ttc gtc cag cca      2832
Asp Asp Gln Glu Gln Gly Ala Glu Pro Arg His Asn Phe Val Gln Pro
930                 935                 940 aat gaa acc aga act tac ttt tgg aaa gtg cag cat cac atg gca ccc      2880
Asn Glu Thr Arg Thr Tyr Phe Trp Lys Val Gln His His Met Ala Pro
945                 950                 955                 960 aca gaa gac gag ttt gac tgc aaa gcc tgg gcc tac ttt tct gat gtt      2928
Thr Glu Asp Glu Phe Asp Cys Lys Ala Trp Ala Tyr Phe Ser Asp Val
                965                 970                 975 gac ctg gaa aaa gat gtg cac tca ggc ttg atc ggc ccc ctt ctg atc      2976
Asp Leu Glu Lys Asp Val His Ser Gly Leu Ile Gly Pro Leu Leu Ile
            980                 985                 990
```

```
tgc cgc gcc aac acc ctg aac gct gct cac ggt aga caa gtg acc gtg    3024
Cys Arg Ala Asn Thr Leu Asn Ala Ala His Gly Arg Gln Val Thr Val
        995                 1000                1005 caa gaa ttt gct ctg ttt ttc act att ttt gat gag aca aag agc tgg    3072
Gln Glu Phe Ala Leu Phe Phe Thr Ile Phe Asp Glu Thr Lys Ser Trp
    1010                1015                1020 tac ttc act gaa aat gtg gaa agg aac tgc cgg gcc ccc tgc cat ctg    3120
Tyr Phe Thr Glu Asn Val Glu Arg Asn Cys Arg Ala Pro Cys His Leu
1025                1030                1035                1040 cag atg gag gac ccc act ctg aaa gaa aac tat cgc ttc cat gca atc    3168
Gln Met Glu Asp Pro Thr Leu Lys Glu Asn Tyr Arg Phe His Ala Ile
                1045                1050                1055 aat ggc tat gtg atg gat aca ctc cct ggc tta gta atg gct cag aat    3216
Asn Gly Tyr Val Met Asp Thr Leu Pro Gly Leu Val Met Ala Gln Asn
            1060                1065                1070 caa agg atc cga tgg tat ctg ctc agc atg ggc agc aat gaa aat atc    3264
Gln Arg Ile Arg Trp Tyr Leu Leu Ser Met Gly Ser Asn Glu Asn Ile
        1075                1080                1085 cat tcg att cat ttt agc gga cac gtg ttc agt gta cgg aaa aag gag    3312
His Ser Ile His Phe Ser Gly His Val Phe Ser Val Arg Lys Lys Glu
    1090                1095                1100 gag tat aaa atg gcc gtg tac aat ctc tat ccg ggt gtc ttt gag aca    3360
Glu Tyr Lys Met Ala Val Tyr Asn Leu Tyr Pro Gly Val Phe Glu Thr
1105                1110                1115                1120 gtg gaa atg cta ccg tcc aaa gtt gga att tgg cga ata gaa tgc ctg    3408
Val Glu Met Leu Pro Ser Lys Val Gly Ile Trp Arg Ile Glu Cys Leu
                1125                1130                1135 att ggc gag cac ctg caa gct ggg atg agc acg act ttc ctg gtg tac    3456
Ile Gly Glu His Leu Gln Ala Gly Met Ser Thr Thr Phe Leu Val Tyr
            1140                1145                1150 agc aag aag tgt cag act ccc ctg gga atg gct tct gga cac att aga    3504
Ser Lys Lys Cys Gln Thr Pro Leu Gly Met Ala Ser Gly His Ile Arg
        1155                1160                1165 gat ttt cag att aca gct tca gga caa tat gga cag tgg gcc cca aag    3552
Asp Phe Gln Ile Thr Ala Ser Gly Gln Tyr Gly Gln Trp Ala Pro Lys
    1170                1175                1180 ctg gcc aga ctt cat tat tcc gga tca atc aat gcc tgg agc acc aag    3600
Leu Ala Arg Leu His Tyr Ser Gly Ser Ile Asn Ala Trp Ser Thr Lys
1185                1190                1195                1200 gag ccc ttt tct tgg atc aag gtg gat ctg ttg gca cca atg att att    3648
Glu Pro Phe Ser Trp Ile Lys Val Asp Leu Leu Ala Pro Met Ile Ile
                1205                1210                1215 cac ggc atc aag acc cag ggt gcc cgt cag aag ttc tcc agc ctc tac    3696
His Gly Ile Lys Thr Gln Gly Ala Arg Gln Lys Phe Ser Ser Leu Tyr
            1220                1225                1230 atc tct cag ttt atc atc atg tat agt ctt gat ggg aag aag tgg cag    3744
Ile Ser Gln Phe Ile Ile Met Tyr Ser Leu Asp Gly Lys Lys Trp Gln
        1235                1240                1245 act tat cga gga aat tcc act gga acc tta atg gtc ttc ttt ggc aat    3792
Thr Tyr Arg Gly Asn Ser Thr Gly Thr Leu Met Val Phe Phe Gly Asn
    1250                1255                1260 gtg gat tca tct ggg ata aaa cac aat att ttt aac cct cca att att    3840
Val Asp Ser Ser Gly Ile Lys His Asn Ile Phe Asn Pro Pro Ile Ile
1265                1270                1275                1280 gct cga tac atc cgt ttg cac cca act cat tat agc att cgc agc act    3888
Ala Arg Tyr Ile Arg Leu His Pro Thr His Tyr Ser Ile Arg Ser Thr
                1285                1290                1295 ctt cgc atg gag ttg atg ggc tgt gat tta aat agt tgc agc atg cca    3936
Leu Arg Met Glu Leu Met Gly Cys Asp Leu Asn Ser Cys Ser Met Pro
            1300                1305                1310
```

```
ttg gga atg gag agt aaa gca ata tca gat gca cag att act gct tca    3984
Leu Gly Met Glu Ser Lys Ala Ile Ser Asp Ala Gln Ile Thr Ala Ser
        1315                1320                1325 tcc tac ttt acc aat atg ttt gcc acc tgg tct cct tca aaa gct cga    4032
Ser Tyr Phe Thr Asn Met Phe Ala Thr Trp Ser Pro Ser Lys Ala Arg
    1330                1335                1340 ctt cac ctc caa ggg agg agt aat gcc tgg aga cct cag gtg aat aat    4080
Leu His Leu Gln Gly Arg Ser Asn Ala Trp Arg Pro Gln Val Asn Asn
1345                1350                1355                1360 cca aaa gag tgg ctg caa gtg gac ttc cag aag aca atg aaa gtc aca    4128
Pro Lys Glu Trp Leu Gln Val Asp Phe Gln Lys Thr Met Lys Val Thr
                1365                1370                1375 gga gta act act cag gga gta aaa tct ctg ctt acc agc atg tat gtg    4176
Gly Val Thr Thr Gln Gly Val Lys Ser Leu Leu Thr Ser Met Tyr Val
        1380                1385                1390 aag gag ttc ctc atc tcc agc agt caa gat ggc cat cag tgg act ctc    4224
Lys Glu Phe Leu Ile Ser Ser Ser Gln Asp Gly His Gln Trp Thr Leu
    1395                1400                1405 ttt ttt cag aat ggc aaa gta aag gtt ttt cag gga aat caa gac tcc    4272
Phe Phe Gln Asn Gly Lys Val Lys Val Phe Gln Gly Asn Gln Asp Ser
1410                1415                1420 ttc aca cct gtg gtg aac tct cta gac cca ccg tta ctg act cgc tac    4320
Phe Thr Pro Val Val Asn Ser Leu Asp Pro Pro Leu Leu Thr Arg Tyr
1425                1430                1435                1440 ctt cga att cac ccc cag agt tgg gtg cac cag att gcc ctg agg atg    4368
Leu Arg Ile His Pro Gln Ser Trp Val His Gln Ile Ala Leu Arg Met
        1445                1450                1455 gag gtt ctg ggc tgc gag gca cag gac ctc tac                         4401
Glu Val Leu Gly Cys Glu Ala Gln Asp Leu Tyr
    1460                1465

<210> SEQ ID NO 15
<211> LENGTH: 1467
<212> TYPE: PRT
<213> ORGANISM: Artificial Sequence
<220> FEATURE:
<223> OTHER INFORMATION: HP44/OL-- factor VIII having the following
      domains: A1p-A2p-app-A3p-C1h-C2h

<400> SEQUENCE: 15

Met Gln Leu Glu Leu Ser Thr Cys Val Phe Leu Cys Leu Leu Pro Leu
1               5                   10                  15

Gly Phe Ser Ala Ile Arg Arg Tyr Tyr Leu Gly Ala Val Glu Leu Ser
                20                  25                  30

Trp Asp Tyr Arg Gln Ser Glu Leu Leu Arg Glu Leu His Val Asp Thr
            35                  40                  45

Arg Phe Pro Ala Thr Ala Pro Gly Ala Leu Pro Leu Gly Pro Ser Val
        50                  55                  60

Leu Tyr Lys Lys Thr Val Phe Val Glu Phe Thr Asp Gln Leu Phe Ser
65                  70                  75                  80

Val Ala Arg Pro Arg Pro Pro Trp Met Gly Leu Leu Gly Pro Thr Ile
                85                  90                  95

Gln Ala Glu Val Tyr Asp Thr Val Val Thr Leu Lys Asn Met Ala
                100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140
```

```
Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
            195                 200                 205

Thr Gln Asn Leu His Glu Phe Val Leu Leu Phe Ala Val Phe Asp Glu
        210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285

Ile Phe Leu Glu Gly His Thr Phe Leu Val Arg His His Arg Gln Ala
        290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                325                 330                 335

His Gly Gly Met Glu Ala His Val Arg Val Glu Ser Cys Ala Glu Glu
            340                 345                 350

Pro Gln Leu Arg Arg Lys Ala Asp Glu Glu Asp Tyr Asp Asp Asn
        355                 360                 365

Leu Tyr Asp Ser Asp Met Asp Val Val Arg Leu Asp Gly Asp Asp Val
    370                 375                 380

Ser Pro Phe Ile Gln Ile Arg Ser Val Ala Lys Lys His Pro Lys Thr
385                 390                 395                 400

Trp Val His Tyr Ile Ser Ala Glu Glu Asp Trp Asp Tyr Ala Pro
                405                 410                 415

Ala Val Pro Ser Pro Ser Asp Arg Ser Tyr Lys Ser Leu Tyr Leu Asn
            420                 425                 430

Ser Gly Pro Gln Arg Ile Gly Arg Lys Tyr Lys Lys Ala Arg Phe Val
        435                 440                 445

Ala Tyr Thr Asp Val Thr Phe Lys Thr Arg Lys Ala Ile Pro Tyr Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Lys Ala Ser Arg Pro Tyr Asn Ile Tyr Pro
                485                 490                 495

His Gly Ile Thr Asp Val Ser Ala Leu His Pro Gly Arg Leu Leu Lys
            500                 505                 510

Gly Trp Lys His Leu Lys Asp Met Pro Ile Leu Pro Gly Glu Thr Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Ser Ile Asn Leu Glu Lys
545                 550                 555                 560
```

-continued

```
Asp Leu Ala Ser Gly Leu Ile Gly Pro Leu Leu Ile Cys Tyr Lys Glu
            565                 570                 575

Ser Val Asp Gln Arg Gly Asn Gln Met Met Ser Asp Lys Arg Asn Val
        580                 585                 590

Ile Leu Phe Ser Val Phe Asp Glu Asn Gln Ser Trp Tyr Leu Ala Glu
    595                 600                 605

Asn Ile Gln Arg Phe Leu Pro Asn Pro Asp Gly Leu Gln Pro Gln Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Val Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Val Leu Gly Cys His Asn Ser Asp Leu Arg Asn Arg Gly
705                 710                 715                 720

Met Thr Ala Leu Leu Lys Val Tyr Ser Cys Asp Arg Asp Ile Gly Asp
                725                 730                 735

Tyr Tyr Asp Asn Thr Tyr Glu Asp Ile Pro Gly Phe Leu Leu Ser Gly
            740                 745                 750

Lys Asn Val Ile Glu Pro Arg Ser Phe Ala Gln Asn Ser Arg Pro Pro
        755                 760                 765

Ser Ala Ser Ala Pro Lys Pro Pro Val Leu Arg Arg His Gln Arg Asp
770                 775                 780

Ile Ser Leu Pro Thr Phe Gln Pro Glu Glu Asp Lys Met Asp Tyr Asp
785                 790                 795                 800

Asp Ile Phe Ser Thr Glu Thr Lys Gly Glu Asp Phe Asp Ile Tyr Gly
                805                 810                 815

Glu Asp Glu Asn Gln Asp Pro Arg Ser Phe Gln Lys Arg Thr Arg His
            820                 825                 830

Tyr Phe Ile Ala Ala Val Glu Gln Leu Trp Asp Tyr Gly Met Ser Glu
        835                 840                 845

Ser Pro Arg Ala Leu Arg Asn Arg Ala Gln Asn Gly Glu Val Pro Arg
    850                 855                 860

Phe Lys Lys Val Val Phe Arg Glu Phe Ala Asp Gly Ser Phe Thr Gln
865                 870                 875                 880

Pro Ser Tyr Arg Gly Glu Leu Asn Lys His Leu Gly Leu Leu Gly Pro
                885                 890                 895

Tyr Ile Arg Ala Glu Val Glu Asp Asn Ile Met Val Thr Phe Lys Asn
            900                 905                 910

Gln Ala Ser Arg Pro Tyr Ser Phe Tyr Ser Ser Leu Ile Ser Tyr Pro
        915                 920                 925

Asp Asp Gln Glu Gln Gly Ala Glu Pro Arg His Asn Phe Val Gln Pro
    930                 935                 940

Asn Glu Thr Arg Thr Tyr Phe Trp Lys Val Gln His His Met Ala Pro
945                 950                 955                 960

Thr Glu Asp Glu Phe Asp Cys Lys Ala Trp Ala Tyr Phe Ser Asp Val
                965                 970                 975
```

-continued

Asp Leu Glu Lys Asp Val His Ser Gly Leu Ile Gly Pro Leu Leu Ile
              980                 985                 990

Cys Arg Ala Asn Thr Leu Asn Ala Ala His Gly Arg Gln Val Thr Val
              995                 1000                1005

Gln Glu Phe Ala Leu Phe Phe Thr Ile Phe Asp Glu Thr Lys Ser Trp
              1010                1015                1020

Tyr Phe Thr Glu Asn Val Glu Arg Asn Cys Arg Ala Pro Cys His Leu
1025                1030                1035                1040

Gln Met Glu Asp Pro Thr Leu Lys Glu Asn Tyr Arg Phe His Ala Ile
              1045                1050                1055

Asn Gly Tyr Val Met Asp Thr Leu Pro Gly Leu Val Met Ala Gln Asn
              1060                1065                1070

Gln Arg Ile Arg Trp Tyr Leu Leu Ser Met Gly Ser Asn Glu Asn Ile
              1075                1080                1085

His Ser Ile His Phe Ser Gly His Val Phe Ser Val Arg Lys Lys Glu
              1090                1095                1100

Glu Tyr Lys Met Ala Val Tyr Asn Leu Tyr Pro Gly Val Phe Glu Thr
1105                1110                1115                1120

Val Glu Met Leu Pro Ser Lys Val Gly Ile Trp Arg Ile Glu Cys Leu
              1125                1130                1135

Ile Gly Glu His Leu Gln Ala Gly Met Ser Thr Thr Phe Leu Val Tyr
              1140                1145                1150

Ser Lys Lys Cys Gln Thr Pro Leu Gly Met Ala Ser Gly His Ile Arg
              1155                1160                1165

Asp Phe Gln Ile Thr Ala Ser Gly Gln Tyr Gly Gln Trp Ala Pro Lys
              1170                1175                1180

Leu Ala Arg Leu His Tyr Ser Gly Ser Ile Asn Ala Trp Ser Thr Lys
1185                1190                1195                1200

Glu Pro Phe Ser Trp Ile Lys Val Asp Leu Leu Ala Pro Met Ile Ile
              1205                1210                1215

His Gly Ile Lys Thr Gln Gly Ala Arg Gln Lys Phe Ser Ser Leu Tyr
              1220                1225                1230

Ile Ser Gln Phe Ile Ile Met Tyr Ser Leu Asp Gly Lys Lys Trp Gln
              1235                1240                1245

Thr Tyr Arg Gly Asn Ser Thr Gly Thr Leu Met Val Phe Phe Gly Asn
1250                1255                1260

Val Asp Ser Ser Gly Ile Lys His Asn Ile Phe Asn Pro Pro Ile Ile
1265                1270                1275                1280

Ala Arg Tyr Ile Arg Leu His Pro Thr His Tyr Ser Ile Arg Ser Thr
              1285                1290                1295

Leu Arg Met Glu Leu Met Gly Cys Asp Leu Asn Ser Cys Ser Met Pro
              1300                1305                1310

Leu Gly Met Glu Ser Lys Ala Ile Ser Asp Ala Gln Ile Thr Ala Ser
              1315                1320                1325

Ser Tyr Phe Thr Asn Met Phe Ala Thr Trp Ser Pro Ser Lys Ala Arg
              1330                1335                1340

Leu His Leu Gln Gly Arg Ser Asn Ala Trp Arg Pro Gln Val Asn Asn
1345                1350                1355                1360

Pro Lys Glu Trp Leu Gln Val Asp Phe Gln Lys Thr Met Lys Val Thr
              1365                1370                1375

Gly Val Thr Thr Gln Gly Val Lys Ser Leu Leu Thr Ser Met Tyr Val
              1380                1385                1390

```
Lys Glu Phe Leu Ile Ser Ser Gln Asp Gly His Gln Trp Thr Leu
        1395                1400                1405

Phe Phe Gln Asn Gly Lys Val Lys Val Phe Gln Gly Asn Gln Asp Ser
    1410                1415                1420

Phe Thr Pro Val Val Asn Ser Leu Asp Pro Pro Leu Leu Thr Arg Tyr
1425                1430                1435                1440

Leu Arg Ile His Pro Gln Ser Trp Val His Gln Ile Ala Leu Arg Met
            1445                1450                1455

Glu Val Leu Gly Cys Glu Ala Gln Asp Leu Tyr
        1460                1465

<210> SEQ ID NO 16
<211> LENGTH: 4371
<212> TYPE: DNA
<213> ORGANISM: Artificial Sequence
<220> FEATURE:
<223> OTHER INFORMATION: hybrid human and porcine factor VIII sequence
<220> FEATURE:
<221> NAME/KEY: CDS
<222> LOCATION: (1)...(4371)
<223> OTHER INFORMATION: HP46/SQ-- factor VIII having the following
      domains:  A1p-A2h-aph-A3h-C1h-C2h

<400> SEQUENCE: 16
```

| | | | | | | | | | | | | | | | | |
|---|---|---|---|---|---|---|---|---|---|---|---|---|---|---|---|---|
| atg | cag | cta | gag | ctc | tcc | acc | tgt | gtc | ttt | ctg | tgt | ctc | ttg | cca | ctc | 48 |
| Met | Gln | Leu | Glu | Leu | Ser | Thr | Cys | Val | Phe | Leu | Cys | Leu | Leu | Pro | Leu | |
| 1 | | | | 5 | | | | | 10 | | | | | 15 | | |
| ggc | ttt | agt | gcc | atc | agg | aga | tac | tac | ctg | ggc | gca | gtg | gaa | ctg | tcc | 96 |
| Gly | Phe | Ser | Ala | Ile | Arg | Arg | Tyr | Tyr | Leu | Gly | Ala | Val | Glu | Leu | Ser | |
| | | | 20 | | | | | 25 | | | | | 30 | | | |
| tgg | gac | tac | cgg | caa | agt | gaa | ctc | ctc | cgt | gag | ctg | cac | gtg | gac | acc | 144 |
| Trp | Asp | Tyr | Arg | Gln | Ser | Glu | Leu | Leu | Arg | Glu | Leu | His | Val | Asp | Thr | |
| | | 35 | | | | | 40 | | | | | 45 | | | | |
| aga | ttt | cct | gct | aca | gcg | cca | gga | gct | ctt | ccg | ttg | ggc | ccg | tca | gtc | 192 |
| Arg | Phe | Pro | Ala | Thr | Ala | Pro | Gly | Ala | Leu | Pro | Leu | Gly | Pro | Ser | Val | |
| | 50 | | | | | 55 | | | | | 60 | | | | | |
| ctg | tac | aaa | aag | act | gtg | ttc | gta | gag | ttc | acg | gat | caa | ctt | ttc | agc | 240 |
| Leu | Tyr | Lys | Lys | Thr | Val | Phe | Val | Glu | Phe | Thr | Asp | Gln | Leu | Phe | Ser | |
| 65 | | | | | 70 | | | | | 75 | | | | | 80 | |
| gtt | gcc | agg | ccc | agg | cca | cca | tgg | atg | ggt | ctg | ctg | ggt | cct | acc | atc | 288 |
| Val | Ala | Arg | Pro | Arg | Pro | Pro | Trp | Met | Gly | Leu | Leu | Gly | Pro | Thr | Ile | |
| | | | | 85 | | | | | 90 | | | | | 95 | | |
| cag | gct | gag | gtt | tac | gac | acg | gtg | gtc | gtt | acc | ctg | aag | aac | atg | gct | 336 |
| Gln | Ala | Glu | Val | Tyr | Asp | Thr | Val | Val | Val | Thr | Leu | Lys | Asn | Met | Ala | |
| | | | 100 | | | | | 105 | | | | | 110 | | | |
| tct | cat | ccc | gtt | agt | ctt | cac | gct | gtc | ggc | gtc | tcc | ttc | tgg | aaa | tct | 384 |
| Ser | His | Pro | Val | Ser | Leu | His | Ala | Val | Gly | Val | Ser | Phe | Trp | Lys | Ser | |
| | | 115 | | | | | 120 | | | | | 125 | | | | |
| tcc | gaa | ggc | gct | gaa | tat | gag | gat | cac | acc | agc | caa | agg | gag | aag | gaa | 432 |
| Ser | Glu | Gly | Ala | Glu | Tyr | Glu | Asp | His | Thr | Ser | Gln | Arg | Glu | Lys | Glu | |
| | 130 | | | | | 135 | | | | | 140 | | | | | |
| gac | gat | aaa | gtc | ctt | ccc | ggt | aaa | agc | caa | acc | tac | gtc | tgg | cag | gtc | 480 |
| Asp | Asp | Lys | Val | Leu | Pro | Gly | Lys | Ser | Gln | Thr | Tyr | Val | Trp | Gln | Val | |
| 145 | | | | | 150 | | | | | 155 | | | | | 160 | |
| ctg | aaa | gaa | aat | ggt | cca | aca | gcc | tct | gac | cca | cca | tgt | ctt | acc | tac | 528 |
| Leu | Lys | Glu | Asn | Gly | Pro | Thr | Ala | Ser | Asp | Pro | Pro | Cys | Leu | Thr | Tyr | |
| | | | | 165 | | | | | 170 | | | | | 175 | | |
| tca | tac | ctg | tct | cac | gtg | gac | ctg | gtg | aaa | gac | ctg | aat | tcg | ggc | ctc | 576 |
| Ser | Tyr | Leu | Ser | His | Val | Asp | Leu | Val | Lys | Asp | Leu | Asn | Ser | Gly | Leu | |
| | | | 180 | | | | | 185 | | | | | 190 | | | |

```
att gga gcc ctg ctg gtt tgt aga gaa ggg agt ctg acc aga gaa agg      624
Ile Gly Ala Leu Leu Val Cys Arg Glu Gly Ser Leu Thr Arg Glu Arg
            195                 200                 205 acc cag aac ctg cac gaa ttt gta cta ctt ttt gct gtc ttt gat gaa      672
Thr Gln Asn Leu His Glu Phe Val Leu Leu Phe Ala Val Phe Asp Glu
        210                 215                 220 ggg aaa agt tgg cac tca gca aga aat gac tcc tgg aca cgg gcc atg      720
Gly Lys Ser Trp His Ser Ala Arg Asn Asp Ser Trp Thr Arg Ala Met
225                 230                 235                 240 gat ccc gca cct gcc agg gcc cag cct gca atg cac aca gtc aat ggc      768
Asp Pro Ala Pro Ala Arg Ala Gln Pro Ala Met His Thr Val Asn Gly
                245                 250                 255 tat gtc aac agg tct ctg cca ggt ctg atc gga tgt cat aag aaa tca      816
Tyr Val Asn Arg Ser Leu Pro Gly Leu Ile Gly Cys His Lys Lys Ser
            260                 265                 270 gtc tac tgg cac gtg att gga atg ggc acc agc ccg gaa gtg cac tcc      864
Val Tyr Trp His Val Ile Gly Met Gly Thr Ser Pro Glu Val His Ser
        275                 280                 285 att ttt ctt gaa ggc cac acg ttt ctc gtg agg cac cat cgc cag gct      912
Ile Phe Leu Glu Gly His Thr Phe Leu Val Arg His His Arg Gln Ala
    290                 295                 300 tcc ttg gag atc tcg cca cta act ttc ctc act gct cag aca ttc ctg      960
Ser Leu Glu Ile Ser Pro Leu Thr Phe Leu Thr Ala Gln Thr Phe Leu
305                 310                 315                 320 atg gac ctt ggc cag ttc cta ctg ttt tgt cat atc tct tcc cac cac     1008
Met Asp Leu Gly Gln Phe Leu Leu Phe Cys His Ile Ser Ser His His
                325                 330                 335 cat ggt ggc atg gag gct cac gtc aga gta gaa agc tgc gcc gag gag     1056
His Gly Gly Met Glu Ala His Val Arg Val Glu Ser Cys Ala Glu Glu
            340                 345                 350 ccc cag ctg cgg agg aaa gct gat gaa gag gaa gat tat gat gac aat     1104
Pro Gln Leu Arg Arg Lys Ala Asp Glu Glu Glu Asp Tyr Asp Asp Asn
        355                 360                 365 ttg tac gac tcg gac atg gac gtg gtc cgg ctc gat ggt gac gac gtg     1152
Leu Tyr Asp Ser Asp Met Asp Val Val Arg Leu Asp Gly Asp Asp Val
    370                 375                 380 tct ccc ttt atc caa atc cgc tca gtt gcc aag aag cat cct aaa act     1200
Ser Pro Phe Ile Gln Ile Arg Ser Val Ala Lys Lys His Pro Lys Thr
385                 390                 395                 400 tgg gta cat tac att gct gct gaa gag gag gac tgg gac tat gct ccc     1248
Trp Val His Tyr Ile Ala Ala Glu Glu Glu Asp Trp Asp Tyr Ala Pro
                405                 410                 415 tta gtc ctc gcc ccc gat gac aga agt tat aaa agt caa tat ttg aac     1296
Leu Val Leu Ala Pro Asp Asp Arg Ser Tyr Lys Ser Gln Tyr Leu Asn
            420                 425                 430 aat ggc cct cag cgg att ggt agg aag tac aaa aaa gtc cga ttt atg     1344
Asn Gly Pro Gln Arg Ile Gly Arg Lys Tyr Lys Lys Val Arg Phe Met
        435                 440                 445 gca tac aca gat gaa acc ttt aag acg cgt gaa gct att cag cat gaa     1392
Ala Tyr Thr Asp Glu Thr Phe Lys Thr Arg Glu Ala Ile Gln His Glu
    450                 455                 460 tca gga atc ttg gga cct tta ctt tat ggg gaa gtt gga gac aca ctg     1440
Ser Gly Ile Leu Gly Pro Leu Leu Tyr Gly Glu Val Gly Asp Thr Leu
465                 470                 475                 480 ttg att ata ttt aag aat caa gca agc aga cca tat aac atc tac cct     1488
Leu Ile Ile Phe Lys Asn Gln Ala Ser Arg Pro Tyr Asn Ile Tyr Pro
                485                 490                 495 cac gga atc act gat gtc cgt cct ttg tat tca agg aga tta cca aaa     1536
His Gly Ile Thr Asp Val Arg Pro Leu Tyr Ser Arg Arg Leu Pro Lys
            500                 505                 510
```

```
ggt gta aaa cat ttg aag gat ttt cca att ctg cca gga gaa ata ttc      1584
Gly Val Lys His Leu Lys Asp Phe Pro Ile Leu Pro Gly Glu Ile Phe
        515                 520                 525 aaa tat aaa tgg aca gtg act gta gaa gat ggg cca act aaa tca gat      1632
Lys Tyr Lys Trp Thr Val Thr Val Glu Asp Gly Pro Thr Lys Ser Asp
    530                 535                 540 ccg cgg tgc ctg acc cgc tat tac tct agt ttc gtt aat atg gag aga      1680
Pro Arg Cys Leu Thr Arg Tyr Tyr Ser Ser Phe Val Asn Met Glu Arg
545                 550                 555                 560 gat cta gct tca gga ctc att ggc cct ctc ctc atc tgc tac aaa gaa      1728
Asp Leu Ala Ser Gly Leu Ile Gly Pro Leu Leu Ile Cys Tyr Lys Glu
                565                 570                 575 tct gta gat caa aga gga aac cag ata atg tca gac aag agg aat gtc      1776
Ser Val Asp Gln Arg Gly Asn Gln Ile Met Ser Asp Lys Arg Asn Val
            580                 585                 590 atc ctg ttt tct gta ttt gat gag aac cga agc tgg tac ctc aca gag      1824
Ile Leu Phe Ser Val Phe Asp Glu Asn Arg Ser Trp Tyr Leu Thr Glu
        595                 600                 605 aat ata caa cgc ttt ctc ccc aat cca gct gga gtg cag ctt gag gat      1872
Asn Ile Gln Arg Phe Leu Pro Asn Pro Ala Gly Val Gln Leu Glu Asp
    610                 615                 620 cca gag ttc caa gcc tcc aac atc atg cac agc atc aat ggc tat gtt      1920
Pro Glu Phe Gln Ala Ser Asn Ile Met His Ser Ile Asn Gly Tyr Val
625                 630                 635                 640 ttt gat agt ttg cag ttg tca gtt tgt ttg cat gag gtg gca tac tgg      1968
Phe Asp Ser Leu Gln Leu Ser Val Cys Leu His Glu Val Ala Tyr Trp
                645                 650                 655 tac att cta agc att gga gca cag act gac ttc ctt tct gtc ttc ttc      2016
Tyr Ile Leu Ser Ile Gly Ala Gln Thr Asp Phe Leu Ser Val Phe Phe
            660                 665                 670 tct gga tat acc ttc aaa cac aaa atg gtc tat gaa gac aca ctc acc      2064
Ser Gly Tyr Thr Phe Lys His Lys Met Val Tyr Glu Asp Thr Leu Thr
        675                 680                 685 cta ttc cca ttc tca gga gaa act gtc ttc atg tcg atg gaa aac cca      2112
Leu Phe Pro Phe Ser Gly Glu Thr Val Phe Met Ser Met Glu Asn Pro
    690                 695                 700 ggt cta tgg att ctg ggg tgc cac aac tca gac ttt cgg aac aga ggc      2160
Gly Leu Trp Ile Leu Gly Cys His Asn Ser Asp Phe Arg Asn Arg Gly
705                 710                 715                 720 atg acc gcc tta ctg aag gtt tct agt tgt gac aag aac act ggt gat      2208
Met Thr Ala Leu Leu Lys Val Ser Ser Cys Asp Lys Asn Thr Gly Asp
                725                 730                 735 tat tac gag gac agt tat gaa gat att tca gca tac ttg ctg agt aaa      2256
Tyr Tyr Glu Asp Ser Tyr Glu Asp Ile Ser Ala Tyr Leu Leu Ser Lys
            740                 745                 750 aac aat gcc att gaa cct agg agc ttc tct cag aat cca cca gtc ttg      2304
Asn Asn Ala Ile Glu Pro Arg Ser Phe Ser Gln Asn Pro Pro Val Leu
        755                 760                 765 aaa cgc cat caa cgg gaa ata act cgt act act ctt cag tca gat caa      2352
Lys Arg His Gln Arg Glu Ile Thr Arg Thr Thr Leu Gln Ser Asp Gln
    770                 775                 780 gag gaa att gac tat gat gat acc ata tca gtt gaa atg aag aag gaa      2400
Glu Glu Ile Asp Tyr Asp Asp Thr Ile Ser Val Glu Met Lys Lys Glu
785                 790                 795                 800 gat ttt gac att tat gat gag gat gaa aat cag agc ccc cgc agc ttt      2448
Asp Phe Asp Ile Tyr Asp Glu Asp Glu Asn Gln Ser Pro Arg Ser Phe
                805                 810                 815 caa aag aaa aca cga cac tat ttt att gct gca gtg gag agg ctc tgg      2496
Gln Lys Lys Thr Arg His Tyr Phe Ile Ala Ala Val Glu Arg Leu Trp
            820                 825                 830
```

```
                                               -continued gat tat ggg atg agt agc tcc cca cat gtt cta aga aac agg gct cag      2544
Asp Tyr Gly Met Ser Ser Pro His Val Leu Arg Asn Arg Ala Gln
            835                 840                 845 agt ggc agt gtc cct cag ttc aag aaa gtt gtt ttc cag gaa ttt act      2592
Ser Gly Ser Val Pro Gln Phe Lys Lys Val Val Phe Gln Glu Phe Thr
850                 855                 860 gat ggc tcc ttt act cag ccc tta tac cgt gga gaa cta aat gaa cat      2640
Asp Gly Ser Phe Thr Gln Pro Leu Tyr Arg Gly Glu Leu Asn Glu His
865                 870                 875                 880 ttg gga ctc ctg ggg cca tat ata aga gca gaa gtt gaa gat aat atc      2688
Leu Gly Leu Leu Gly Pro Tyr Ile Arg Ala Glu Val Glu Asp Asn Ile
                885                 890                 895 atg gta act ttc aga aat cag gcc tct cgt ccc tat tcc ttc tat tct      2736
Met Val Thr Phe Arg Asn Gln Ala Ser Arg Pro Tyr Ser Phe Tyr Ser
            900                 905                 910 agc ctt att tct tat gag gaa gat cag agg caa gga gca gaa cct aga      2784
Ser Leu Ile Ser Tyr Glu Glu Asp Gln Arg Gln Gly Ala Glu Pro Arg
        915                 920                 925 aaa aac ttt gtc aag cct aat gaa acc aaa act tac ttt tgg aaa gtg      2832
Lys Asn Phe Val Lys Pro Asn Glu Thr Lys Thr Tyr Phe Trp Lys Val
930                 935                 940 caa cat cat atg gca ccc act aaa gat gag ttt gac tgc aaa gcc tgg      2880
Gln His His Met Ala Pro Thr Lys Asp Glu Phe Asp Cys Lys Ala Trp
945                 950                 955                 960 gct tat ttc tct gat gtt gac ctg gaa aaa gat gtg cac tca ggc ctg      2928
Ala Tyr Phe Ser Asp Val Asp Leu Glu Lys Asp Val His Ser Gly Leu
                965                 970                 975 att gga ccc ctt ctg gtc tgc cac act aac aca ctg aac cct gct cat      2976
Ile Gly Pro Leu Leu Val Cys His Thr Asn Thr Leu Asn Pro Ala His
            980                 985                 990 ggg aga caa gtg aca gta cag gaa ttt gct ctg ttt ttc acc atc ttt      3024
Gly Arg Gln Val Thr Val Gln Glu Phe Ala Leu Phe Phe Thr Ile Phe
        995                 1000                1005 gat gag acc aaa agc tgg tac ttc act gaa aat atg gaa aga aac tgc      3072
Asp Glu Thr Lys Ser Trp Tyr Phe Thr Glu Asn Met Glu Arg Asn Cys
    1010                1015                1020 agg gct ccc tgc aat atc cag atg gaa gat ccc act ttt aaa gag aat      3120
Arg Ala Pro Cys Asn Ile Gln Met Glu Asp Pro Thr Phe Lys Glu Asn
1025                1030                1035                1040 tat cgc ttc cat gca atc aat ggc tac ata atg gat aca cta cct ggc      3168
Tyr Arg Phe His Ala Ile Asn Gly Tyr Ile Met Asp Thr Leu Pro Gly
                1045                1050                1055 tta gta atg gct cag gat caa agg att cga tgg tat ctg ctc agc atg      3216
Leu Val Met Ala Gln Asp Gln Arg Ile Arg Trp Tyr Leu Leu Ser Met
            1060                1065                1070 ggc agc aat gaa aac atc cat tct att cat ttc agt gga cat gtg ttc      3264
Gly Ser Asn Glu Asn Ile His Ser Ile His Phe Ser Gly His Val Phe
        1075                1080                1085 act gta cga aaa aaa gag gag tat aaa atg gca ctg tac aat ctc tat      3312
Thr Val Arg Lys Lys Glu Glu Tyr Lys Met Ala Leu Tyr Asn Leu Tyr
    1090                1095                1100 cca ggt gtt ttt gag aca gtg gaa atg tta cca tcc aaa gct gga att      3360
Pro Gly Val Phe Glu Thr Val Glu Met Leu Pro Ser Lys Ala Gly Ile
1105                1110                1115                1120 tgg cgg gtg gaa tgc ctt att ggc gag cat cta cat gct ggg atg agc      3408
Trp Arg Val Glu Cys Leu Ile Gly Glu His Leu His Ala Gly Met Ser
                1125                1130                1135 aca ctt ttt ctg gtg tac agc aat aag tgt cag act ccc ctg gga atg      3456
Thr Leu Phe Leu Val Tyr Ser Asn Lys Cys Gln Thr Pro Leu Gly Met
            1140                1145                1150
```

| | |
|---|---|
| gct tct gga cac att aga gat ttt cag att aca gct tca gga caa tat<br>Ala Ser Gly His Ile Arg Asp Phe Gln Ile Thr Ala Ser Gly Gln Tyr<br>              1155                   1160                  1165 | 3504 |
| gga cag tgg gcc cca aag ctg gcc aga ctt cat tat tcc gga tca atc<br>Gly Gln Trp Ala Pro Lys Leu Ala Arg Leu His Tyr Ser Gly Ser Ile<br>1170                   1175                   1180 | 3552 |
| aat gcc tgg agc acc aag gag ccc ttt tct tgg atc aag gtg gat ctg<br>Asn Ala Trp Ser Thr Lys Glu Pro Phe Ser Trp Ile Lys Val Asp Leu<br>1185                   1190                   1195                  1200 | 3600 |
| ttg gca cca atg att att cac ggc atc aag acc cag ggt gcc cgt cag<br>Leu Ala Pro Met Ile Ile His Gly Ile Lys Thr Gln Gly Ala Arg Gln<br>              1205                   1210                  1215 | 3648 |
| aag ttc tcc agc ctc tac atc tct cag ttt atc atc atg tat agt ctt<br>Lys Phe Ser Ser Leu Tyr Ile Ser Gln Phe Ile Ile Met Tyr Ser Leu<br>              1220                   1225                  1230 | 3696 |
| gat ggg aag aag tgg cag act tat cga gga aat tcc act gga acc tta<br>Asp Gly Lys Lys Trp Gln Thr Tyr Arg Gly Asn Ser Thr Gly Thr Leu<br>              1235                   1240                  1245 | 3744 |
| atg gtc ttc ttt ggc aat gtg gat tca tct ggg ata aaa cac aat att<br>Met Val Phe Phe Gly Asn Val Asp Ser Ser Gly Ile Lys His Asn Ile<br>              1250                   1255                  1260 | 3792 |
| ttt aac cct cca att att gct cga tac atc cgt ttg cac cca act cat<br>Phe Asn Pro Pro Ile Ile Ala Arg Tyr Ile Arg Leu His Pro Thr His<br>1265                   1270                   1275                  1280 | 3840 |
| tat agc att cgc agc act ctt cgc atg gag ttg atg ggc tgt gat tta<br>Tyr Ser Ile Arg Ser Thr Leu Arg Met Glu Leu Met Gly Cys Asp Leu<br>                       1285                   1290                  1295 | 3888 |
| aat agt tgc agc atg cca ttg gga atg gag agt aaa gca ata tca gat<br>Asn Ser Cys Ser Met Pro Leu Gly Met Glu Ser Lys Ala Ile Ser Asp<br>              1300                   1305                  1310 | 3936 |
| gca cag att act gct tca tcc tac ttt acc aat atg ttt gcc acc tgg<br>Ala Gln Ile Thr Ala Ser Ser Tyr Phe Thr Asn Met Phe Ala Thr Trp<br>              1315                   1320                  1325 | 3984 |
| tct cct tca aaa gct cga ctt cac ctc caa ggg agg agt aat gcc tgg<br>Ser Pro Ser Lys Ala Arg Leu His Leu Gln Gly Arg Ser Asn Ala Trp<br>              1330                   1335                  1340 | 4032 |
| aga cct cag gtg aat aat cca aaa gag tgg ctg caa gtg gac ttc cag<br>Arg Pro Gln Val Asn Asn Pro Lys Glu Trp Leu Gln Val Asp Phe Gln<br>1345                   1350                   1355                  1360 | 4080 |
| aag aca atg aaa gtc aca gga gta act act cag gga gta aaa tct ctg<br>Lys Thr Met Lys Val Thr Gly Val Thr Thr Gln Gly Val Lys Ser Leu<br>              1365                   1370                  1375 | 4128 |
| ctt acc agc atg tat gtg aag gag ttc ctc atc tcc agc agt caa gat<br>Leu Thr Ser Met Tyr Val Lys Glu Phe Leu Ile Ser Ser Gln Asp<br>              1380                   1385                  1390 | 4176 |
| ggc cat cag tgg act ctc ttt ttt cag aat ggc aaa gta aag gtt ttt<br>Gly His Gln Trp Thr Leu Phe Phe Gln Asn Gly Lys Val Lys Val Phe<br>              1395                   1400                  1405 | 4224 |
| cag gga aat caa gac tcc ttc aca cct gtg gtg aac tct cta gac cca<br>Gln Gly Asn Gln Asp Ser Phe Thr Pro Val Val Asn Ser Leu Asp Pro<br>              1410                   1415                  1420 | 4272 |
| ccg tta ctg act cgc tac ctt cga att cac ccc cag agt tgg gtg cac<br>Pro Leu Leu Thr Arg Tyr Leu Arg Ile His Pro Gln Ser Trp Val His<br>1425                   1430                   1435                  1440 | 4320 |
| cag att gcc ctg agg atg gag gtt ctg ggc tgc gag gca cag gac ctc<br>Gln Ile Ala Leu Arg Met Glu Val Leu Gly Cys Glu Ala Gln Asp Leu<br>              1445                   1450                  1455 | 4368 |
| tac<br>Tyr | 4371 |

```
<210> SEQ ID NO 17
<211> LENGTH: 1457
<212> TYPE: PRT
<213> ORGANISM: Artificial Sequence
<220> FEATURE:
<223> OTHER INFORMATION: HP46/SQ-- factor VIII having the following
      domains:  A1p-A2h-aph-A3h-C1h-C2h

<400> SEQUENCE: 17

Met Gln Leu Glu Leu Ser Thr Cys Val Phe Leu Cys Leu Leu Pro Leu
 1               5                  10                  15

Gly Phe Ser Ala Ile Arg Arg Tyr Tyr Leu Gly Ala Val Glu Leu Ser
             20                  25                  30

Trp Asp Tyr Arg Gln Ser Glu Leu Leu Arg Glu Leu His Val Asp Thr
         35                  40                  45

Arg Phe Pro Ala Thr Ala Pro Gly Ala Leu Pro Leu Gly Pro Ser Val
     50                  55                  60

Leu Tyr Lys Lys Thr Val Phe Val Glu Phe Thr Asp Gln Leu Phe Ser
 65                  70                  75                  80

Val Ala Arg Pro Arg Pro Pro Trp Met Gly Leu Leu Gly Pro Thr Ile
                 85                  90                  95

Gln Ala Glu Val Tyr Asp Thr Val Val Val Thr Leu Lys Asn Met Ala
            100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285

Ile Phe Leu Glu Gly His Thr Phe Leu Val Arg His His Arg Gln Ala
    290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                325                 330                 335

His Gly Gly Met Glu Ala His Val Arg Val Glu Ser Cys Ala Glu Glu
            340                 345                 350

Pro Gln Leu Arg Arg Lys Ala Asp Glu Glu Glu Asp Tyr Asp Asp Asn
        355                 360                 365
```

-continued

```
Leu Tyr Asp Ser Asp Met Asp Val Val Arg Leu Asp Gly Asp Val
        370                 375                 380

Ser Pro Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780
```

-continued

```
Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
                900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
            930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
                980                 985                 990

Gly Arg Gln Val Thr Val Gln Glu Phe Ala Leu Phe Phe Thr Ile Phe
            995                 1000                1005

Asp Glu Thr Lys Ser Trp Tyr Phe Thr Glu Asn Met Glu Arg Asn Cys
1010                1015                1020

Arg Ala Pro Cys Asn Ile Gln Met Glu Asp Pro Thr Phe Lys Glu Asn
1025                1030                1035                1040

Tyr Arg Phe His Ala Ile Asn Gly Tyr Ile Met Asp Thr Leu Pro Gly
                1045                1050                1055

Leu Val Met Ala Gln Asp Gln Arg Ile Arg Trp Tyr Leu Leu Ser Met
                1060                1065                1070

Gly Ser Asn Glu Asn Ile His Ser Ile His Phe Ser Gly His Val Phe
            1075                1080                1085

Thr Val Arg Lys Lys Glu Glu Tyr Lys Met Ala Leu Tyr Asn Leu Tyr
    1090                1095                1100

Pro Gly Val Phe Glu Thr Val Glu Met Leu Pro Ser Lys Ala Gly Ile
1105                1110                1115                1120

Trp Arg Val Glu Cys Leu Ile Gly Glu His Leu His Ala Gly Met Ser
                1125                1130                1135

Thr Leu Phe Leu Val Tyr Ser Asn Lys Cys Gln Thr Pro Leu Gly Met
                1140                1145                1150

Ala Ser Gly His Ile Arg Asp Phe Gln Ile Thr Ala Ser Gly Gln Tyr
            1155                1160                1165

Gly Gln Trp Ala Pro Lys Leu Ala Arg Leu His Tyr Ser Gly Ser Ile
    1170                1175                1180

Asn Ala Trp Ser Thr Lys Glu Pro Phe Ser Trp Ile Lys Val Asp Leu
1185                1190                1195                1200
```

```
Leu Ala Pro Met Ile Ile His Gly Ile Lys Thr Gln Gly Ala Arg Gln
            1205                1210                1215

Lys Phe Ser Ser Leu Tyr Ile Ser Gln Phe Ile Ile Met Tyr Ser Leu
        1220                1225                1230

Asp Gly Lys Lys Trp Gln Thr Tyr Arg Gly Asn Ser Thr Gly Thr Leu
    1235                1240                1245

Met Val Phe Phe Gly Asn Val Asp Ser Ser Gly Ile Lys His Asn Ile
1250                1255                1260

Phe Asn Pro Pro Ile Ile Ala Arg Tyr Ile Arg Leu His Pro Thr His
1265                1270                1275                1280

Tyr Ser Ile Arg Ser Thr Leu Arg Met Glu Leu Met Gly Cys Asp Leu
            1285                1290                1295

Asn Ser Cys Ser Met Pro Leu Gly Met Glu Ser Lys Ala Ile Ser Asp
        1300                1305                1310

Ala Gln Ile Thr Ala Ser Ser Tyr Phe Thr Asn Met Phe Ala Thr Trp
    1315                1320                1325

Ser Pro Ser Lys Ala Arg Leu His Leu Gln Gly Arg Ser Asn Ala Trp
1330                1335                1340

Arg Pro Gln Val Asn Asn Pro Lys Glu Trp Leu Gln Val Asp Phe Gln
1345                1350                1355                1360

Lys Thr Met Lys Val Thr Gly Val Thr Gln Gly Val Lys Ser Leu
            1365                1370                1375

Leu Thr Ser Met Tyr Val Lys Glu Phe Leu Ile Ser Ser Ser Gln Asp
        1380                1385                1390

Gly His Gln Trp Thr Leu Phe Phe Gln Asn Gly Lys Val Lys Val Phe
    1395                1400                1405

Gln Gly Asn Gln Asp Ser Phe Thr Pro Val Val Asn Ser Leu Asp Pro
1410                1415                1420

Pro Leu Leu Thr Arg Tyr Leu Arg Ile His Pro Gln Ser Trp Val His
1425                1430                1435                1440

Gln Ile Ala Leu Arg Met Glu Val Leu Gly Cys Glu Ala Gln Asp Leu
            1445                1450                1455

Tyr

<210> SEQ ID NO 18
<211> LENGTH: 4401
<212> TYPE: DNA
<213> ORGANISM: Artificial Sequence
<220> FEATURE:
<223> OTHER INFORMATION: hybrid human and porcine factor VIII sequence
<220> FEATURE:
<221> NAME/KEY: CDS
<222> LOCATION: (1)...(4401)
<223> OTHER INFORMATION: HP47/OL -- factor VIII having the following
      domains:  A1p-A2h-app-A3p-C1h-C2h

<400> SEQUENCE: 18 atg cag cta gag ctc tcc acc tgt gtc ttt ctg tgt ctc ttg cca ctc      48
Met Gln Leu Glu Leu Ser Thr Cys Val Phe Leu Cys Leu Leu Pro Leu
 1               5                  10                  15 ggc ttt agt gcc atc agg aga tac tac ctg ggc gca gtg gaa ctg tcc      96
Gly Phe Ser Ala Ile Arg Arg Tyr Tyr Leu Gly Ala Val Glu Leu Ser
             20                  25                  30 tgg gac tac cgg caa agt gaa ctc ctc cgt gag ctg cac gtg gac acc     144
Trp Asp Tyr Arg Gln Ser Glu Leu Leu Arg Glu Leu His Val Asp Thr
         35                  40                  45
```

```
aga ttt cct gct aca gcg cca gga gct ctt ccg ttg ggc ccg tca gtc        192
Arg Phe Pro Ala Thr Ala Pro Gly Ala Leu Pro Leu Gly Pro Ser Val
    50                  55                  60 ctg tac aaa aag act gtg ttc gta gag ttc acg gat caa ctt ttc agc        240
Leu Tyr Lys Lys Thr Val Phe Val Glu Phe Thr Asp Gln Leu Phe Ser
 65                  70                  75                  80 gtt gcc agg ccc agg cca cca tgg atg ggt ctg ctg ggt cct acc atc        288
Val Ala Arg Pro Arg Pro Pro Trp Met Gly Leu Leu Gly Pro Thr Ile
                 85                  90                  95 cag gct gag gtt tac gac acg gtg gtc gtt acc ctg aag aac atg gct        336
Gln Ala Glu Val Tyr Asp Thr Val Val Val Thr Leu Lys Asn Met Ala
            100                 105                 110 tct cat ccc gtt agt ctt cac gct gtc ggc gtc tcc ttc tgg aaa tct        384
Ser His Pro Val Ser Leu His Ala Val Gly Val Ser Phe Trp Lys Ser
        115                 120                 125 tcc gaa ggc gct gaa tat gag gat cac acc agc caa agg gag aag gaa        432
Ser Glu Gly Ala Glu Tyr Glu Asp His Thr Ser Gln Arg Glu Lys Glu
130                 135                 140 gac gat aaa gtc ctt ccc ggt aaa agc caa acc tac gtc tgg cag gtc        480
Asp Asp Lys Val Leu Pro Gly Lys Ser Gln Thr Tyr Val Trp Gln Val
145                 150                 155                 160 ctg aaa gaa aat ggt cca aca gcc tct gac cca cca tgt ctt acc tac        528
Leu Lys Glu Asn Gly Pro Thr Ala Ser Asp Pro Pro Cys Leu Thr Tyr
                165                 170                 175 tca tac ctg tct cac gtg gac ctg gtg aaa gac ctg aat tcg ggc ctc        576
Ser Tyr Leu Ser His Val Asp Leu Val Lys Asp Leu Asn Ser Gly Leu
            180                 185                 190 att gga gcc ctg ctg gtt tgt aga gaa ggg agt ctg acc aga gaa agg        624
Ile Gly Ala Leu Leu Val Cys Arg Glu Gly Ser Leu Thr Arg Glu Arg
        195                 200                 205 acc cag aac ctg cac gaa ttt gta cta ctt ttt gct gtc ttt gat gaa        672
Thr Gln Asn Leu His Glu Phe Val Leu Leu Phe Ala Val Phe Asp Glu
    210                 215                 220 ggg aaa agt tgg cac tca gca aga aat gac tcc tgg aca cgg gcc atg        720
Gly Lys Ser Trp His Ser Ala Arg Asn Asp Ser Trp Thr Arg Ala Met
225                 230                 235                 240 gat ccc gca cct gcc agg gcc cag cct gca atg cac aca gtc aat ggc        768
Asp Pro Ala Pro Ala Arg Ala Gln Pro Ala Met His Thr Val Asn Gly
                245                 250                 255 tat gtc aac agg tct ctg cca ggt ctg atc gga tgt cat aag aaa tca        816
Tyr Val Asn Arg Ser Leu Pro Gly Leu Ile Gly Cys His Lys Lys Ser
            260                 265                 270 gtc tac tgg cac gtg att gga atg ggc acc agc ccg gaa gtg cac tcc        864
Val Tyr Trp His Val Ile Gly Met Gly Thr Ser Pro Glu Val His Ser
        275                 280                 285 att ttt ctt gaa ggc cac acg ttt ctc gtg agg cac cat cgc cag gct        912
Ile Phe Leu Glu Gly His Thr Phe Leu Val Arg His His Arg Gln Ala
    290                 295                 300 tcc ttg gag atc tcg cca cta act ttc ctc act gct cag aca ttc ctg        960
Ser Leu Glu Ile Ser Pro Leu Thr Phe Leu Thr Ala Gln Thr Phe Leu
305                 310                 315                 320 atg gac ctt ggc cag ttc cta ctg ttt tgt cat atc tct tcc cac cac       1008
Met Asp Leu Gly Gln Phe Leu Leu Phe Cys His Ile Ser Ser His His
                325                 330                 335 cat ggt ggc atg gag gct cac gtc aga gta gaa agc tgc gcc gag gag       1056
His Gly Gly Met Glu Ala His Val Arg Val Glu Ser Cys Ala Glu Glu
            340                 345                 350 ccc cag ctg cgg agg aaa gct gat gaa gag gaa gat tat gat gac aat       1104
Pro Gln Leu Arg Arg Lys Ala Asp Glu Glu Glu Asp Tyr Asp Asp Asn
        355                 360                 365
```

```
ttg tac gac tcg gac atg gac gtg gtc cgg ctc gat ggt gac gac gtg      1152
Leu Tyr Asp Ser Asp Met Asp Val Val Arg Leu Asp Gly Asp Asp Val
    370                 375                 380 tct ccc ttt atc caa atc cgc tca gtt gcc aag aag cat cct aaa act      1200
Ser Pro Phe Ile Gln Ile Arg Ser Val Ala Lys Lys His Pro Lys Thr
385                 390                 395                 400 tgg gta cat tac att gct gct gaa gag gag gac tgg gac tat gct ccc      1248
Trp Val His Tyr Ile Ala Ala Glu Glu Glu Asp Trp Asp Tyr Ala Pro
                405                 410                 415 tta gtc ctc gcc ccc gat gac aga agt tat aaa agt caa tat ttg aac      1296
Leu Val Leu Ala Pro Asp Asp Arg Ser Tyr Lys Ser Gln Tyr Leu Asn
                420                 425                 430 aat ggc cct cag cgg att ggt agg aag tac aaa aaa gtc cga ttt atg      1344
Asn Gly Pro Gln Arg Ile Gly Arg Lys Tyr Lys Lys Val Arg Phe Met
            435                 440                 445 gca tac aca gat gaa acc ttt aag acg cgt gaa gct att cag cat gaa      1392
Ala Tyr Thr Asp Glu Thr Phe Lys Thr Arg Glu Ala Ile Gln His Glu
450                 455                 460 tca gga atc ttg gga cct tta ctt tat ggg gaa gtt gga gac aca ctg      1440
Ser Gly Ile Leu Gly Pro Leu Leu Tyr Gly Glu Val Gly Asp Thr Leu
465                 470                 475                 480 ttg att ata ttt aag aat caa gca agc aga cca tat aac atc tac cct      1488
Leu Ile Ile Phe Lys Asn Gln Ala Ser Arg Pro Tyr Asn Ile Tyr Pro
                485                 490                 495 cac gga atc act gat gtc cgt cct ttg tat tca agg aga tta cca aaa      1536
His Gly Ile Thr Asp Val Arg Pro Leu Tyr Ser Arg Arg Leu Pro Lys
                500                 505                 510 ggt gta aaa cat ttg aag gat ttt cca att ctg cca gga gaa ata ttc      1584
Gly Val Lys His Leu Lys Asp Phe Pro Ile Leu Pro Gly Glu Ile Phe
            515                 520                 525 aaa tat aaa tgg aca gtg act gta gaa gat ggg cca act aaa tca gat      1632
Lys Tyr Lys Trp Thr Val Thr Val Glu Asp Gly Pro Thr Lys Ser Asp
530                 535                 540 ccg cgg tgc ctg acc cgc tat tac tct agt ttc gtt aat atg gag aga      1680
Pro Arg Cys Leu Thr Arg Tyr Tyr Ser Ser Phe Val Asn Met Glu Arg
545                 550                 555                 560 gat cta gct tca gga ctc att ggc cct ctc ctc atc tgc tac aaa gaa      1728
Asp Leu Ala Ser Gly Leu Ile Gly Pro Leu Leu Ile Cys Tyr Lys Glu
                565                 570                 575 tct gta gat caa aga gga aac cag ata atg tca gac aag agg aat gtc      1776
Ser Val Asp Gln Arg Gly Asn Gln Ile Met Ser Asp Lys Arg Asn Val
                580                 585                 590 atc ctg ttt tct gta ttt gat gag aac cga agc tgg tac ctc aca gag      1824
Ile Leu Phe Ser Val Phe Asp Glu Asn Arg Ser Trp Tyr Leu Thr Glu
            595                 600                 605 aat ata caa cgc ttt ctc ccc aat cca gct gga gtg cag ctt gag gat      1872
Asn Ile Gln Arg Phe Leu Pro Asn Pro Ala Gly Val Gln Leu Glu Asp
610                 615                 620 cca gag ttc caa gcc tcc aac atc atg cac agc atc aat ggc tat gtt      1920
Pro Glu Phe Gln Ala Ser Asn Ile Met His Ser Ile Asn Gly Tyr Val
625                 630                 635                 640 ttt gat agt ttg cag ttg tca gtt tgt ttg cat gag gtg gca tac tgg      1968
Phe Asp Ser Leu Gln Leu Ser Val Cys Leu His Glu Val Ala Tyr Trp
                645                 650                 655 tac att cta agc att gga gca cag act gac ttc ctt tct gtc ttc ttc      2016
Tyr Ile Leu Ser Ile Gly Ala Gln Thr Asp Phe Leu Ser Val Phe Phe
                660                 665                 670 tct gga tat acc ttc aaa cac aaa atg gtc tat gaa gac aca ctc acc      2064
Ser Gly Tyr Thr Phe Lys His Lys Met Val Tyr Glu Asp Thr Leu Thr
                675                 680                 685
```

```
cta ttc cca ttc tca gga gaa act gtc ttc atg tcg atg gaa aac cca    2112
Leu Phe Pro Phe Ser Gly Glu Thr Val Phe Met Ser Met Glu Asn Pro
        690                 695                 700 ggt cta tgg att ctg ggg tgc cac aac tca gac ttt cgg aac aga ggc    2160
Gly Leu Trp Ile Leu Gly Cys His Asn Ser Asp Phe Arg Asn Arg Gly
705                 710                 715                 720 atg acc gcc tta ctg aag gtt tct agt tgt gac aag aac act ggt gat    2208
Met Thr Ala Leu Leu Lys Val Ser Ser Cys Asp Lys Asn Thr Gly Asp
                725                 730                 735 tat tac gag gac agt tat gaa gat att tca gca tac ttg ctg agt aaa    2256
Tyr Tyr Glu Asp Ser Tyr Glu Asp Ile Ser Ala Tyr Leu Leu Ser Lys
            740                 745                 750 aac aat gcc att gaa cct agg agc ttt gcc cag aat tca aga ccc cct    2304
Asn Asn Ala Ile Glu Pro Arg Ser Phe Ala Gln Asn Ser Arg Pro Pro
        755                 760                 765 agt gcg agc gct cca aag cct ccg gtc ctg cga cgg cat cag agg gac    2352
Ser Ala Ser Ala Pro Lys Pro Pro Val Leu Arg Arg His Gln Arg Asp
770                 775                 780 ata agc ctt cct act ttt cag ccg gag gaa gac aaa atg gac tat gat    2400
Ile Ser Leu Pro Thr Phe Gln Pro Glu Glu Asp Lys Met Asp Tyr Asp
785                 790                 795                 800 gat atc ttc tca act gaa acg aag gga gaa gat ttt gac att tac ggt    2448
Asp Ile Phe Ser Thr Glu Thr Lys Gly Glu Asp Phe Asp Ile Tyr Gly
                805                 810                 815 gag gat gaa aat cag gac cct cgc agc ttt cag aag aga acc cga cac    2496
Glu Asp Glu Asn Gln Asp Pro Arg Ser Phe Gln Lys Arg Thr Arg His
            820                 825                 830 tat ttc att gct gcg gtg gag cag ctc tgg gat tac ggg atg agc gaa    2544
Tyr Phe Ile Ala Ala Val Glu Gln Leu Trp Asp Tyr Gly Met Ser Glu
        835                 840                 845 tcc ccc cgg gcg cta aga aac agg gct cag aac gga gag gtg cct cgg    2592
Ser Pro Arg Ala Leu Arg Asn Arg Ala Gln Asn Gly Glu Val Pro Arg
850                 855                 860 ttc aag aag gtg gtc ttc cgg gaa ttt gct gac ggc tcc ttc acg cag    2640
Phe Lys Lys Val Val Phe Arg Glu Phe Ala Asp Gly Ser Phe Thr Gln
865                 870                 875                 880 ccg tcg tac cgc ggg gaa ctc aac aaa cac ttg ggg ctc ttg gga ccc    2688
Pro Ser Tyr Arg Gly Glu Leu Asn Lys His Leu Gly Leu Leu Gly Pro
                885                 890                 895 tac atc aga gcg gaa gtt gaa gac aac atc atg gta act ttc aaa aac    2736
Tyr Ile Arg Ala Glu Val Glu Asp Asn Ile Met Val Thr Phe Lys Asn
            900                 905                 910 cag gcg tct cgt ccc tat tcc ttc tac tcg agc ctt att tct tat ccg    2784
Gln Ala Ser Arg Pro Tyr Ser Phe Tyr Ser Ser Leu Ile Ser Tyr Pro
        915                 920                 925 gat gat cag gag caa ggg gca gaa cct cga cac aac ttc gtc cag cca    2832
Asp Asp Gln Glu Gln Gly Ala Glu Pro Arg His Asn Phe Val Gln Pro
930                 935                 940 aat gaa acc aga act tac ttt tgg aaa gtg cag cat cac atg gca ccc    2880
Asn Glu Thr Arg Thr Tyr Phe Trp Lys Val Gln His His Met Ala Pro
945                 950                 955                 960 aca gaa gac gag ttt gac tgc aaa gcc tgg gcc tac ttt tct gat gtt    2928
Thr Glu Asp Glu Phe Asp Cys Lys Ala Trp Ala Tyr Phe Ser Asp Val
                965                 970                 975 gac ctg gaa aaa gat gtg cac tca ggc ttg atc ggc ccc ctt ctg atc    2976
Asp Leu Glu Lys Asp Val His Ser Gly Leu Ile Gly Pro Leu Leu Ile
            980                 985                 990 tgc cgc gcc aac acc ctg aac gct gct cac ggt aga caa gtg acc gtg    3024
Cys Arg Ala Asn Thr Leu Asn Ala Ala His Gly Arg Gln Val Thr Val
        995                 1000                1005
```

```
caa gaa ttt gct ctg ttt ttc act att ttt gat gag aca aag agc tgg      3072
Gln Glu Phe Ala Leu Phe Phe Thr Ile Phe Asp Glu Thr Lys Ser Trp
    1010                1015                1020 tac ttc act gaa aat gtg gaa agg aac tgc cgg gcc ccc tgc cat ctg      3120
Tyr Phe Thr Glu Asn Val Glu Arg Asn Cys Arg Ala Pro Cys His Leu
1025                1030                1035                1040 cag atg gag gac ccc act ctg aaa gaa aac tat cgc ttc cat gca atc      3168
Gln Met Glu Asp Pro Thr Leu Lys Glu Asn Tyr Arg Phe His Ala Ile
                1045                1050                1055 aat ggc tat gtg atg gat aca ctc cct ggc tta gta atg gct cag aat      3216
Asn Gly Tyr Val Met Asp Thr Leu Pro Gly Leu Val Met Ala Gln Asn
1060                1065                1070 caa agg atc cga tgg tat ctg ctc agc atg ggc agc aat gaa aat atc      3264
Gln Arg Ile Arg Trp Tyr Leu Leu Ser Met Gly Ser Asn Glu Asn Ile
            1075                1080                1085 cat tcg att cat ttt agc gga cac gtg ttc agt gta cgg aaa aag gag      3312
His Ser Ile His Phe Ser Gly His Val Phe Ser Val Arg Lys Lys Glu
    1090                1095                1100 gag tat aaa atg gcc gtg tac aat ctc tat ccg ggt gtc ttt gag aca      3360
Glu Tyr Lys Met Ala Val Tyr Asn Leu Tyr Pro Gly Val Phe Glu Thr
1105                1110                1115                1120 gtg gaa atg cta ccg tcc aaa gtt gga att tgg cga ata gaa tgc ctg      3408
Val Glu Met Leu Pro Ser Lys Val Gly Ile Trp Arg Ile Glu Cys Leu
                1125                1130                1135 att ggc gag cac ctg caa gct ggg atg agc acg act ttc ctg gtg tac      3456
Ile Gly Glu His Leu Gln Ala Gly Met Ser Thr Thr Phe Leu Val Tyr
                1140                1145                1150 agc aag aag tgt cag act ccc ctg gga atg gct tct gga cac att aga      3504
Ser Lys Lys Cys Gln Thr Pro Leu Gly Met Ala Ser Gly His Ile Arg
            1155                1160                1165 gat ttt cag att aca gct tca gga caa tat gga cag tgg gcc cca aag      3552
Asp Phe Gln Ile Thr Ala Ser Gly Gln Tyr Gly Gln Trp Ala Pro Lys
    1170                1175                1180 ctg gcc aga ctt cat tat tcc gga tca atc aat gcc tgg agc acc aag      3600
Leu Ala Arg Leu His Tyr Ser Gly Ser Ile Asn Ala Trp Ser Thr Lys
1185                1190                1195                1200 gag ccc ttt tct tgg atc aag gtg gat ctg ttg gca cca atg att att      3648
Glu Pro Phe Ser Trp Ile Lys Val Asp Leu Leu Ala Pro Met Ile Ile
                1205                1210                1215 cac ggc atc aag acc cag ggt gcc cgt cag aag ttc tcc agc ctc tac      3696
His Gly Ile Lys Thr Gln Gly Ala Arg Gln Lys Phe Ser Ser Leu Tyr
                1220                1225                1230 atc tct cag ttt atc atc atg tat agt ctt gat ggg aag aag tgg cag      3744
Ile Ser Gln Phe Ile Ile Met Tyr Ser Leu Asp Gly Lys Lys Trp Gln
            1235                1240                1245 act tat cga gga aat tcc act gga acc tta atg gtc ttc ttt ggc aat      3792
Thr Tyr Arg Gly Asn Ser Thr Gly Thr Leu Met Val Phe Phe Gly Asn
    1250                1255                1260 gtg gat tca tct ggg ata aaa cac aat att ttt aac cct cca att att      3840
Val Asp Ser Ser Gly Ile Lys His Asn Ile Phe Asn Pro Pro Ile Ile
1265                1270                1275                1280 gct cga tac atc cgt ttg cac cca act cat tat agc att cgc agc act      3888
Ala Arg Tyr Ile Arg Leu His Pro Thr His Tyr Ser Ile Arg Ser Thr
                1285                1290                1295 ctt cgc atg gag ttg atg ggc tgt gat tta aat agt tgc agc atg cca      3936
Leu Arg Met Glu Leu Met Gly Cys Asp Leu Asn Ser Cys Ser Met Pro
                1300                1305                1310 ttg gga atg gag agt aaa gca ata tca gat gca cag att act gct tca      3984
Leu Gly Met Glu Ser Lys Ala Ile Ser Asp Ala Gln Ile Thr Ala Ser
            1315                1320                1325
```

```
tcc tac ttt acc aat atg ttt gcc acc tgg tct cct tca aaa gct cga    4032
Ser Tyr Phe Thr Asn Met Phe Ala Thr Trp Ser Pro Ser Lys Ala Arg
    1330                1335                1340 ctt cac ctc caa ggg agg agt aat gcc tgg aga cct cag gtg aat aat    4080
Leu His Leu Gln Gly Arg Ser Asn Ala Trp Arg Pro Gln Val Asn Asn
1345                1350                1355                1360 cca aaa gag tgg ctg caa gtg gac ttc cag aag aca atg aaa gtc aca    4128
Pro Lys Glu Trp Leu Gln Val Asp Phe Gln Lys Thr Met Lys Val Thr
        1365                1370                1375 gga gta act act cag gga gta aaa tct ctg ctt acc agc atg tat gtg    4176
Gly Val Thr Thr Gln Gly Val Lys Ser Leu Leu Thr Ser Met Tyr Val
            1380                1385                1390 aag gag ttc ctc atc tcc agc agt caa gat ggc cat cag tgg act ctc    4224
Lys Glu Phe Leu Ile Ser Ser Ser Gln Asp Gly His Gln Trp Thr Leu
                1395                1400                1405 ttt ttt cag aat ggc aaa gta aag gtt ttt cag gga aat caa gac tcc    4272
Phe Phe Gln Asn Gly Lys Val Lys Val Phe Gln Gly Asn Gln Asp Ser
    1410                1415                1420 ttc aca cct gtg gtg aac tct cta gac cca ccg tta ctg act cgc tac    4320
Phe Thr Pro Val Val Asn Ser Leu Asp Pro Pro Leu Leu Thr Arg Tyr
1425                1430                1435                1440 ctt cga att cac ccc cag agt tgg gtg cac cag att gcc ctg agg atg    4368
Leu Arg Ile His Pro Gln Ser Trp Val His Gln Ile Ala Leu Arg Met
        1445                1450                1455 gag gtt ctg ggc tgc gag gca cag gac ctc tac                        4401
Glu Val Leu Gly Cys Glu Ala Gln Asp Leu Tyr
            1460                1465

<210> SEQ ID NO 19
<211> LENGTH: 1467
<212> TYPE: PRT
<213> ORGANISM: Artificial Sequence
<220> FEATURE:
<223> OTHER INFORMATION: HP47/OL -- factor VIII having the following
      domains: A1p-A2h-app-A3p-C1h-C2h

<400> SEQUENCE: 19

Met Gln Leu Glu Leu Ser Thr Cys Val Phe Leu Cys Leu Leu Pro Leu
1               5                   10                  15

Gly Phe Ser Ala Ile Arg Arg Tyr Tyr Leu Gly Ala Val Glu Leu Ser
            20                  25                  30

Trp Asp Tyr Arg Gln Ser Glu Leu Leu Arg Glu Leu His Val Asp Thr
        35                  40                  45

Arg Phe Pro Ala Thr Ala Pro Gly Ala Leu Pro Leu Gly Pro Ser Val
    50                  55                  60

Leu Tyr Lys Lys Thr Val Phe Val Glu Phe Thr Asp Gln Leu Phe Ser
65                  70                  75                  80

Val Ala Arg Pro Arg Pro Pro Trp Met Gly Leu Leu Gly Pro Thr Ile
                85                  90                  95

Gln Ala Glu Val Tyr Asp Thr Val Val Thr Leu Lys Asn Met Ala
            100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175
```

```
Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285

Ile Phe Leu Glu Gly His Thr Phe Leu Val Arg His His Arg Gln Ala
    290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                325                 330                 335

His Gly Gly Met Glu Ala His Val Arg Val Glu Ser Cys Ala Glu Glu
            340                 345                 350

Pro Gln Leu Arg Arg Lys Ala Asp Glu Glu Asp Tyr Asp Asp Asn
        355                 360                 365

Leu Tyr Asp Ser Asp Met Asp Val Val Arg Leu Asp Gly Asp Asp Val
    370                 375                 380

Ser Pro Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590
```

-continued

```
Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ala Gln Asn Ser Arg Pro Pro
        755                 760                 765

Ser Ala Ser Ala Pro Lys Pro Pro Val Leu Arg Arg His Gln Arg Asp
    770                 775                 780

Ile Ser Leu Pro Thr Phe Gln Pro Glu Glu Asp Lys Met Asp Tyr Asp
785                 790                 795                 800

Asp Ile Phe Ser Thr Glu Thr Lys Gly Glu Asp Phe Asp Ile Tyr Gly
                805                 810                 815

Glu Asp Glu Asn Gln Asp Pro Arg Ser Phe Gln Lys Arg Thr Arg His
            820                 825                 830

Tyr Phe Ile Ala Ala Val Glu Gln Leu Trp Asp Tyr Gly Met Ser Glu
        835                 840                 845

Ser Pro Arg Ala Leu Arg Asn Arg Ala Gln Asn Gly Glu Val Pro Arg
    850                 855                 860

Phe Lys Lys Val Val Phe Arg Glu Phe Ala Asp Gly Ser Phe Thr Gln
865                 870                 875                 880

Pro Ser Tyr Arg Gly Glu Leu Asn Lys His Leu Gly Leu Leu Gly Pro
                885                 890                 895

Tyr Ile Arg Ala Glu Val Glu Asp Asn Ile Met Val Thr Phe Lys Asn
            900                 905                 910

Gln Ala Ser Arg Pro Tyr Ser Phe Tyr Ser Ser Leu Ile Ser Tyr Pro
        915                 920                 925

Asp Asp Gln Glu Gln Gly Ala Glu Pro Arg His Asn Phe Val Gln Pro
    930                 935                 940

Asn Glu Thr Arg Thr Tyr Phe Trp Lys Val Gln His His Met Ala Pro
945                 950                 955                 960

Thr Glu Asp Glu Phe Asp Cys Lys Ala Trp Ala Tyr Phe Ser Asp Val
                965                 970                 975

Asp Leu Glu Lys Asp Val His Ser Gly Leu Ile Gly Pro Leu Leu Ile
            980                 985                 990

Cys Arg Ala Asn Thr Leu Asn Ala Ala His Gly Arg Gln Val Thr Val
        995                 1000                1005
```

-continued

```
Gln Glu Phe Ala Leu Phe Phe Thr Ile Phe Asp Glu Thr Lys Ser Trp
    1010                1015                1020
Tyr Phe Thr Glu Asn Val Glu Arg Asn Cys Arg Ala Pro Cys His Leu
1025                1030                1035                1040
Gln Met Glu Asp Pro Thr Leu Lys Glu Asn Tyr Arg Phe His Ala Ile
                1045                1050                1055
Asn Gly Tyr Val Met Asp Thr Leu Pro Gly Leu Val Met Ala Gln Asn
            1060                1065                1070
Gln Arg Ile Arg Trp Tyr Leu Leu Ser Met Gly Ser Asn Glu Asn Ile
        1075                1080                1085
His Ser Ile His Phe Ser Gly His Val Phe Ser Val Arg Lys Lys Glu
    1090                1095                1100
Glu Tyr Lys Met Ala Val Tyr Asn Leu Tyr Pro Gly Val Phe Glu Thr
1105                1110                1115                1120
Val Glu Met Leu Pro Ser Lys Val Gly Ile Trp Arg Ile Glu Cys Leu
                1125                1130                1135
Ile Gly Glu His Leu Gln Ala Gly Met Ser Thr Thr Phe Leu Val Tyr
            1140                1145                1150
Ser Lys Lys Cys Gln Thr Pro Leu Gly Met Ala Ser Gly His Ile Arg
        1155                1160                1165
Asp Phe Gln Ile Thr Ala Ser Gly Gln Tyr Gly Gln Trp Ala Pro Lys
    1170                1175                1180
Leu Ala Arg Leu His Tyr Ser Gly Ser Ile Asn Ala Trp Ser Thr Lys
1185                1190                1195                1200
Glu Pro Phe Ser Trp Ile Lys Val Asp Leu Leu Ala Pro Met Ile Ile
                1205                1210                1215
His Gly Ile Lys Thr Gln Gly Ala Arg Gln Lys Phe Ser Ser Leu Tyr
            1220                1225                1230
Ile Ser Gln Phe Ile Ile Met Tyr Ser Leu Asp Gly Lys Lys Trp Gln
        1235                1240                1245
Thr Tyr Arg Gly Asn Ser Thr Gly Thr Leu Met Val Phe Phe Gly Asn
    1250                1255                1260
Val Asp Ser Ser Gly Ile Lys His Asn Ile Phe Asn Pro Pro Ile Ile
1265                1270                1275                1280
Ala Arg Tyr Ile Arg Leu His Pro Thr His Tyr Ser Ile Arg Ser Thr
                1285                1290                1295
Leu Arg Met Glu Leu Met Gly Cys Asp Leu Asn Ser Cys Ser Met Pro
            1300                1305                1310
Leu Gly Met Glu Ser Lys Ala Ile Ser Asp Ala Gln Ile Thr Ala Ser
        1315                1320                1325
Ser Tyr Phe Thr Asn Met Phe Ala Thr Trp Ser Pro Ser Lys Ala Arg
    1330                1335                1340
Leu His Leu Gln Gly Arg Ser Asn Ala Trp Arg Pro Gln Val Asn Asn
1345                1350                1355                1360
Pro Lys Glu Trp Leu Gln Val Asp Phe Gln Lys Thr Met Lys Val Thr
                1365                1370                1375
Gly Val Thr Thr Gln Gly Val Lys Ser Leu Leu Thr Ser Met Tyr Val
            1380                1385                1390
Lys Glu Phe Leu Ile Ser Ser Ser Gln Asp Gly His Gln Trp Thr Leu
        1395                1400                1405
Phe Phe Gln Asn Gly Lys Val Lys Val Phe Gln Gly Asn Gln Asp Ser
    1410                1415                1420
```

```
Phe Thr Pro Val Val Asn Ser Leu Asp Pro Pro Leu Thr Arg Tyr
1425                1430                1435                1440

Leu Arg Ile His Pro Gln Ser Trp Val His Gln Ile Ala Leu Arg Met
            1445                1450                1455

Glu Val Leu Gly Cys Glu Ala Gln Asp Leu Tyr
        1460                1465

<210> SEQ ID NO 20
<211> LENGTH: 4401
<212> TYPE: DNA
<213> ORGANISM: Artificial Sequence
<220> FEATURE:
<223> OTHER INFORMATION: hybrid human and porcine factor VIII sequence
<220> FEATURE:
<221> NAME/KEY: CDS
<222> LOCATION: (1)...(4401)
<223> OTHER INFORMATION: HP63/OL -- factor VIII variant

<400> SEQUENCE: 20 atg cag cta gag ctc tcc acc tgt gtc ttt ctg tgt ctc ttg cca ctc     48
Met Gln Leu Glu Leu Ser Thr Cys Val Phe Leu Cys Leu Leu Pro Leu
1               5                   10                  15 ggc ttt agt gcc atc agg aga tac tac ctg ggc gca gtg gaa ctg tcc     96
Gly Phe Ser Ala Ile Arg Arg Tyr Tyr Leu Gly Ala Val Glu Leu Ser
            20                  25                  30 tgg gac tac cgg caa agt gaa ctc ctc cgt gag ctg cac gtg gac acc    144
Trp Asp Tyr Arg Gln Ser Glu Leu Leu Arg Glu Leu His Val Asp Thr
        35                  40                  45 aga ttt cct gct aca gcg cca gga gct ctt ccg ttg ggc ccg tca gtc    192
Arg Phe Pro Ala Thr Ala Pro Gly Ala Leu Pro Leu Gly Pro Ser Val
    50                  55                  60 ctg tac aaa aag act gtg ttc gta gag ttc acg gat caa ctt ttc agc    240
Leu Tyr Lys Lys Thr Val Phe Val Glu Phe Thr Asp Gln Leu Phe Ser
65                  70                  75                  80 gtt gcc agg ccc agg cca cca tgg atg ggt ctg ctg ggt cct acc atc    288
Val Ala Arg Pro Arg Pro Pro Trp Met Gly Leu Leu Gly Pro Thr Ile
                85                  90                  95 cag gct gag gtt tac gac acg gtg gtc gtt acc ctg aag aac atg gct    336
Gln Ala Glu Val Tyr Asp Thr Val Val Val Thr Leu Lys Asn Met Ala
            100                 105                 110 tct cat ccc gtt agt ctt cac gct gtc ggc gtc tcc ttc tgg aaa tct    384
Ser His Pro Val Ser Leu His Ala Val Gly Val Ser Phe Trp Lys Ser
        115                 120                 125 tcc gaa ggc gct gaa tat gag gat cac acc agc caa agg gag aag gaa    432
Ser Glu Gly Ala Glu Tyr Glu Asp His Thr Ser Gln Arg Glu Lys Glu
    130                 135                 140 gac gat aaa gtc ctt ccc ggt aaa agc caa acc tac gtc tgg cag gtc    480
Asp Asp Lys Val Leu Pro Gly Lys Ser Gln Thr Tyr Val Trp Gln Val
145                 150                 155                 160 ctg aaa gaa aat ggt cca aca gcc tct gac cca cca tgt ctt acc tac    528
Leu Lys Glu Asn Gly Pro Thr Ala Ser Asp Pro Pro Cys Leu Thr Tyr
                165                 170                 175 tca tac ctg tct cac gtg gac ctg gtg aaa gac ctg aat tcg ggc ctc    576
Ser Tyr Leu Ser His Val Asp Leu Val Lys Asp Leu Asn Ser Gly Leu
            180                 185                 190 att gga gcc ctg ctg gtt tgt aga gaa ggg agt ctg acc aga gaa agg    624
Ile Gly Ala Leu Leu Val Cys Arg Glu Gly Ser Leu Thr Arg Glu Arg
        195                 200                 205 acc cag aac ctg cac gaa ttt gta cta ctt ttt gct gtc ttt gat gaa    672
Thr Gln Asn Leu His Glu Phe Val Leu Leu Phe Ala Val Phe Asp Glu
    210                 215                 220
```

```
ggg aaa agt tgg cac tca gca aga aat gac tcc tgg aca cgg gcc atg        720
Gly Lys Ser Trp His Ser Ala Arg Asn Asp Ser Trp Thr Arg Ala Met
225                 230                 235                 240 gat ccc gca cct gcc agg gcc cag cct gca atg cac aca gtc aat ggc        768
Asp Pro Ala Pro Ala Arg Ala Gln Pro Ala Met His Thr Val Asn Gly
                245                 250                 255 tat gtc aac agg tct ctg cca ggt ctg atc gga tgt cat aag aaa tca        816
Tyr Val Asn Arg Ser Leu Pro Gly Leu Ile Gly Cys His Lys Lys Ser
            260                 265                 270 gtc tac tgg cac gtg att gga atg ggc acc agc ccg gaa gtg cac tcc        864
Val Tyr Trp His Val Ile Gly Met Gly Thr Ser Pro Glu Val His Ser
        275                 280                 285 att ttt ctt gaa ggc cac acg ttt ctc gtg agg cac cat cgc cag gct        912
Ile Phe Leu Glu Gly His Thr Phe Leu Val Arg His His Arg Gln Ala
290                 295                 300 tcc ttg gag atc tcg cca cta act ttc ctc act gct cag aca ttc ctg        960
Ser Leu Glu Ile Ser Pro Leu Thr Phe Leu Thr Ala Gln Thr Phe Leu
305                 310                 315                 320 atg gac ctt ggc cag ttc cta ctg ttt tgt cat atc tct tcc cac cac       1008
Met Asp Leu Gly Gln Phe Leu Leu Phe Cys His Ile Ser Ser His His
                325                 330                 335 cat ggt ggc atg gag gct cac gtc aga gta gaa agc tgc gcc gag gag       1056
His Gly Gly Met Glu Ala His Val Arg Val Glu Ser Cys Ala Glu Glu
            340                 345                 350 ccc cag ctg cgg agg aaa gct gat gaa gag gaa gat tat gat gac aat       1104
Pro Gln Leu Arg Arg Lys Ala Asp Glu Glu Glu Asp Tyr Asp Asp Asn
        355                 360                 365 ttg tac gac tcg gac atg gac gtg gtc cgg ctc gat ggt gac gac gtg       1152
Leu Tyr Asp Ser Asp Met Asp Val Val Arg Leu Asp Gly Asp Asp Val
370                 375                 380 tct ccc ttt atc caa atc cgc tca gtt gcc aag aag cat cct aaa act       1200
Ser Pro Phe Ile Gln Ile Arg Ser Val Ala Lys Lys His Pro Lys Thr
385                 390                 395                 400 tgg gta cat tac att gct gct gaa gag gag gac tgg gac tat gct ccc       1248
Trp Val His Tyr Ile Ala Ala Glu Glu Glu Asp Trp Asp Tyr Ala Pro
                405                 410                 415 tta gtc ctc gcc ccc gat gac aga agt tat aaa agt caa tat ttg aac       1296
Leu Val Leu Ala Pro Asp Asp Arg Ser Tyr Lys Ser Gln Tyr Leu Asn
            420                 425                 430 aat ggc cct cag cgg att ggt agg aag tac aaa aaa gtc cga ttt atg       1344
Asn Gly Pro Gln Arg Ile Gly Arg Lys Tyr Lys Lys Val Arg Phe Met
        435                 440                 445 gca tac aca gat gaa acc ttt aag act cgt gaa gct att cag cat gaa       1392
Ala Tyr Thr Asp Glu Thr Phe Lys Thr Arg Glu Ala Ile Gln His Glu
450                 455                 460 tca gga atc ttg gga cct tta ctt tat ggg gaa gtt gga gac aca ctg       1440
Ser Gly Ile Leu Gly Pro Leu Leu Tyr Gly Glu Val Gly Asp Thr Leu
465                 470                 475                 480 ttg att ata ttt aag aat caa gca agc aga cca tat aac atc tac cct       1488
Leu Ile Ile Phe Lys Asn Gln Ala Ser Arg Pro Tyr Asn Ile Tyr Pro
                485                 490                 495 cac gga atc act gat gtc cgt cct ttg tat tca agg aga tta cca aaa       1536
His Gly Ile Thr Asp Val Arg Pro Leu Tyr Ser Arg Arg Leu Pro Lys
            500                 505                 510 ggt gta aaa cat ttg aag gat ttt cca att ctg cca gga gaa ata ttc       1584
Gly Val Lys His Leu Lys Asp Phe Pro Ile Leu Pro Gly Glu Ile Phe
        515                 520                 525 aaa tat aaa tgg aca gtg act gta gaa gat ggg cca act aaa tca gat       1632
Lys Tyr Lys Trp Thr Val Thr Val Glu Asp Gly Pro Thr Lys Ser Asp
530                 535                 540
```

-continued

| | |
|---|---|
| cct cgg tgc ctg acc cgc tat tac tct agt ttc gtt aat atg gag aga<br>Pro Arg Cys Leu Thr Arg Tyr Tyr Ser Ser Phe Val Asn Met Glu Arg<br>545                  550                    555                  560 | 1680 |
| gat cta gct tca gga ctc att ggc cct ctc ctc atc tgc tac aaa gaa<br>Asp Leu Ala Ser Gly Leu Ile Gly Pro Leu Leu Ile Cys Tyr Lys Glu<br>                  565                    570                    575 | 1728 |
| tct gta gat caa aga gga aac cag ata atg tca gac aag agg aat gtc<br>Ser Val Asp Gln Arg Gly Asn Gln Ile Met Ser Asp Lys Arg Asn Val<br>                          580                    585                    590 | 1776 |
| atc ctg ttt tct gta ttt gat gag aac cga agc tgg tac ctc aca gag<br>Ile Leu Phe Ser Val Phe Asp Glu Asn Arg Ser Trp Tyr Leu Thr Glu<br>                  595                    600                    605 | 1824 |
| aat ata caa cgc ttt ctc ccc aat cca gct gga gtg cag ctt gag gat<br>Asn Ile Gln Arg Phe Leu Pro Asn Pro Ala Gly Val Gln Leu Glu Asp<br>610                  615                    620 | 1872 |
| cca gag ttc caa gcc tcc aac atc atg cac agc atc aat ggc tat gtt<br>Pro Glu Phe Gln Ala Ser Asn Ile Met His Ser Ile Asn Gly Tyr Val<br>625                  630                    635                    640 | 1920 |
| ttt gat agt ttg cag ttg tca gtt tgt ttg cat gag gtg gca tac tgg<br>Phe Asp Ser Leu Gln Leu Ser Val Cys Leu His Glu Val Ala Tyr Trp<br>                          645                    650                    655 | 1968 |
| tac att cta agc att gga gca cag act gac ttc ctt tct gtc ttc ttc<br>Tyr Ile Leu Ser Ile Gly Ala Gln Thr Asp Phe Leu Ser Val Phe Phe<br>                  660                    665                    670 | 2016 |
| tct gga tat acc ttc aaa cac aaa atg gtc tat gaa gac aca ctc acc<br>Ser Gly Tyr Thr Phe Lys His Lys Met Val Tyr Glu Asp Thr Leu Thr<br>                  675                    680                    685 | 2064 |
| cta ttc cca ttc tca gga gaa act gtc ttc atg tcg atg gaa aac cca<br>Leu Phe Pro Phe Ser Gly Glu Thr Val Phe Met Ser Met Glu Asn Pro<br>690                  695                    700 | 2112 |
| ggt cta tgg att ctg ggg tgc cac aac tca gac ttt cgg aac aga ggc<br>Gly Leu Trp Ile Leu Gly Cys His Asn Ser Asp Phe Arg Asn Arg Gly<br>705                  710                    715                    720 | 2160 |
| atg acc gcc tta ctg aag gtt tct agt tgt gac aag aac act ggt gat<br>Met Thr Ala Leu Leu Lys Val Ser Ser Cys Asp Lys Asn Thr Gly Asp<br>                  725                    730                    735 | 2208 |
| tat tac gag gac agt tat gaa gat att tca gca tac ttg ctg agt aaa<br>Tyr Tyr Glu Asp Ser Tyr Glu Asp Ile Ser Ala Tyr Leu Leu Ser Lys<br>                          740                    745                    750 | 2256 |
| aac aat gcc att gaa cct agg agc ttc tcc cag aat tca aga cac cct<br>Asn Asn Ala Ile Glu Pro Arg Ser Phe Ser Gln Asn Ser Arg His Pro<br>755                  760                    765 | 2304 |
| agc act agg tct caa aac cca cca gtc ttg aaa cgc cat caa cgg gaa<br>Ser Thr Arg Ser Gln Asn Pro Pro Val Leu Lys Arg His Gln Arg Glu<br>770                  775                    780 | 2352 |
| ata act cgt act act ctt cag tca gat caa gag gaa att gac tat gat<br>Ile Thr Arg Thr Thr Leu Gln Ser Asp Gln Glu Glu Ile Asp Tyr Asp<br>785                  790                    795                    800 | 2400 |
| gat acc ata tca gtt gaa atg aag aag gaa gat ttt gac att tat gat<br>Asp Thr Ile Ser Val Glu Met Lys Lys Glu Asp Phe Asp Ile Tyr Asp<br>                          805                    810                    815 | 2448 |
| gag gat gaa aat cag agc ccc cgc agc ttt caa aag aga acc cga cac<br>Glu Asp Glu Asn Gln Ser Pro Arg Ser Phe Gln Lys Arg Thr Arg His<br>                  820                    825                    830 | 2496 |
| tat ttc att gct gcg gtg gag cag ctc tgg gat tac ggg atg agc gaa<br>Tyr Phe Ile Ala Ala Val Glu Gln Leu Trp Asp Tyr Gly Met Ser Glu<br>                  835                    840                    845 | 2544 |
| tcc ccc cgg gcg cta aga aac agg gct cag aac gga gag gtg cct cgg<br>Ser Pro Arg Ala Leu Arg Asn Arg Ala Gln Asn Gly Glu Val Pro Arg<br>850                    855                    860 | 2592 |

-continued

| | |
|---|---|
| ttc aag aag gtg gtc ttc cgg gaa ttt gct gac ggc tcc ttc acg cag<br>Phe Lys Lys Val Val Phe Arg Glu Phe Ala Asp Gly Ser Phe Thr Gln<br>865                    870                    875                    880 | 2640 |
| ccg tcg tac cgc ggg gaa ctc aac aaa cac ttg ggg ctc ttg gga ccc<br>Pro Ser Tyr Arg Gly Glu Leu Asn Lys His Leu Gly Leu Leu Gly Pro<br>                    885                    890                    895 | 2688 |
| tac atc aga gcg gaa gtt gaa gac aac atc atg gta act ttc aaa aac<br>Tyr Ile Arg Ala Glu Val Glu Asp Asn Ile Met Val Thr Phe Lys Asn<br>900                    905                    910 | 2736 |
| cag gcg tct cgt ccc tat tcc ttc tac tcg agc ctt att tct tat ccg<br>Gln Ala Ser Arg Pro Tyr Ser Phe Tyr Ser Ser Leu Ile Ser Tyr Pro<br>                    915                    920                    925 | 2784 |
| gat gat cag gag caa ggg gca gaa cct cga aaa aac ttt gtc aag cct<br>Asp Asp Gln Glu Gln Gly Ala Glu Pro Arg Lys Asn Phe Val Lys Pro<br>930                    935                    940 | 2832 |
| aat gaa acc aaa act tac ttt tgg aaa gtg cag cat cac atg gca ccc<br>Asn Glu Thr Lys Thr Tyr Phe Trp Lys Val Gln His His Met Ala Pro<br>945                    950                    955                    960 | 2880 |
| aca gaa gac gag ttt gac tgc aaa gcc tgg gcc tac ttt tct gat gtt<br>Thr Glu Asp Glu Phe Asp Cys Lys Ala Trp Ala Tyr Phe Ser Asp Val<br>                    965                    970                    975 | 2928 |
| gac ctg gaa aaa gat gtg cac tca ggc ttg atc ggc ccc ctt ctg atc<br>Asp Leu Glu Lys Asp Val His Ser Gly Leu Ile Gly Pro Leu Leu Ile<br>980                    985                    990 | 2976 |
| tgc cgc gcc aac acc ctg aac gct gct cac ggt aga caa gtg acc gtg<br>Cys Arg Ala Asn Thr Leu Asn Ala Ala His Gly Arg Gln Val Thr Val<br>                    995                    1000                  1005 | 3024 |
| caa gaa ttt gct ctg ttt ttc act att ttt gat gag aca aag agc tgg<br>Gln Glu Phe Ala Leu Phe Phe Thr Ile Phe Asp Glu Thr Lys Ser Trp<br>1010                    1015                  1020 | 3072 |
| tac ttc act gaa aat gtg gaa agg aac tgc cgg gcc ccc tgc cat ctg<br>Tyr Phe Thr Glu Asn Val Glu Arg Asn Cys Arg Ala Pro Cys His Leu<br>1025                    1030                  1035                  1040 | 3120 |
| cag atg gag gac ccc act ctg aaa gaa aac tat cgc ttc cat gca atc<br>Gln Met Glu Asp Pro Thr Leu Lys Glu Asn Tyr Arg Phe His Ala Ile<br>                    1045                  1050                  1055 | 3168 |
| aat ggc tat gtg atg gat aca ctc cct ggc tta gta atg gct cag aat<br>Asn Gly Tyr Val Met Asp Thr Leu Pro Gly Leu Val Met Ala Gln Asn<br>1060                    1065                  1070 | 3216 |
| caa agg atc cga tgg tat ctg ctc agc atg ggc agc aat gaa aat atc<br>Gln Arg Ile Arg Trp Tyr Leu Leu Ser Met Gly Ser Asn Glu Asn Ile<br>1075                    1080                  1085 | 3264 |
| cat tcg att cat ttt agc gga cac gtg ttc agt gta cgg aaa aag gag<br>His Ser Ile His Phe Ser Gly His Val Phe Ser Val Arg Lys Lys Glu<br>1090                    1095                  1100 | 3312 |
| gag tat aaa atg gcc gtg tac aat ctc tat ccg ggt gtc ttt gag aca<br>Glu Tyr Lys Met Ala Val Tyr Asn Leu Tyr Pro Gly Val Phe Glu Thr<br>1105                    1110                  1115                  1120 | 3360 |
| gtg gaa atg cta ccg tcc aaa gtt gga att tgg cgg aat aga tgc ctg<br>Val Glu Met Leu Pro Ser Lys Val Gly Ile Trp Arg Asn Arg Cys Leu<br>                    1125                  1130                  1135 | 3408 |
| att ggc gag cac ctg caa gct ggg atg agc acg act ttc ctg gtg tac<br>Ile Gly Glu His Leu Gln Ala Gly Met Ser Thr Thr Phe Leu Val Tyr<br>1140                    1145                  1150 | 3456 |
| agc aag aag tgt cag act ccc ctg gga atg gct tct gga cac att aga<br>Ser Lys Lys Cys Gln Thr Pro Leu Gly Met Ala Ser Gly His Ile Arg<br>1155                    1160                  1165 | 3504 |
| gat ttt cag att aca gct tca gga caa tat gga cag tgg gcc cca aag<br>Asp Phe Gln Ile Thr Ala Ser Gly Gln Tyr Gly Gln Trp Ala Pro Lys<br>1170                    1175                  1180 | 3552 |

-continued

| | | |
|---|---|---|
| ctg gcc aga ctt cat tat tcc gga tca atc aat gcc tgg agc acc aag<br>Leu Ala Arg Leu His Tyr Ser Gly Ser Ile Asn Ala Trp Ser Thr Lys<br>1185          1190          1195          1200 | 3600 |
| gag ccc ttt tct tgg atc aag gtg gat ctg ttg gca cca atg att att<br>Glu Pro Phe Ser Trp Ile Lys Val Asp Leu Leu Ala Pro Met Ile Ile<br>                   1205          1210          1215 | 3648 |
| cac ggc atc aag acc cag ggt gcc cgt cag aag ttc tcc agc ctc tac<br>His Gly Ile Lys Thr Gln Gly Ala Arg Gln Lys Phe Ser Ser Leu Tyr<br>1220          1225          1230 | 3696 |
| atc tct cag ttt atc atc atg tat agt ctt gat ggg aag aag tgg cag<br>Ile Ser Gln Phe Ile Ile Met Tyr Ser Leu Asp Gly Lys Lys Trp Gln<br>                   1235          1240          1245 | 3744 |
| act tat cga gga aat tcc act gga acc tta atg gtc ttc ttt ggc aat<br>Thr Tyr Arg Gly Asn Ser Thr Gly Thr Leu Met Val Phe Phe Gly Asn<br>1250          1255          1260 | 3792 |
| gtg gat tca tct ggg ata aaa cac aat att ttt aac cct cca att att<br>Val Asp Ser Ser Gly Ile Lys His Asn Ile Phe Asn Pro Pro Ile Ile<br>1265          1270          1275          1280 | 3840 |
| gct cga tac atc cgt ttg cac cca act cat tat agc att cgc agc act<br>Ala Arg Tyr Ile Arg Leu His Pro Thr His Tyr Ser Ile Arg Ser Thr<br>                   1285          1290          1295 | 3888 |
| ctt cgc atg gag ttg atg ggc tgt gat tta aat agt tgc agc atg cca<br>Leu Arg Met Glu Leu Met Gly Cys Asp Leu Asn Ser Cys Ser Met Pro<br>1300          1305          1310 | 3936 |
| ttg gga atg gag agt aaa gca ata tca gat gca cag att act gct tca<br>Leu Gly Met Glu Ser Lys Ala Ile Ser Asp Ala Gln Ile Thr Ala Ser<br>                   1315          1320          1325 | 3984 |
| tcc tac ttt acc aat atg ttt gcc acc tgg tct cct tca aaa gct cga<br>Ser Tyr Phe Thr Asn Met Phe Ala Thr Trp Ser Pro Ser Lys Ala Arg<br>1330          1335          1340 | 4032 |
| ctt cac ctc caa ggg agg agt aat gcc tgg aga cct cag gtg aat aat<br>Leu His Leu Gln Gly Arg Ser Asn Ala Trp Arg Pro Gln Val Asn Asn<br>1345          1350          1355          1360 | 4080 |
| cca aaa gag tgg ctg caa gtg gac ttc cag aag aca atg aaa gtc aca<br>Pro Lys Glu Trp Leu Gln Val Asp Phe Gln Lys Thr Met Lys Val Thr<br>                   1365          1370          1375 | 4128 |
| gga gta act act cag gga gta aaa tct ctg ctt acc agc atg tat gtg<br>Gly Val Thr Thr Gln Gly Val Lys Ser Leu Leu Thr Ser Met Tyr Val<br>1380          1385          1390 | 4176 |
| aag gag ttc ctc atc tcc agc agt caa gat ggc cat cag tgg act ctc<br>Lys Glu Phe Leu Ile Ser Ser Ser Gln Asp Gly His Gln Trp Thr Leu<br>1395          1400          1405 | 4224 |
| ttt ttt cag aat ggc aaa gta aag gtt ttt cag gga aat caa gac tcc<br>Phe Phe Gln Asn Gly Lys Val Lys Val Phe Gln Gly Asn Gln Asp Ser<br>1410          1415          1420 | 4272 |
| ttc aca cct gtg gtg aac tct cta gac cca ccg tta ctg act cgc tac<br>Phe Thr Pro Val Val Asn Ser Leu Asp Pro Pro Leu Leu Thr Arg Tyr<br>1425          1430          1435          1440 | 4320 |
| ctt cga att cac ccc cag agt tgg gtg cac cag att gcc ctg agg atg<br>Leu Arg Ile His Pro Gln Ser Trp Val His Gln Ile Ala Leu Arg Met<br>                   1445          1450          1455 | 4368 |
| gag gtt ctg ggc tgc gag gca cag gac ctc tac<br>Glu Val Leu Gly Cys Glu Ala Gln Asp Leu Tyr<br>1460          1465 | 4401 |

```
<210> SEQ ID NO 21
<211> LENGTH: 1467
<212> TYPE: PRT
<213> ORGANISM: Artificial Sequence
<220> FEATURE:
<223> OTHER INFORMATION: HP63/OL -- factor VIII variant
```

<400> SEQUENCE: 21

```
Met Gln Leu Glu Leu Ser Thr Cys Val Phe Leu Cys Leu Leu Pro Leu
 1               5                  10                  15

Gly Phe Ser Ala Ile Arg Arg Tyr Tyr Leu Gly Ala Val Glu Leu Ser
             20                  25                  30

Trp Asp Tyr Arg Gln Ser Glu Leu Leu Arg Glu Leu His Val Asp Thr
         35                  40                  45

Arg Phe Pro Ala Thr Ala Pro Gly Ala Leu Pro Leu Gly Pro Ser Val
     50                  55                  60

Leu Tyr Lys Lys Thr Val Phe Val Glu Phe Thr Asp Gln Leu Phe Ser
 65                  70                  75                  80

Val Ala Arg Pro Arg Pro Pro Trp Met Gly Leu Leu Gly Pro Thr Ile
                 85                  90                  95

Gln Ala Glu Val Tyr Asp Thr Val Val Val Thr Leu Lys Asn Met Ala
                100                 105                 110

Ser His Pro Val Ser Leu His Ala Val Gly Val Ser Phe Trp Lys Ser
            115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285

Ile Phe Leu Glu Gly His Thr Phe Leu Val Arg His His Arg Gln Ala
    290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                325                 330                 335

His Gly Gly Met Glu Ala His Val Arg Val Glu Ser Cys Ala Glu Glu
            340                 345                 350

Pro Gln Leu Arg Arg Lys Ala Asp Glu Glu Asp Tyr Asp Asp Asn
        355                 360                 365

Leu Tyr Asp Ser Asp Met Asp Val Val Arg Leu Asp Gly Asp Val
    370                 375                 380

Ser Pro Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415
```

-continued

```
Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Ser Gln Asn Pro Pro Val Leu Lys Arg His Gln Arg Glu
    770                 775                 780

Ile Thr Arg Thr Thr Leu Gln Ser Asp Gln Glu Glu Ile Asp Tyr Asp
785                 790                 795                 800

Asp Thr Ile Ser Val Glu Met Lys Lys Glu Asp Phe Asp Ile Tyr Asp
                805                 810                 815

Glu Asp Glu Asn Gln Ser Pro Arg Ser Phe Gln Lys Arg Thr Arg His
            820                 825                 830
```

-continued

```
Tyr Phe Ile Ala Ala Val Glu Gln Leu Trp Asp Tyr Gly Met Ser Glu
            835                 840                 845

Ser Pro Arg Ala Leu Arg Asn Arg Ala Gln Asn Gly Glu Val Pro Arg
        850                 855                 860

Phe Lys Lys Val Val Phe Arg Glu Phe Ala Asp Gly Ser Phe Thr Gln
865                 870                 875                 880

Pro Ser Tyr Arg Gly Glu Leu Asn Lys His Leu Gly Leu Leu Gly Pro
            885                 890                 895

Tyr Ile Arg Ala Glu Val Glu Asp Asn Ile Met Val Thr Phe Lys Asn
            900                 905                 910

Gln Ala Ser Arg Pro Tyr Ser Phe Tyr Ser Ser Leu Ile Ser Tyr Pro
            915                 920                 925

Asp Asp Gln Glu Gln Gly Ala Glu Pro Arg Lys Asn Phe Val Lys Pro
        930                 935                 940

Asn Glu Thr Lys Thr Tyr Phe Trp Lys Val Gln His His Met Ala Pro
945                 950                 955                 960

Thr Glu Asp Glu Phe Asp Cys Lys Ala Trp Ala Tyr Phe Ser Asp Val
            965                 970                 975

Asp Leu Glu Lys Asp Val His Ser Gly Leu Ile Gly Pro Leu Leu Ile
            980                 985                 990

Cys Arg Ala Asn Thr Leu Asn Ala Ala His Gly Arg Gln Val Thr Val
            995                 1000                1005

Gln Glu Phe Ala Leu Phe Phe Thr Ile Phe Asp Glu Thr Lys Ser Trp
        1010                1015                1020

Tyr Phe Thr Glu Asn Val Glu Arg Asn Cys Arg Ala Pro Cys His Leu
1025                1030                1035                1040

Gln Met Glu Asp Pro Thr Leu Lys Glu Asn Tyr Arg Phe His Ala Ile
            1045                1050                1055

Asn Gly Tyr Val Met Asp Thr Leu Pro Gly Leu Val Met Ala Gln Asn
            1060                1065                1070

Gln Arg Ile Arg Trp Tyr Leu Leu Ser Met Gly Ser Asn Glu Asn Ile
        1075                1080                1085

His Ser Ile His Phe Ser Gly His Val Phe Ser Val Arg Lys Lys Glu
        1090                1095                1100

Glu Tyr Lys Met Ala Val Tyr Asn Leu Tyr Pro Gly Val Phe Glu Thr
1105                1110                1115                1120

Val Glu Met Leu Pro Ser Lys Val Gly Ile Trp Arg Asn Arg Cys Leu
            1125                1130                1135

Ile Gly Glu His Leu Gln Ala Gly Met Ser Thr Thr Phe Leu Val Tyr
            1140                1145                1150

Ser Lys Lys Cys Gln Thr Pro Leu Gly Met Ala Ser Gly His Ile Arg
        1155                1160                1165

Asp Phe Gln Ile Thr Ala Ser Gly Gln Tyr Gly Gln Trp Ala Pro Lys
        1170                1175                1180

Leu Ala Arg Leu His Tyr Ser Gly Ser Ile Asn Ala Trp Ser Thr Lys
1185                1190                1195                1200

Glu Pro Phe Ser Trp Ile Lys Val Asp Leu Leu Ala Pro Met Ile Ile
            1205                1210                1215

His Gly Ile Lys Thr Gln Gly Ala Arg Gln Lys Phe Ser Ser Leu Tyr
            1220                1225                1230

Ile Ser Gln Phe Ile Ile Met Tyr Ser Leu Asp Gly Lys Lys Trp Gln
            1235                1240                1245
```

```
                                        -continued
Thr Tyr Arg Gly Asn Ser Thr Gly Thr Leu Met Val Phe Phe Gly Asn
        1250                1255                1260

Val Asp Ser Ser Gly Ile Lys His Asn Ile Phe Asn Pro Pro Ile Ile
1265                1270                1275                1280

Ala Arg Tyr Ile Arg Leu His Pro Thr His Tyr Ser Ile Arg Ser Thr
                1285                1290                1295

Leu Arg Met Glu Leu Met Gly Cys Asp Leu Asn Ser Cys Ser Met Pro
            1300                1305                1310

Leu Gly Met Glu Ser Lys Ala Ile Ser Asp Ala Gln Ile Thr Ala Ser
        1315                1320                1325

Ser Tyr Phe Thr Asn Met Phe Ala Thr Trp Ser Pro Ser Lys Ala Arg
    1330                1335                1340

Leu His Leu Gln Gly Arg Ser Asn Ala Trp Arg Pro Gln Val Asn Asn
1345                1350                1355                1360

Pro Lys Glu Trp Leu Gln Val Asp Phe Gln Lys Thr Met Lys Val Thr
                1365                1370                1375

Gly Val Thr Thr Gln Gly Val Lys Ser Leu Leu Thr Ser Met Tyr Val
            1380                1385                1390

Lys Glu Phe Leu Ile Ser Ser Ser Gln Asp Gly His Gln Trp Thr Leu
        1395                1400                1405

Phe Phe Gln Asn Gly Lys Val Lys Val Phe Gln Gly Asn Gln Asp Ser
    1410                1415                1420

Phe Thr Pro Val Val Asn Ser Leu Asp Pro Pro Leu Leu Thr Arg Tyr
1425                1430                1435                1440

Leu Arg Ile His Pro Gln Ser Trp Val His Gln Ile Ala Leu Arg Met
                1445                1450                1455

Glu Val Leu Gly Cys Glu Ala Gln Asp Leu Tyr
            1460                1465
```

NUCLEIC ACID AND AMINO ACID SEQUENCES ENCODING HIGH-LEVEL EXPRESSOR FACTOR VIII POLYPEPTIDES AND METHODS OF USE

CROSS-REFERENCE TO RELATED APPLICATIONS

This application is a U.S. Continuation of PCT Application No. PCT/US02/33403 filed on Oct. 7, 2002, and which claims priority to U.S. Provisional Application No. 60/327,388, filed Oct. 5, 2001, all of which are incorporated herein by reference in its entirety.

FEDERALLY SPONSORED RESEARCH OR DEVELOPMENT

This invention was made with government support under grant number HL040921 awarded by the National Institutes of Health. The government has certain rights in the invention.

FIELD OF THE INVENTION

The present invention relates the field of recombinant molecular biology, particularly a modified factor VIII polypeptide and methods of use.

BACKGROUND OF THE INVENTION

Factor VIII is a large (~300 kDa) glycoprotein that functions as an integral component of the intrinsic pathway of blood coagulation. It contains a series of domains designated A1-A2-B-ap-A3-$C_1$-$C_2$. The B domain of factor VIII has no known function and can be deleted without loss of coagulant activity. Mutations in the factor VIII gene that result in decreased or defective factor VIII protein give rise to the genetic disease, hemophilia A, which is characterized by recurrent bleeding episodes. Treatment of hemophilia A requires intravenous infusion of either plasma-derived or recombinant factor VIII.

Since the introduction of recombinant factor VIII for the treatment of hemophilia A, supply has struggled to keep up with demand because factor VIII is expressed and recovered at low levels in the heterologous mammalian cell culture systems used for commercial manufacture (Garber et al. (2000) *Nature Biotechnology* 18:1133). Additionally, factor VIII levels during hemophilia A gene therapy trials indicate that expression levels will be a limiting feature (Roth, et al. (2001) *N. Engl. J. Med.* 344:1735-1742). The importance of this problem has resulted in significant research efforts to overcome the low factor VIII expression barrier. Several factors that limit expression have been identified, including low mRNA levels (Lynch et al. (1993) *Hum. Gene Ther.* 4:259-272; Hoeben et al. (1995) *Blood* 85:2447-2454; Koeberl et al. (1995) *Hum. Gene Ther.* 6:469-479), interaction with protein chaperones and inefficient secretion (Pipe et al. (1998) *J. Biol. Chem.* 273:8537-8544; Tagliavacca et al. (2000) *Biochemistry* 39:1973-1981; Kaufman et al. (1997) *Blood Coagul Fibrinolysis* 8 Suppl 2:S3-14) and rapid decay in the absence of von Willebrand factor (Kaufman et al. (1988) *J. Biol. Chem.* 263:6352-6362 and Kaufman et al. (1989) *Mol. Cell Biol.* 9:1233-1242). Deletion of the B-domain has been shown to increase factor VIII protein production in heterologous systems (Toole et al. (1986) *Proc. Natl. Acad. Sci. U.S.A.* 83:5939-5942). A B-domain deleted form of human factor VIII (Lind et al. (1995) *Eur. J. Biochem.* 232:19-27) has been approved for clinical use.

Despite these insights into factor VIII regulation, expression continues to be significantly lower than other recombinant proteins in the heterologous systems used in commercial manufacture (Kaufman et al. (1997) *Blood Coagul. Fibrinolysis* 8 Suppl 2:S3-14), as well as in ex-vivo (Roth, et al. (2001) *N. Engl. J. Med.* 344:1735-1742) and in vivo gene therapy applications (Chuah et al. (1995) *Hum. Gene Ther.* 6:1363-1377). Methods and compositions are needed for the increased expression of factor VIII.

SUMMARY OF THE INVENTION

Methods and compositions are provided that allow for high-level expression of a factor VIII polypeptide. More specifically, the present invention provides methods and compositions comprising nucleic acid and amino acid sequences comprising a modified factor VIII that results in high-level expression of the polypeptide. The methods and compositions of the invention find use in the treatment of factor VIII deficiency, including, for example, hemophilia A.

In particular, one embodiment of the present invention provides an isolated polypeptide comprising an amino acid sequence set forth in SEQ ID NO:15, 17, or 19; an amino acid sequence having at least 85%, 90%, 95%, 97%, 98%, or 99% sequence identity to SEQ ID NO:15, 17, or 19, wherein said polypeptide is characterized by high-level expression, or a fragment thereof.

In another embodiment of the invention, isolated nucleic acid molecules are provided comprising a nucleotide sequence set forth in SEQ ID NO:14, 16, or 18; a nucleotide sequence encoding a polypeptide comprising the amino acid sequence set forth in SEQ ID NO:15, 17, or 19; and, a nucleotide sequence having at least 85%, 90%, 95%, 97%, 98%, or 99% sequence identity to SEQ ID NO:14, 16, or 18, wherein said nucleotide sequence encodes a polypeptide that is characterized by high-level expression. Expression cassettes, vectors, and cells comprising the nucleic acid molecules of the invention are further provided.

Pharmaceutical compositions comprising the nucleic acid molecules and the polypeptides of the invention are also provided.

Methods for the production of a polypeptide are provided. In one embodiment, the method comprises introducing into a cell a nucleic acid molecule comprising a nucleotide sequence encoding a polypeptide comprising the amino acid sequence set forth in SEQ ID NO:15, 17, or 19; a nucleotide sequence comprising the sequence set forth in SEQ ID NO:14, 16, or 18; a nucleotide sequence having at least 85%, 90%, 95%, 97%, 98%, or 99% sequence identity to SEQ ID NO:14, 16, or 18, wherein the nucleotide sequence encodes a polypeptide characterized by high-level expression, or a fragment thereof; and, culturing the cell under conditions that allow expression of the nucleotide sequence.

Also provided are methods for increasing the level of expression of the factor VIII polypeptide. In one embodiment, the method comprises introducing into a cell a nucleic acid molecule comprising a nucleotide sequence encoding a polypeptide comprising the amino acid sequence set forth in SEQ ID NO:15, 17, or 19; a nucleotide sequence comprising the sequence set forth in SEQ ID NO:14, 16, or 18; a nucleotide sequence having at least 85%, 90%, 95%, 97%, 98%, or 99% sequence identity to SEQ ID NO:14, 16, or 18, wherein the nucleotide sequence encodes a polypeptide characterized by high-level expression, or a fragment thereof; and, culturing the cell under conditions that allow expression of the nucleotide sequence.

Also provided is a method for the treatment of factor VIII deficiencies, including, for example, hemophilia A. The method comprises administering to a subject in need thereof a composition comprising a therapeutically effective amount of a polypeptide, where the polypeptide comprises an amino acid sequence set forth in SEQ ID NO: 15, 17, or 19, an amino acid sequence having at least 85%, 90%, 95%, 97%, 98%, or 99% sequence identity to SEQ ID NO:15, 17, or 19, wherein said polypeptide is characterized by high-level expression, or a fragment thereof.

Other methods include treating a factor VIII deficiency by administering to a subject in need thereof a composition comprising a therapeutically effective amount of a nucleic acid molecule, where said nucleic acid molecule comprises a nucleotide sequence set forth in SEQ ID NO:14, 16, or 18; a nucleotide sequence encoding a polypeptide comprising the amino acid sequence set forth in SEQ ID NO:15, 17, or 19; a nucleotide sequence having at least 85%, 90%, 95%, 97%, 98%, or 99% sequence identity to SEQ ID NO:14, 16, or 18, wherein said nucleic acid molecule encodes a polypeptide characterized by high-level expression, or a fragment thereof.

BRIEF DESCRIPTION OF THE DRAWINGS

FIG. 1A-1H taken together provide an aligned amino acid sequence comparison of the human (SEQ ID NO:6), porcine (SEQ ID NO:2), and mouse (SEQ ID NO:8) factor VIII polypeptide sequences.

FIG. 4 provides the amino acid sequence for the factor VIII$_{SEP}$ polypeptide designated herein as HP44/OL (SEQ ID NO:15).

FIG. 5A-5D provides the nucleotide sequence (SEQ ID NO: 14) encoding the factor VIII$_{SEP}$ polypeptide designated herein as HP44/OL.

FIG. 6 provides the amino acid sequence for the factor VIII$_{SEP}$ polypeptide designated herein as HP46/SQ (SEQ ID NO: 17).

FIG. 7A-7D provides the nucleotide sequence (SEQ ID NO: 16) encoding the factor VIII$_{SEP}$ polypeptide designated herein as HP46/SQ.

FIG. 8 provides the amino acid sequence for the factor VIII$_{SEP}$ polypeptide designated herein as HP47/SQ (SEQ ID NO:19).

FIG. 9A-9D provides the nucleotide sequence (SEQ ID NO: 18) encoding the factor VIII$_{SEP}$ polypeptide designated herein as HP47/SQ.

FIG. 10A-10D provides the amino acid sequence for the human factor VIII B-domain deleted polypeptide (SEQ ID NO:13).

FIG. 11A-11B provides the nucleotide sequence (SEQ ID NO:12) encoding the human factor VIII B-domain deleted polypeptide.

FIG. 13 provides the amino acid sequence (SEQ ID NO:21) encoding the factor VIII$_{SEP}$ polypeptide designated herein as HP63/OL.

FIG. 14A-14B provides the nucleotide sequence (SEQ ID NO: 20) encoding the factor VIII$_{SEP}$ polypeptide designated herein as HP63/OL.

DETAILED DESCRIPTION OF THE INVENTION

Overview

Figure 2:
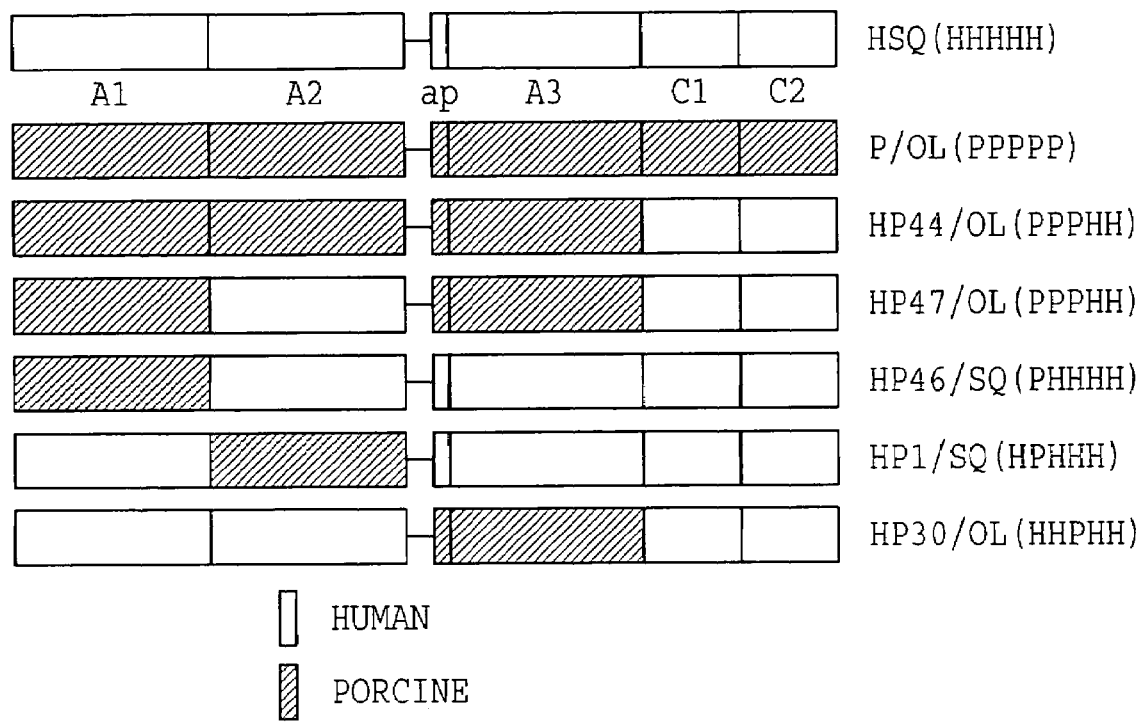
FIG. 2 provides a schematic of B domain-deleted human, porcine, and hybrid human/porcine factor VIII constructs. The solid line between the A2 and ap domains represents linker sequences.

The present invention provides methods and compositions that allow for high-level expression of the factor VIII polypeptide. The factor VIII polypeptide contains homology-defined proteins domains having the following nomenclature: A1-A2-B-ap-A3-C$_1$-C$_2$. The present invention has identified regions within the domains of a non-human factor VIII polypeptide that promote high-level expression of the factor VIII polypeptide. More particularly, regions of the porcine factor VIII polypeptide that comprises the A1 and ap-A3 regions, and variants and fragments thereof, have been identified which impart high-level expression to both the porcine and human factor VIII polypeptide. The present invention thus provides methods and compositions that use the non-human factor VIII polypeptide sequences which impart high-level expression, and active variants or fragments of these sequences, to construct nucleic acid and polypeptide sequences encoding a modified factor VIII polypeptide that results in high-level expression of the encoded factor VIII polypeptide. The modified factor VIII polypeptides characterized by high-level expression are referred to herein as "factor VIII$_{SEP}$" (Super Expression).

By "high-level expression" is intended the production of a polypeptide at increased levels when compared to the expression levels of the corresponding human factor VIII polypeptide expressed under the same conditions. An increase in polypeptide levels (i.e., high-level expression) comprises at least about 0.5, 1, 2, 3, 4, 5, 6, 7, 8, 9, 10, 11, 12, 13, 14, 15, 20 fold or greater expression of the factor VIII$_{SEP}$ polypeptide compared to the expression levels of the corresponding human factor VIII polypeptide. Alternatively, "high-level expression" can comprise an increase in polypeptide expression levels of at least 1-25 fold, 1-5 fold, 5-10 fold, 10-15 fold, 15-20 fold, 20-25 fold or greater expression levels of the factor VIII$_{SEP}$ when compared to the corresponding human factor VIII polypeptide. Methods for assaying "high-level expression" are routine in the art and are outlined in more detail below.

By "corresponding" factor VIII polypeptide is intended a factor VIII polypeptide that comprises an equivalent amino acid sequence. For instance, when a modified factor VIII polypeptide comprising the A1-A2-ap-A3-C$_1$-C$_2$ domains is tested for high-level expression, a human or porcine factor VIII polypeptide containing corresponding domains will be used (i.e., A1-A2-ap-A3-C$_1$-C$_2$). When a fragment of a modified factor VIII polypeptide is tested for high-level expression (i.e., A1-A2-ap-A3), a human or porcine factor VIII polypeptide having the corresponding domains will be tested (i.e., A1-A2-ap-A3).

Compositions

Compositions of the invention include the nucleic acid molecules encoding factor VIII polypeptides characterized by high-level expression. As outlined in further detail below, the A1 domain of porcine factor VIII (amino acid residues 20-391 of SEQ ID NO:19) and the ap-A3 domain of porcine factor VIII (amino acids 1450-1820 of SEQ ID NO:19) allow for high-level expression of factor VIII. The present invention thus provides methods and compositions comprising factor VIII$_{SEP}$ polypeptides and active variant and active fragments of factor VIII$_{SEP}$ polypeptides characterized by high-level expression.

In particular, the present invention provides for isolated nucleic acid molecules comprising nucleotide sequences encoding the amino acid sequence shown in SEQ ID NOS:15, 17, or 19 and active fragments or active variants thereof. Also provided are isolated nucleic acid molecules comprising nucleotide sequences set forth in SEQ ID NOS:14, 16, or 18 and active fragments or active variants thereof. Further provided are polypeptides having an amino acid sequence encoded by a nucleic acid molecule described herein, for example, those set forth in SEQ ID NOS:15, 17, and 19 and active fragments and active variants thereof.

Table 1 provides a summary of structure of the sequences provided in SEQ ID NOS:14-19, where the subscript "P" designates a domain from porcine factor VIII and the subscript "H" designates a domain from human factor VIII.

TABLE 1

Summary of Sequence Structure

| SEQ ID NO | Factor VIII domains |
|---|---|
| 14 and 15 | A1$_P$-A2$_P$-ap$_P$-A3$_P$-C1$_H$-C2$_H$ |
| 16 and 17 | A1$_P$-A2$_H$-ap$_H$-A3$_H$-C1$_H$-C2$_H$ |
| 18 and 19 | A1$_P$-A2$_H$-ap$_P$-A3$_P$-C1$_H$-C2$_H$ |

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed factor VIII$_{SEP}$ nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the polypeptides set forth in SEQ ID NO:15, 17, or 19 and hence are characterized by high-level expression of the factor VIII polypeptide. Thus, fragments of a nucleotide sequence may range from at least about 10, about 20 nucleotides, about 50 nucleotides, about 100 nucleotides, about 500 nucleotides, about 1000 nucleotides, about 2000 nucleotides, about 3000 nucleotides, about 4000 nucleotides, about 5000 nucleotides, about 6000 nucleotides, about 7000 nucleotides, about 8000 nucleotides, and up to the full-length nucleotide sequence encoding the factor VIII polypeptide of the invention about 9000 nucleotides.

A fragment of a nucleotide sequence of the present invention that encodes a biologically active portion of a factor VIII$_{SEP}$ protein of the invention will encode at least 12, 25, 30, 50, 100, 150, 200, 300, 400, 500, 600, 700, 800, 900, 1000, 1100, 1200, 1300, 1400, 1500, 1600, 1700, 1800, 1900, 2000, 2100, 2200, 2300 contiguous amino acids, or up to the total number of amino acids present in a full-length factor VIII protein of the invention (for example, 1457, 1467, or 1467 amino acids for SEQ ID NO:15, 17, or 19 respectively) and will allow high-level expression of the factor VIII polypeptide.

By "variant" is intended substantially similar sequences. For nucleotide sequences, conservative variants include those sequences that, because of the degeneracy of the genetic code, encode the amino acid sequence of one of the polypeptides of the invention. Variant nucleotide sequences include synthetically derived nucleotide sequences, such as those generated, for example, by using site-directed mutagenesis but which still encode a factor VIII$_{SEP}$ protein characterized by high-level expression. Generally, variants of a particular nucleotide sequence of the invention will have at least at least 75%, 80%, 85%, 86%, 87%, 88%, 89%, preferably about 90%, 91%, 92%, 93%, 94%, 95%, 96%, 97%, and more preferably about 98%, 99%, or more sequence identity to that particular nucleotide sequence as determined by sequence alignment programs described elsewhere herein.

By "variant" protein is intended a protein derived from the polypeptide of SEQ ID NO:15, 17, or 19 by deletion (so-called truncation) or addition of one or more amino acids to the N-terminal and/or C-terminal end of the protein; deletion or addition of one or more amino acids at one or more sites in the protein; or substitution of one or more amino acids at one or more sites in the protein. Variant proteins encompassed by the present invention are biologically active, that is they continue to possess the desired biological activity of SEQ ID NO:15, 17, or 19, hence they will continue to allow for the high-level expression of the factor VIII polypeptide. Such variants may result from, for example, genetic polymorphism or from human manipulation. Biologically active variants of a polypeptide of the invention will have at least 75%, 80%, 85%, 86%, 87%, 88%, 89%, preferably about 90%, 91%, 92%, 93%, 94%, 95%, 96%, 97%, 98%, 99% or more sequence identity to the amino acid sequence for SEQ ID NO:15, 17, or 19 as determined by sequence alignment programs described elsewhere herein using default parameters. A biologically active variant of a protein of the invention may differ from that protein by as few as 1-100, 1-50, 1-25, 1-15 amino acid residues, as few as 1-10, such as 6-10, as few as 5, as few as 4, 3, 2, or even 1 amino acid residue.

Biological activity of the factor VIII$_{SEP}$ polypeptides of the present invention can be assayed by any method known in the art. As discussed above, the factor VIII$_{SEP}$ polypeptides of the invention are characterized by high-level expression. Assays to measure high-level expression are known in the art. For example, the level of expression of the factor VIII$_{SEP}$ polypeptide can be measured by Western blot analysis or ELISA. Other methods include, for example, labeling cell lines expressing the factor VIII polypeptide with $^{35}$S-methionine, followed by immunoprecipitation of radiolabeled factor VIII molecules. Alternatively, the level of expression of the factor VIII$_{SEP}$ polypeptide can be assayed for by measuring the activity of the factor VIII polypeptide. For example, increased factor VIII expression could be assayed by measuring factor VIII activity using standard assays known in the art, including a one-stage coagulation assay or a two-stage activity assay. See, for example, U.S. Pat. No. 6,458,561 and the Experimental section below.

Briefly, coagulation assays are based on the ability of factor VIII to shorten the clotting time of plasma derived from a patient with hemophilia A. For example, in the one-stage assay, 0.1 ml hemophilia A plasma (George King Biomedical, Inc.) is incubated with 0.1 ml activated partial thromboplastin reagent (APTT) (Organon Teknika) and 0.01 ml sample or standard, consisting of diluted, citrated normal human plasma, for 5 min at 37° C. in a water bath. Incubation is followed by addition of 0.1 ml 20 mM CaCl$_2$, and the time for development of a fibrin clot is determined by visual inspection. A unit of factor VIII is defined as the amount present in 1 ml of citrated normal human plasma.

The one-stage assay relies on endogenous activation of factor VIII by activators formed in the hemophilia A plasma, whereas the two-stage assay measures the procoagulant activity of preactivated factor VIII. In the two-stage assay, samples containing factor VIII that are reacted with thrombin are added to a mixture of activated partial thromboplastin and human hemophilia A plasma that is preincubated for 5 min at 37° C. The resulting clotting times are converted to units/ml, based on the same human standard curve described above. See, for example, U.S. Pat. No. 6,376,463.

The factor VIII$_{SEP}$ polypeptides of the invention may be altered in various ways including amino acid substitutions, deletions, truncations, and insertions. Methods for such manipulations are generally known in the art. For example, amino acid sequence variants of the factor VIII$_{SEP}$ proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity (i.e., high-level expression) of the factor VIII$_{SEP}$ may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred. Alternatively, methods to minimize the number of porcine amino acids in the A$_1$ and ap-A$_3$ domains of factor VIII$_{SEP}$ and still continue to retain the high-level expression of the factor VIII$_{SEP}$ are known in the art and include, for example, established site-directed mutagenesis such as by splicing overlap extension as described elsewhere herein. Obviously, the mutations that will be made in the DNA encoding the variant must not place the sequence out of reading frame and preferably will not create complementary regions that could produce secondary mRNA structure. See, EP Patent Application Publication No. 75,444.

When it is difficult to predict the exact effect of the substitution, deletion, or insertion in advance of doing so, one skilled in the art will appreciate that the effect will be evaluated by routine screening assays. That is, the activity can be evaluated by high-level expression of the factor VIII polypeptide as discussed in detail elsewhere herein.

By "sequence identity" is intended the same nucleotides or amino acid residues are found within the variant sequence and a reference sequence when a specified, contiguous segment of the nucleotide sequence or amino acid sequence of the variant is aligned and compared to the nucleotide sequence or amino acid sequence of the reference sequence. Methods for sequence alignment and for determining identity between sequences are well known in the art. See, for example, Ausubel et al., eds. (1995) *Current Protocols in Molecular Biology*, Chapter 19 (Greene Publishing and Wiley-Interscience, New York); and the ALIGN program (Dayhoff (1978) in *Atlas of Polypeptide Sequence and Structure* 5:Suppl. 3 (National Biomedical Research Foundation, Washington, D.C.). With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. The contiguous segment used for comparison to the reference nucleotide sequence or reference amino acid sequence will comprise at least 20 contiguous nucleotides, or amino acid residues, and may be 30, 40, 50, 100, or more nucleotides or amino acid residues. Corrections for increased sequence identity associated with inclusion of gaps in the variant's nucleotide sequence or amino acid sequence can be made by assigning gap penalties. Methods of sequence alignment are well known in the art.

The determination of percent identity between two sequences is accomplished using a mathematical algorithm. Specifically, for the purpose of the present invention percent identity of an amino acid sequence is determined using the Smith-Waterman homology search algorithm using an affine 6 gap search with a gap open penalty of 12 and a gap extension penalty of 2, BLOSUM matrix 62. The Smith-Waterman homology search algorithm is taught in Smith and Waterman (1981) *Adv. Appl. Math* 2:482-489, herein incorporated by reference. Alternatively, for the purposes of the present invention percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic.

It is further recognized that when considering percentage of amino acid identity, some amino acid positions may differ as a result of conservative amino acid substitutions, which do not effect the properties of polynucleotide function. In these instances, percent sequence identity may be adjusted upwards to account for the similarity in conservatively substituted amino acids. Such adjustments are well known in the art. See, for example, Meyers et al. (1988) *Computer Applic. Biol. Sci.* 4:11-17.

It is recognized that variants of sequences of the invention may encode factor VIII$_{SEP}$ polypeptides that contain only the amino acid residues of the Al$_p$ and ap-A3$_p$ domains that confer the high-level expression to the factor VIII polypeptide. Consequently, the A1$_p$ and A3$_p$ domains can be progressively humanized such that only the residues required to retain high-level expression are retained in the factor VIII$_{SEP}$ polypeptide. Such methods are known by those skilled in the art and also discussed in more detail below. See also, for example, U.S. Pat. Nos. 6,376,463; 6,458,563; 5,744,466; 5,888,974; 5,663,060; 5,364,771; 5,859,204; and, 6,180,371; all of which are herein incorporated by reference. In addition, it is recognized that a three-dimensional model of the human factor VIII A1-A2-A3 domains can be used to identify regions away from the domain interface. One of skill will be able to use this model to identify target amino acids residues for humanization.

It is recognized that the variant factor $VIII_{SEP}$ or fragments thereof can be made (1) by substitution of isolated, plasma-derived animal subunits or human subunits (heavy or light chains) for corresponding human subunits or animal subunits; (2) by substitution of human domains or animal domains (A1, A2, A3, B, C1, and C2) for corresponding animal domains or human domains; (3) by substitution of parts of human domains or animal domains for parts of animal domains or human domains; (4) by substitution of at least one specific sequence including one or more unique human or animal amino acid(s) for the corresponding animal or human amino acid(s); or (5) by substitution of amino acid sequence that has no known sequence identity to factor VIII for at least one sequence including one or more specific amino acid residue(s) in human, animal, or variant factor VIII or fragments thereof. Individual amino acid replacements can be obtain by site-directed mutagenesis of the corresponding segment coding DNA.

In a factor VIII molecule, a "domain", as used herein, is a continuous sequence of amino acids that is defined by internal amino acid sequence identity and sites of proteolytic cleavage by thrombin. Unless otherwise specified, factor VIII domains include the following amino acid residues, when the sequences are aligned with the human amino acid sequence (SEQ ID NO:6): A1, residues Ala1-Arg372; A2, residues Ser373-Arg740; B, residues Ser741-Arg1648; A3, residues Ser1690-Ile2032; C1, residues Arg2033-Asn2172; C2, residues Ser2173-Tyr2332. The A3-$C_1$-$C_2$ sequence includes residues Ser1690-Tyr2332. The remaining sequence, residues Glu1649-Arg1689, is usually referred to as the factor VIII light chain activation peptide. factor VIII is proteolytically activated by thrombin or factor Xa, which dissociates it from von Willebrand factor, forming factor VIII, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-$C_1$-$C_2$ heterotrimer that forms a complex with factor IXa and factor X on the surface of platelets or monocytes. A "partial domain" as used herein is a continuous sequence of amino acids forming part of a domain. "Subunits" of human or animal (i.e., mouse, pig, dog etc.) factor VIII, as used herein, are the heavy and light chains of the protein. The heavy chain of factor VIII contains three domains, A1, A2, and B. The light chain of factor VIII also contains three domains, A3, C1, and C2. A "unique" amino acid residue or sequence, as used herein, refers to an amino acid sequence or residue in the factor VIII molecule of one species that is different from the homologous residue or sequence in the factor VIII molecule of another species. As used herein, "mammalian factor VIII" includes factor VIII with amino acid sequence derived from any non-human mammal, unless otherwise specified. "Animal", as used herein, refers to pig and other non-human mammals.

Since current information indicates that the B domain has no inhibitory epitope and has no known effect on factor VIII function, factor $VIII_{SEP}$ variants of the present invention may have a B domain or a portion thereof. In addition, factor $VIII_{SEP}$ variants may also have the factor VIII B-domain with the B-domain from porcine or human factor V. See, for example, U.S. Pat. No. 5,004,803. A "B-domainless" variant factor $VIII_{SEP}$ or fragment thereof, as used herein, refers to any one of the variant factor $VIII_{SEP}$ constructs described herein that lacks the B domain, or a portion thereof.

One of skill in the art will be aware of techniques that allow individual subunits, domains, or continuous parts of domains of animal or human factor VIII cDNA to be cloned and substituted for the corresponding human or porcine subunits, domains, or parts of domains by established mutagenesis techniques and thereby generate a factor $VIII_{SEP}$ or variant or fragment thereof. For example, Lubin et al. (1994) *J. Biol. Chem.* 269(12):8639-8641 describes techniques for substituting the porcine A2 domain for the human domain using convenient restriction sites. Other methods for substituting a region of the factor VIII cDNA of one species for the factor VIII cDNA of another species include splicing by overlap extension ("SOE"), as described by Horton et al. (1993) *Meth. Enzymol* 217:270-279.

DNA Constructs and Vectors

The nucleotide sequence encoding the factor $VIII_{SEP}$ polypeptides or active variants or fragments thereof can be contained in a DNA construct. The DNA construct can include a variety of enhancers/promoters from both viral and mammalian sources that drive expression of the factor $VIII_{SEP}$ polypeptide in the desired cell type. The DNA construct can further contain 3' regulatory sequences and nucleic acid sequences that facilitate subcloning and recovery of the DNA.

The transcriptional promoter and, if desired, the transcriptional enhancer element are operably linked to the nucleic acid sequence of the factor VIII polypeptide. A "promoter" is defined as a minimal DNA sequence that is sufficient to direct transcription of a nucleic acid sequence. A "transcriptional enhancer element" refers to a regulatory DNA sequence that stimulates the transcription of the adjacent gene. The nucleic acid sequence encoding the factor VIII polypeptide is operably linked to the promoter sequence. See, for example, Goeddel (1990) *Gene Expression Technology: Methods in Enzymology* 185 (Academic Press, San Diego, Calif.).

By "operably linked" is intended a functional linkage between the regulatory promoter and the nucleic acid sequence encoding the factor VIII polypeptide. The functional linkage permits gene expression of factor VIII when the appropriate transcription activator proteins are present.

Thus, the DNA construct can include a promoter that may be native or foreign. By "foreign" it is meant a sequence not found in the native organism. Furthermore, the transcription regulatory elements may be heterologous to the nucleotide sequence encoding factor VIII. By "heterologous" is intended any nucleotide sequence not naturally found upstream of the sequence encoding the factor VIII polypeptide. The promoter may be a natural sequence or a synthetic sequence. In addition, the promoter may be constitutively active, tissue-specific, or inducible. A tissue-specific promoter is preferentially activated in a given tissue and results in expression of a gene product in the tissue where activated.

For use in mammalian cells, the promoters may be derived from a virus. For example, commonly used promoters are derived from polyoma, Simian Virus 40 (SV40) and Adenovirus 2. The early and late promoters of SV40 virus are useful as is the major late promoter of adenovirus. Further, it is also possible, and often desirable, to utilize promoter or control sequences normally associated with the desired gene sequence, provided such control sequences are compatible with the host cell system.

In certain embodiments, the introduction of the nucleotide sequence encoding factor VIII into a cell can be identified in vitro or in vivo by including a marker in the DNA construct. The marker will result in an identifiable change in the genetically transformed cell. Drug selection markers include for example neomycin, puromycin, hygromycin, DHFR, GPT, zeocin and histidinol. Alternatively, enzymes such as herpes simplex virus thymidine kinase (TK) or immunological markers can be used. Further examples of selectable markers are well known in the art.

It is recognized that multiple alterations can be envisioned for the design of the DNA construct used in the methods of the present invention. For instance, the construct may be designed for the insertion of the nucleotide sequence encoding the factor VIII$_{SEP}$ polypeptide using homologous or site-specific recombination systems (i.e., Cre or FLP recombination systems).

The DNA construct may also contain at least one additional gene to be co-introduced into the host cells.

The nucleotide sequences of the present invention can be contained in an expression vector. An "expression vector" is a DNA element, often of circular structure, having the ability to replicate autonomously in a desired host cell, or to integrate into a host cell genome and also possessing certain well-known features which, for example, permit expression of a coding DNA inserted into the vector sequence at the proper site and in proper orientation. Such features can include, but are not limited to, one or more promoter sequences to direct transcription initiation of the coding DNA and other DNA elements such as enhancers, polyadenylation sites and the like, all as well known in the art.

Other vectors, including both plasmid and eukaryotic viral vectors, may be used to express a recombinant gene construct in eukaryotic cells depending on the preference and judgment of the skilled practitioner (see, for example, Sambrook et al., Chapter 16). For example, many viral vectors are known in the art including, for example, retroviruses, adeno-associated viruses, and adenoviruses. Other viruses useful for introduction of a gene into a cell include, but a not limited to, herpes virus, mumps virus, poliovirus, Sindbis virus, and vaccinia virus, such as, canary pox virus. The methods for producing replication-deficient viral particles and for manipulating the viral genomes are well known. See, for examples, Rosenfeld et al. (1991) *Science* 252:431-434, Rosenfeld et al. (1992) *Cell* 68:143-155, and U.S. Pat. No. 5,882,877 (adenovirus); U.S. Pat. No. 5,139,941 (adeno-associated virus); U.S. Pat. No. 4,861,719, U.S. Pat. No. 5,681,746, and Miller et al. (1993) *Methods in Enzymology* 217:581 (retrovirus), all of which are herein incorporated by reference. Therefore, given the knowledge in the art, viral vectors can be readily constructed for use in the introduction of the factor VIII sequences into a cell. Other vectors and expression systems, including bacterial, yeast, and insect cell systems, can be used but are not preferred due to differences in, or lack of, glycosylation.

Factor VIII polypeptides of the invention can be expressed in a variety of cells commonly used for culture and recombinant mammalian protein expression. In particular, a number of rodent cell lines have been found to be especially useful hosts for expression of large proteins. Preferred cell lines, available from the American Type Culture Collection, Rockville, Md., include, but are not limited to, baby hamster kidney cells, and chinese hamster ovary (CHO) cells which are cultured using routine procedures and media. Additional cells of interest can include vertebrate cells such as VERO, HeLa cells, W138, COS-7, and MDCK cell lines. For other suitable expression systems see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.).

Methods of Expression and Isolation

The DNA construct of the present invention may be introduced into a cell (prokaryotic or eukaryotic) by standard methods. As used herein, the terms "transformation" and "transfection" are intended to refer to a variety of art recognized techniques to introduce a DNA into a host cell. Such methods include, for example, transfection, including, but not limited to, liposome-polybrene, DEAE dextran-mediated transfection, electroporation, calcium phosphate precipitation, microinjection, or velocity driven microprojectiles ("biolistics"). Such techniques are well known by one skilled in the art. See, Sambrook et al. (1989) *Molecular Cloning: A Laboratory Manaual* (2 ed. Cold Spring Harbor Lab Press, Plainview, N.Y.). Alternatively, one could use a system that delivers the DNA construct in a gene delivery vehicle. The gene delivery vehicle may be viral or chemical. Various viral gene delivery vehicles can be used with the present invention. In general, viral vectors are composed of viral particles derived from naturally occurring viruses. The naturally occurring virus has been genetically modified to be replication defective and does not generate additional infectious viruses. The viral vector also contains a DNA construct capable of expressing the factor VIII protein.

The DNA construct containing nucleic acid sequences encoding the factor VIII$_{SEP}$ polypeptide may also be administered to cell by a non-viral gene delivery vehicle. Such chemical gene delivery vehicles include, for example, a DNA- or RNA-liposome complex formulation or a naked DNA. See, for example, Wang et al. (1987) *Proc. Natl. Acad. Sci. U.S.A.* 84:7851, U.S. Pat. No. 5,844,107, U.S. Pat. No. 5,108,921, and Wagner et al. (1991) *Proc. Natl. Acad. Sci. U.S.A.* 88:4255-4259, all of which are herein incorporated by reference.

It is recognized that the method of introducing the factor VIII$_{SEP}$ polypeptide or variant or fragment thereof into a cell can result in either stable integration into the cell genome or transient, episomal expression.

As defined herein, the "expression product" of a DNA encoding a factor VIII$_{SEP}$ polypeptide or a fragment or variant thereof is the product obtained from expression of the referenced DNA in a suitable host cell, including such features of pre- or post-translational modification of protein encoded by the referenced DNA, including but not limited to glycosylation, proteolytic cleavage and the like. It is known in the art that such modifications can occur and can differ somewhat depending upon host cell type and other factors, and can result in molecular isoforms of the product, with retention of procoagulant activity. See, for example, Lind et al, (1995) *Eur. J. Biochem.* 232:1927 incorporated herein by reference.

In a one embodiment, cDNA encoding factor VIII$_{SEP}$ or a variant or fragment thereof, is inserted in a mammalian expression vector, such as ReNeo. Preliminary characterization of the factor VIII$_{SEP}$ is accomplished by transient expression in the ReNeo expression vector containing the factor VIII$_{SEP}$ construct in COS-7 cells. A determination of whether active factor VIII$_{SEP}$ protein is expressed can then be made. The expression vector construct is used further to stably transfect cells in culture, such as baby hamster kidney cells, using methods that are routine in the art, such as liposome-mediated transfection (Lipofectin™, Life Technologies, Inc.). Expression of the factor VIII$_{SEP}$ protein can be confirmed, for example, by sequencing, Northern and Western blotting, or polymerase chain reaction (PCR).

Factor VIII$_{SEP}$ polypeptides or fragments or variants thereof in the culture media in which the transfected cells stably expressing the protein are maintained can be precipitated, pelleted, washed, and resuspended in an appropriate buffer, and the factor VIII$_{SEP}$ protein or variant or fragment thereof is purified by standard techniques, including immunoaffinity chromatography using, for example, monoclonal anti-A2-Sepharose™.

A "fusion protein" or "fusion factor VIII$_{SEP}$ or fragment thereof", as used herein, is the product of a hybrid gene in which the coding sequence for one protein is extensively altered, for example, by fusing part of it to the coding sequence for a second protein from a different gene to produce a hybrid gene that encodes the fusion protein.

In a further embodiment, the factor VIII$_{SEP}$ or variant or fragment thereof is expressed as a fusion protein from a recombinant molecule in which sequence encoding a protein or peptide that enhances, for example, stability, secretion, detection, isolation, or the like is inserted in place adjacent to the factor VIII encoding sequence. See, for example, U.S. Pat. No. 4,965,199 which discloses a recombinant DNA method for producing factor VIII in mammalian host cells and purification of human factor VIII. Human factor VIII expression on CHO (Chinese hamster ovary) cells and BHKC (baby hamster kidney cells) has been reported. Established protocols for use of homologous or heterologous species expression control sequences including, for example, promoters, operators, and regulators, in the preparation of fusion proteins are known and routinely used in the art. See, Ausubel et al. *Current Protocols in Molecular Biology*, Wiley Interscience, N.Y, herein incorporated by reference. It is further noted that expression is enhanced by including portions of the B-domain. In particular, the inclusion of those parts of the B domain designated "SQ" (Lind et al. (1995) *Eur. J. Biochem.* 232:1927, herein incorporated herein by reference) results in favorable expression. "SQ" constructs lack all of the human B domain except for 5 amino acids of the B domain N-terminus and 9 amino acids of the B domain C-terminus.

It is further recognized that the factor VIII$_{SEP}$ polypeptide or variant or fragment thereof of the invention may be prepared via reconstitution methods. In this embodiment factor VIII$_{SEP}$, variants or fragments thereof are made by isolation of subunits, domains, or continuous parts of domains of plasma-derived factor VIII, followed by reconstitution and purification to produce a factor VIII$_{SEP}$ polypeptide of the invention. Alternatively, the factor VIII$_{SEP}$, variant or fragment thereof can be made by recombinant DNA methods, followed by reconstitution and purification.

More particularly, the method of preparing a factor VIII$_{SEP}$ by reconstitution methods can be performed via a modification of procedures reported by Fay et al. (1990) *J. Biol. Chem.* 265:6197; and Lollar et al. (1988) *J. Biol. Chem.* 263:10451, which involves the isolation of subunits (heavy and light chains) of human and animal factor VIII, followed by recombination of human heavy chain and animal light chain or by recombination of human light chain and animal heavy chain.

Isolation of both human and animal individual subunits involves dissociation of the light chain/heavy chain dimer. This is accomplished, for example, by chelation of calcium with ethylenediaminetetraacetic acid (EDTA), followed by monoS™ HPLC (Pharmacia-LKB, Piscataway, N.J.). Hybrid human/animal factor VIII molecules are reconstituted from isolated subunits in the presence of calcium. Hybrid human light chain/animal heavy chain or animal light chain/human heavy chain factor VIII is isolated from unreacted heavy chains by monoS™ HPLC by procedures for the isolation of porcine factor VIII, such as described by Lollar et al. (1988) *Blood* 71:137-143 and in U.S. Pat. No. 6,376,463, both of which is herein incorporated by reference.

Diagnostic Assays

As used herein, "diagnostic assays" include assays that in some manner utilize the antigen-antibody interaction to detect and/or quantify the amount of a particular antibody that is present in a test sample to assist in the selection of medical therapies. There are many such assays known to those of skill in the art. As used herein, however, the factor VIII$_{SEP}$ DNA or variant or fragment thereof and protein expressed therefrom, in whole or in part, can be substituted for the corresponding reagents in the otherwise known assays, whereby the modified assays may be used to detect and/or quantify antibodies to factor VIII. It is the use of these reagents, the factor VIII$_{SEP}$ DNA or variants or fragments thereof or protein expressed therefrom, that permits modification of known assays for detection of antibodies to human or animal factor VIII or to hybrid human/animal factor VIII. As used herein, the factor $VIII_{SEP}$ or variants or fragment thereof that includes at least one epitope of the protein can be used as the diagnostic reagent.

The DNA or amino acid sequence of the factor $VIII_{SEP}$ or variant or fragment thereof can be used in assays as diagnostic reagents for the detection of inhibitory antibodies to human or animal factor VIII, including, for example, samples of serum and body fluids of human patients with factor VIII deficiency. These antibody assays include assays such as ELISA assays, immunoblots, radioimmunoassays, immunodiffusion assays, and assay of factor VIII biological activity (e.g., by coagulation assay). Examples of other assays in which the factor $VIII_{SEP}$ or variant or fragment thereof can be used include the Bethesda assay and anticoagulation assays. Techniques for preparing these reagents and methods for use thereof are known to those skilled in the art. For example, an immunoassay for detection of inhibitory antibodies in a patient serum sample can include reacting the test sample with a sufficient amount of the factor $VIII_{SEP}$ that contains at least one antigenic site, wherein the amount is sufficient to form a detectable complex with the inhibitory antibodies in the sample.

Nucleic acid and amino acid probes can be prepared based on the sequence of the factor $VIII_{SEP}$ DNA or protein molecule or fragments or variants thereof. In some embodiments, these can be labeled using dyes or enzymatic, fluorescent, chemiluminescent, or radioactive labels that are commercially available. The amino acid probes can be used, for example, to screen sera or other body fluids where the presence of inhibitors to human, animal, or hybrid human/animal factor VIII is suspected. Levels of inhibitors can be quantitated in patients and compared to healthy controls, and can be used, for example, to determine whether a patient with a factor VIII deficiency can be treated with a factor $VIII_{SEP}$ or active fragment or variant thereof. The cDNA probes can be used, for example, for research purposes in screening DNA libraries.

Pharmaceutical Compositions

The present invention further provides pharmaceutical compositions comprising the nucleic acid molecules and the polypeptides encoding the high-level expression factor $VIII_{SEP}$ of the present invention or variants and fragments thereof. Such compositions can comprise nucleic acids and polypeptides of the invention either alone or in combination with appropriate pharmaceutical stabilization compounds, delivery vehicles, and/or carrier vehicles, are prepared according to known methods, as described in Martin et al. *Remington's Pharmaceutical Sciences*, herein incorporated by reference.

In one embodiment, the preferred carriers or delivery vehicles for intravenous infusion are physiological saline or phosphate buffered saline.

In another embodiment, suitable stabilization compounds, delivery vehicles, and carrier vehicles include but are not limited to other human or animal proteins such as albumin.

Phospholipid vesicles or liposomal suspensions may also be used as pharmaceutically acceptable carriers or delivery vehicles. These can be prepared according to methods known to those skilled in the art and can contain, for example, phosphatidylserine-phosphatidylcholine or other compositions of phospholipids or detergents that together impart a negative charge to the surface, since factor VIII binds to negatively charged phospholipid membranes. Liposomes may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the factor $VIII_{SEP}$ of the present invention is then introduced into the container. The container is then swirled by hand to free lipid material from the sides of the container and to disperse lipid aggregates, thereby forming the liposomal suspension.

The factor $VIII_{SEP}$ molecules of the invention can be combined with other suitable stabilization compounds, delivery vehicles, and/or carrier vehicles, including vitamin K dependent clotting factors, tissue factor, and von Willebrand factor (vWf) or a fragment of vWf that contains the factor VIII binding site, and polysaccharides such as sucrose.

Factor $VIII_{SEP}$ molecules of the invention can also be delivered by gene therapy using delivery means such as retroviral vectors. This method consists of incorporation of a nucleotide sequence encoding desired factor $VIII_{SEP}$ polypeptide of the invention into human cells that are transplanted directly into a factor $VIII_{SEP}$ deficient patient or that are placed in an implantable device, permeable to the factor VIII molecules but impermeable to cells, that is then transplanted.

In one embodiment, the method will be retroviral-mediated gene transfer. In this method, a nucleotide sequence encoding a factor VIII polypeptide of the invention is cloned into the genome of a modified retrovirus. The gene is inserted into the genome of the host cell by viral machinery where it will be expressed by the cell. The retroviral vector is modified so that it will not produce virus, preventing viral infection of the host. The general principles for this type of therapy are known to those skilled in the art and have been reviewed in the literature (Kohn et al. (1989) *Transfusion* 29:812-820).

The factor $VIII_{SEP}$ polypeptide of the invention can be stored bound to vWf to increase the half-life and shelf-life of the polypeptide molecule. Additionally, lyophilization of factor $VIII_{SEP}$ can improve the yields of active molecules in the presence of vWf. Current methods for storage of human and animal factor VIII used by commercial suppliers can be employed for storage of recombinant factor VIII. These methods include: (1) lyophilization of factor $VIII_{SEP}$ in a partially-purified state (as a factor VIII "concentrate" that is infused without further purification); (2) immunoaffinity-purification of factor $VIII_{SEP}$ by the Zimmerman method and lyophilization in the presence of albumin, which stabilizes the factor VIII; (3) lyophilization of recombinant factor $VIII_{SEP}$ in the presence of albumin.

Additionally, the factor VIII polypeptides can be stored at 4° C. in 0.6 M NaCl, 20 mM MES, and 5 mM $CaCl_2$ at pH 6.0. The polypeptides can also be stored frozen in these buffers and thawed with minimal loss of activity.

Methods of Treatment

Factor $VIII_{SEP}$ or fragments and variant thereof can be used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. The active materials are preferably administered intravenously.

"Factor VIII deficiency," as used herein, includes deficiency in clotting activity caused by production of defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII protein it encodes.

Additionally, factor $VIII_{SEP}$ or fragments and variant thereof can be administered by transplantation of cells genetically engineered to produce the factor $VIII_{SEP}$ or by implantation of a device containing such cells, as described above.

In one embodiment, pharmaceutical compositions of factor $VIII_{SEP}$ or fragments and variants thereof alone or in combination with stabilizers, delivery vehicles, and/or carriers are infused into patients intravenously according to the same procedure that is used for infusion of factor $VIII_{SEP}$.

The treatment dosages of the factor $VIII_{SEP}$ composition or variants or fragments thereof that must be administered to a patient in need of such treatment will vary depending on the severity of the factor VIII deficiency. Generally, dosage level is adjusted in frequency, duration, and units in keeping with the severity and duration of each patient's bleeding episode. Accordingly, the factor $VIII_{SEP}$ or variants or fragments thereof is included in the pharmaceutically acceptable carrier, delivery vehicle, or stabilizer in an amount sufficient to deliver to a patient a therapeutically effective amount of the hybrid to stop bleeding, as measured by standard clotting assays.

"Specific activity" as used herein, refers to the activity that will correct the coagulation defect of human factor VIII deficient plasma. Specific activity is measured in units of clotting activity per milligram total factor VIII protein in a standard assay in which the clotting time of human factor VIII deficient plasma is compared to that of normal human plasma. One unit of factor VIII activity is the activity present in one milliliter of normal human plasma. In the assay, the shorter the time for clot formation, the greater the activity of the factor VIII being assayed. The specific activity of the factor VIII polypeptides, variant or fragments thereof, may be less than, equal to, or greater than that of either plasma-derived or recombinant human factor VIII.

Factor VIII is classically defined as that substance present in normal blood plasma that corrects the clotting defect in plasma derived from individuals with hemophilia A. The coagulant activity in vitro of purified and partially-purified forms of factor $VIII_{SEP}$ is used to calculate the dose of factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher et al. *New Engl. J. Med.* 328: 453-459; Pittman et al. (1992) *Blood* 79:389-397; and Brinkhous et al. (1985) *Proc. Natl. Acad. Sci.* 82:8752-8755.

The increase of factor $VIII_{SEP}$ in the plasma will be sufficient to produce a therapeutic effect. A "therapeutic effect" is defined as an increase in the blood coagulation activity in the plasma of patients that is greater than the coagulation activity observed in the subject before administration of the factor VIII$_{SEP}$ molecule. In a standard blood clotting assay, the shorter time for clot formation, the greater the activity of factor VIII being assayed. An increase in factor VIII activity in the factor VIII deficient plasma of at least 1% or higher will be therapeutically beneficial.

Usually, the desired plasma factor VIII level to be achieved in the patient through administration of the factor VIII$_{SEP}$ or variant or fragment thereof is in the range of 30-100% of normal. In a one mode of administration of the factor VIII$_{SEP}$ or fragment or variant thereof, the composition is given intravenously at a preferred dosage in the range from about 5 to 50 units/kg body weight, more preferably in a range of 10-50 units/kg body weight, and most preferably at a dosage of 20-40 units/kg body weight; the interval frequency is in the range from about 8 to 24 hours (in severely affected hemophiliacs); and the duration of treatment in days is in the range from 1 to 10 days or until the bleeding episode is resolved. See, for example, Roberts et al. (1990) *Hematology*, Williams et al. ed. Ch. 153, 1453-1474, herein incorporated by reference. Patients with inhibitors may require more factor VIII$_{SEP}$ or variants or fragments thereof, or patients may require less factor VIII$_{SEP}$ or fragments or variants thereof. As in treatment with human or porcine factor VIII, the amount of factor VIII$_{SEP}$ or fragments or variants infused is defamed by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

Treatment can take the form of a single intravenous administration of the composition or periodic or continuous administration over an extended period of time, as required. Alternatively, factor VIII SEP or fragments or variants thereof can be administered subcutaneously or orally with liposomes in one or several doses at varying intervals of time.

Factor VIII SEP or fragments or variants thereof can also be used to treat uncontrolled bleeding due to factor VIII deficiency in hemophiliacs who have developed antibodies to human factor VIII.

EXPERIMENTAL

Example 1

Sequence Characterization of Factor VIII

Both porcine and human factor VIII are isolated from plasma as a two subunit protein. The subunits, known as the heavy chain and light chain, are held together by a non-covalent bond that requires calcium or other divalent metal ions. The heavy chain of factor VIII contains three domains, A1, A2, and B, which are linked covalently. The light chain of factor VIII also contains three domains, designated A3, C1, and C2. The B domain has no known biological function and can be removed, or partially removed from the molecule proteolytically or by recombinant DNA technology methods without significant alteration in any measurable parameter of factor VIII. Human recombinant factor VIII has a similar structure and function to plasma-derived factor VIII, though it is not glycosylated unless expressed in mammalian cells. Both human and porcine activated factor VIII ("factor VIIIa") have three subunits due to cleavage of the heavy chain between the A1 and A2 domains. This structure is designated A1/A2/A3-C1-C2.

The cDNA sequence of porcine factor VIII corresponding the signal peptide coding region, the A1, B, light chain activity peptide region A3, C1, and C2 domains is provided in SEQ ID NO:1. The translation of the porcine cDNA is provided in SEQ ID NO:2.

The alignment of the predicted amino acid sequence of full-length porcine factor VIII (SEQ ID NO:2) with the published human (Wood et al. (1984) *Nature* 312:330-337) (SEQ ID NO:6) and murine (Elder et al. (1993) supra) (SEQ ID NO:8) sequences are shown in FIGS. 1A-1H along with sites for post-translational modification, proteolytic cleavage, and recognition by other macromolecules.

Potential N-linked glycosylation sites (NXS/T where X is not proline) can be seen in FIGS. 1A-1H. There are eight conserved N-linked glycosylation sites: one in the A1 domain, one in the A2 domain, four in the B domain, one in the A3 domain, and one in the C1 domain. The 19 A and C domain cysteines are conserved, whereas there is divergence of B domain cysteines. Six of the seven disulfide linkages in factor VIII are found at homologous sites in factor V and Ceruloplasmin, and both C domain disulfide linkages are found in factor V (McMullen et al. (1995) *Protein Sci.* 4:740-746). Human factor VIII contains sulfated tyrosines at positions 346, 718, 719, 723, 1664, and 1680 (Pittman et al. (1992) *Biochemistry* 31:3315-3325; Michnick et al. (1994) *J. Biol. Chem.* 269:20095-20102). These residues are conserved in mouse factor VIII and porcine factor VIII (FIG. 1), although the CLUSTALW program failed to align the mouse tyrosine corresponding to Tyr346 in human factor VIII. Epitopes of the various domain of the factor VIII polypeptide are outlined in FIG. 1.

Example 2

Summary

Human factor VIII expression levels are significantly lower than levels of other coagulation proteins in vivo and in heterologous expression systems in vitro. Low-level expression of recombinant human factor VIII has constrained the treatment of hemophilia A using recombinant protein infusion and gene therapy protocols. However, recombinant B-domain-deleted porcine factor VIII is expressed at levels 10-14 fold greater than recombinant B-domain-deleted human factor VIII in vitro. To identify sequences of porcine factor VIII necessary for this property, B-domain-deleted human/porcine hybrid factor VIII cDNAs were produced that contained substitution of human sequences with the corresponding porcine sequences. These cDNAs were transiently transfected into COS-7 cells or stably transfected into BHK-derived cells and factor VIII expression into the extracellular media was measured by one-stage coagulation assay. Human/porcine hybrid factor VIII cDNAs containing 1) the A1, A2 and A3 domains of porcine factor VIII and the C1 and C2 domains of human factor VIII, or 2) the A1 and A3 domains of porcine factor VIII and the A2, C1, and C2 domains of human factor VIII demonstrated factor VIII expression levels comparable to porcine factor VIII. A human/porcine hybrid factor VIII molecule demonstrating high-level expression may be valuable for improving factor VIII production for intravenous infusion or for somatic cell gene therapy of hemophilia A.

Materials

Dulbecco's phosphate-buffered saline, fetal bovine serum (FBS), penicillin, streptomycin, DMEM:F12, serum-free AIM V culture media, Lipofectin, Lipofectamine 2000 and geneticin were purchased from Invitrogen. Baby hamster kidney—derived cells, designated BHK-M cells (Funk et al. (1990) *Biochemistry* 29:1654-1660), were a gift from Dr. Ross Macgillivray, University of British Columbia. Transient transfections were controlled for transfection efficiency using the RL-CMV vector and Dual-Luciferase Assay Kit (Promega, Madison, Wis.). Citrated factor VIII-deficient plasma and pooled citrated normal human plasma (FACT) were purchased from George King Biomedical (Overland Park, Kans.). Activated partial thromboplastin reagent (aPTT) was purchased from Organon Teknika (Durham, N.C.). Oligonucleotide primers were synthesized by Life Technologies. Pfu DNA polymerase and *E. coli* XL-1 Blue cells were purchased from Stratagene (La Jolla, Calif.).

Construction of Factor VIII Expression Vectors

All of the factor VIII expression vectors in this study were contained in the ReNeo mammalian expression plasmid (Lind et al. (1995) *Eur. J. Biochem.* 232:19-27). The factor VIII cDNA inserts lack endogenous factor VIII 5'-UTR sequence and contain the first 749 of the 1805 nt human factor VIII 3'-UTR.

A human B domain-deleted factor VIII cDNA designed HSQ (FIG. 2) was created by cloning the human factor VIII cDNA into the mammalian expression vector ReNeo as described previously (Doering et al. (2002) *J. Biol. Chem.* 277: 38345-38349). The HSQ cDNA encodes an S F S Q N P P V L K R H Q R (SEQ ID NO:9) linker sequence between the A2 and ap domains. This linker includes the R H Q R (SEQ ID NO:10) recognition sequence for intracellular proteolytic processing by PACE/furin (Seidah et al. (1997) *Current Opinion in Biotechnology* 8:602-607). This cleavage event converts single chain factor VIII into a heterodimer (Lind et al. (1995) *Eur. J. Biochem.* 232:19-27). Heterodimeric factor VIII is considered the physiologic form of factor VIII (Fass et al. (1982) *Blood* 59:594-600).

A B-domain-deleted form of porcine factor VIII cDNA was ligated into ReNeo as described previously (Doering et al. (2002) *J. Biol. Chem.* 277: 38345-38349). The cDNA, designated P/OL (FIG. 2), encodes a porcine-derived linker sequence S F A Q N S R P P S A S A P K P P V L R R H Q R (SEQ ID NO:11) between the A2 and ap domains for PACE/furin recognition.

A B-domainless hybrid human/porcine factor VIII molecule designated HP 1, which contains the porcine A2 domain and human A1, ap-A3, C1 and C2 domains, was prepared as described previously (Lubin et al. (1994) *J. Biol. Chem.* 269: 8639-8641). The cDNA encoding the human-derived linker sequence S F S Q N P P V L K R H Q R (SEQ ID NO:9) was inserted between the A2 and ap domains of HP1 by splicing-by-overlap extension (SOE) mutagenesis (Horton et al. (1993) *Methods Enzymol.* 217:270-279), producing HP1/SQ (FIG. 2).

HP30, which contains the porcine ap-A3 domain and human A1, A2, C1 and C2 domains, was prepared as described previously (Barrow et al. (2000) *Blood* 95:557-561). The cDNA encoding the porcine-derived linker sequence S F A Q N S R P P S A S A P K P P V L R R H Q R (SEQ ID NO:11) was inserted between the A2 and ap domains of HP30 by SOE mutagenesis, producing HP30/OL (FIG. 2).

HP44/OL, which contains the porcine A1, A2, ap-A3 domains, the porcine-derived linker sequence S F A Q N S R P P S A S A P K P P V L R R H Q R (SEQ ID NO:11) and the human C1 and C2 domains (FIG. 2), was prepared as follows. P/OL ReNeo was digested with AvrII and the fragment containing A1, A2 and ReNeo sequence was gel purified. HP30/OL was digested with AvrII and the fragment containing porcine ap-A3 and human C1 and C2 sequences was gel purified. Ligation of the products, transformation of *E. coli* XL-1 cells and plasmid purification were performed as described previously (Healey et al. (1998) *Blood* 92:3701-3709).

HP46/SQ, which contains the porcine A1 domain and human A2, ap-A3, C1 and C2 domains and the human S F S Q N P P V L K R H Q R (SEQ ID NO:11) linker sequence (FIG. 2), was prepared by SOE mutagenesis. P/OL in ReNeo and HSQ in ReNeo were used as templates in the first round SOE reactions. The 5' primer in the P/OL reaction was complementary to ReNeo sequence 5' to the factor VIII cDNA. The 3' primer flanked the porcine A1 domain. The 5' primer in the HSQ reaction was partially complementary to the 3' primer used in the first reaction. The 3' primer was complementary to human A2 sequence. Following gel purification of the products from the first round reactions, the second SOE reaction was performed, yielding a product containing ReNeo sequence 5' to the factor VIII cDNA insert, the porcine A1 domain, and part of the human A2 domain. This product was digested with XhoI, at the junction of ReNeo and the factor VIII insert, and MluI, in the human A2 domain, and ligated into XhoI/MluI digested HSQ/ReNeo. The resulting plasmid was amplified by transformation into *E. coli* XL-1 Blue cells as described above.

HP47/OL, which contains the porcine A1, ap-A3 domains, porcine-derived linker sequence S F A Q N S R P P S A S A P K P P V L R R H Q R (SEQ ID NO:11) and human A2, C1 and C2 domains (FIG. 2) was prepared as follows. HP46/SQ in ReNeo was digested with AvrII, which cleaves the plasmid in the ReNeo sequence 5 to the factor VIII insert and at the A2-ap junction. The fragment containing the A1 and A2 domains was gel purified ligated to a fragment of HP30/OL in ReNeo produced by AvrII digestion.

Sequences produced by SOE mutagenesis were confirmed by dideoxy DNA sequencing.

Transient Expression of Factor VIII From COS-7 Cells

COS-7 cells were grown to 70-80% confluence in 2 cm$^2$ wells containing 1 ml DMEM:F12 supplemented with 10% FBS, 100 units/ml penicillin and 100 µg/ml streptomycin. Cells were transfected with a 2000:1 mass ratio of factor VIII plasmid:luciferase plasmid DNA using Lipofectamine 2000. Twenty-four hours after transfection the cells were rinsed twice with 1 ml of PBS and 0.5 ml of serum-free AIM V medium was added to each well. Cells were cultured 24 hr before the conditioned media was harvested and factor VIII activity was measured as described below.

Stable Expression of Factor VIII From Baby Hamster Kidney-Derived (BHK-M) Cells

BHK-M cells were transfected using Lipofectin along with an ReNeo plasmid containing factor VIII cDNA and cultured in the presence of DMEM:F12 containing 10% FBS, 100 units/ml penicillin, 100 µg/ml streptomycin and 500 µg/ml geneticin for 10 days. The ReNeo vector contains the neomycin phosphotransferase gene for resistance to the antibiotic geneticin. Twenty-four to 72 geneticin resistant clones were screened for factor VIII production. The clone from each cDNA construct that displayed the highest level of factor VIII activity was transferred into a 75 cm$^2$ flask, grown to 90-95% confluence and then switched to 25 ml serum-free AIM V media. After 24 hr, the conditioned media was replaced with 25 ml fresh serum-free media AIM V and cultured for an additional 24 hr. Harvested media from each time point was assayed for factor VIII activity as described below.

Factor VIII Assay

Factor VIII activity was measured by one-stage coagulation assay using a ST art Coagulation Instrument (Diagnostica Stago, Asnieres, France). Five µl of sample or standard was added to 50 µl of factor VIII-deficient plasma, followed by addition of 50 µl aPTT reagent and incubation for 3 min at 37° C. Fifty microliters of 20 mM $CaCl_2$ was added to initiate the reaction, and the time required to develop a fibrin clot was measured viscometrically. Standard curves were generated using several dilutions of pooled normal human plasma and subjected to linear regression analysis of the clotting time versus the logarithm of the reciprocal plasma dilution. For determination of factor VIII activity, samples were diluted in HEPES buffered saline to a concentration within the range of the standard curve.

Results

Figure 3:
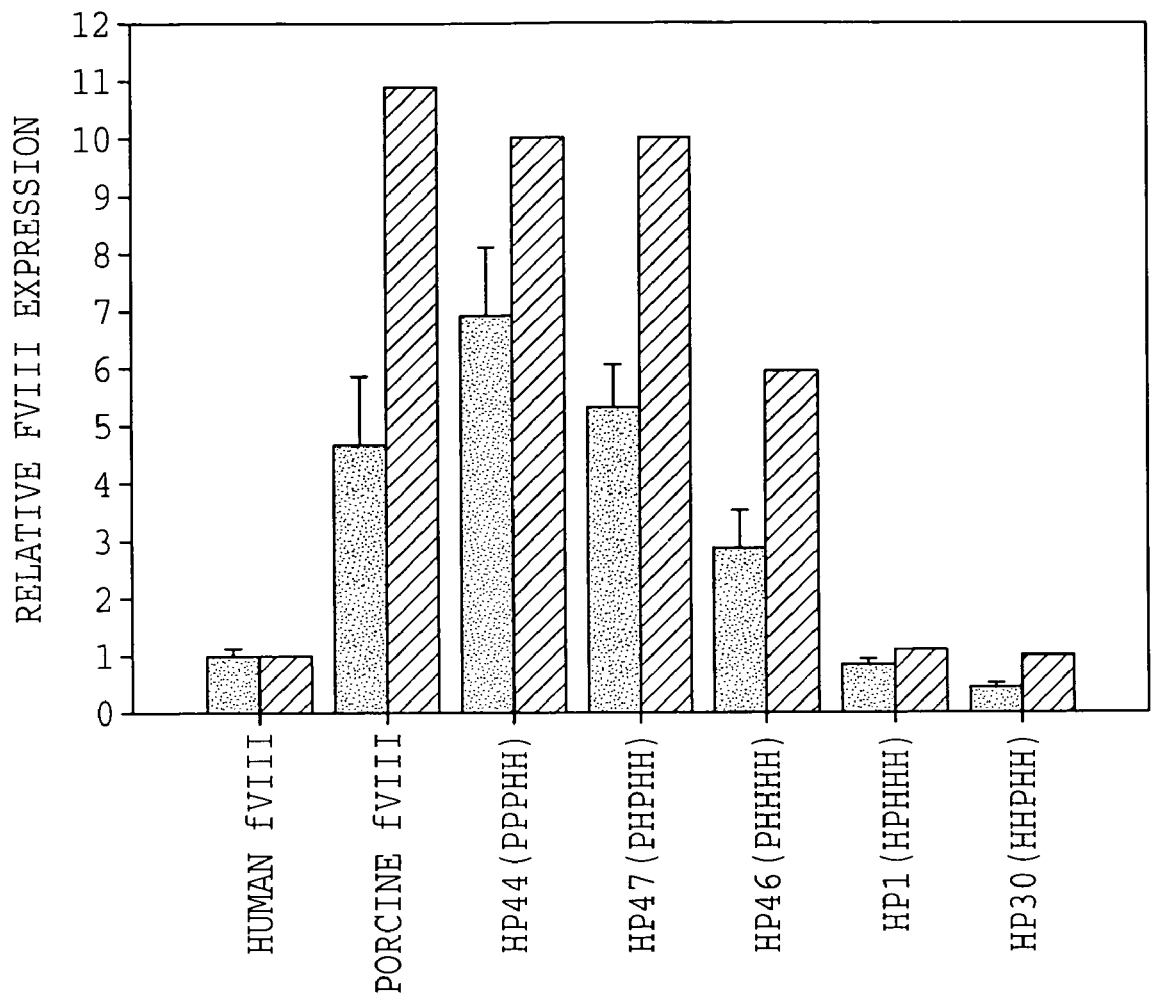
FIG. 3 provides graphical data showing heterologous expression of a recombinant B domain-deleted porcine factor VIII protein, designated P/OL, recombinant B domain-deleted human factor VIII protein, and five recombinant B domain-deleted hybrid human/porcine factor VIII proteins, designated HP1, HP30, HP44, HP46, and HP47. COS-7 cells (solid bars) and baby hamster kidney-derived cells, designated BMK-M cells, (hatched bars) were transfected with the individual factor VIII expression constructs and luciferase plasmid DNA and cultured in serum-free media for 24 hr. The data illustrates that there is a significant increase in expression of P/OL, HP44, HP47, and HP46 compared to HSQ. In contrast, expression of HP1 and HP30 were not increased compared to HSQ.

To identify regions in porcine factor VIII that confer high-level expression, human/porcine hybrid factor VIII molecules shown in FIG. 2 were constructed and their expression levels in COS-7 and BHK-M cells were measured. After COS-7 cell transfection, the expression plasmid is not integrated into genomic DNA, but is present transiently as an episomal DNA. Expression levels from COS-7 cells represent an average of the cell population. FIG. 3 shows the results of COS-7 wells transfected in quadruplicate. There is a significant increase in expression of P/OL, HP44, HP47, and HP46 compared to HSQ. In contrast, expression of HP 1 and HP30 were not increased compared to HSQ.

Expression of factor VIII from BHK-M cells was consistent with the results in COS-7 cells. After BHK-M cell transfection, clones containing plasmid DNA that is stably incorporated into the genome are selected using the antibiotic geneticin. Cells that do not contain the neomycin phosphotransferase gene contained in the plasmid do not survive in the presence of geneticin. Approximately 50% of the clones resulting from transfection of BHK-M cells with the constructs shown in FIG. 2 did not express detectable levels of factor VIII (data not shown). This is consistent with previous results with HSQ and P/OL (Doering et al. (2002) *J. Biol. Chem.* 277: 38345-38349) and is expected because factor VIII expression per se is not selected for during geneticin selection. Average expression levels for factor VIII-producing clones were significantly higher for the P/OL, HP44, HP47, and HP46, but not the HP1 and HP30 constructs, compared to HSQ (data not shown). For each factor VIII cDNA construct, the clone producing the highest levels of factor VIII was expanded and switched to serum-free AIM V medium. Consistent with the above results, factor VIII levels for the HP44, HP47, and HP46, but not the HP1 and HP30, were comparable to P/OL (FIG. 3).

FIG. 3 shows heterologous expression of recombinant porcine factor VIII OL and recombinant human factor VIII SQ. COS-7 cells (solid bars) were transfected with the individual factor VIII expression constructs and luciferase plasmid DNA and cultured in serum-free media for 24 hr as described in Experimental Procedures. Conditioned media was assayed for factor VIII activity by one-stage coagulation assay. After media harvest, cells were lysed and assayed for luciferase activity. Data are presented as the ratio of factor VIII activity: luciferase activity (mean+/−standard deviation of four wells of transfected cells for each sample) normalized to the mean HSQ level. Data shown are representative of experiments involving three separate cultures of COS-7 cells. BHK-M cells (hatched bars) were transfected with the individual factor VIII expression constructs and selected for stable transgene integration. The top producing clone for each construct was split to a 75 $cm^2$ flask, grown to greater than 90% confluence, rinsed twice with PBS and cultured 24 hr in serum-free media. After 24 hr, the media was harvested and assayed for factor VIII activity. The data are expressed relative to HSQ expression, which was 2.8 units/$10^6$ cells/24 h in BHK-M cells.

Discussion

Recombinant B domain-deleted porcine factor VIII is expressed at levels up to 14-fold greater than recombinant human factor VIII (Doering et al. (2002) *J. Biol. Chem.* 277: 38345-38349). The levels are substantially greater than in previously published reports of factor VIII expression (Table II). The mechanism for the high expression phenomenon has not been established. However, high-level expression is due to a difference between human and porcine B domain-deleted factor VIII in translated sequence because the P/OL and HSQ expression cassettes do not contain endogenous factor VIII 5'-UTR sequence, while both possess the first 749 nt (of 1805 nt) of the human factor VIII 3'UTR. Furthermore, the effect occurs at the post-transcriptional level, because there is no difference in P/OL and HSQ mRNA levels in BHK-M cells (Doering et al. (2002) *J. Biol. Chem.* 277: 38345-38349).

TABLE II

Previous Reports of FACTOR VIII Expression.

| FACTOR VIII Construct | FVIII Level | Assay | Serum | vWf | Cell Line | Reference |
|---|---|---|---|---|---|---|
| Human, full length | 0.07[a] | Coatest | + | − | BHK | Wood et al. (1984) Nature 312: 330-337 |
| Human, full length | 0.16[a] 0.33[a] | Coatest Coagulation | + | − | COS | Toole et al. (1986) Proc. Natl. Acad. Sci. U.S.A. 83: 5939-5942 |
| Human, B domain-deleted | 0.34[a] | Coatest | − | − | CHO[c] | Kaufman et al. (1988) J. Biol. Chem. 263: 6352-6362 |
| Human, full length | 1.4[b] | Coatest | − | + | CHO | Kaufman et al. (1989) Mol. Cell Biol. 9: 1233-1242 |
| Human, B domain-deleted | 5[a] | Coatest | − | + | CHO | Pittman et al. (1993) Blood 81: 2925-2935 |

TABLE II-continued

Previous Reports of FACTOR VIII Expression.

| FACTOR VIII Construct | FVIII Level | Assay | Serum | vWf | Cell Line | Reference |
|---|---|---|---|---|---|---|
| Human, B domain-deleted | 1.5[a] | Coatest | − | − | CHO | Lind et al. (1995) Eur. J. Biochem. 232: 19-27 |
| Human, B domain-deleted | 2.5[b] | Coagulation | + | − | CHO | Plantier et al. (2001) Thromb. Haemost. 86: 596-603 |
| Human, B domain-deleted | 3.1[a] 10[b] | Coagulation | − | − | BHK | Doering et al. (2002) J. Biol. Chem. 277, 38345-38349 |
| Porcine, B domain-deleted | 41[a] 140[b] | Coagulation | − | − | BHK | Doering et al. (2002) J. Biol. Chem. 277, 38345-38349 |

[a]units/milliliter/24 hours
[b]units/10$^6$ cells/24 hours
[c]Chinese hamster ovary Example 3

Figure 12:
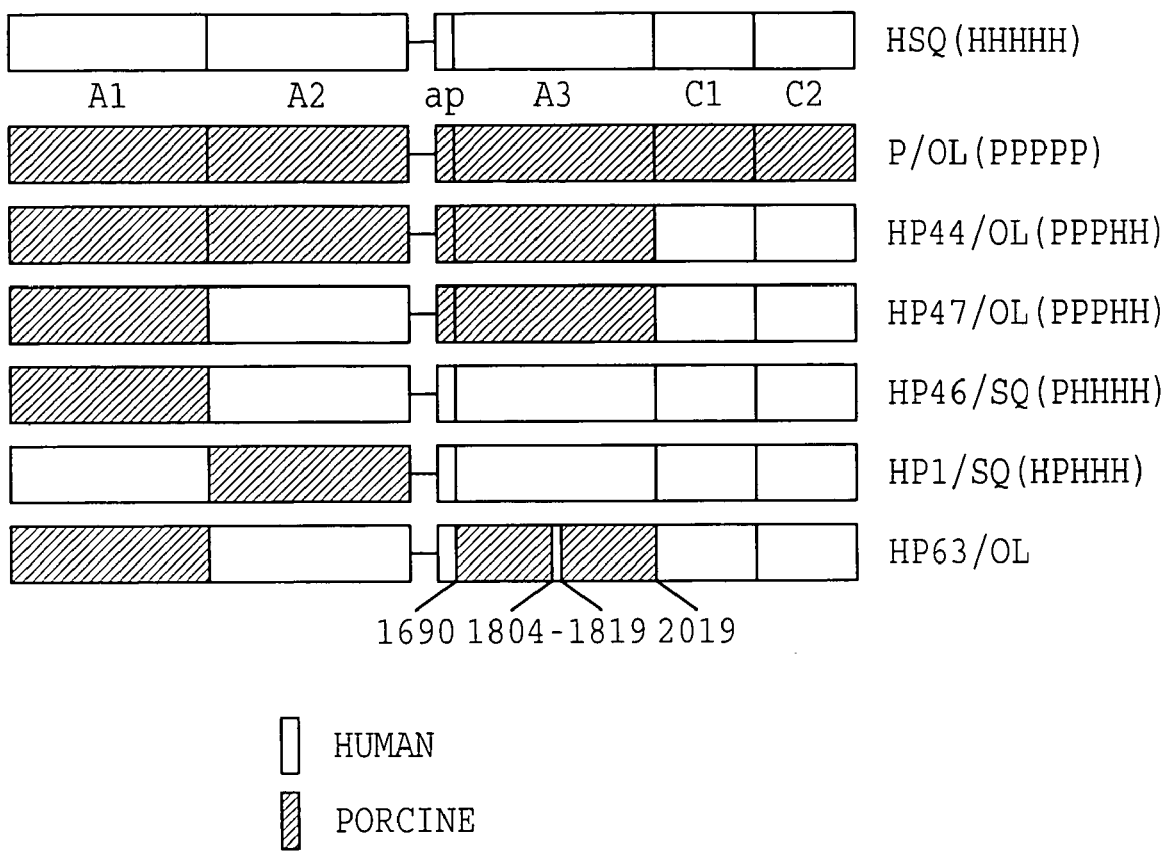
FIG. 12 provides a schematic representation of one possible factor VIII$_{SEP}$ variant of the present invention. The variant, referred to as HP63/OL, contains the porcine A1 domain and a partially humanized ap-A3 domain that comprises porcine amino acids from about 1690 to about 1804 and from about 1819 to about 2019.

Variants of the factor VIII$_{SEP}$ sequences of the invention may be generated. For example, the HP63/OL factor VIII$_{SEP}$ may be generated. See FIGS. 12-14.

Two major human factor VIII epitopes that are recognized by inhibitory antibodies have been identified: in the A2 domain in a segment bound by residues 484-508 (Healey et al. (1995) *J. Biol. Chem.* 270:14505-14509) and in the C2 domain in a segment bounded by residues 2181-2252 (Healey et al. (1998) *Blood* 92:3701-3709 and Barrow et al. (2001) *Blood* 97:169-174, all of which are herein incorporated by reference). The sequence numbering refers to the fill-length, mature human factor VIII according to standard convention (Vehar et al. (1984) *Nature* 312:337-342). Antibodies also have been identified that recognize the light chain activation peptide, ap, (Barrow et al. (2000) *Blood* 95:557-561) and the A3 domain in a region bounded by residues 1804-1819 (Zhong et al. (1998) *Blood* 92:136-142), but they are less common (Prescott et al. (1997) *Blood* 89:3663-3671). Other epitopes occasionally have been identified, but they are considered unusual.

A variant of a factor VIII$_{SEP}$ molecule can be generated to contain the human A2, ap, and C2 domains, human sequence 1804-1819 and the porcine A1 domain and porcine A3 sequences from about 1690 to 1803 and from about 1820 to 2019. This factor VIII$_{SEP}$ variant is diagramed in FIG. 12 as HP63. The amino acid and nucleotide sequences are provided in SEQ ID NO: 20 and 21. Such a molecule is predicted to be a super-expresser that has the antigenic characteristics of human factor VIII. Assays to measure the high-level expression activity of the HP63 variant are disclosed elsewhere herein.

TABLE III

Sequence ID Listing

| SEQ ID NO | Type | Species | Description |
|---|---|---|---|
| 1 | NT | *Sus scrofa* | Factor VIII |
| 2 | AA | *Sus scrofa* | Factor VIII |
| 3 | NT | *Sus scrofa* | Factor VIII - B-domain deleted (retains first 12 and last 12 amino acids of B-domain) |
| 4 | AA | *Sus scrofa* | Factor VIII - B-domain deleted (retains first 12 and last 12 amino acids of B-domain) |
| 5 | NT | *Homo sapiens* | Factor VIII with 5' and 3' UTR sequences |
| 6 | AA | *Homo sapiens* | Factor VIII |
| 7 | NT | *Homo sapiens* | Factor VIII cDNA |
| 8 | AA | *Mus musculus* | Factor VIII |
| 9 | AA | *Homo sapiens* | Linker sequence between A2 and ap domains |
| 10 | AA | *Homo sapiens* | Recognition sequence for PACE/furin |
| 11 | AA | *Sus scrofa* | Linker sequence between A2 and ap domains |
| 12 | NT | *Homo sapiens* | Factor VIII - B-domain deleted |
| 13 | AA | *Homo sapiens* | Factor VIII - B domain deleted |
| 14 | NT | Artificial | HP44/OL Factor VIII which has the following domains: A1$_P$-A2$_P$-ap$_P$-A3$_P$-C1$_H$-C2$_H$ |
| 15 | AA | Artificial | HP44/OL Factor VIII which has the following domains: A1$_P$-A2$_P$-ap$_P$-A3$_P$-C1$_H$-C2$_H$ |
| 16 | NT | Artificial | HP46/SQ Factor VIII which has the following domains: A1$_P$-A2$_H$-ap$_H$-A3$_H$-C1$_H$-C2$_H$ |
| 17 | AA | Artificial | HP46/SQ Factor VIII which has the following domains: A1$_P$-A2$_H$-ap$_H$-A3$_H$-C1$_H$-C2$_H$ |
| 18 | NT | Artificial | HP47/OL Factor VIII which has the following domains: A1$_P$-A2$_H$-ap$_P$-A3$_P$-C1$_H$-C2$_H$ |
| 19 | AA | Artificial | HP47/OL Factor VIII which has the following domains: A1$_P$-A2$_H$-ap$_P$-A3$_P$-C1$_H$-C2$_H$ |
| 20 | NT | Artificial | HP63/OL |
| 21 | AA | Artificial | HP63/OL |

The present invention has been described above with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

What is claimed is:

1. An isolated nucleic acid molecule encoding a modified factor VIII polypeptide comprising a nucleotide sequence having at least 95% sequence identity to the polynucleotide sequence shown in SEQ ID NO: 18, wherein said nucleotide sequence encodes a polypeptide characterized by high-level expression when compared to a corresponding human factor VIII polypeptide expressed under the same conditions.

2. The isolated nucleic acid molecule of claim 1, wherein said nucleotide sequence is selected from the group consisting of:
   a) a nucleotide sequence comprising the sequence set forth in SEQ ID NO: 18; and,
   b) a nucleotide sequence comprising the sequence encoding a polypeptide comprising the amino acid sequence at least 95% identical to that set forth in SEQ ID NO: 19.

3. A DNA construct comprising the nucleic acid molecule of claim 1.

4. A DNA construct comprising the nucleic acid molecule of claim 2.

5. A vector comprising the nucleic acid molecule of claim 1.

6. A vector comprising the nucleic acid molecule of claim 2.

7. A cell comprising the nucleic acid molecule of claim 1.

8. A cell comprising the nucleic acid molecule of claim 2.

9. A cell comprising the vector of claim 5.

10. A cell comprising the vector of claim 6.

11. A method of producing a modified factor VIII polypeptide comprising:
   a) introducing into a cell a nucleic acid molecule comprising the nucleotide sequence having at least 95% sequence identity to SEQ NO: 18, wherein said sequence encodes said polypeptide and said polypeptide is characterized by high-level expression when compared to a corresponding human factor VIII polypeptide expressed under the same conditions; and
   b) culturing said cell under conditions that allow expression of said nucleotide sequence.

12. The method of claim 11, wherein said nucleotide sequence is selected from the group consisting of:
   a) a nucleotide sequence comprising the sequence set forth in SEQ ID NO: 18; and,
   b) a nucleotide sequence comprising the sequence encoding a polypeptide comprising the amino acid sequence at least 95% identical to that set forth in SEQ ID NO: 19.

13. The method of claim 11 further comprising isolating said polypeptide.

14. The method of claim 12 further comprising isolating said polypeptide.

* * * * *

UNITED STATES PATENT AND TRADEMARK OFFICE
CERTIFICATE OF CORRECTION

PATENT NO. : 7,635,763 B2  Page 1 of 1
APPLICATION NO. : 10/813507
DATED : December 22, 2009
INVENTOR(S) : John S. Lollar It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1229 days.

Signed and Sealed this

Ninth Day of November, 2010

David J. Kappos
*Director of the United States Patent and Trademark Office*